US009452228B2

(12) United States Patent
Liu et al.

(10) Patent No.: US 9,452,228 B2
(45) Date of Patent: *Sep. 27, 2016

(54) ANTIBODIES REACTIVE WITH AN EPITOPE LOCATED IN THE N-TERMINAL REGION OF MUC5AC COMPRISING CYSTEINE-RICH SUBDOMAIN 2 (CYS2)

(71) Applicant: Immunomedics, Inc., Morris Plains, NJ (US)

(72) Inventors: Donglin Liu, Kendall Park, NJ (US); Chien-Hsing Chang, Downingtown, PA (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/753,249

(22) Filed: Jun. 29, 2015

(65) Prior Publication Data

US 2015/0315289 A1 Nov. 5, 2015

Related U.S. Application Data

(60) Continuation-in-part of application No. 14/632,480, filed on Feb. 26, 2015, now Pat. No. 9,238,084, which is a division of application No. 14/242,138, filed on Apr. 1, 2014, now Pat. No. 9,005,613.

(60) Provisional application No. 61/807,176, filed on Apr. 1, 2013, provisional application No. 61/818,708, filed on May 2, 2013, provisional application No. 61/896,909, filed on Oct. 29, 2013, provisional application No. 62/018,989, filed on Jun. 30, 2014, provisional application No. 62/091,932, filed on Dec. 15, 2014, provisional application No. 62/148,428, filed on Apr. 16, 2015.

(51) Int. Cl.

| | |
|---|---|
| *A61K 39/395* | (2006.01) |
| *A61K 51/10* | (2006.01) |
| *A61K 38/19* | (2006.01) |
| *A61K 38/20* | (2006.01) |
| *A61K 38/21* | (2006.01) |
| *A61K 38/28* | (2006.01) |
| *A61K 38/29* | (2006.01) |
| *A61B 5/055* | (2006.01) |
| *A61K 45/06* | (2006.01) |
| *A61K 47/48* | (2006.01) |
| *A61K 51/04* | (2006.01) |
| *A61K 51/08* | (2006.01) |
| *A61K 31/404* | (2006.01) |
| *A61K 31/519* | (2006.01) |
| *A61K 31/5377* | (2006.01) |
| *A61K 31/7068* | (2006.01) |
| *A61K 33/24* | (2006.01) |
| *B82Y 5/00* | (2011.01) |
| *C07K 16/30* | (2006.01) |

(Continued)

(52) U.S. Cl.
CPC ............ *A61K 51/1093* (2013.01); *A61B 5/055* (2013.01); *A61K 31/404* (2013.01); *A61K 31/519* (2013.01); *A61K 31/5377* (2013.01); *A61K 31/7068* (2013.01); *A61K 33/24* (2013.01); *A61K 38/19* (2013.01); *A61K 38/193* (2013.01); *A61K 38/20* (2013.01); *A61K 38/21* (2013.01); *A61K 38/212* (2013.01); *A61K 38/215* (2013.01); *A61K 38/217* (2013.01); *A61K 38/28* (2013.01); *A61K 38/29* (2013.01); *A61K 39/39558* (2013.01); *A61K 45/06* (2013.01); *A61K 47/486* (2013.01); *A61K 47/48746* (2013.01); *A61K 51/0406* (2013.01); *A61K 51/0491* (2013.01); *A61K 51/08* (2013.01); *A61K 51/088* (2013.01); *A61K 51/109* (2013.01); *A61K 51/1057* (2013.01); *B82Y 5/00* (2013.01); *C07K 16/303* (2013.01); *C07K 16/3092* (2013.01); *C07K 16/44* (2013.01); *G01N 33/57438* (2013.01); *A61K 2039/505* (2013.01); *A61K 2039/507* (2013.01); *B82Y 15/00* (2013.01); *C07K 2317/24* (2013.01); *C07K 2317/30* (2013.01); *C07K 2317/31* (2013.01); *C07K 2317/34* (2013.01); *C07K 2317/54* (2013.01); *C07K 2317/55* (2013.01); *C07K 2317/565* (2013.01); *C07K 2317/567* (2013.01); *G01N 2333/4725* (2013.01)

(58) Field of Classification Search
None
See application file for complete search history.

(56) References Cited

U.S. PATENT DOCUMENTS

| | | | |
|---|---|---|---|
| 4,046,722 | A | 9/1977 | Rowland |
| 4,699,784 | A | 10/1987 | Shih et al. |

(Continued)

FOREIGN PATENT DOCUMENTS

| | | |
|---|---|---|
| WO | 0068248 | 11/2000 |
| WO | 03106495 | 12/2003 |

(Continued)

OTHER PUBLICATIONS

Gold et al. (Int. J. Cancer, vol. 57, 204-210, 1994).*

(Continued)

*Primary Examiner* — Laura B Goddard
*Assistant Examiner* — Meera Natarajan
(74) *Attorney, Agent, or Firm* — Richard A. Nakashima

(57) ABSTRACT

The present invention concerns compositions and methods of use of antibodies or antibody fragments that bind to an epitope located within the second cysteine-rich domain (Cys2, amino acid residues 1575-1725) of MUC5AC. The antibodies bind with high specificity and selectivity to pancreatic cancer and are of use for therapy, detection and/or diagnosis of pancreatic cancer. In preferred embodiments, therapeutic antibody may be conjugated to at least one therapeutic agent, such as $^{90}$Y. Both in vivo and in vitro detection of pancreatic cancer may be performed with the subject methods and compositions. Specific dosages of radiolabeled antibody and/or gemcitabine, of use in human pancreatic cancer patients, are disclosed herein.

11 Claims, 38 Drawing Sheets

(51) Int. Cl.
  *C07K 16/44* (2006.01)
  *G01N 33/574* (2006.01)
  *B82Y 15/00* (2011.01)
  *A61K 39/00* (2006.01)

(56) References Cited

U.S. PATENT DOCUMENTS

| | | | |
|---|---|---|---|
| 4,868,109 A | 9/1989 | Lansdorp et al. | |
| 4,935,498 A | 6/1990 | Sessler et al. | |
| 5,530,101 A | 6/1996 | Queen et al. | |
| 5,693,762 A | 12/1997 | Queen et al. | |
| 5,770,198 A | 6/1998 | Coller et al. | |
| 5,776,427 A | 7/1998 | Thorpe et al. | |
| 5,859,205 A | 1/1999 | Adair et al. | |
| 6,017,514 A | 1/2000 | Epstein et al. | |
| 6,120,995 A | 9/2000 | Waldman et al. | |
| 6,176,842 B1 | 1/2001 | Tachibana et al. | |
| 6,261,537 B1 | 7/2001 | Klaveness et al. | |
| 6,306,393 B1 | 10/2001 | Goldenberg | |
| 6,342,219 B1 | 1/2002 | Thorpe et al. | |
| 6,524,854 B1 | 2/2003 | Monia et al. | |
| 6,632,926 B1 | 10/2003 | Chen et al. | |
| 6,989,140 B2 | 1/2006 | Tidmarsh et al. | |
| 7,060,506 B2 | 6/2006 | Craig | |
| 7,138,103 B2 | 11/2006 | Goldenberg et al. | |
| 7,547,441 B2 * | 6/2009 | Ranson | C07K 14/8132 424/193.1 |
| 8,574,854 B2 | 11/2013 | Gold et al. | |
| 8,795,662 B2 | 8/2014 | Gold et al. | |
| 2002/0041847 A1 | 4/2002 | Goldenberg et al. | |
| 2003/0096249 A1 | 5/2003 | Westphal et al. | |
| 2003/0198595 A1 | 10/2003 | Goldenberg et al. | |
| 2003/0198956 A1 | 10/2003 | Makowski et al. | |
| 2004/0018587 A1 | 1/2004 | Makowski et al. | |
| 2004/0126361 A1 | 7/2004 | Saifer et al. | |
| 2005/0002945 A1 | 1/2005 | McBride et al. | |
| 2005/0003403 A1 | 1/2005 | Rossi et al. | |
| 2005/0014207 A1 | 1/2005 | Goldenberg et al. | |
| 2005/0053606 A1 | 3/2005 | Kufe et al. | |
| 2006/0210475 A1 | 9/2006 | Goldenberg et al. | |
| 2007/0044171 A1 | 2/2007 | Kovalic et al. | |
| 2007/0048217 A1 | 3/2007 | McBride et al. | |
| 2007/0264265 A1 | 11/2007 | Goldenberg et al. | |
| 2008/0171067 A1 | 7/2008 | Govindan et al. | |
| 2009/0111143 A1 | 4/2009 | Goldenberg et al. | |
| 2009/0304580 A1 | 12/2009 | Goldenberg et al. | |
| 2012/0301400 A1 | 11/2012 | Williams et al. | |
| 2013/0005598 A1 | 1/2013 | Haab et al. | |
| 2013/0247232 A1 | 9/2013 | Wang | |
| 2014/0170063 A1 | 6/2014 | Govindan et al. | |
| 2014/0227179 A1 | 8/2014 | Liu et al. | |

FOREIGN PATENT DOCUMENTS

| | | |
|---|---|---|
| WO | 2011133609 | 10/2011 |
| WO | 2012112443 | 8/2012 |

OTHER PUBLICATIONS

Alisauskus et al., "Initial studies of monoclonal antibody PAM4 targeting to xenografted orthotopic pancreatic cancer", Cancer Res. Dec. 1, 1995;55(23 Suppl):5743s-5748s.

Chopra et al., "125I-Labeled trivalent, bispecific monoclonal antibody construct TF10 that targets mucin-1 and is reactive against a histamine-succinyl-glycine hapten IMP-288", Molecular Imaging and Contrast Agent Database (MICAD) [Internet]. Bethesda (MD): National Center for Biotechnology Information (US); 2004-2013. Jun. 29, 2011 [updated Aug. 25, 2011].

Chopra et al., "111In/125/131I-Labeled anti-mucin-1 murine, chimeric or humanized antibody hPAM4", Molecular Imaging and Contrast Agent Database (MICAD) [Internet]. Bethesda (MD): National Center for Biotechnology Information (US); 2004-2013. Jun. 16, 2011 [updated Jul. 26, 2011].

Eguia et al., "Early detection of pancreatic cancer", JOP. Mar. 10, 2012;13(2):131-4.

Glazer et al., "Noninvasive radiofrequency field destruction of pancreatic adenocarcinoma xenografts treated with targeted gold nanoparticles", Clin Cancer Res. Dec. 1, 2010;16(23):5712-21.

Gold et al., "Combined 90Yttrium-DOTA-labeled PAM4 antibody radioimmunotherapy and gemcitabine radiosensitization for the treatment of a human pancreatic cancer xenograft", Int J Cancer. Apr. 20, 2004;109(4):618-26.

Gold et al., "Low-dose radioimmunotherapy ((90)Y-PAM4) combined with gemcitabine for the treatment of experimental pancreatic cancer", Clin Cancer Res. Sep. 1, 2003;9(10 Pt 2):3929S-37S.

Gold et al., "Targeting of xenografted pancreatic cancer with a new monoclonal antibody, PAM4", Cancer Res. Mar. 1, 1995;55(5):1105-10.

Han et al., "The role of PAM4 in the management of pancreatic cancer: diagnosis, radioimmunodetection, and radioimmunotherapy", J Immunol Res. 2014;2014:268479.

Hoimes et al., "Biomarkers for early detection and screening in pancreatic cancer", Highlights from the 45th ASCO annual meeting. Orlando, FL, USA. May 29-Jun. 2, 2009, JOP. Jul. 6, 2009;10(4):352-6.

Liu et al., "Identification of PAM4 (clivatuzumab)-reactive epitope on MUC5AC: A promising biomarker and therapeutic target for pancreatic cancer", Oncotarget. Feb. 28, 2015;6(6):4274-85.

Schmidt, C., "Early detection tools for pancreatic cancer", J Natl Cancer Inst. Aug. 8, 2012;104(15):1117-8.

Matarrese et al., "Type I Interferon Gene Transfer Sensitizes Melanoma Cells to Apoptosis via a Target Activity on Mitochondrial Function" Am. J. Pathol. 2002, 160(4):1507-1520.

Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.

Newlon et al., "A Novel Mechanism of PKA Anchoring Revealed by Solution Structures of Anchoring Complexes", EMBO J. 2001;20(7):1651-1662.

Newlon et al., "The Molecular Basis for Protein Kinase A Anchoring Revealed by Solution NMR", Nat. Struct Biol. 1999;6(3):222-227.

Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.

Osborn et al., "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).

Oyen et al., "Human testis cDNA for the regulatory subunit RIIα of cAMP-dependent protein kinase encodes an alternate amino-terminal region", FEBS Letters 246:57-64, 1989.

Ozzello et al., "Conjugation of interferon alpha to a humanized monoclonal antibody (HuBrE-3vl) enhances the selective localization and antitumor effects of interferon in breast cancer xenografts" Breast Cancer Res. Treat. 48: 135-147 (1998).

Paquette et al., "Interferon-α and granulocyte-macrophage colony-stimulating factor differentiate peripheral blood monocytes into potent antigen-presenting cells" J. Leukoc. Biol. 64:358-367; 1998.

Patel et al., "Anti-tumor activity of a novel monoclonal antibody, NPC-1C, optimized for recognition of tumor antigen MUC5AC variant in preclinical models", Cancer Immunol Immunother. Jun. 2013;62(6):1011-9.

Pelham et al., "Interferon-α conjugation to human osteogenic sarcoma monoclonal antibody 791T/36" Cancer Immunol. Immuother 1983;15(3):210-216.

Pepinsky et al., "Improved Pharmacokinetic Properties of a Polyethylene Glycol-Modified Form of Interferon-β-1a With Preserved in Vitro Bioactivity", Pharmacol. Exp. Ther. 2001;297(3):1059-1066.

Pilling et al., "Interferon-β mediates stromal cell rescue of T cells from apoptosis" Eur. J. Immunol. 29:1041-1050 (1999).

(56) References Cited

OTHER PUBLICATIONS

Rabjohn et al., "Molecular Cloning and Epitope Analysis of the Peanut Allergen Ara h 3" J. Clinical Investigation 103 (4):535-542 (1999).
Raefsky et al., "Studies of Interferon as a regulator of hematopoietic cells proliferation" J. Immunol. 135 (4):2507-2512 (1985).
Reis et al. "Immunohistochemical study of MUC5AC expression in human gastric carcinomas using a novel monoclonal antibody", Int J Cancer. Feb. 20, 1997;74(1):112-21.
Rose et al., "Structural basis of dimerization, coactivator recognition and MODY3 mutations in HNF-1α", Nature Struct. Biol. 2000; 7:744-748.
Rosendahl et al., "A Long-Acting, Highly Potent Interferon α-2 Conjugate Created Using Site-Specific PEGylation", Bioconjugate Chem. 2005;16:200-207.
Rossi et al., "Novel Designs of Multivalent Anti-CD20 Humanized Antibodies as Improved Lymphoma Therapeutics", Cancer Res. 68:8384-92, 2008.
Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.
Rustandi et al., "The Ca2+-Dependent Interaction of S100B(ββ) with a Peptide Derived from p53", Biochemistry 1998; 37: 1951-1960.
Sabaawy et al., "Enhancement of 5-fluorouracil cytotoxicity on human colon cancer cells by retrovirus-mediated interferon-α gene transfer" Int. J. Oncol. Jun. 1999; 14(6):1143-51.
Salles et al., "Rituximab combined with chemotherapy and interferon in follicular lymphoma patients: results of the GELA-GOELAMS FL2000 study" Blood 2008; 112:4824-4831.
Santini et al., "Type I Interferon as a Powerful Adjuvant for Monocyte-derived Dendritic Cell Development and Activity in Vivo and in Hu-PBL-SCID Mice" J. Exp. Med. 191(10):1777-1788 (2000).
Scott et al., "Type II Regulatory Subunit Dimerization Determines the Subcellular Localization of the cAMP-dependent Protein Kinase", J. Biol. Chem. 265:21561-66 (1990).
Scott et al., "Cyclic nucleotide-dependent protein kinases" Pharmacol. Ther. 1991;50(1):123-45.
Seffernick et al., "Melamine Deaminase and Atrazine Chlorohydrolase: 98 Percent Identical but Functionally Different" J. Bacteriol. Apr. 2001;183(8):2405-10.
Sharkey et al., "Improved Therapeutic Results by Pretargeted Radioimmunotherapy of Non-Hodgkin's Lymphoma with a New Recombinant, Trivalent, Anti-CD20, Bispecific Antibody", Cancer Res. 68:5282-90, 2008.
Sharkey et al., "Metastatic Human Colonic Carcinoma: Molecular Imaging with Pretargeted SPECT and PET in a Mouse Model", Radiology 246:497-507, 2008.
Sidky et al., "Inhibition of Angiogenesis by Interferons: Effects on Tumor- and Lymphocyte-induced Vascular Responses" Cancer Res. 47:5155-5161, Oct. 1, 1987.
Silsirivanit et al., "A novel serum carbohydrate marker on mucin 5AC: values for diagnostic and prognostic indicators for cholangiocarcinoma", Cancer. Aug. 1, 2011;117(15)3393-403.
Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma" Clin. Cancer Res. vol. 10, 2868-2878, Apr. 15, 2004.
Stein et al., "Characterization of a humanized IgG4 anti-HLA-DR monoclonal antibody that lacks effector cell functions but retains direct antilymphoma activity and increases the potency of rituximab" Blood 2006;108:2736-2744.
Stokka et al., "Characterization of A-kinase-anchoring disruption using a solution-based assay" Biochem. J. (2006) 400, 493-499.
Stryer et al., "Levels of Structure in Protein Architecture", Biochemistry, 3rd Ed., pp. 31-33, W.H. Freeman & Co., New York, 1988.
Takaoka et al., Integration of interferon-α/β signalling to p53 responses in tumour suppression and antiviral defence Nature Jul. 31, 2003;424(6948):516-23.
Taylor, S., "cAMP-dependent Protein Kinase" J. Biol. Chem. 1989;264(15):8443-8446.
Walsh et al., "An Adenosine 3', 5'-Monophosphate-dependant Protein Kinase from Rabbit Skeletal Muscle" J. Biol. Chem. 243(13):3763-3774 (1968).
Wang et al., "Diagnostic value of mucins (MUC1, MUC2 and MUC5AC) expression profile in endoscopic ultrasound-guided fine-needle aspiration specimens of the pancreas", Int J Cancer. Dec. 15, 2007;121(12):2716-22.
Weck et al., "Comparison of the Antiviral Activities of Various Cloned Human Interferon-α Subtypes in Mammalian Cell Cultures" J. Gen. Virol. (1981), 57, 233-237.
Winkler et al., "Changing the Antigen Binding Specificity by Single Point Mutations of an Anti-p24 (HIV-1) Antibody", J. Immunol. 165:4505-14, 2000.
Witkowski et al., "Conversion of a β-Ketoacyl Synthase to a Malonyl Decarboxylase by Replacement of the Active-Site Cysteine with Glutamine" Biochemistry 38(36):11643-50 (1999).
Wong et al., "AKAP Signalling Complexes: Focal Points in Space and Time", Nat. Rev. Mol. Cell Biol. 2004;5:959-970.
Wongkham et al. "Serum MUC5AC mucin as a potential marker for cholangiocarcinoma", Cancer Lett. May 30, 2003;195(1):93-9.
Zhu et al., "Inhibition of tumor growth and metastasis by targeting tumor-associated angiogenesis with antagonists to the receptors of vascular endothelial growth factor", Invest. New Drugs 17:195-212, 1999.
Von Hoff et al., "Increased survival in pancreatic cancer with nab-paclitaxel plus gemcitabine", N Engl J Med. Oct. 31, 2013;369(18):1691-703.
Abbas et al., Cellular and Molecular Immunology, W.B. Saunders Comp. 1991, p. 43.
Alto et al., "Bioinformatic Design of A-kinase Anchoring Protein-in Silico: A Potent and Selective Peptide Antagonist of Type II Protein Kinase A Anchoring", Proc. Natl. Acad. Sci, USA. 2003;100:4445.
Backer et al., "Self-Assembled "Dock and Lock" System for Linking Payloads to Targeting Proteins" Bioconjugate Chem., 2006, 17(4):912-919.
Baillie et al., "Compartmentalisation of phosphodiesterases and protein kinase A: opposites attract", FEBS Letters 2005; 579:3264-3270.
Banky et al., "Dimerization/Docking Domain of the Type Iα Regulatory Subunit of cAMP-dependent Protein Kinase", J. Biol. Chem. 273:35048-55, 1998.
Basu et al., "Structure-Function Engineering of Interferon-β-1b for Improving Stability, Solubility, Potency, Immunogenicity, and Pharmacokinetic Properties by Site-Selective Mono-PEGylation", Bioconjugate Chem. 2006;17:618-630.
Belardelli et al., "Interferon-alpha in tumor immunity and immunotherapy" Cytokine Growth Factor Rev. 13(2):119-134 (2002).
Belardelli et al., "International Meeting on Cancer Vaccines: How Can We Enhance Efficacy of Therapeutic Vaccines?" Cancer Res. 64:6827-6830 (2004).
Belardelli et al., "The neglected role of type I interferon in the T-cell response: implications for its clinical use" Immunol. Today 17(8):369-72 (1996).
Biron et al., "Natural killer cells in antiviral defense: function and regulation by innate cytokines" Annu. Rev. Immunol. 17:189-220 (1999).
Brunda et al., "Modulation of Murine Natural Killer Cell Activity in Vitro and in Vivo by Recombinant Human Interferons" Cancer Res. 44:597-601 (1984).
Burns-Hamuro et al., "Distinct interaction modes of an AKAP bound to two regulatory subunit isoforms of protein kinase A revealed by amide hydrogen/deuterium exchange" Protein Science (2005), 14:2982-2992.
Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).

(56) References Cited

OTHER PUBLICATIONS

Carr et al., "Interaction of the Regulatory Subunit (RII) of cAMP-dependent Protein Kinase with RII-anchoring Proteins Occurs through an Amphipathic Helix Binding Motif", J. Biol. Chem. 1991;266:14188-14192.

Carrero et al., "Lymphocytes are detrimental during the early innate immune response against Listeria monocytogenes" J. Exp. Med. 203(4):933-940 (2006).

Chang et al., "The Dock and Lock Method: A Novel Platform Technology for Building Multivalent, Multifunctional Structures of Defined Composition with Retained Bioactivity", Clin. Cancer Res. 13:5586s-5591s, 2007.

Chmura et al., "Antibodies with infinite affinity" Proc. Natl. Acad. Sci. USA 98(15):8480-8484 (2001).

Colledge et al., "AKAPs: from structure to function", Trends Cell Biol. 1999; 9(6):216-21.

Corbin et al., "Regulation of Adenosine 3',5'—Monophosphate-dependent Protein Kinase", J. Biol. Chem. 248:1813-21 (1973).

Dhalluin et al.,"Structural and Biophysical Characterization of the 40 kDa PEG-Interferon-α2a and Its Individual Positional Isomers", Bioconjugate Chem. 2005;16:504-517.

Dodart et al., "Immunotherapy for Alzheimer's Disease: will vaccination work?" Trends Mol. Med. 9(3):85-87 (2003).

Doherty et al., "Site-Specific PEGylation of Engineered Cysteine Analogues of Recombinant Human Granulocyte-Macrophage Colony-Stimulating Factor", Bioconjugate Chem. 2005;16:1291-1298.

Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).

Ferrantini et al., "Interferon-α and cancer: Mechanisms of action and new perspectives of clinical use" Biochimie 89: 884-893 (2007).

Gillies et al., "High-level expression of chimeric antibodies using adapted cDNA variable region cassettes", J. Immunol. Methods 125 (1989) 191-202.

Glennie et al., "Mechanisms of killing by anti-CD20 monoclonal antibodies" Mol. Immunol. 44:3823-3837 (2007).

Gold et al., "A Novel Bispecific, Trivalent Antibody Construct for Targeting Pancreatic Carcinoma", Cancer Res. 68:4819-26, 2008.

Gold et al., "Molecular Basis of AKAP Specificity for PKA Regulatory Subunits" Mol. Cell Nov. 3, 2006;24(3):383-95.

Goldenberg et al., "Multifunctional Antibodies by the Dock-and-Lock Method for Improved Cancer Imaging and Therapy by Pretargeting", J. Nucl. Med. 49:158-63, 2008.

Goldenberg et al., "Properties and structure-function relationships of veltuzumab (hA20), a humanized anti-CD20 monoclonal antibody" Blood 113:1062-70 (2009).

Goodson et al., "Site-Directed PEGylation of Recombinant Interleukin-2 at its Glycosylation Site", Biotechnology Apr. 1990;8(4):343-6.

Grace et al., "Site of Pegylation and Polyethylene Glycol Molecule Size Attenuate Interferon-α Antiviral and Antiproliferative Activities Through the JAK/STAT Signaling Pathway", J. Biol. Chem. 2005;280(8):6327-6336.

Grimley et al., "Prolonged STAT1 Activation Related to the Growth Arrest of Malignant Lymphoma Cells by Interferon-α" Blood 91(8):3017-27 (1998).

Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).

Gutterman et al., "Cytokine therapeutics: Lessons from interferon α" Proc. Natl. Acad. Sci. USA 91:1198-205 (1994).

Harris et al., "Effect of pegylation on pharmaceuticals" Nat. Rev. Drug. Discov. 2:214-221 (2003).

Hausken et al., "Mutational Analysis of the A-Kinase Anchoring Protein (AKAP)-binding Site on RII", J. Biol. Chem. 271:29016-22 (1996).

Hodneland et al., "Selective immobilization of proteins to self-assembled monolayers presenting active site-directed capture ligands", Proc. Natl. Acd. Sci. USA 2002; 99:5048-5052.

Huang et al., "Targeting IFN-α to B Cell Lymphoma by a Tumor-Specific Antibody Elicits Potent Antitumor Activities" J. Immunol. 179:6881-88 (2007).

Hundsrucker et al., "High-affinity AKAP7δ-protein kinase A interaction yields novel protein kinase A-anchoring disruptor peptides" Biochem. J. (2006) 396, 297-306.

Kimby et al. "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).

Kinderman et al., "A Dynamic Mechanism for AKAP Binding to RII Isoforms of cAMP-Dependent Protein Kinase" Mol. Cell 24(3):397-408 (2006).

Kinstler et al., "Characterization and Stability of N-terminally PEGylated rhG-CSF", Pharm. Res. 1996;13 (7):996-1002.

Kramer et al., "Cell and virus sensitivity studies with recombinant human alpha interferons" J. Interferon. Res. 3 (4):425-35 (1983).

Le Bon et al., "Type I Interferons Potently Enhance Humoral Immunity and Can Promote Isotype Switching by Stimulating Dendritic Cells in Vivo" Immunity 14:461-470 (2001).

Lee et al., "Solid-Phase PEGylation of Recombinant Interferon α-2a for Site-Specific Modification: Process Performance, Characterization, and in Vitro Bioactivity", Bioconjug. Chem. 2007; 18:1728-34.

Lohmann et al., "High-affinity binding of the regulatory subunit (RII) of cAMP-dependent protein kinase to microtubule-associated and other cellular proteins", Proc. Natl. Acad. Sci. USA 81:6723-27 (1984).

Luft et al., "Type I IFNs Enhance the Terminal Differentiation of Dendritic Cells" J. Immunol. 161:1947-1953 (1998).

Mason, A., "Functional Analysis of the Cysteine Residues of Activin A", Mol. Endocrinol. 8:325-32, 1994.

Arlen et al., "The use of specific monoclonal antibodies to target immunogenic tumor membrane proteins in patients with recurrent pancreatic and colon cancer", Curr Drug Deily. Jan. 2012;9(1):52-6.

Bamrungphon et al., "A new mucin antibody/enzyme-linked lectin-sandwich assay of serum MUC5AC mucin for the diagnosis of cholangiocarcinoma", Cancer Lett. Mar. 18, 2007;247(2):301-8.

Brennan et al., "Novel agents for the treatment of pancreatic cancer", JOP. Mar. 10, 2014;15(2):110-3.

Bu et al., "Altered expression of MUC2 and MUC5AC in progression of colorectal carcinoma", World J Gastroenterol. Aug. 28, 2010;16(32):4089-94.

Cardillo et al., "Therapeutic Advantage of 90Yttrium-versus 131Iodine-labeled PAM4 Antibody in Experimental Pancreatic Cancer" Clin. Cancer Res. 7(10):3186-3192, Oct. 2001.

Cardillo et al., "Combined Gemcitabine and Radioimmunotherapy for the Treatment of Pancreatic Cancer" Int. J. Cancer: 97(3):386-392 (2002).

Cardillo et al., "Improved targeting of pancreatic cancer: experimental studies of a new bispecific antibody, pretargeting enhancement system for immunoscintigraphy", Clin Cancer Res. May 15, 2004;10(10):3552-61.

Cham et al., A solvent system for delipidation of plasma or serum without protein precipitation, J Lipid Res. Mar. 1976;17(2):176-81.

Clark et al., "Antibody humanization: a case of the Emeror's new clothes?" Immunol. Today 21(8):397-402 (2000).

Dall'Acqua et al., "Antibody Engineering" Curr. Opin. Struct. Biol., Aug. 1998; 8(4):443-50.

Daniel et al., "Mapping of Linear Antigenic Sites on the S Glycoprotein of a Neurotropic Murine Coronavirus with Synthetic Peptides: A Combination of Nine Prediction Algorithms Fails to Identify Relevant Epitopes and Peptide Immunogenicity Is Drastically Influenced by the Nature of the Protein Carrier" Virology 202, 540-549 (1994).

Emery et al., "Humanised monoclonal antibodies for therapeutic applications" Exp. Opin. Invest. Drugs (1994) 3(3):241-251.

Forgue-Lafitte et al., "Abnormal expression of M1/MUC5AC mucin in distal colon of patients with diverticulitis, ulcerative colitis and cancer", Int J Cancer. Oct. 1, 2007;121(7):1543-9.

(56) References Cited

OTHER PUBLICATIONS

Foser et al., "Improved biological and transcriptional activity of monopegylated interferon-alpha-2a isomers", Pharmacogenomics J. 2003;3(6):312-9.
Gold et al., "Radioimmunotherapy of Experimental Pancreatic Cancer with 131I-Labeled Monoclonal Antibody PAM4" Int. J. Cancer: 71(4):660-667 (1997).
Gold et al., "Chimerization and CDR-grafted humanization of PAM4, a murine monoclonal anti-pancreatic cancer antibody" Proc AACR 1993; 34:480, abstract 2866.
Gold et al., "Characterization of Monoclonal Antibody PAM4 Reactive with a pancreatic Cancer Mucin" Int. J. Cancer 57(2): 204-210 (1994).
Gold et al., "Localization of pancreatic cancer with radiolabeled monoclonal antibody PAM4" Crit. Rev. Oncol. Hematol. Jul.-Aug. 2001;39(1-2):147-154.
Gold et al., "New MUC1 serum immunoassay differentiates pancreatic cancer from pancreatitis", J Clin Oncol. Jan. 10, 2006;24(2):252-8.
Gold et al., "PAM4-Reactive MUC1 is a Biomarker for Early Pancreatic Adenocarcinoma", Clin. Cancer Res. 13 (24):7380-7387 (2007).
Gold et al., "Detection of early-stage pancreatic adenocarcinoma", Cancer Epidemiol Biomarkers Prev. Nov. 2010;19(11):2786-94.
Gold et al., "PAM4 enzyme immunoassay alone and in combination with CA 19-9 for the detection of pancreatic adenocarcinoma", Cancer. Feb. 1, 2013;119(3):522-8.
Gold et al., "Mapping PAM4 (clivatuzumab), a monoclonal antibody in clinical trials for early detection and therapy of pancreatic ductal adenocarcinoma, to MUC5AC mucin", Mol Cancer. Nov. 20, 2013;12(1):143.
Greenspan et al., "Defining epitopes: Its not as easy as it seems" Nat. Biotech. 17:936-937 (1999).
Gulec et al., "Treatment of advanced pancreatic carcinoma with 90Y-Clivatuzumab Tetraxetan: a phase I single-dose escalation trial", Clin Cancer Res. Jun. 15, 2011;17(12):4091-100. Epub Apr. 28, 2011.
Haab et al., "Glycosylation variants of mucins and CEACAMs as candidate biomarkers for the diagnosis of pancreatic cystic neoplasms", Ann Surg. May 2010;251(5):937-45.
Han et al., "Combination of MUC5ac and WT-1 immunohistochemistry is useful in distinguishing pancreatic ductal carcinoma from ovarian serous carcinoma in effusion cytology", Diagn Cytopathol. May 2010;38(5):333-6.
Ho et al., "Antisense Oligonucleaotides as Therapeutics for Malignant Diseases" Semin. Oncol. 24(2):187-202 (1997).
Ho et al., "Secretion of MUC5AC mucin from pancreatic cancer cells in response to forskolin and VIP", Biochem Biophys Res Commun. Jun. 14, 2002;294(3):680-6.
Ho et al., "Methylation status of promoters and expression of MUC2 and MUC5AC mucins in pancreatic cancer cells", Int J Oncol. Feb. 2003;22(2):273-9.
Hoshi et al., "Tumor-associated MUC5AC stimulates in vivo tumorigenicity of human pancreatic cancer", Int J Oncol. Mar. 2011;38(3):619-27.
Jones, DT., "Critically assessing the state-of-the-art in protein structure prediction" Pharmacogenomics J.; 1:126-134, 2001.
Kanno et al., "The expression of MUC4 and MUC5AC is related to the biologic malignancy of intraductal papillary mucinous neoplasms of the pancreas", Pancreas. Nov. 2006;33(4):391-6.
Karacay et al., "A Pretargeting Bispecific Antibody Method for Improved Imaging and Therapy of Pancreatic Cancer" J. Nucl. Med., vol. 43, No. 5(Suppl.), May 2002, p. 369P, No. 1484.
Karacay et al., "Pretargeted radioimmunotherapy of pancreatic cancer xenografts: TF10-90Y-IMP-288 alone and combined with gemcitabine", J Nucl Med. Dec. 2009;50(12):2008-16.
Kipriyanov et al., "Generation of Recombinant Antibodies" Mol. Biotechnol., vol. 12, Sep. 1999; pp. 173-201.
Klivenyi et al., "Gallium-68 Chelate Imaging of Human Colon Carcinoma Xenografts Pretargeted with Bispecific Anti-CD44V6/Anti-Gallium Chelate Antibodies" J. Nucl. Med. 39(10): pp. 1769-1776, Oct. 1998.
Kunze et al., "Tumor-associated neoexpression of the pS2 peptide and MUC5AC mucin in primary adenocarcinomas and signet ring cell carcinomas of the urinary bladder", Histol Histopathol. May 2008;23(5):539-48.
Luka et al., "Development of a serum biomarker assay that differentiates tumor-associated MUC5AC (NPC-1C Antigen) from normal MUC5AC", J Biomed Biotechnol. 2011;2011:934757.
Mariani et al., "Initial Tumor Targeting, Biodistribution, and Pharmacokinetic Evaluation of the Monoclonal Antibody PAM4 in Patients with Pancreatic Cancer" Cancer Res. Suppl. 55, 5911s-5915s, Dec. 1, 1995.
Maurin et al. "Progression of tumors arising from large ACF is associated with the MUC5AC expression during rat colon MNNG carcinogenis", Int J Cancer. Feb. 1, 2007;120(3):477-83.
Modrak et al., "Colonic tumor CEA, CSAp and MUC-1 expression following radioimmunotherapy or chemotherapy", Tumour Biol. Jan.-Feb. 2003;24(1):32-9.
Ocean et al., "Fractionated radioimmunotherapy with (90) Y-clivatuzumab tetraxetan and low-dose gemcitabine is active in advanced pancreatic cancer: A phase 1 trial", Cancer. Nov. 15, 2012;118(22):5497-506.
Price et al., "Summary Report on the ISOBM TD-4 Workshop: Analysis of 56 Monoclonal Antibodies against the MUC1 Mucin" Tumor Biol. 1998, 19(Suppl. 1):1-20.
Schuhmacher et al., "Pretargeting of human mammary carcinoma xenografts with bispecific anti-MUC1/anti-Ga chelate antibodies and immunoscintigraphy with PET" Nucl. Med. Biol. 28 (2001) 821-828.
Shi et al., "Differentiation of pancreatic ductal adenocarcinoma from chronic pancreatitis by PAM4 immunohistochemistry", Arch Pathol Lab Med. Feb. 2014;138(2):220-8.
Skolnick et al., "From genes to protein structure and function: novel applications of computational approaches in the genomic era" Trends Biotechnol. 2000; 18:34-39.
Takasaki et al., "Correlative study on expression of CA 19-9 and DU-PAN-2 in tumor tissue and in serum of pancreatic cancer patients", Cancer Res. Mar. 15, 1988;48(6):1435-8.
Tosatto et al., "Large-Scale Prediction of Protein Structure and Function from Sequence" Curr. Pharm. Des., 12, 2006, 2067-2086.
Walker et al., "Improved Cellular Delivery of Antisense Oligonucleotides Using Transferrin Receptor Antibody-Oligonucleotide Conjugates" Pharm. Res., 12(10):1548-53, (1995).

\* cited by examiner

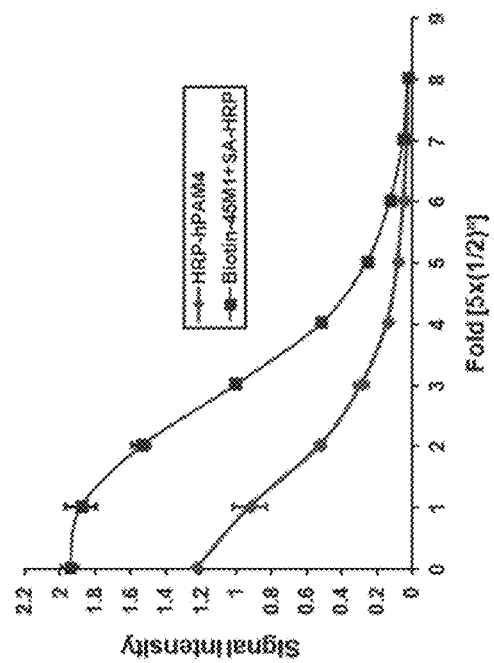
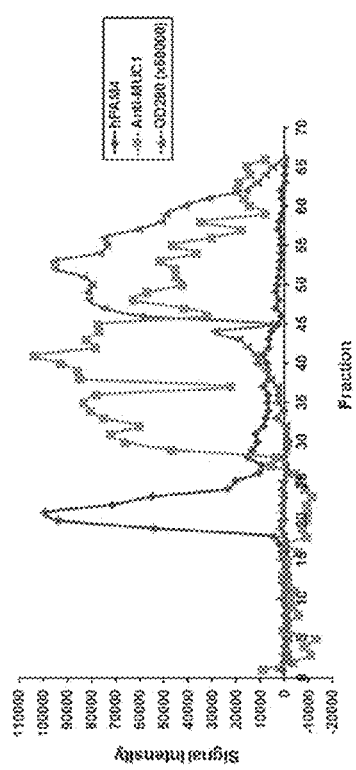
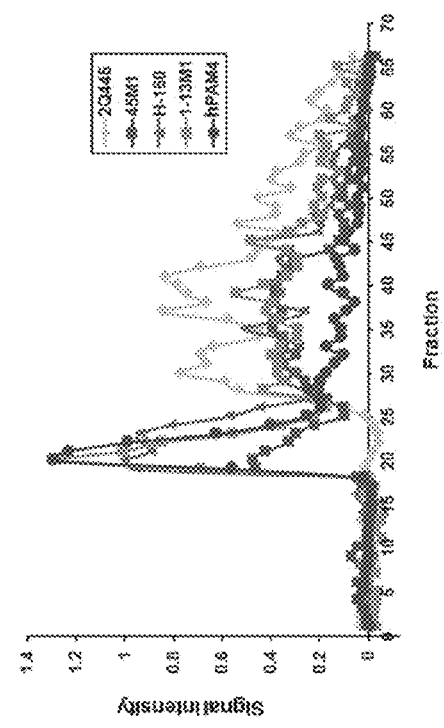

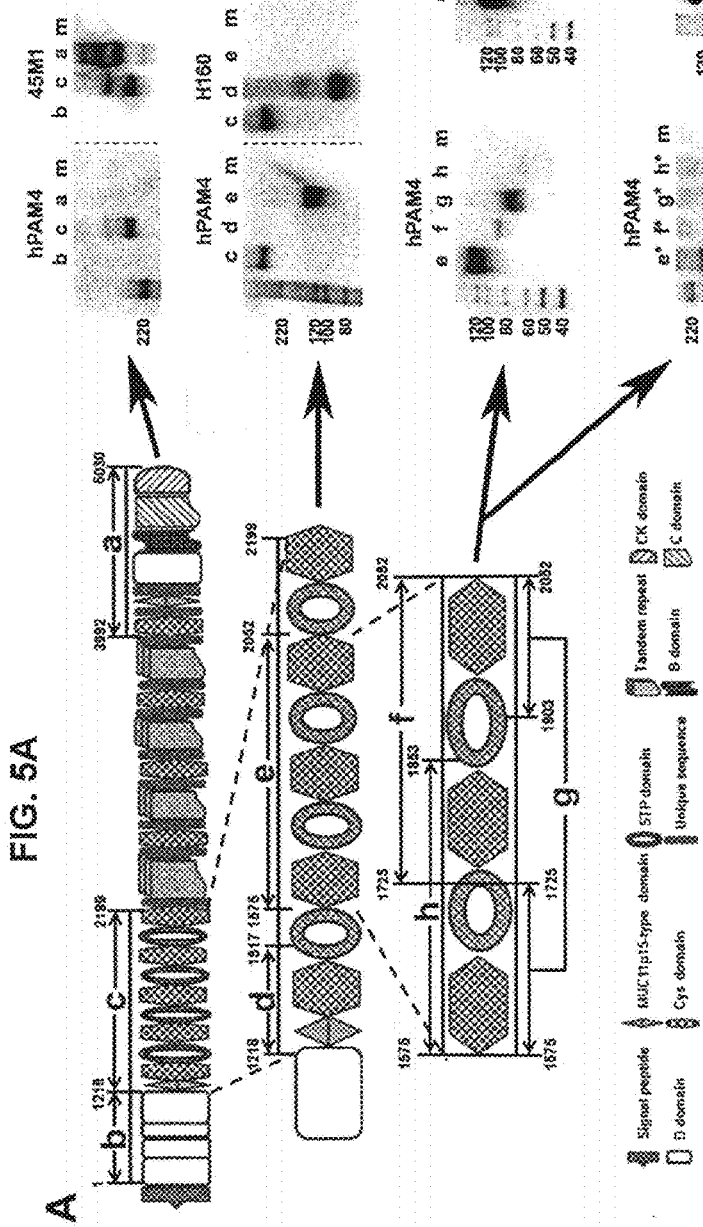

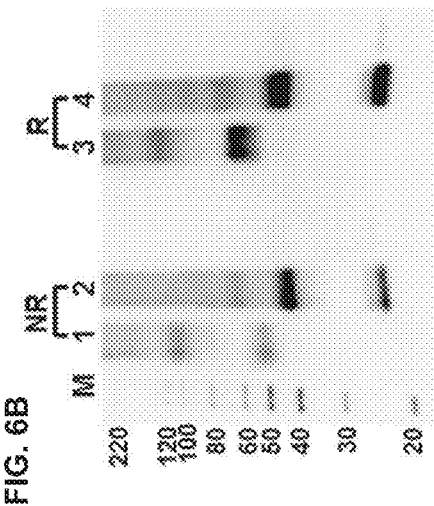
FIG. 6A Coomassie blue
FIG. 6B Anti-Myc
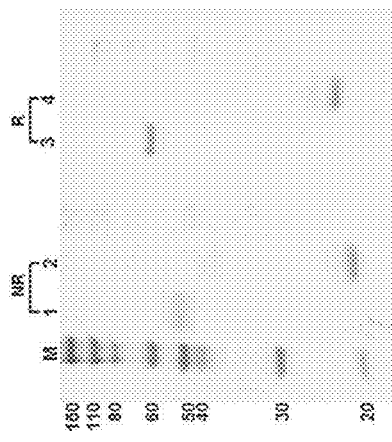
FIG. 6C hPAM4
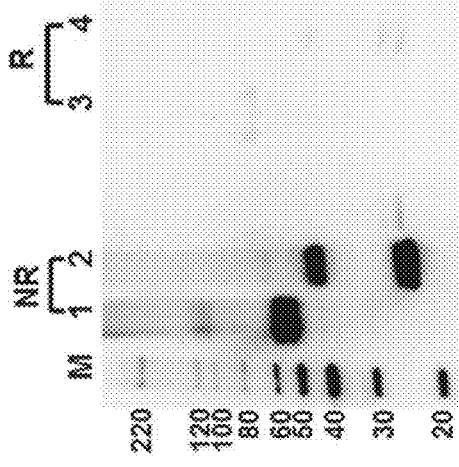
FIG. 6D 1-13M1
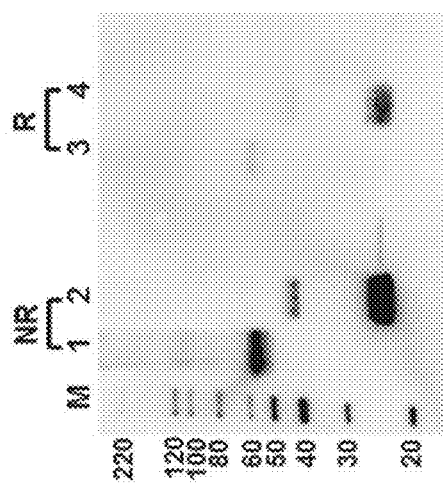

PAM4 V<sub>k</sub>

```
GATATTGTGATGACCCAGTCTCCAGCAATCATGTCTGCAGTCTCCTGGGGAGAAGGTCACCATGACCTGCAGTGCCAGCTCAAGTGTAAGT    90
 1                    10                    20        27 A
 D  I  V  M  T  Q  S  P  A  I  M  S  A  S  P  G  E  K  V  T  M  T  C  S  A  S  S  S  V  S
                                                                           ─────────────────
                                                                                  CDR1

TCCAGCTACTTGTACTGGTACCAGCAGAAGCCAGGATCCTCCCCCAAACTCTGGATTTATAGCACATCCAACCTGGCTTCTGGAGTCCCT   180
         30                    40                    50
 S  S  Y  L  Y  W  Y  Q  Q  K  P  G  S  S  P  K  L  W  I  Y  S  T  S  N  L  A  S  G  V  P
 ────────────                                              ──────────────────────
     CDR3                                                           CDR2

GCTCGGCTTCAGTGGCAGTGGGTCTGGGACCTCTTACTCTCTCACAATCAGCAGCATGGAGGCTGAAGATGCTGCCTCTTATTTCTGCCAT   270
                60                    70                    80
 A  R  F  S  G  S  G  S  G  T  S  Y  S  L  T  I  S  S  M  E  A  E  D  A  A  S  Y  F  C  H

CAGTGGAATAGGTACCCGTACACGTTCGGAGGGGGGACCAAGCTGGAAATAAAA                                        324
         90                   100       107
 Q  W  N  R  Y  P  Y  T  F  G  G  G  T  K  L  E  I  K
 ─────────────────────
         CDR3
```

FIG. 8A

PAM4 V$_H$

```
GAGGTTCAGCTGCAGGAGTCTGGACCTGAGCTGGTAAAGCCTGGGGCTTCAGTGAAGATGTCCTGCAAGGCTTCTGGATACACATTCCCT  90
 1                        10                       20                       30
 E  V  Q  L  Q  E  S  G  P  E  L  V  K  P  G  A  S  V  K  M  S  C  K  A  S  G  Y  T  F  P

AGCTATGTTTTGCACTGGGTGAAGCAGAAGCCTGGGCAGGGCCTTGAGTGGATTGGATATATTAATCCTTACAATGATGGTACTCAGTAC  180
                         40                       50    52 A               Y  I  N  P  Y  N  D  G  T  Q  Y
 S  Y  V  L  H  W  V  K  Q  K  P  G  Q  G  L  E  W  I  G
       CDR1                                                                    CDR2

AATGAGAAGTTCAAAGGCAAGGCCACACTGACTTCAGACAAATCGTCCAGCACAGCCTACATGGAGCTCAGCCGCCTGACCTCTGAGGAC  270
 60                       70                       80  82 A B C
 N  E  K  F  K  G  K  A  T  L  T  S  D  K  S  S  S  T  A  Y  M  E  L  S  R  L  T  S  E  D
       CDR2

TCTGCGGTCTATTACTGTGCAAGAGGGTTCGGTGGTAGCTACGGATTTGCTTACTGGGGCCAAGGGACTCTGATCACTGTCTCTGCA  357
                          90                 100 A B                   110         113
 S  A  V  Y  Y  C  A  R  G  F  G  G  S  Y  G  F  A  Y  W  G  Q  G  T  L  I  T  V  S  A
                          CDR3
```

FIG. 8B

```
            1          10         20        27 A    30              40
DIQLTQSPAIMSASPGEKVTMTCSASSSVSSSYLYWYQQKPGSSPKLWIY
                                   ‾‾‾‾‾‾‾‾‾‾‾‾‾
                                       CDR1
      50          60         70              80              90
STSNLASGVPARFSGSGSGTSYSLTISSMEAEDAASYFCHQWNRYPYTFG
‾‾‾‾‾‾‾                                      ‾‾‾‾‾‾‾‾‾‾‾
  CDR2                                           CDR3
     100      108
GGTKLEIKR
```

FIG. 9A

```
        1          10         20         30              40            50
QVQLQESGPELVKPGASVKMSCKASGYTFPSYVLHWVKQKPGQGLEWIGY
                              ‾‾‾‾‾‾                              ‾‾‾‾‾
                               CDR1
   52 A                 60         70              80  82 A B C         90
INPYNDGTQYNEKFKGKATLTSDKSSSTAYMELSRLTSEDSAVYYCARGE
‾‾‾‾‾‾‾‾‾‾‾‾‾‾‾‾‾                                                 ‾‾‾‾‾‾
       CDR2
         100 A B          110  113
GGSYGFAYWGQGTLITVSS
‾‾‾‾‾‾‾‾
  CDR3
```

FIG. 9B

```
                        10                  20         27A   30
Walker V_K    DIQMTQSPSSLSASVGDRVTITCRASQ-SISNYLSWYQQK
PAM4 V_K      ····V·····AIM···P·EK··M···S··SSVS·S··Y····
hPAM4 V_K     DIQLTQSPSSLSASVGDRVTMTCSASSSVSSSYLYWYQQK
                        40                  50         60                70
Walker V_K    PGKAPKLLIYAASSLQSGVTSRFSGSGSGTDFTLTISSLQ
PAM4 V_K      ··SS···W··ST·N·A···PA·······SYS····ME
hPAM4 V_K     PGKAPKLWIYSTSNLASGVPARFSGSGSGTDFTLTISSLQ
                        80                  90         100               108
Walker V_K    PEDSATYYCQQSYSTLITFGQGTRLEIK-
PAM4 V_K      A··A·S·F·H·WNRYPY···G··K····-
hPAM4 V_K     PEDSASYFCHQWNRYPYTFGGGTRLEIKR
```

FIG. 10A

```
                              10                  20              30                40
                    1  QVQLVQSGAEVKKPGSSVKVSCKASGGTFSSYAISWVRQA
Wil2  V_H              
PAM4  V_H              E···QE··P·LV····A····M····Y··P··VLH··K·K
hPAM4 V_H              ···Q·········A········E··Y··P··VLH··K·K 50 52 A                    60                  70
                    PGQGLEWMGGIIPIFGTANYAQKFQGRVTITADESTSTAY
Wil2  V_H              
PAM4  V_H              ·····I·Y·N·YNDGTQ·NE··K··KA·L·S·K·S····
hPAM4 V_H              ·····I·Y·N·YNDGTQ·NE··K··KA·L·R·T·IN···

80 82 A B C           90              100 A B
                    MELSSLRSEDTAVYYCARGPRLLADVLL
Wil2  V_H              
PAM4  V_H              ····R·T···S·······EGGSYGFAY
hPAM4 V_H              ····R····D········EGGSYGFAY 103            110 113
                    WGQGTLVTVSS
NEWM  V_H              
PAM4  V_H              ·······I···A
hPAM4 V_H              ···········
```

FIG. 10B

```
                                                                                        PvuII
GACATCCAGCTGACCCAGTCCTCCATCCTCCCTGTCTCTGCATCTGTAGGAGAGACAGAGTCACCATGACCTGCAGTGCCAGCTCAAGTGTAAGT    90
  1                     10                    20                    27 A
  D  I  Q  L  T  Q  S  P  S  S  L  S  A  S  V  G  D  R  V  T  M  T  C  S  A  S  S  S  V  S
                                                                               CDR1

TCCAGCTACTTGTACTGGTACCAACAGAAACCAGGGAAAGCCCCCAAACTCTGGATTTATAGCACACATCCAACCTGGCTTCTGGAGTCCCT    180
  30                    40                    50
  S  S  Y  L  Y  W  Y  Q  Q  K  P  G  K  A  P  K  L  W  I  Y  S  T  S  N  L  A  S  G  V  P
                                                                CDR2

GCTCGCTTCAGTGGCAGTGGATCTGGGACAGACTTCACTCTCACCATCAGCAGTCTGCAACCTGAAGATTCTGCCTCTTATTTCTGCCAT    270
  60                    70                    80
  A  R  F  S  G  S  G  S  G  T  D  F  T  L  T  I  S  S  L  Q  P  E  D  S  A  S  Y  F  C  H

BglII/BclI
CAGTGGAATAGGTACCCGTACACGTTCGGAGGGGGGACACGACTGGAGATCAAACGA    327
  90                     100                   108
  Q  W  N  R  Y  P  Y  T  F  G  G  G  T  R  L  E  I  K  R
  CDR3
```

FIG. 11A

```
PstI
CAGGTGCAGCTGCAGCAGTCTGGGGCTGAGGTGAAGAAGCCTGGGGCCTCAGTGAAGGTCTCCTGCGAGGCTTCTGGATACACATTCCCT    90
 1              10              20              30
 Q  V  Q  L  Q  Q  S  G  A  E  V  K  K  P  G  A  S  V  K  V  S  C  E  A  S  G  Y  T  F  P

AGCTATGTTTTGCACTGGGTGAAGCAGGCCCCTGGACAAGGCCTTGAGTGGATTGGATATATTAATCCTTACAATGATGGTACTCAGTAC   180
            40              50      52 A        A
 S  Y  V  L  H  W  V  K  Q  A  P  G  Q  G  L  E  W  I  G  Y  I  N  P  Y  N  D  G  T  Q  Y
    CDR1                                              CDR2

AATGAGAAGTTCAAAGGCAAGGCCACACTGACTAGGGACACGTCCATCAACACAGCCTACATGGAGCTGAGCAGGCTGAGATCTGACGAC   270
 60                     70              80     82 A B C
 N  E  K  F  K  G  K  A  T  L  T  R  D  T  S  I  N  T  A  Y  M  E  L  S  R  L  R  S  D  D
    CDR2
                                                          BstEII
ACGGCCGTGTATTACTGTGCAAGAGGCTTCGGTGGTAGCTACGGATTTGCTTACTGGGGCCAGGGGAACCCTGGTCACCGTCTCCTCA    357
         90             100 A B              103                   110
 T  A  V  Y  Y  C  A  R  G  F  G  G  S  Y  G  F  A  Y  W  G  Q  G  T  L  V  T  V  S  S
                             CDR3
```

FIG. 11B

SEQUENCE LISTING

```
<160> NUMBER OF SEQ ID NOS: 121

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ala Ser Ser Ser Val Ser Ser Ser Tyr Leu Tyr
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Thr Ser Asn Leu Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Gln Trp Asn Arg Tyr Pro Tyr Thr
1               5

<210> SEQ ID NO 4
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 4

Ser Tyr Val Leu His
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ile Asn Pro Tyr Asn Asp Gly Thr Gln Tyr Asn Glu Lys Phe Lys
1               5                   10                  15
Gly

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Gly Gly Ser Tyr Gly Phe Ala Tyr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Thr Trp Asn Ile Thr Lys Ala Tyr Pro Leu Pro
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Cys Pro Glu Trp Trp Gly Thr Thr Cys
1               5                   10

<210> SEQ ID NO 9
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 9 gat att gtg atg acc cag tct cca gca atc atg tct gca tct cct ggg        48
```

```
Asp Ile Val Met Thr Gln Ser Pro Ala Ile Met Ser Ala Ser Pro Gly
1               5                   10                  15 gag aag gtc acc atg acc tgc agt gcc agc tca agt gta agt tcc agc        96
Glu Lys Val Thr Met Thr Cys Ser Ala Ser Ser Val Ser Ser Ser
                20                  25                  30 tac ttg tac tgg tac cag cag aag cca gga tcc tcc ccc aaa ctc tgg       144
Tyr Leu Tyr Trp Tyr Gln Gln Lys Pro Gly Ser Ser Pro Lys Leu Trp
            35                  40                  45 att tat agc aca tcc aac ctg gct tct gga gtc cct gct cgc ttc agt       192
Ile Tyr Ser Thr Ser Asn Leu Ala Ser Gly Val Pro Ala Arg Phe Ser
    50                  55                  60 ggc agt ggg tct ggg acc tct tac tct ctc aca atc agc agc atg gag       240
Gly Ser Gly Ser Gly Thr Ser Tyr Ser Leu Thr Ile Ser Ser Met Glu
65                  70                  75                  80 gct gaa gat gct gcc tct tat ttc tgc cat cag tgg aat agg tac ccg       288
Ala Glu Asp Ala Ala Ser Tyr Phe Cys His Gln Trp Asn Arg Tyr Pro
                85                  90                  95 tac acg ttc gga ggg ggg acc aag ctg gaa ata aaa                        324
Tyr Thr Phe Gly Gly Gly Thr Lys Leu Glu Ile Lys
            100                 105
```

<210> SEQ ID NO 10
<211> LENGTH: 108
<212> TYPE: PRT
<213> ORGANISM: Mus sp.

<400> SEQUENCE: 10

```
Asp Ile Val Met Thr Gln Ser Pro Ala Ile Met Ser Ala Ser Pro Gly
1               5                   10                  15

Glu Lys Val Thr Met Thr Cys Ser Ala Ser Ser Val Ser Ser Ser
                20                  25                  30

Tyr Leu Tyr Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Asn Arg Tyr Pro
                85                  90                  95

Tyr Thr Phe Gly Gly Gly Thr Lys Leu Glu Ile Lys
            100                 105
```

<210> SEQ ID NO 11
<211> LENGTH: 357
<212> TYPE: DNA
<213> ORGANISM: Mus sp.
<220> FEATURE:
<221> NAME/KEY: CDS
<222> LOCATION: (1)..(357)

<400> SEQUENCE: 11

```
gag gtt cag ctg cag gag tct gga cct gag ctg gta aag cct ggg gct        48
Glu Val Gln Leu Gln Glu Ser Gly Pro Glu Leu Val Lys Pro Gly Ala
1               5                   10                  15 tca gtg aag atg tcc tgc aag gct tct gga tac aca ttc cct agc tat        96
Ser Val Lys Met Ser Cys Lys Ala Ser Gly Tyr Thr Phe Pro Ser Tyr
                20                  25                  30 gtt ttg cac tgg gtg aag cag aag cct ggg cag ggc ctt gag tgg att       144
Val Leu His Trp Val Lys Gln Lys Pro Gly Gln Gly Leu Glu Trp Ile
            35                  40                  45
```

```
gga tat att aat cct tac aat gat ggt act cag tac aat gag aag ttc    192
Gly Tyr Ile Asn Pro Tyr Asn Asp Gly Thr Gln Tyr Asn Glu Lys Phe
 50                  55                  60 aaa ggc aag gcc aca ctg act tca gac aaa tcg tcc agc aca gcc tac    240
Lys Gly Lys Ala Thr Leu Thr Ser Asp Lys Ser Ser Ser Thr Ala Tyr
 65                  70                  75                  80 atg gag ctc agc cgc ctg acc tct gag gac tct gcg gtc tat tac tgt    288
Met Glu Leu Ser Arg Leu Thr Ser Glu Asp Ser Ala Val Tyr Tyr Cys
                 85                  90                  95 gca aga ggc ttc ggt ggt agc tac gga ttt gct tac tgg ggc caa ggg    336
Ala Arg Gly Phe Gly Gly Ser Tyr Gly Phe Ala Tyr Trp Gly Gln Gly
            100                 105                 110 act ctg atc act gtc tct gca                                        357
Thr Leu Ile Thr Val Ser Ala
        115
```

<210> SEQ ID NO 12
<211> LENGTH: 119
<212> TYPE: PRT
<213> ORGANISM: Mus sp.

<400> SEQUENCE: 12

```
Glu Val Gln Leu Gln Glu Ser Gly Pro Glu Leu Val Lys Pro Gly Ala
 1               5                  10                  15

Ser Val Lys Met Ser Cys Lys Ala Ser Gly Tyr Thr Phe Pro Ser Tyr
            20                  25                  30

Val Leu His Trp Val Lys Gln Lys Pro Gly Gln Gly Leu Glu Trp Ile
        35                  40                  45

Gly Tyr Ile Asn Pro Tyr Asn Asp Gly Thr Gln Tyr Asn Glu Lys Phe
 50                  55                  60

Lys Gly Lys Ala Thr Leu Thr Ser Asp Lys Ser Ser Ser Thr Ala Tyr
 65                  70                  75                  80

Met Glu Leu Ser Arg Leu Thr Ser Glu Asp Ser Ala Val Tyr Tyr Cys
                 85                  90                  95

Ala Arg Gly Phe Gly Gly Ser Tyr Gly Phe Ala Tyr Trp Gly Gln Gly
            100                 105                 110

Thr Leu Ile Thr Val Ser Ala
        115
```

<210> SEQ ID NO 13
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Asp Ile Gln Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Ser Tyr Phe Cys His Gln Trp Asn Arg Tyr Pro
```

```
                    85                  90                  95

Tyr Thr Phe Gly Gly Gly Thr Lys Leu Glu Ile Lys Arg
            100                 105

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Glu Ser Gly Pro Glu Leu Val Lys Pro Gly Ala
1               5                   10                  15

Ser Val Lys Met Ser Cys Lys Ala Ser Gly Tyr Thr Phe Pro Ser Tyr
            20                  25                  30

Val Leu His Trp Val Lys Gln Lys Pro Gly Gln Gly Leu Glu Trp Ile
        35                  40                  45

Gly Tyr Ile Asn Pro Tyr Asn Asp Gly Thr Gln Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Arg Leu Thr Ser Glu Asp Ser Ala Val Tyr Tyr Cys
                85                  90                  95

Ala Arg Gly Phe Gly Gly Ser Tyr Gly Phe Ala Tyr Trp Gly Gln Gly
            100                 105                 110

Thr Leu Ile Thr Val Ser Ser
        115

<210> SEQ ID NO 15
<211> LENGTH: 107
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ser Trp Tyr Gln Gln Lys Pro Gly Lys Ala Pro Lys Leu Leu Ile
        35                  40                  45

Tyr Ala Ala Ser Ser Leu Gln Ser Gly Val Thr Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Ser Thr Leu Ile
                85                  90                  95

Thr Phe Gly Gln Gly Thr Arg Leu Glu Ile Lys
            100                 105

<210> SEQ ID NO 16
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16
```

```
Asp Ile Gln Leu Thr Gln Ser Pro Ser Leu Ser Ala Ser Val Gly
1               5                   10                  15

Asp Arg Val Thr Met Thr Cys Ser Ala Ser Ser Ser Val Ser Ser
            20                  25                  30

Tyr Leu Tyr Trp Tyr Gln Gln Lys Pro Gly Lys Ala Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Ser Ala Ser Tyr Phe Cys His Gln Trp Asn Arg Tyr Pro
                85                  90                  95

Tyr Thr Phe Gly Gly Gly Thr Arg Leu Glu Ile Lys Arg
            100                 105
```

```
<210> SEQ ID NO 17
<211> LENGTH: 108
<212> TYPE: PRT
<213> ORGANISM: Homo sapiens

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Arg Leu Leu Ala Asp Val Leu Leu
            100                 105
```

```
<210> SEQ ID NO 18
<211> LENGTH: 11
<212> TYPE: PRT
<213> ORGANISM: Homo sapiens

<400> SEQUENCE: 18

Trp Gly Gln Gly Thr Leu Val Thr Val Ser Ser
1               5                   10
```

```
<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Gln Ser Gly Ala Glu Val Lys Lys Pro Gly Ala
1               5                   10                  15

Ser Val Lys Val Ser Cys Glu Ala Ser Gly Tyr Thr Phe Pro Ser Tyr
            20                  25                  30
```

```
Val Leu His Trp Val Lys Gln Ala Pro Gly Gln Gly Leu Glu Trp Ile
         35                  40                  45

Gly Tyr Ile Asn Pro Tyr Asn Asp Gly Thr Gln Tyr Asn Glu Lys Phe
 50                  55                  60

Lys Gly Lys Ala Thr Leu Thr Arg Asp Thr Ser Ile Asn Thr Ala Tyr
 65                  70                  75                  80

Met Glu Leu Ser Arg Leu Arg Ser Asp Thr Ala Val Tyr Tyr Cys
                 85                  90                  95

Ala Arg Gly Phe Gly Gly Ser Tyr Gly Phe Ala Tyr Trp Gly Gln Gly
                100                 105                 110

Thr Leu Val Thr Val Ser Ser
        115
```

<210> SEQ ID NO 20
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(327)

<400> SEQUENCE: 20

```
gac atc cag ctg acc cag tct cca tcc tcc ctg tct gca tct gta gga      48
Asp Ile Gln Leu Thr Gln Ser Pro Ser Ser Leu Ser Ala Ser Val Gly
 1               5                  10                  15 gac aga gtc acc atg acc tgc agt gcc agc tca agt gta agt tcc agc      96
Asp Arg Val Thr Met Thr Cys Ser Ala Ser Ser Ser Val Ser Ser Ser
             20                  25                  30 tac ttg tac tgg tac caa cag aaa cca ggg aaa gcc ccc aaa ctc tgg     144
Tyr Leu Tyr Trp Tyr Gln Gln Lys Pro Gly Lys Ala Pro Lys Leu Trp
         35                  40                  45 att tat agc aca tcc aac ctg gct tct gga gtc cct gct cgc ttc agt     192
Ile Tyr Ser Thr Ser Asn Leu Ala Ser Gly Val Pro Ala Arg Phe Ser
 50                  55                  60 ggc agt gga tct ggg aca gac ttc act ctc acc atc agc agt ctg caa     240
Gly Ser Gly Ser Gly Thr Asp Phe Thr Leu Thr Ile Ser Ser Leu Gln
 65                  70                  75                  80 cct gaa gat tct gcc tct tat ttc tgc cat cag tgg aat agg tac ccg     288
Pro Glu Asp Ser Ala Ser Tyr Phe Cys His Gln Trp Asn Arg Tyr Pro
                 85                  90                  95 tac acg ttc gga ggg ggg aca cga ctg gag atc aaa cga                 327
Tyr Thr Phe Gly Gly Gly Thr Arg Leu Glu Ile Lys Arg
                100                 105
```

<210> SEQ ID NO 21
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(357)

<400> SEQUENCE: 21

```
cag gtg cag ctg cag cag tct ggg gct gag gtg aag aag cct ggg gcc      48
Gln Val Gln Leu Gln Gln Ser Gly Ala Glu Val Lys Lys Pro Gly Ala
 1               5                  10                  15 tca gtg aag gtc tcc tgc gag gct tct gga tac aca ttc cct agc tat      96
Ser Val Lys Val Ser Cys Glu Ala Ser Gly Tyr Thr Phe Pro Ser Tyr
```

```
Ser Val Lys Val Ser Cys Glu Ala Ser Gly Tyr Thr Phe Pro Ser Tyr
            20                  25                  30 gtt ttg cac tgg gtg aag cag gcc cct gga caa ggg ctt gag tgg att      144
Val Leu His Trp Val Lys Gln Ala Pro Gly Gln Gly Leu Glu Trp Ile
            35                  40                  45 gga tat att aat cct tac aat gat ggt act cag tac aat gag aag ttc      192
Gly Tyr Ile Asn Pro Tyr Asn Asp Gly Thr Gln Tyr Asn Glu Lys Phe
 50                  55                  60 aaa ggc aag gcc aca ctg acc agg gac acg tcc atc aac aca gcc tac      240
Lys Gly Lys Ala Thr Leu Thr Arg Asp Thr Ser Ile Asn Thr Ala Tyr
 65                  70                  75                  80 atg gag ctg agc agg ctg aga tct gac gac acg gcc gtg tat tac tgt      288
Met Glu Leu Ser Arg Leu Arg Ser Asp Asp Thr Ala Val Tyr Tyr Cys
                85                  90                  95 gca aga ggc ttc ggt ggt agc tac gga ttt gct tac tgg ggc cag gga      336
Ala Arg Gly Phe Gly Gly Ser Tyr Gly Phe Ala Tyr Trp Gly Gln Gly
                100                 105                 110 acc ctg gtc acc gtc tcc tca                                          357
Thr Leu Val Thr Val Ser Ser
        115

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aatgcggcgg tggtgacagt a                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aagctcagca cacagaaaga c                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
uaaaaucuuc cugcccacct t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 25
ggaagcuguu ggcugaaaat t                                              21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aagaccagcc ucuuugccca g                                              21

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggaccaggca gaaaacgag                                                 19

<210> SEQ ID NO 28
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
cuaucaggau gacgcgg                                                   17

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ugacacaggc aggcuugacu u                                              21

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggtgaagaag ggcgtccaa                                                 19

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gatccgttgg agctgttggc gtagttcaag agactcgcca acagctccaa cttttggaaa    60

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aggtggtgtt aacagcagag    20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aaggtggagc aagcggtgga g    21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aaggagttga aggccgacaa a    21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
uauggagcug cagaggaugt t    21

<210> SEQ ID NO 36
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tttgaatatc tgtgctgaga acacagttct cagcacagat attcttttt    49

<210> SEQ ID NO 37
<211> LENGTH: 29
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 37
aatgagaaaa gcaaaaggtg ccctgtctc                                           29

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
aaucaucauc aagaaagggc a                                                   21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
augacuguca ggauguugct t                                                   21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gaacgaaucc ugaagacauc u                                                   21

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
aagcctggct acagcaatat gcctgtctc                                           29

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
ugaccaucac cgaguuuaut t                                                   21

-continued

```
<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aagtcggacg caacagagaa a                                                  21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
cuaccuuucu acggacgugt t                                                  21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctgcctaagg cggatttgaa t                                                  21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
ttauuccuuc uucgggaagu c                                                  21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aaccttctgg aacccgccca c                                                  21

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 48
gagcatcttc gagcaagaa                                                19

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
catgtggcac cgtttgcct                                                19

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aactaccaga aaggtatacc t                                             21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
ucacaguguc cuuuauguat t                                             21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
gcaugaaccg gaggcccaut t                                             21

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ccggacagtt ccatgtata                                                19

<210> SEQ ID NO 54
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 54
ggagcctgat catccagca                                                    19

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Gln Lys Leu Ile Ser Glu Glu Asp Leu
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Glu Gly Tyr Thr Phe Cys Glu Ser Pro Arg
1               5                   10

<210> SEQ ID NO 57
<211> LENGTH: 173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
agtctggggc tgaggtgaag aagcctgggg cctcagtgaa ggtctcctgc gaggcttctg       60
gatacacatt ccctagctat gttttgcact gggtgaagca ggcccctgga caagggcttg      120
agtggattgg atatattaat ccttacaatg atggtactca gtacaatgag aag             173

<210> SEQ ID NO 58
<211> LENGTH: 173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
agggttccct ggccccagta agcaaatccg tagctaccac cgaagcctct tgcacagtaa       60
tacacggccg tgtcgtcaga tctcagcctg ctcagctcca tgtaggctgt gttgatggac      120
gtgtccctgg tcagtgtggc cttgcctttg aacttctcat tgtactgagt acc             173

<210> SEQ ID NO 59
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 59
caggtgcagc tgcagcagtc tggggctgag gtga                                        34

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tgaggagacg gtgaccaggg ttccctggcc cca                                         33

<210> SEQ ID NO 61
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
cagtctccat cctccctgtc tgcatctgta ggagacagag tcaccatgac ctgcagtgcc            60
agctcaagtg taagttccag ctacttgtac tggtaccaac agaaaccagg gaaagccccc           120
aaactctgga tttatagcac atccaacctg gcttctg                                   157

<210> SEQ ID NO 62
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62 gtccccctc cgaacgtgta cgggtaccta ttccactgat ggcagaaata agaggcagaa             60
tcttcaggtt gcagactgct gatggtgaga gtgaagtctg tcccagatcc actgccactg          120
aagcgagcag ggactccaga agccaggttg gatgtg                                    156

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gacatccagc tgacccagtc tccatcctcc ctg                                         33

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ttagatctcc agtcgtgtcc cccctccgaa cgt                                         33

```
<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Trp Thr Trp Asn Ile Thr Lys Glu Tyr Pro Gln Pro
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Cys Pro Glu Trp Trp Gly Thr Thr Cys
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Thr Thr Gly Thr Thr Cys
1               5

<210> SEQ ID NO 68
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 69
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
```

```
                        35                  40                  45

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Ile Glu Tyr Leu Ala Lys Gln Ile Val Asp Asn Ala Ile Gln Gln
1               5                   10                  15

Ala

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 72
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 73
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
```

```
                  50                  55

<210> SEQ ID NO 74
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 75
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gly Ser Gly Gly Gly Gly Ser Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 76
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ser Gly Gly Gly Gly Ser Gly Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 77
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45
```

Glu Ala Lys
    50

<210> SEQ ID NO 78
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
    50

<210> SEQ ID NO 79
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 80
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Ile Glu Tyr Val Ala Lys Gln Ile Val Asp Tyr Ala Ile His Gln
1               5                   10                  15

Ala

```
<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82
```

Gln Ile Glu Tyr Lys Ala Lys Gln Ile Val Asp His Ala Ile His Gln
1               5                   10                  15

Ala

```
<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83
```

Gln Ile Glu Tyr His Ala Lys Gln Ile Val Asp His Ala Ile His Gln
1               5                   10                  15

Ala

```
<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84
```

Gln Ile Glu Tyr Val Ala Lys Gln Ile Val Asp His Ala Ile His Gln
1               5                   10                  15

Ala

```
<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85
```

Pro Leu Glu Tyr Gln Ala Gly Leu Leu Val Gln Asn Ala Ile Gln Gln
1               5                   10                  15

Ala Ile

```
<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86
```

Leu Leu Ile Glu Thr Ala Ser Ser Leu Val Lys Asn Ala Ile Gln Leu

```
1               5                   10                  15

Ser Ile

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Ile Glu Glu Ala Ala Ser Arg Ile Val Asp Ala Val Ile Glu Gln
1               5                   10                  15

Val Lys

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Leu Tyr Gln Phe Ala Asp Arg Phe Ser Glu Leu Val Ile Ser Glu
1               5                   10                  15

Ala Leu

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Glu Gln Val Ala Asn Gln Leu Ala Asp Gln Ile Ile Lys Glu Ala
1               5                   10                  15

Thr

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Phe Glu Glu Leu Ala Trp Lys Ile Ala Lys Met Ile Trp Ser Asp Val
1               5                   10                  15

Phe

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91
```

```
Glu Leu Val Arg Leu Ser Lys Arg Leu Val Glu Asn Ala Val Leu Lys
1               5                   10                  15

Ala Val

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Thr Ala Glu Glu Val Ser Ala Arg Ile Val Gln Val Val Thr Ala Glu
1               5                   10                  15

Ala Val

<210> SEQ ID NO 93
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Ile Lys Gln Ala Ala Phe Gln Leu Ile Ser Gln Val Ile Leu Glu
1               5                   10                  15

Ala Thr

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Leu Ala Trp Lys Ile Ala Lys Met Ile Val Ser Asp Val Met Gln Gln
1               5                   10                  15

<210> SEQ ID NO 95
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96
```

```
Leu Glu Gln Tyr Ala Asn Gln Leu Ala Asp Gln Ile Ile Lys Glu Ala
1               5                   10                  15

Thr Glu

<210> SEQ ID NO 97
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Phe Glu Glu Leu Ala Trp Lys Ile Ala Lys Met Ile Trp Ser Asp Val
1               5                   10                  15

Phe Gln Gln Cys
            20

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Ile Glu Tyr Leu Ala Lys Gln Ile Pro Asp Asn Ala Ile Gln Gln
1               5                   10                  15

Ala

<210> SEQ ID NO 99
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 100
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 101

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 102
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 103
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 104
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 105
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

```
<210> SEQ ID NO 106
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 107
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 108
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 109
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 110
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Leu Glu Lys Gln Tyr Gln Glu Gln Leu Glu Glu Glu Val Ala Lys Val
```

```
                1               5                  10                  15
Ile Val Ser Met Ser Ile Ala Phe Ala
                20                  25

<210> SEQ ID NO 111
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asn Thr Asp Glu Ala Gln Glu Glu Leu Ala Trp Lys Ile Ala Lys Met
1               5                   10                  15

Ile Val Ser Asp Ile Met Gln Gln Ala
                20                  25

<210> SEQ ID NO 112
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Val Asn Leu Asp Lys Lys Ala Val Leu Ala Glu Lys Ile Val Ala Glu
1               5                   10                  15

Ala Ile Glu Lys Ala Glu Arg Glu Leu
                20                  25

<210> SEQ ID NO 113
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asn Gly Ile Leu Glu Leu Glu Thr Lys Ser Ser Lys Leu Val Gln Asn
1               5                   10                  15

Ile Ile Gln Thr Ala Val Asp Gln Phe
                20                  25

<210> SEQ ID NO 114
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Gln Asp Lys Asn Tyr Glu Asp Glu Leu Thr Gln Val Ala Leu Ala
1               5                   10                  15

Leu Val Glu Asp Val Ile Asn Tyr Ala
                20                  25

<210> SEQ ID NO 115
<211> LENGTH: 25
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 115

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asn or Asp
<220> FEATURE:
<221> NAME/KEY: MOD_RES
<222> LOCATION: (6)..(6)
<223> OTHER INFORMATION: Thr or Arg
<220> FEATURE:
<221> NAME/KEY: MOD_RES
<222> LOCATION: (7)..(7)
<223> OTHER INFORMATION: Lys, Arg, Thr, Asn or Gly
<220> FEATURE:
<221> NAME/KEY: MOD_RES
<222> LOCATION: (8)..(8)
<223> OTHER INFORMATION: Ala, Glu, Thr, Arg, Phe or Cys
<220> FEATURE:
<221> NAME/KEY: MOD_RES
<222> LOCATION: (9)..(9)
<223> OTHER INFORMATION: Tyr or Thr
<220> FEATURE:
<221> NAME/KEY: MOD_RES
<222> LOCATION: (10)..(10)
<223> OTHER INFORMATION: Pro or Arg
<220> FEATURE:
<221> NAME/KEY: MOD_RES
<222> LOCATION: (11)..(11)
<223> OTHER INFORMATION: Leu, Gln, Ile, Met or Cys

<400> SEQUENCE: 116

Trp Thr Trp Xaa Ile Xaa Xaa Xaa Xaa Xaa Xaa Pro
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro or Tyr
<220> FEATURE:
<221> NAME/KEY: MOD_RES
<222> LOCATION: (7)..(7)
<223> OTHER INFORMATION: Gly or Ser
<220> FEATURE:
<221> NAME/KEY: MOD_RES
<222> LOCATION: (8)..(8)
<223> OTHER INFORMATION: Thr, Gly or Ser
<220> FEATURE:
<221> NAME/KEY: MOD_RES
<222> LOCATION: (9)..(9)
<223> OTHER INFORMATION: Thr, Met, Ser, Gln or Pro

<400> SEQUENCE: 117

```
Ala Cys Xaa Glu Trp Trp Xaa Xaa Xaa Cys
1               5                   10
```

<210> SEQ ID NO 118
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

```
Pro Lys Ser Cys
1
```

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Gly Gly Gly Gly Ser Gly Gly Gly Gly Ser
1               5                   10
```

<210> SEQ ID NO 120
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Gln Val Gln Leu Gln Gln Ser Gly Ala Glu Val Lys Lys Pro Gly Ala
1               5                   10                  15

Ser Val Lys Val Ser Cys Glu Ala Ser Gly Tyr Thr Phe Pro Ser Tyr
            20                  25                  30

Val Leu His Trp Val Lys Gln Ala Pro Gly Gln Gly Leu Glu Trp Ile
        35                  40                  45

Gly Tyr Ile Asn Pro Tyr Asn Asp Gly Thr Gln Tyr Asn Glu Lys Phe
    50                  55                  60

Lys Gly Lys Ala Thr Leu Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Phe Gly Gly Ser Tyr Gly Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

Lys

<210> SEQ ID NO 121
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Asp Ile Gln Leu Thr Gln Ser Pro Ser Ser Leu Ser Ala Ser Val Gly
1               5                   10                  15

Asp Arg Val Thr Met Thr Cys Ser Ala Ser Ser Ser Val Ser Ser Ser
            20                  25                  30

Tyr Leu Tyr Trp Tyr Gln Gln Lys Pro Gly Lys Ala Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Ser Ala Ser Tyr Phe Cys His Gln Trp Asn Arg Tyr Pro
                85                  90                  95
```

-continued

```
Tyr Thr Phe Gly Gly Gly Thr Arg Leu Glu Ile Lys Arg Thr Val Ala
            100             105             110

Ala Pro Ser Val Phe Ile Phe Pro Pro Ser Asp Glu Gln Leu Lys Ser
        115             120             125

Gly Thr Ala Ser Val Val Cys Leu Leu Asn Asn Phe Tyr Pro Arg Glu
        130             135             140

Ala Lys Val Gln Trp Lys Val Asp Asn Ala Leu Gln Ser Gly Asn Ser
145             150             155             160

Gln Glu Ser Val Thr Glu Gln Asp Ser Lys Asp Ser Thr Tyr Ser Leu
                165             170             175

Ser Ser Thr Leu Thr Leu Ser Lys Ala Asp Tyr Glu Lys His Lys Val
            180             185             190

Tyr Ala Cys Glu Val Thr His Gln Gly Leu Ser Ser Pro Val Thr Lys
        195             200             205

Ser Phe Asn Arg Gly Glu Cys
    210             215
```

ANTIBODIES REACTIVE WITH AN EPITOPE LOCATED IN THE N-TERMINAL REGION OF MUC5AC COMPRISING CYSTEINE-RICH SUBDOMAIN 2 (CYS2)

RELATED APPLICATIONS

This application is a continuation-in-part of U.S. patent application Ser. No. 14/632,480, filed Feb. 26, 2015, which was a divisional of U.S. patent application Ser. No. 14/242,138 (now U.S. Pat. No. 9,005,613), filed Apr. 1, 2014, which claimed the benefit under 35 U.S.C. 119(e) of provisional U.S. Patent Application Ser. Nos. 61/807,176, filed Apr. 1, 2013, 61/818,708, filed May 2, 2013, and 61/896,909, filed Oct. 29, 2013. This application claims the benefit under 35 U.S.C. 119(e) of provisional U.S. Patent Application Ser. Nos. 62/018,989, filed Jun. 30, 2014, 62/091,932, filed Dec. 15, 2014, and 62/148,428, filed Apr. 16, 2015, the entire text of each priority application incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 16, 2015, is named IMM352US1_SL.txt and is 56,774 bytes in size.

FIELD OF THE INVENTION

This invention relates to anti-pancreatic cancer antibodies and antigen-binding fragments thereof that bind to MUC5AC mucin in pancreatic cancer. Preferably, the antibodies or fragments thereof bind to an epitope located within the second to fourth cysteine-rich subdomains of MUC5AC (amino acid residues 1575-2052, Cys2-Cys4). More preferably, the antibodies bind to an epitope located in amino acid residues 1575-1725 and 1903-2052 (Cys2 and Cys4). Even more preferably, the antibodies bind to an epitope located in amino acid residues 1575-1725 (Cys2+). Most preferably, the antibodies bind to an epitope located in the Cys2 subdomain of MUC5AC. In preferred embodiments, the anti-pancreatic cancer antibody binds to the same epitope as, or competes for binding to MUC5AC with a PAM4 antibody comprising the light chain variable region complementarity-determining region (CDR) sequences CDR1 (SASSSVSSYLY, SEQ ID NO:1); CDR2 (STSNLAS, SEQ ID NO:2); and CDR3 (HQWNRYPYT, SEQ ID NO:3); and the heavy chain CDR sequences CDR1 (SYVLH, SEQ ID NO:4); CDR2 (YINPYNDGTQYNEKFKG, SEQ ID NO:5) and CDR3 (GFGGSYGFAY, SEQ ID NO:6). The subject antibodies or antibody fragments bind with high selectivity to pancreatic cancer cells to allow detection and/or diagnosis of pancreatic adenocarcinoma at the earliest stages of the disease. Most preferably, antibody-based assays are capable of detecting about 85% or more of pancreatic adenocarcinomas, with a false positive rate of about 5% or less for healthy controls. In particular embodiments, the methods and compositions can be used to detect and/or diagnose pancreatic adenocarcinoma by screening serum samples from subjects and preferably can detect 60% or more of stage I pancreatic cancers and 80% or more of stage II cancers by serum sample analysis. In still other embodiments, reactivity with the anti-pancreatic cancer antibody can be used to detect occult pancreatic cancer or neoplastic precursor lesions against a background of pancreatitis or benign pancreatic hyperplasia.

The anti-pancreatic cancer antibody is of use for diagnosis, detection and/or treatment of pancreatic cancer. For therapy, the antibody or fragment thereof may be administered as a naked antibody, as an antibody complex, as an antibody fusion protein, or conjugated to at least one therapeutic agent, such as a radionuclide, an immunomodulator, a hormone, a hormone antagonist, an enzyme, an oligonucleotide such as an anti-sense oligonucleotide or a siRNA, an enzyme inhibitor, a photoactive therapeutic agent, a cytotoxic agent such as a drug or toxin, an angiogenesis inhibitor and a pro-apoptotic agent. Most preferably, the antibody is a $^{90}$Y-hPAM4 antibody and the radiolabeled antibody may be administered in fractionated dosages for treating pancreatic cancer.

BACKGROUND

The number of patients who succumb to pancreatic ductal adenocarcinoma (PDAC) each year continues to rise, unlike other leading cancers where surveillance and/or screening technologies have led to a decrease in cancer-related mortality rates (Cardin & Berlin, 2013, J Natl Cancer Inst 105:1675-6; Ma et al., 2013, J Natl Cancer Inst 105:1694-1700; Siegel et al. 2012, Cancer statistics, 62:10-29). Unfortunately, the mortality rate for PDAC is nearly equal to the incidence. The overall survival rate for all stages of pancreatic cancer diagnosed between 2001 and 2007 is only 20% after one year, and about 6% after 5 years (Siegel et al. 2012, Cancer statistics, 62:10-29). With the alarming increase in PDAC incidence, it is projected that by the year 2030, pancreatic cancer will become the second leading cause of cancer deaths in the United States (Rahib et al., 2014, Cancer Res 74:2913-21). The major reason for this poor prognosis is the inability to detect the disease at an early stage, when curative measures may have a greater opportunity to provide successful outcomes.

Biomarkers, whether they are biological, chemical, or physical in nature, have proven of significant value in providing information leading to the earlier detection and diagnosis of cancer, such as breast (Goldhirsch et al., 2003, Ann Oncol 14:1212-4), colon (Mandel et al., 1993, N Engl J Med 328:1365-71), and prostate (Jacobsen et al., 1995, JAMA 274:1445-9), resulting in improved patient outcomes. Unfortunately, this has not been the case for PDAC. Despite considerable attention directed towards discovery of biomarkers for PDAC (Lennon et al., 2014, Cancer Research 74:1-9), to date no FDA-approved means for early detection/diagnosis exists. A need exists for more effective compositions and methods for early detection and/or diagnosis of prostate cancer, preferably at the earliest stages of the disease.

In addition to more effective and earlier means of detection, a need also exists for better therapeutic treatments for pancreatic cancer. The outlook for patients with advanced pancreatic adenocarcinoma remains poor (Hidalgo, 2010, N Engl J Med 362:1605-17). In the frontline, median survival was 6.2-6.7 months with gemcitabine alone (Burris et al., 1997, J Clin Oncol 15:2403-13) or with erlotinib (Moore et al., 2007, J Clin Oncol 25:1960-6), 8.5 months combined with albumin-bound paclitaxel (Von Hoff et al., 2013, N Engl J Med 369:1691-1703), and 11.1 months for those able to tolerate combination chemotherapy (FOLFIRINOX) (Conroy et al., 2011, N Engl J Med 364:1817-25). Beyond 1st line, the survival advantage with chemotherapy remains limited (Rahma et al., 2013, Ann Oncol 24:1972-9; Oettle et al., 2014, J Clin Oncol 32:2423-9) and after two prior treatments (one usually gemcitabine-based, the other fluoropyrimidine-based), there are no accepted treatments (Seufferlein et al., 2012, Ann Oncol 23(suppl 7):vii33-40; Almhanna & Kim, 2008, Oncology (Williston Park) 22:1176-83).

There is an unmet need for more effective therapies in pancreatic cancer patients who have received and shown resistance to or relapsed from two or more prior therapies.

SUMMARY

In various embodiments, the present invention concerns antibodies, antigen-binding antibody fragments and fusion proteins that bind to the MUC5AC pancreatic cancer mucin. Preferably, the antibodies or fragments thereof bind to an epitope located within the second to fourth cysteine-rich subdomains of MUC5AC (amino acid residues 1575-2052, Cys2-Cys4). More preferably, the antibodies bind to an epitope located in amino acid residues 1575-1725 and 1903-2052 (Cys2 and Cys 4). Even more preferably, the antibodies bind to an epitope located in amino acid residues 1575-1725 (Cys2+). Most preferably, the antibodies bind to an epitope located in Cys2.

In preferred embodiments, the subject antibodies or fragments thereof bind specifically to pancreatic cancer cells, with little or no binding to normal or non-neoplastic pancreatic cells. The antibodies are capable of binding to the earliest stages of pancreatic cancer, with detection rates of about 50-60% for PanIN-1A, 70-80% for Pan1B and 80-90% for PanIN-2. More preferably, the antibodies bind to 80 to 90% or more of human invasive pancreatic adenocarcinoma, intraductal papillary mucinous neoplasia, PanIN-1A, PanIN-1B and PanIN-2 lesions. Most preferably, the antibodies can distinguish between early stage pancreatic cancer and non-malignant conditions such as pancreatitis.

Such antibodies are of particular use for early detection of cancer and differential diagnosis between early stage pancreatic cancer and benign pancreatic conditions. In preferred embodiments, such antibodies are of use for in vivo or ex vivo analysis of samples from individuals suspected of having early stage pancreatic or certain other cancers. More preferably, the antibodies are of use for detection and diagnosis of early stage pancreatic cancer by analysis of serum samples.

In alternative embodiments, the antibodies, antibody fragments or fusion proteins are capable of binding to synthetic peptide sequences, for example to phage display peptides, such as WTWNITKAYPLP (SEQ ID NO:7) and ACPEWWGTTC (SEQ ID NO:8). Such synthetic peptides may be linear or cyclic and may or may not compete with antibody binding to the endogenous pancreatic cancer antigen. Amino acids in certain positions of the synthetic peptide sequences may be less critical for antibody binding than others. For example, in SEQ ID NO:7 the residues K, A and L at positions 7, 8 and 11 of the peptide sequence may be varied while still retaining antibody binding. Similarly, in SEQ ID NO:8 the threonine residues at positions 8 and 9 of the sequence may be varied, although substitution of the threonine at position 9 may significantly affect antibody binding to the peptide.

Binding of the antibodies to a target pancreatic cancer antigen may be inhibited by treatment of the target antigen with reagents such as dithiothreitol (DTT) and/or periodate. Thus, binding of the antibodies to a pancreatic cancer antigen may be dependent upon the presence of disulfide bonds and/or the glycosylation state of the target antigen. In more preferred embodiments, the epitope recognized by the subject antibodies is not cross-reactive with other reported mucin-specific antibodies, such as the MA5 antibody, the CLH2-2 antibody and/or the 45M1 antibody (see, e.g., Major et al., J Histochem Cytochem. 35:139-48, 1987; Dion et al., Hybridoma 10:595-610, 1991).

The subject antibodies or fragments may be naked antibodies or fragments or preferably are conjugated to at least one therapeutic and/or diagnostic agent for delivery of the agent to target tissues. In alternative embodiments, the subject antibodies or fragments may be part of a bispecific antibody with a first binding site for an epitope of MUC5AC as discussed above and a second binding site for a hapten conjugated to a targetable construct. The targetable construct may in turn be attached to at least one therapeutic and/or diagnostic agent, of use in pretargeting techniques.

In preferred embodiments, the subject antibody, antibody fragment or fusion protein is a humanized PAM4 antibody or fragment, comprising the light chain variable region CDR sequences CDR1 (SASSSVSSSYLY, SEQ ID NO:1); CDR2 (STSNLAS, SEQ ID NO:2); and CDR3 (HQWNRYPYT, SEQ ID NO:3); and the heavy chain variable region CDR sequences CDR1 (SYVLH, SEQ ID NO:4); CDR2 (YINPYNDGTQYNEKFKG, SEQ ID NO:5) and CDR3 (GFGGSYGFAY, SEQ ID NO:6) and human antibody framework region (FR) and constant region sequences. More preferably, the FRs of the light and heavy chain variable regions of the humanized PAM4 antibody or fragment thereof comprise at least one amino acid substituted from amino acid residues 5, 27, 30, 38, 48, 66, 67 and 69 of the murine PAM4 heavy chain variable region (SEQ ID NO:12) and/or at least one amino acid selected from amino acid residues 21, 47, 59, 60, 85, 87 and 100 of the murine PAM4 light chain variable region (SEQ ID NO:10). Most preferably, the antibody or fragment thereof comprises the hPAM4 $V_H$ amino acid sequence of SEQ ID NO:19 and the hPAM4 $V_K$ amino acid sequence of SEQ ID NO:16.

In alternative embodiments, the anti-pancreatic cancer antibody may be a chimeric, humanized or human antibody that binds to the same antigenic determinant (epitope) as, or competes for binding to MUC5AC with, a chimeric PAM4 (cPAM4) antibody. As discussed below, the cPAM4 antibody is one that comprises the light chain variable region CDR sequences CDR1 (SASSSVSSSYLY, SEQ ID NO:1); CDR2 (STSNLAS, SEQ ID NO:2); and CDR3 (HQWNRYPYT, SEQ ID NO:3); and the heavy chain variable region CDR sequences CDR1 (SYVLH, SEQ ID NO:4); CDR2 (YINPYNDGTQYNEKFKG, SEQ ID NO:5) and CDR3 (GFGGSYGFAY, SEQ ID NO:6). Antibodies that bind to the same antigenic determinant may be identified by a variety of techniques known in the art, such as by competitive binding studies using the cPAM4 antibody as the competing antibody and human pancreatic mucin or MUC5AC as the target antigen. Antibodies that block (compete for) binding to human pancreatic mucin by a cPAM4 antibody are referred to as cross-blocking antibodies. Preferably, such cross-blocking antibodies are ones that bind to an epitope located within the second to fourth cysteine-rich subdomains of MUC5AC, or that compete for binding to amino acid residues 1575-2052 with a PAM4 antibody. More preferably, the antibodies bind to an epitope located in Cys2.

Other embodiments concern cancer cell-targeting therapeutic immunoconjugates comprising an antibody or fragment thereof or fusion protein bound to at least one therapeutic agent. Preferably, the therapeutic agent is selected from the group consisting of a radionuclide, an immunomodulator, a hormone, a hormone antagonist, an enzyme, an oligonucleotide such as an anti-sense oligonucleotide or a siRNA, an enzyme inhibitor, a photoactive therapeutic agent, a cytotoxic agent such as a drug or toxin, an angiogenesis inhibitor and a pro-apoptotic agent. In embodiments where more than one therapeutic agent is used, the therapeutic agents may comprise multiple copies of the same therapeutic agent or else combinations of different therapeutic agents. More preferably, the therapeutic agent is a radionuclide, such as $^{90}$Y. The labeled antibody may be administered alone, or in combination with one or more other therapeutic agents, such as low-dose gemcitabine.

In certain embodiments, the therapeutic agent is a cytotoxic agent, such as a drug or a toxin. Also preferred, the drug is selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicins and their analogs, antimetabolites, alkylating agents, antimitotics, anti-angiogenic agents, tyrosine kinase inhibitors, Bruton tyrosine kinase inhibitors, mTOR inhibitors, heat shock protein (HSP90) inhibitors, proteosome inhibitors, HDAC inhibitors, pro-apoptotic agents, methotrexate, CPT-11, SN-38, 2-PDOX, pro-2-PDOX, and a combination thereof.

In another preferred embodiment, the therapeutic agent is a toxin selected from the group consisting of ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin and combinations thereof. Or an immunomodulator selected from the group consisting of a cytokine, a stem cell growth factor, a lymphotoxin, a hematopoietic factor, a colony stimulating factor (CSF), an interferon (IFN), a stem cell growth factor, erythropoietin, thrombopoietin and a combinations thereof.

Alternatively, the therapeutic agent is an enzyme selected from the group consisting of malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Such enzymes may be used, for example, in combination with prodrugs that are administered in relatively non-toxic form and converted at the target site by the enzyme into a cytotoxic agent. In other alternatives, a drug may be converted into less toxic form by endogenous enzymes in the subject but may be reconverted into a cytotoxic form by the therapeutic enzyme.

Other therapeutic agents include radionuclides such as $^{14}$C, $^{13}$N, $^{15}$O, $^{32}$P, $^{33}$P, $^{47}$Sc, $^{51}$Cr, $^{57}$Co, $^{58}$Co, $^{59}$Fe, $^{62}$Cu, $^{67}$Cu, $^{67}$Ga, $^{67}$Ga, $^{75}$Br, $^{75}$Se, $^{75}$Se, $^{75}$Br, $^{77}$As, $^{77}$Br, $^{80m}$Br, $^{89}$Sr, $^{90}$Y, $^{95}$Ru, $^{97}$Ru, $^{99}$Mo, $^{99m}$Tc, $^{103m}$Rh, $^{103}$Ru, $^{105}$Rh, $^{105}$Ru, $^{107}$Hg, $^{109}$Pd, $^{109}$Pt, $^{111}$Ag, $^{111}$In, $^{113m}$In, $^{119}$Sb, $^{121m}$Te, $^{122m}$Te, $^{125}$I, $^{125m}$Te, $^{126}$I, $^{131}$I, $^{133}$I, $^{142}$Pr, $^{143}$Pr, $^{149}$Pm, $^{152}$Dy, $^{153}$Sm, $^{161}$Ho, $^{161}$Tb, $^{165}$Tm, $^{166}$Dy, $^{166}$Ho, $^{167}$Tm, $^{168}$Tm, $^{169}$Er, $^{169}$Yb, $^{177}$Lu, $^{186}$Re, $^{188}$Re, $^{189m}$Os, $^{189}$Re, $^{192}$Ir, $^{194}$Ir, $^{197}$Pt, $^{198}$Au, $^{199}$Au, $^{201}$Tl, $^{203}$Hg, $^{211}$At, $^{211}$Bi, $^{211}$Pb, $^{212}$Bi, $^{212}$Pb, $^{213}$Bi, $^{215}$Po, $^{217}$At, $^{219}$Rn, $^{221}$Fr, $^{223}$Ra, $^{224}$Ac, $^{225}$Ac, $^{255}$Fm or $^{227}$Th.

A variety of tyrosine kinase inhibitors are known in the art and any such known therapeutic agent may be utilized. Exemplary tyrosine kinase inhibitors include, but are not limited to canertinib, dasatinib, erlotinib, gefitinib, imatinib, lapatinib, leflunomide, nilotinib, pazopanib, semaxinib, sorafenib, sunitinib, sutent and vatalanib. A specific class of tyrosine kinase inhibitor is the Bruton tyrosine kinase inhibitor. Bruton tyrosine kinase (Btk) has a well-defined role in B-cell development. Bruton kinase inhibitors include, but are not limited to, PCI-32765 (ibrutinib), PCI-45292, GDC-0834, LFM-A13 and RN486.

The subject antibody or fragment may be conjugated to at least one diagnostic (or detection) agent. Preferably, the diagnostic agent is selected from the group consisting of a radionuclide, a contrast agent, a fluorescent agent, a chemiluminescent agent, a bioluminescent agent, a paramagnetic ion, an enzyme and a photoactive diagnostic agent. Still more preferred, the diagnostic agent is a radionuclide with an energy between 20 and 4,000 keV or is a radionuclide selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. In a particularly preferred embodiment, the diagnostic radionuclide $^{18}$F is used for labeling and PET imaging, as described in the Examples below. The $^{18}$F may be attached to an antibody, antibody fragment or peptide by complexation to a metal, such as aluminum, and binding of the $^{18}$F-metal complex to a chelating moiety that is conjugated to a targeting protein, peptide or other molecule.

Also preferred, the diagnostic agent is a paramagnetic ion, such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), or a radiopaque material, such as barium, diatrizoate, ethiodized oil, gallium citrate, iocarmic acid, iocetamic acid, iodamide, iodipamide, iodoxamic acid, iogulamide, iohexol, iopamidol, iopanoic acid, iprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

In still other embodiments, the diagnostic agent is a fluorescent labeling compound selected from the group consisting of fluorescein isothiocyanate, rhodamine, phycoerytherin, phycocyanin, allophycocyanin, o-phthaldehyde and fluorescamine, a chemiluminescent labeling compound selected from the group consisting of luminol, isoluminol, an aromatic acridinium ester, an imidazole, an acridinium salt and an oxalate ester, or a bioluminescent compound selected from the group consisting of luciferin, luciferase and aequorin. In another embodiment, the diagnostic immunoconjugates are used in intraoperative, endoscopic, or intravascular tumor diagnosis.

Also contemplated are multivalent, multispecific antibodies or fragments thereof comprising at least one binding site that binds to an epitope of MUC5AC as discussed above and one or more hapten binding sites having affinity towards hapten molecules. Preferably, the antibody or fragment thereof is a chimeric, humanized or fully human antibody or fragment thereof. The hapten molecule may be conjugated to a targetable construct for delivery of one or more therapeutic and/or diagnostic agents. In certain preferred embodiments, the multivalent antibodies or fragments thereof may be prepared by the DOCK-AND-LOCK™ (DNL™) technique, as described below. An exemplary DNL™ construct incorporating hPAM4 antibody fragments is designated TF10, as described below.

Also contemplated is a bispecific antibody or fragment thereof comprising at least one binding site with an affinity toward an epitope of MUC5AC as discussed above and at least one binding site with an affinity toward a targetable construct which is capable of carrying at least one diagnostic and/or therapeutic agent. Targetable constructs suitable for use are disclosed, for example, in U.S. Pat. Nos. 6,576,746; 6,962,702; 7,052,872; 7,138,103; 7,172,751; 7,405,320; 7,597,876; 7,563,433; 7,993,626; 147,799; 8,153,100; 8,153,101; 8,202,509; 8,343,460; 8,444,956, 8,496,912; 8,545,809; 8,617,518; and 8,632,752, the Examples section of each of which is incorporated herein by reference.

Other embodiments concern fusion proteins comprising at least two anti-pancreatic cancer antibodies and fragments thereof as described herein. Alternatively, the fusion protein or fragment thereof may comprise at least one first antibody or fragment thereof that binds to an epitope of MUC5AC as discussed above and at least one second MAb or fragment thereof. Preferably, the second MAb binds to a tumor-associated antigen, for example selected from the group consisting of CA19.9, DUPAN2, SPAN1, Nd2, B72.3, CC49, CEA (CEACAM5), CEACAM6, Le$^a$, the Lewis antigen Le(y), CSAp, insulin-like growth factor (IGF), epithelial glycoprotein-1 (EGP-1), epithelial glycoprotein-2 (EGP-2), CD-80, placental growth factor (PlGF), carbonic anhydrase IX, tenascin, IL-6, HLA-DR, CD40, CD74 (e.g., milatuzumab), CD138 (syndecan-1), CTLA-4, PD-1, PD-L1, TIM-3, LAG-3, matrix metalloproteinase-1 (MMP-1), MMP-2, MMP-7, MMP-9, MMP-14, MUC1, MUC2, MUC3, MUC4, MUC5AC, MUC16, MUC17, TAG-72, EGFR, platelet-derived growth factor (PDGF), angiogenesis factors (e.g., VEGF and PlGF), products of oncogenes (e.g., bcl-2, Kras, p53), cMET, HER2/neu, and antigens associated with gastric cancer and colorectal cancer. The second MAb may also bind to a different epitope of MUC5AC than the first MAb. The antibody fusion protein or fragments thereof may further comprise at least one diagnostic and/or therapeutic agent.

Also described herein are DNA sequences comprising a nucleic acid encoding an anti-pancreatic cancer antibody, fusion protein, multispecific antibody, bispecific antibody or fragment thereof as described herein. Other embodiments concern expression vectors and/or host cells comprising the antibody-encoding DNA sequences. In certain preferred embodiments, the host cell may be an Sp2/0 cell line transformed with a mutant Bcl-2 gene, for example with a triple mutant Bcl-2 gene (T69E, S70E, S87E), that has been adapted to cell transformation and growth in serum free medium. (See, e.g., U.S. Pat. Nos. 7,531,327; 7,537,930; and 7,608,425, the Examples section of each of which is incorporated herein by reference.)

Another embodiment concerns methods of delivering a diagnostic or therapeutic agent, or a combination thereof, to a target comprising (i) providing a composition that comprises an anti-pancreatic cancer antibody or fragment that binds to an epitope located within the second to fourth cysteine-rich subdomains of MUC5AC (amino acid residues 1575-2052), more preferably to an epitope located in amino acid residues 1575-1725 and 1903-2052 (Cys2 and Cys 4), even more preferably to an epitope located in amino acid residues 1575-1725 (Cys2+), most preferably, to an epitope located in Cys2, conjugated to at least one diagnostic and/or therapeutic agent and (ii) administering to a subject in need thereof the diagnostic or therapeutic conjugate of any one of the antibodies, antibody fragments or fusion proteins claimed herein.

Also contemplated is a method of delivering a diagnostic agent, a therapeutic agent, or a combination thereof to a target, comprising: (a) administering to a subject any one of the multivalent, multispecific or bispecific antibodies or fragments thereof that have an affinity toward an epitope of MUC5AC as discussed above and comprising one or more hapten binding sites; (b) waiting a sufficient amount of time for antibody that does not bind to MUC5AC to clear the subject's blood stream; and (c) administering to said subject a carrier molecule comprising a diagnostic agent, a therapeutic agent, or a combination thereof, that binds to a binding site of the antibody. Preferably, the carrier molecule binds to more than one binding site of the antibody.

Described herein is a method for diagnosing or treating cancer, comprising: (a) administering to a subject any one of the multivalent, multispecific antibodies or fragments thereof claimed herein that have an affinity toward an epitope of MUC5AC as discussed above and comprising one or more hapten binding sites; (b) waiting a sufficient amount of time for an amount of the non-bound antibody to clear the subject's blood stream; and (c) administering to said subject a carrier molecule comprising a diagnostic agent, a therapeutic agent, or a combination thereof, that binds to a binding site of the antibody. In a preferred embodiment the cancer is pancreatic cancer. Also preferred, the method can be used for intraoperative identification of diseased tissues, endoscopic identification of diseased tissues, or intravascular identification of diseased tissues.

Another embodiment is a method of treating a malignancy in a subject comprising administering to said subject a therapeutically effective amount of an antibody or fragment thereof that binds to an epitope of MUC5AC as discussed above, optionally conjugated to at least one therapeutic agent, such as $^{90}$Y. The antibody or fragment thereof may alternatively be a naked antibody or fragment thereof. In more preferred embodiments, the antibody or fragment is administered either before, simultaneously with, or after administration of another therapeutic agent as described above.

Contemplated herein is a method of diagnosing a malignancy in a subject, particularly a pancreatic cancer, comprising (a) administering to said subject a diagnostic conjugate comprising an antibody or fragment thereof that binds to an epitope of MUC5AC as discussed above, wherein said MAb or fragment thereof is conjugated to at least one diagnostic agent, and (b) detecting the presence of labeled antibody bound to pancreatic cancer cells or other malignant cells, wherein binding of the antibody is diagnostic for the presence of pancreatic cancer or another malignancy. In preferred embodiments, the antibody or fragment binds to pancreatic cancer and not to normal pancreatic tissue, pancreatitis or other non-malignant conditions. In less preferred embodiments, the antibody or fragment binds at a significantly higher level to cancer cells than to non-malignant cells, allowing differential diagnosis of cancer from non-malignant conditions. In a most preferred embodiment, the diagnostic agent may be an F-18 labeled molecule that is detected by PET imaging.

In more preferred embodiments, the use of anti-pancreatic cancer antibodies that bind to an epitope located within the second to fourth cysteine-rich subdomains of MUC5AC (amino acid residues 1575-2052), more preferably to an epitope located in amino acid residues 1575-1725 and 1903-2052 (Cys2 and Cys 4), even more preferably to an epitope located in amino acid residues 1575-1725 (Cys2+), most preferably, to an epitope located in Cys2, allows the detection and/or diagnosis of pancreatic cancer with high specificity and sensitivity at the earliest stages of malignant disease. Preferably, the diagnostic antibody or fragment is capable of labeling at least 70%, more preferably at least 80%, more preferably at least 90%, more preferably at least 95%, most preferably about 100% of well differentiated, moderately differentiated and poorly differentiated pancreatic cancer and 90% or more of invasive pancreatic adenocarcinomas. The anti-pancreatic cancer antibody of use is preferably capable of detecting 85% or more of PanIN-1A, PanIN-1B, PanIN-2, IPMN and MCN precursor lesions. Most preferably, immunoassays using the anti-pancreatic cancer antibody are capable of detecting 89% or more of total PanIN, 86% or more of IPMN, and 92% or more of MCN.

An alternative embodiment is a method of detecting the presence of PAM4-binding MUC5AC and/or diagnosing pancreatic cancer in an individual by in vitro analysis of blood, plasma or serum samples. Preferably, the sample is subjected to an organic phase extraction, using an organic solvent such as butanol, before it is processed for immunodetection using an anti-pancreatic cancer antibody, such as a PAM4 antibody. Following organic phase extraction, the extracted aqueous phase is analyzed for the presence of the epitope of MUC5AC to which PAM4 binds in the sample, using any of a variety of immunoassay techniques known in the art, such as ELISA, sandwich immunoassay, solid phase RIA, and similar techniques. Surprisingly, the organic phase extraction results in the removal of an inhibitor of PAM4 binding to MUC5AC, allowing detection of MUC5AC in fresh serum samples. More surprisingly, using the in vitro analysis techniques described herein, serum samples may be analyzed to detect and/or diagnose pancreatic cancer in a subject at the earliest stages of pancreatic adenocarcinoma. These unexpected results provide the first serum-based assay technique that is diagnostic for the presence of early stage pancreatic cancer.

Another embodiment is a method of treating a cancer cell in a subject comprising administering to said subject a composition comprising a naked antibody or fragment thereof or a naked antibody fusion protein or fragment thereof that binds to an epitope of MUC5AC as discussed above. Preferably, the method further comprises administering a second naked antibody or fragment thereof selected from the group consisting of CA19.9, DUPAN2, SPAN1, Nd2, B72.3, CC49, anti-CEA, anti-CEACAM6, anti-EGP-1, anti-EGP-2, anti-Le$^a$, antibodies defined by the Lewis antigen Le(y), and antibodies against CSAp, MUC1, MUC2, MUC3, MUC4, MUC5AC, MUC16, MUC17, TAG-72, EGFR, CD40, HLA-DR, CD74, CD138, angiogenesis factors (e.g., VEGF and placenta-like growth factor (PlGF), insulin-like growth factor (IGF), tenascin, platelet-derived growth factor, IL-6, products of oncogenes, cMET, and HER2/neu.

Still other embodiments concern a method of diagnosing a malignancy in a subject comprising (i) performing an in vitro diagnosis assay on a specimen from said subject with a composition comprising an antibody or fragment thereof that binds to an epitope of MUC5AC as discussed above; and (ii) detecting the presence of antibody or fragment bound to malignant cells in the specimen. Preferably, the malignancy is a cancer. More preferably, the cancer is pancreatic cancer.

BRIEF DESCRIPTION OF THE DRAWINGS

The following drawings are provided to illustrate preferred embodiments of the invention. However, the claimed subject matter is in no way limited by the illustrative embodiments disclosed in the drawings.

FIG. 3A. Immunoreactivity of fractions eluted from SEP-HAROSE® CL-2B. Capan-1 cell culture supernatant was separated on a SEPHAROSE® CL2B column with the eluted fractions analyzed by hPAM4 and anti-MUC1.

FIG. 3B. Immunoreactivity of fractions eluted from SEP-HAROSE® CL-2B. The void-volume (Vo) fractions of Capan-1 reacted positively with three anti-MUC5AC antibodies (45M1, 1-13M1 and H-160), but not with 2Q445, which recognizes the unglycosylated tandem repeat region of MUC5AC.

FIG. 3C. Immunoreactivity of fractions eluted from SEP-HAROSE® CL-2B. The Capan-1 void-volume peak, following capture by 2-11M1, could be detected directly by HRP-hPAM4, or indirectly by biotin-45M1 plus SA-HRP.

FIG. 5A. Mapping the PAM4-reactive epitope on human MUC5AC. Schematic diagram of different MUC5AC recombinant fragments (a-h) generated in PANC-1 cells for mapping PAM4 epitope; Numbers are AA positions in the MUC5AC protein sequence (UniProtKB/Swiss-Prot: P98088).

FIG. 5B. Mapping the PAM4-reactive epitope on human MUC5AC. Western blot of a-fragment (AA3992-5030), b-fragment (AA1-1218) and c-fragment (AA1218-2199), which spans the five N-terminal cysteine-rich subdomains (Cys1-2-3-4-5), with hPAM4 and 45M1 antibodies. Lane m indicates samples from untransfected cells.

FIG. 5C. Mapping the PAM4-reactive epitope on human MUC5AC. Western blot of c-fragment (AA1218-2199), d-fragment (AA1218-1517) and e-fragment (AA1575-2052), with hPAM4, H160 and 45M1 antibodies. Lane m indicates samples from untransfected cells.

FIG. 5D. Mapping the PAM4-reactive epitope on human MUC5AC. Western blot of e-fragment (AA1575-2052), f-fragment (AA1725-2052), g-fragment (AA1575-1725 and 1903-2052) and h-fragment (AA1575-1853) with hPAM4 and 45M1 antibodies. Lane m indicates samples from untransfected cells.

FIG. 5E. Mapping the PAM4-reactive epitope on human MUC5AC. Western blot of GFP-fused e*-fragment (AA1575-2052), f*-fragment (AA1725-2052), g*-fragment (AA1575-1725 and 1903-2052) and h*-fragment (AA1575-1853) with hPAM4 and anti-GFP antibodies. Lane m indicates samples from untransfected cells.

FIG. 6A. SDS-PAGE and Western blot analyses of recombinant MUC5AC fragments expressed in E. coli. Four gels were run under similar conditions of SDS-PAGE. Gel was stained with coomassie blue. Samples, either reduced (R) or non-reduced (NR), were loaded at 500 ng/well; lane M, markers; lanes 1 & 3, Cys2-3-4 (AA1575-2052); lanes 2 &4, Cys2+ (AA1575-1725).

FIG. 6B. SDS-PAGE and Western blot analyses of recombinant MUC5AC fragments expressed in E. coli. Four gels were run under similar conditions of SDS-PAGE. Gel was transferred onto nitrocellulose membrane and stained with anti-Myc. Samples, either reduced (R) or non-reduced (NR), were loaded at 500 ng/well; lane M, markers; lanes 1 & 3, Cys2-3-4 (AA1575-2052); lanes 2 &4, Cys2+(AA1575-1725).

FIG. 6C. SDS-PAGE and Western blot analyses of recombinant MUC5AC fragments expressed in E. coli. Four gels were run under similar conditions of SDS-PAGE. Gel was transferred onto nitrocellulose membrane and stained with hPAM4. Samples, either reduced (R) or non-reduced (NR), were loaded at 500 ng/well; lane M, markers; lanes 1 & 3, Cys2-3-4 (AA1575-2052); lanes 2 &4, Cys2+(AA1575-1725).

FIG. 6D. SDS-PAGE and Western blot analyses of recombinant MUC5AC fragments expressed in E. coli. Four gels were run under similar conditions of SDS-PAGE. Gel was transferred onto nitrocellulose membrane and stained with 1-13M1. Samples, either reduced (R) or non-reduced (NR), were loaded at 500 ng/well; lane M, markers; lanes 1 & 3, Cys2-3-4 (AA1575-2052); lanes 2 &4, Cys2+(AA1575-1725).

FIG. 8A. Variable region cDNA sequences (SEQ ID NO:9) and the deduced amino acid sequences (SEQ ID NO:10) of the murine PAM4 Vk. Amino acid sequences encoded by the corresponding DNA sequences are given as one-letter codes below the nucleotide sequence. Numbering of the nucleotide sequence is on the right side. The amino acid residues in the CDR regions are shown in bold and underlined. Kabat's Ig molecule numbering is used for amino acid residues as shown by the numbering above the amino acid residues. The amino acid residues numbered by a letter are the insertion residues defined by Kabat numbering scheme. The insertion residues have the same preceding digits as that of the previous residue.

FIG. 8B. Variable region cDNA sequence (SEQ ID NO:11) and the deduced amino acid sequence (SEQ ID NO:12) of the murine PAM4 VH. Amino acid sequences encoded by the corresponding DNA sequences are given as one-letter codes below the nucleotide sequence. Numbering of the nucleotide sequence is on the right side. The amino acid residues in the CDR regions are shown in bold and underlined. Kabat's Ig molecule numbering is used for amino acid residues as shown by the numbering above the amino acid residues. The amino acid residues numbered by a letter are the insertion residues defined by Kabat numbering scheme. The insertion residues have the same preceding digits as that of the previous residue.

FIG. 9A. Amino acid sequence (SEQ ID NO:13) of the chimeric PAM4 (cPAM4) Vk. The sequences are given as one letter codes. The amino acid residues in the CDR regions are shown in bold and underlined. Kabat's Ig molecule number scheme is used to number the residues.

FIG. 9B. Amino acid sequence (SEQ ID NO:14) of the cPAM4 VH. The sequences are given as one letter codes. The amino acid residues in the CDR regions are shown in bold and underlined. Kabat's Ig molecule number scheme is used to number the residues.

FIG. 10A. Alignment of the $V_K$ amino acid sequences of the human antibody Walker (SEQ ID NO:15) with PAM4 (SEQ ID NO:10) and hPAM4 (SEQ ID NO:16). Dots indicate the residues of PAM4 that are identical to the corresponding residues of the human or humanized antibodies. Boxed regions represent the CDR regions. Both N- and C-terminal residues (underlined) of hPAM4 are fixed by the staging vectors used. Kabat's Ig molecule number scheme is used to number the residues.

FIG. 10B. Alignment of the VH amino acid sequences of the human antibody Wil2 (FR1-3) (SEQ ID NO:17) and NEWM (FR4) (SEQ ID NO:18) with PAM4 (SEQ ID NO:12) and hPAM4 (SEQ ID NO:19). Dots indicate the residues of PAM4 that are identical to the corresponding residues of the human or humanized antibodies. Boxed regions represent the CDR regions. Both N- and C-terminal residues (underlined) of hPAM4 are fixed by the staging vectors used. Kabat's Ig molecule number scheme is used to number the residues.

FIG. 11A. DNA (SEQ ID NO:20) and amino acid (SEQ ID NO:16) sequences of the humanized PAM4 (hPAM4) Vk. Numbering of the nucleotide sequence is on the right side. Amino acid sequences encoded by the corresponding DNA sequences are given as one-letter codes. The amino acid residues in the CDR regions are shown in bold and underlined. Kabat's Ig molecule numbering scheme is used for amino acid residues.

FIG. 11B. DNA (SEQ ID NO:21) and amino acid (SEQ ID NO:19) sequences of the hPAM4 VH. Numbering of the nucleotide sequence is on the right side. Amino acid sequences encoded by the corresponding DNA sequences are given as one-letter codes. The amino acid residues in the CDR regions are shown in bold and underlined. Kabat's Ig molecule numbering scheme is used for amino acid residues.

FIG. 15A illustrates mice showing the location of tumors (arrow).

FIG. 15B shows the detected tumors with $^{111}$In-labeled IMP 288 in the presence (above) or absence (below) of TF10 bispecific antibody.

FIG. 18A shows percent of initial dose per gram of tissue in tumor with PAM4 IgG (open circles), blood with PAM4 IgG (open squares), tumor with pretargeted peptide (closed circles) and blood with pretargeted peptide (closed squares).

FIG. 18B shows percent of initial dose per per gram of tissue in liver with PAM4 IgG (open triangles), kidney with PAM4 IgG (open diamonds), liver with pretargeted peptide (closed triangles) and kidney with pretargeted peptide (closed diamonds).

FIG. 18C shows microcuries per gram of tissue in tumor with PAM4 IgG (open circles), blood with PAM4 IgG (open squares), tumor with pretargeted peptide (closed circles) and blood with pretargeted peptide (closed squares).

FIG. 18D shows microcuries per per gram of tissue in liver with PAM4 IgG (open triangles), kidney with PAM4 IgG (open diamonds), liver with pretargeted peptide (closed triangles) and kidney with pretargeted peptide (closed diamonds).

DETAILED DESCRIPTION

Definitions

Figure 1:
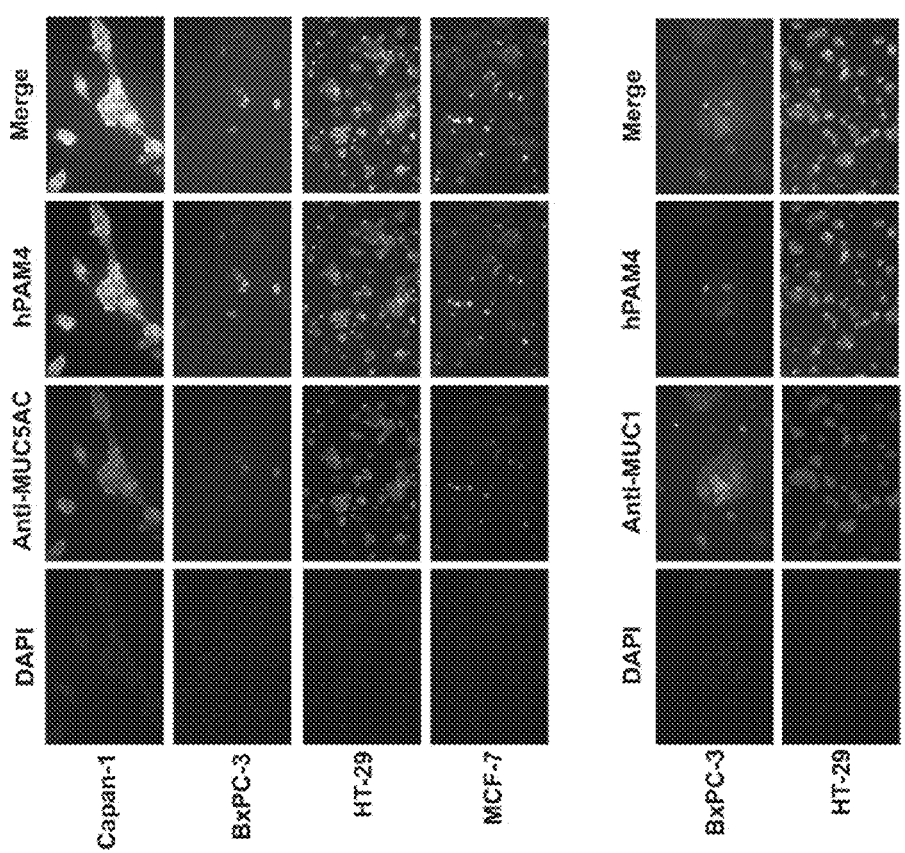
FIG. 1. Co-localization of PAM4 antigen with MUC5AC by cytoflurometric staining. Mucin-expressing cell lines (Capan-1, BxPC-3, HT-29, and MCF-7) were stained with DAPI, 2-11M1 (anti-MUC5AC), hPAM4, and examined by immunofluorescence microcopy. BxPC-3 and HT-29 cells were also stained with anti-MUC1. PAM4 antigen was shown to co-localize with MUC5AC, not MUC1.

Unless otherwise specified, "a" or "an" means one or more.

As used herein, "about" means plus or minus 10%. For example, "about 100" would include any number between 90 and 110.

As described herein, the term "PAM4 antibody" includes murine, chimeric, humanized and human PAM4 antibodies. In preferred embodiments, the PAM4 antibody or antigen-binding fragment thereof comprises the CDR sequences of SEQ ID NO:1 to SEQ ID NO:6.

As used herein, an "anti-pancreatic cancer antibody" is an antibody that exhibits the same diagnostic, therapeutic and binding characteristics as the PAM4 antibody. In preferred embodiments, the "anti-pancreatic cancer antibody" binds to an epitope located within the second to fourth cysteine-rich subdomains of MUC5AC (amino acid residues 1575-2052), more preferably to an epitope located in amino acid residues 1575-1725 and 1903-2052 (Cys2 and Cys 4), even more preferably to an epitope located in amino acid residues 1575-1725 (Cys2+), most preferably, to an epitope located in Cys2.

A "non-endocrine pancreatic cancer" generally refers to cancers arising from the exocrine pancreatic glands. The term excludes pancreatic insulinomas and includes pancreatic carcinoma, pancreatic adenocarcinoma, adenosquamous carcinoma, squamous cell carcinoma and giant cell carcinoma and precursor lesions such as pancreatic intra-epithelial neoplasia (PanIN), mucinous cyst neoplasms (MCN) and intrapancreatic mucinous neoplasms (IPMN), which are neoplastic but not yet malignant. The terms "pancreatic cancer" and "non-endocrine pancreatic cancer" are used interchangeably herein.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as $F(ab')_2$, Fab', Fab, Fv, sFv and the like. Regardless of structure, an antibody fragment binds with the same antigen that is recognized by the full-length antibody. The term "antibody fragment" also includes isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Another form of antibody fragment is a single domain antibody (nanobody).

A naked antibody is an antibody or fragment thereof that is not conjugated to a therapeutic or diagnostic agent. Generally, the Fc portion of the antibody molecule provides effector functions, such as complement-mediated cytotoxicity (CDC) and ADCC (antibody-dependent cellular cytotoxicity), which set mechanisms into action that may result in cell lysis. However, the Fc portion may not be required for therapeutic function, with other mechanisms, such as signaling-induced apoptosis, coming into play. Naked antibodies include both polyclonal and monoclonal antibodies, as well as fusion proteins and certain recombinant antibodies, such as chimeric, humanized or human antibodies.

A chimeric antibody is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, are transferred from the heavy and light variable chains of the rodent antibody into human heavy and light variable domains (e.g., framework region sequences). The constant domains of the antibody molecule are derived from those of a human antibody. In certain embodiments, a limited number of framework region amino acid residues from the parent (rodent) antibody may be substituted into the human antibody framework region sequences.

A human antibody is, e.g., an antibody obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous murine heavy chain and light chain loci. The transgenic mice can synthesize human antibodies specific for particular antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for review, see e.g. Johnson and Chiswell, Current Opinion in Structural Biology 3:5564-571 (1993). Human antibodies may also be generated by in vitro activated B cells. See U.S. Pat. Nos. 5,567,610 and 5,229,275, the Examples sections of which are incorporated herein by reference.

A therapeutic agent is a compound, molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, cytotoxic agents, drugs, toxins, nucleases, hormones, immunomodulators, pro-apoptotic agents, anti-angiogenic agents, boron compounds, photoactive agents or dyes and radioisotopes. Therapeutic agents of use are described in more detail below.

A diagnostic agent is a molecule, atom or other detectable moiety which may be administered conjugated to an antibody moiety or targetable construct and is useful in detecting or diagnosing a disease by locating cells containing the target antigen. Useful diagnostic agents include, but are not limited to, radioisotopes, dyes, contrast agents, fluorescent compounds or molecules and enhancing agents (e.g., paramagnetic ions) for magnetic resonance imaging (MRI) or positron emission tomography (PET) scanning Preferably, the diagnostic agents are selected from the group consisting of radioisotopes, enhancing agents for use in magnetic resonance or PET imaging, and fluorescent compounds. In order to load an antibody component with radioactive metals, paramagnetic ions or other diagnostic cations, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), DOTA, NOTA, NETA, porphyrins, polyamines, crown ethers, bis-thiosemicarbazones, polyoximes, and like groups known to be useful for this purpose. Chelates are coupled to the antibodies using standard chemistries. The chelate is normally linked to the antibody by a group which enables formation of a bond to the molecule with minimal loss of immunoreactivity and minimal aggregation and/or internal cross-linking Other, more unusual, methods and reagents for conjugating chelates to antibodies are disclosed in U.S. Pat. No. 4,824,659, the Examples section of which is incorporated herein by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br, for radioimaging. The same chelates, when complexed with non-radioactive metals, such as manganese, iron and gadolinium are useful for MRI, when used along with the antibodies of the invention. Macrocyclic chelates such as NOTA (1,4,7-triazacyclononane-N,N',N'-triacetic acid), DOTA (1,4,7,10-tetraazacyclododecanetetraacetic acid), and TETA (p-bromoacetamido-benzyl-tetraethylaminetetraacetic acid) are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for radioimmunotherapy (RAIT) are encompassed by the invention. More recently, techniques of general utility for labeling virtually any molecule with an $^{18}$F atom of use in PET imaging have been described in U.S. Pat. Nos. 7,563,433; 7,597,876 and 7,993,626, the Examples section of each incorporated herein by reference.

An immunoconjugate is an antibody, antibody fragment or antibody fusion protein conjugated to at least one therapeutic and/or diagnostic agent. The diagnostic agent and/or therapeutic agent are as defined above.

An expression vector is a DNA molecule comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells, as well as transgenic animals, that have been genetically engineered to contain the cloned gene(s) in the chromosome or genome of the host cell. Suitable mammalian host cells include myeloma cells, such as SP2/0 cells, and NS0 cells, as well as Chinese Hamster Ovary (CHO) cells, hybridoma cell lines and other mammalian host cell useful for expressing antibodies. Also particularly useful to express mAbs and other fusion proteins are Sp2/0 cells transfected with an apoptosis inhibitor, such as a Bcl-EEE gene, and adapted to grow and be further transfected in serum free conditions, as described in U.S. Pat. Nos. 7,531,327; 7,537,930; and 7,608,425, the Examples section of each of which is incorporated herein by reference.

Anti-Pancreatic Cancer Antibodies

Various embodiments of the invention concern antibodies that react with very high selectivity with pancreatic cancer as opposed to normal or benign pancreatic tissues. The anti-pancreatic cancer antibodies and fragments thereof are preferably raised against a crude mucin preparation from a tumor of the human pancreas, although partially purified or even purified MUC5AC may be utilized. A non-limiting example of such antibodies is the PAM4 antibody.

The murine PAM4 (mPAM4) antibody was developed by employing pancreatic cancer mucin derived from the xenografted RIP-1 human pancreatic carcinoma as immunogen. (Gold et al., Int. J. Cancer, 57:204-210, 1994.) As discussed below, antibody cross-reactivity and immunohistochemical staining studies indicate that the PAM4 antibody recognizes a unique and novel epitope on MUC5AC. Immunohistochemical staining studies have shown that the PAM4 MAb binds to an antigen expressed by breast, pancreas and other cancer cells, with limited binding to normal human tissue. However, the highest expression is usually by pancreatic cancer cells. Thus, the PAM4 antibodies are relatively specific to pancreatic cancer and preferentially bind pancreatic cancer cells. The PAM4 antibody is reactive with a target epitope which can be internalized. This epitope is expressed primarily by antigens associated with pancreatic cancer and not with focal pancreatitis or normal pancreatic tissue. Binding of PAM4 antibody to the PAM4 epitope is inhibited by treatment of the antigen with DTT or periodate. Localization and therapy studies using a radiolabeled PAM4 MAb in animal models have demonstrated tumor targeting and therapeutic efficacy.

The PAM4 antibodies bind to an epitope located within the second to fourth cysteine-rich subdomains of MUC5AC (amino acid residues 1575-2052), more preferably to an epitope located in amino acid residues 1575-1725 and 1903-2052 (Cys2 and Cys 4), even more preferably to an epitope located in amino acid residues 1575-1725 (Cys2+), most preferably, to an epitope located in Cys2. The PAM4 epitope is expressed by many organs and tumor types, but is preferentially expressed in pancreatic cancer cells. Studies with a PAM4 MAb, as in the Examples below, indicate that the antibody exhibits several important properties, which make it a good candidate for clinical diagnostic and therapeutic applications. The epitope provides a useful target for diagnosis and therapy of pancreatic and other cancers. The PAM4 antibody apparently recognizes an epitope of MUC5AC that is distinct from the epitopes recognized by non-PAM4 anti-pancreatic cancer antibodies (e.g., CA19.9, DUPAN2, SPAN1, Nd2, CEACAM5, B72.3, anti-Le$^a$, and other anti-Lewis antigens).

Surprisingly, the Examples below indicate that the MUC5AC epitope to which PAM4 binds is present in detectable concentrations in serum of patients with very early stage pancreatic cancer. Also surprisingly, it appears that an endogenous inhibitor of PAM4 antibody binding to MUC5AC is present in fresh human serum. The inhibitor is removed by long-term frozen storage of serum samples, or by organic phase extraction of fresh serum. These unexpected results provide the basis of a relatively non-invasive, early detection test for pancreatic cancer, using blood, serum or plasma samples. In alternative embodiments, the PAM4 antibody may be used alone, or else in conjunction with one or more other antibodies, such as CA19.9 antibody, to detect pancreatic cancer markers in serum.

At the tissue level, the reactivity of PAM4 is highly restricted to PDAC, with the biomarker expressed (or becomes accessible) at the earliest stages of neoplastic development (Gold et al., 1994, Int J Cancer 57:204-10; Gold et al., 2007, Clin Cancer Res 13:7380-7), including pancreatic intraepithelial neoplasia (PanIN), and intraductal papillary mucinous neoplasm (IPMN). Notably, the PAM4-biomarker is absent from normal pancreas and benign, non-neoplastic lesions. In over 50 surgical specimens of chronic pancreatitis, the PAM4-biomarker was identified only within associated PanIN lesions and not by the inflamed parenchyma, including ducts, acinar cells, and acinar-ductal metaplasia (Shi et al., 2014, Arch Pathol Lab Med 138:220-8).

Preclinical studies have demonstrated the potential applications of PAM4 for radioimmunoimaging and radioimmunotherapy of pancreatic carcinoma (Gold et al., 2002, Crit Rev Oncol Hematol 39:147-54; Gold et al., 2004, Int J Cancer 109: 618-26). In patients, $^{90}$Y-labeled, humanized PAM4 ($^{90}$Y-clivatuzumab tetraxetan, hereafter referred to as $^{90}$Y-hPAM4) was well tolerated with manageable hematologic toxicity under maximal tolerated $^{90}$Y dosing, and produced objective responses in both chemotherapy-naïve and -refractory patients with advanced PDAC (Gulec et al., 2011, Clin Cancer Res 17:4091-100). Further, $^{90}$Y-hPAM4 in combination with low-dose gemcitabine showed enhanced therapeutic efficacy in patients with metastatic pancreatic cancer (Ocean et al., 2012, Cancer 118:5497-506). In a recently completed phase Ib study (Picozzi et al., 2014, J Clin Oncol 132:4026) involving 58 patients with metastatic PDAC who had at least 2 prior therapies, multiple cycles of fractionated $^{90}$Y-hPAM4 in combination with low radiosensitizing doses of gemcitabine significantly (P=0.004) improved the Kaplan-Meier median overall survival of this difficult-to-treat population to 7.9 months, compared to those receiving only $^{90}$Y-hPAM4 (3.4 months). These promising results led to the ongoing phase III registration trial of $^{90}$Y-hPAM4 in combination with gemcitabine (NCT01956812).

In addition, PAM4 or hPAM4-based ELISA has been devised and evaluated for detection of PDAC, showing that nearly two-thirds of patients having confirmed stage-1 disease had elevated PAM4 antigen in their serum (Gold et al., 2010, Cancer Epidemiol Biomarkers Prev 19:2786-94). However, the current assay, which employs hPAM4 as the capture antibody and a polyclonal rabbit anti-mucin antiserum (IgG fraction) as a probe, is not optimal, because the polyclonal probe is available in only limited quantities and, more importantly, is not itself specific for the PAM4 antigen. Another concern for further development of the assay has been the unknown nature of the antigen marker to which PAM4 is reactive. Given the clinical merit and ongoing evaluation of hPAM4 as a potential diagnostic and therapeutic agent for PDAC, there is an urgent need to identify the PAM4 epitope. Towards this end, we recently proposed (Gold et al., 2013, Mol Cancer 12:143) that PAM4 was reactive with the human MUC5AC, a polymeric gel-forming mucin with the monomeric form consisting of more than 5,000 amino acid residues organized into three major regions (Thornton et al., 2008, Annu Rev Physiol 70:459-86): a signal peptide and four von Willebrand factor (vWF)-like cysteine-rich domains (D1, D2, D' and D3) in the N-terminal region, a MUC11p15-type domain preceding the heavily 0-glycosylated mucin domain in the central region, and a cluster of vWF-like cysteine-rich domains (D4, B, C, and CK) in the C-terminal region. In addition, 9 cysteine-rich subdomains (designated Cys1, Cys2, Cys3, Cys4, Cys5, Cys6, Cys7, Cys8, and Cys9) are interspersed within the mucin domain. Herein we present further evidence to support MUC5AC as the PAM4-reactive mucin and, importantly, have mapped the PAM4 epitope to Cys2.

For therapeutic use, antibodies suitable for use in combination or conjunction with PAM4 antibodies include, for example, the antibodies CA19.9, DUPAN2, SPAN1, Nd2, B72.3, CC49, anti-CEA, anti-CEACAM6, anti-Le$^a$, anti-HLA-DR, anti-CD40, anti-CD74, anti-CD138, and antibodies defined by the Lewis antigen Le(y), or antibodies against colon-specific antigen-p (CSAp), CTLA-4, PD-1, PD-L1, TIM-3, LAG-3, matrix metalloproteinase-1 (MMP-1), MMP-2, MMP-7, MMP-9, MMP-14, MUC1, MUC2, MUC3, MUC4, MUC5AC, MUC16, MUC17, EGP-1, EGP-2, HER2/neu, EGFR, angiogenesis factors (e.g., VEGF and PlGF), insulin-like growth factor (IGF), tenascin, platelet-derived growth factor, and IL-6, as well as products of oncogenes (bcl-2, Kras, p53), cMET, and antibodies against tumor necrosis substances, such as described in patents by Epstein et al. (U.S. Pat. Nos. 6,071,491, 6,017,514, 5,019,368 and 5,882,626). Such antibodies would be useful for complementing PAM4 antibody immunodetection and immunotherapy methods. These and other therapeutic agents could act synergistically with anti-pancreatic cancer antibodies, such as PAM4 antibody, when administered before, together with or after administration of PAM4 antibody.

In therapeutic applications, antibodies that are agonistic or antagonistic to immunomodulators involved in effector cell function against tumor cells could also be useful in combination with PAM4 antibodies alone or in combination with other tumor-associated antibodies, one example being antibodies against CD40. Todryk et al., J. Immunol Methods, 248:139-147 (2001); Turner et al., J. Immunol, 166:89-94 (2001). Also of use are antibodies against markers or products of oncogenes (e.g., bcl-2, Kras, p53, cMET), or antibodies against angiogenesis factors, such as VEGFR and placenta-like growth factor (PlGF).

The availability of another PAM4-like antibody that binds to a different epitope of MUC5AC is important for the development of a double-determinant enzyme-linked immunosorbent assay (ELISA), of use for MUC5AC in clinical samples. ELISA experiments are described in the Examples below.

The murine, chimeric, humanized and fully human PAM4 antibodies and fragments thereof described herein are exemplary of anti-pancreatic cancer antibodies of use for diagnostic and/or therapeutic methods. The Examples below disclose a preferred embodiment of the construction and use of a humanized PAM4 antibody. Because non-human monoclonal antibodies can be recognized by the human host as a foreign protein, and repeated injections can lead to harmful hypersensitivity reactions, humanization of a murine antibody sequences can reduce the adverse immune response that patients may experience. For murine-based monoclonal antibodies, this is often referred to as a Human Anti-Mouse Antibody (HAMA) response. Preferably some human residues in the framework regions of the humanized anti-pancreatic cancer antibody or fragments thereof are replaced by their murine counterparts. It is also preferred that a combination of framework sequences from two different human antibodies is used for $V_H$. The constant domains of the antibody molecule are derived from those of a human antibody.

Antibody Preparation

Monoclonal antibodies for specific antigens may be obtained by methods known to those skilled in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991) (hereinafter "Coligan"). Briefly, anti-pancreatic cancer MAbs can be obtained by injecting mice with a composition comprising a mixture of pancreatic cancer mucins comprising MUC5AC, or a purified MUC5AC, or a peptide or protein corresponding to an epitope located within the second to fourth cysteine-rich domains of MUC5AC (amino acid residues 1575-2052), more preferably to an epitope located in amino acid residues 1575-1725 and 1903-2052 (Cys2 and Cys 4), even more preferably to an epitope located in amino acid residues 1575-1725 (Cys2+), most preferably, to an epitope located in Cys2, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to MUC5AC, culturing the clones that produce antibodies to an epitope of MUC5AC as discussed above, and isolating anti-pancreatic cancer antibodies from the hybridoma cultures.

After the initial raising of antibodies to the immunogen, the antibodies can be sequenced and subsequently prepared by recombinant techniques to produce chimeric or humanized antibodies. Chimerization of murine antibodies and antibody fragments are well known to those skilled in the art. The use of antibody components derived from chimerized monoclonal antibodies reduces potential problems associated with the immunogenicity of murine constant regions.

General techniques for cloning murine immunoglobulin variable domains are described, for example, by the publication of Orlandi et al., Proc Nat'l Acad. Sci. USA 86: 3833 (1989), incorporated herein by reference. In general, the $V_K$ (variable light chain) and $V_H$ (variable heavy chain) sequences for murine antibodies can be obtained by a variety of molecular cloning procedures, such as RT-PCR, 5'-RACE, and cDNA library screening. Specifically, the $V_H$ and $V_K$ sequences of the murine PAM4 MAb were cloned by PCR amplification from the hybridoma cells by RT-PCR, and their sequences determined by DNA sequencing. To confirm their authenticity, the cloned $V_K$ and $V_H$ genes can be expressed in cell culture as a chimeric Ab as described by Orlandi et al., (Proc Natl. Acad. Sci., USA, 86: 3833, 1989).

In a preferred embodiment, a chimerized PAM4 antibody or antibody fragment comprises the complementarity-determining regions (CDRs) and framework regions (FR) of a murine PAM4 MAb and the light and heavy chain constant regions of a human antibody, wherein the CDRs of the light chain variable region of the chimerized PAM4 comprises CDR1 (SASSSVSSSYLY, SEQ ID NO:1); CDR2 (STSNLAS, SEQ ID NO:2); and CDR3 (HQWNRYPYT, SEQ ID NO:3); and the CDRs of the heavy chain variable region of the chimerized PAM4 MAb comprises CDR1 (SYVLH, SEQ ID NO:4); CDR2 (YINPYNDGTQYNEKFKG, SEQ ID NO:5) and CDR3 (GFGGSYGFAY, SEQ ID NO:6). The use of antibody components derived from chimerized monoclonal antibodies reduces potential problems associated with the immunogenicity of murine constant regions.

Humanization of murine antibodies and antibody fragments is also well known to those skilled in the art. Techniques for producing humanized MAbs are disclosed, for example, by Carter et al., Proc Nat'l Acad. Sci. USA 89: 4285 (1992), Singer et al., J. Immun. 150: 2844 (1992), Mountain et al. Biotechnol Genet Eng Rev. 10:1 (1992), and Coligan at pages 10.19.1-10.19.11, each of which is incorporated herein by reference. For example, humanized monoclonal antibodies may be produced by transferring murine complementary determining regions from heavy and light variable chains of the mouse immunoglobulin into a human variable domain, and then substituting selected human residues in the framework regions with their the murine FR counterparts. The use of human framework region sequences, in addition to human constant region sequences, further reduces the chance of inducing HAMA reactions.

Humanized antibodies can be designed and constructed as described by Leung et al. (Mol Immunol. 32: 1413 (1995)).

Example 3 describes the humanization process utilized for construction of the hPAM4 MAb.

The nucleotide sequences of the primers used to prepare the hPAM4 antibodies are discussed in Example 3, below. In a preferred embodiment, a humanized PAM4 antibody or antibody fragment comprises the light and heavy chain CDR sequences (SEQ ID NO:1 to SEQ ID NO:6) disclosed above. Also preferred, the FRs of the light and heavy chain variable regions of the humanized antibody comprise at least one amino acid substituted from said corresponding FRs of the murine PAM4 MAb.

A fully human antibody, e.g., human PAM4 can be obtained from a transgenic non-human animal. See, e.g., Mendez et al., Nature Genetics, 15: 146-156 (1997); U.S. Pat. No. 5,633,425. For example, a human antibody can be recovered from a transgenic mouse possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization. However, these techniques are not limiting and other methods known in the art for producing human antibodies, such as the use of phage display, may also be utilized to produce human anti-pancreatic cancer antibodies.

Antibodies can be produced by cell culture techniques using methods known in the art. In one example transfectoma cultures are adapted to serum-free medium. For production of humanized antibody, cells may be grown as a 500 ml culture in roller bottles using HSFM. Cultures are centrifuged and the supernatant filtered through a 0.2 μm membrane. The filtered medium is passed through a protein-A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 μl of 3 M Tris (pH 8.6), and protein concentrations determined from the absorbance at 280/260 nm. Peak fractions are pooled, dialyzed against PBS, and the antibody concentrated, for example, with a Centricon 30 filter (Amicon, Beverly, Mass.). The antibody concentration is determined by ELISA and its concentration adjusted to about 1 mg/ml using PBS. Sodium azide, 0.01% (w/v), is conveniently added to the sample as preservative.

Antibodies can be isolated and purified from hybridoma cultures by a variety of well-established techniques. Such isolation techniques include affinity chromatography with Protein-A SEPHAROSE®, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

Anti-pancreatic cancer MAbs can be characterized by a variety of techniques that are well-known to those of skill in the art. For example, the ability of an antibody to bind to an epitope of MUC5AC as discussed above can be verified using an indirect enzyme immunoassay, flow cytometry analysis, ELISA or Western blot analysis.

Antibody Fragments

Antibody fragments are antigen binding portions of an antibody, such as F(ab')$_2$, Fab', F(ab)$_2$, Fab, Fv, sFv, scFv and the like. Antibody fragments which recognize specific epitopes can be generated by known techniques. F(ab')$_2$ fragments, for example, can be produced by pepsin digestion of the antibody molecule. These and other methods are described, for example, by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a $V_L$ domain and a $V_H$ domain. The $V_L$ and $V_H$ domains associate to form a target binding site. These two domains are further covalently linked by a peptide linker (L). A scFv molecule is denoted as either $V_L$-L-$V_H$ if the $V_L$ domain is the N-terminal part of the scFv molecule, or as $V_H$-L-$V_L$ if the $V_H$ domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, Single Chain Antibody Variable Regions, TIBTECH, Vol 9: 132-137 (1991).

Other antibody fragments, for example single domain antibody fragments, are known in the art and may be used in the claimed constructs. Single domain antibodies (VHH) may be obtained, for example, from camels, alpacas or llamas by standard immunization techniques. (See, e.g., Muyldermans et al., TIBS 26:230-235, 2001; Yau et al., J Immunol Methods 281:161-75, 2003; Maass et al., J Immunol Methods 324:13-25, 2007). The VHH may have potent antigen-binding capacity and can interact with novel epitopes that are inaccessible to conventional $V_H$-$V_L$ pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007). Commercially available single domain antibodies, also known as nanobodies, may be purchased for example from Ablynx (Ghent, Belgium).

An antibody fragment can also be prepared by proteolytic hydrolysis of a full-length antibody or by expression in *E. coli* or another host of the DNA coding for the fragment. An antibody fragment can be obtained by pepsin or papain digestion of full-length antibodies by conventional methods. For example, an antibody fragment can be produced by enzymatic cleavage of antibodies with pepsin to provide an approximate 100 Kd fragment denoted F(ab')$_2$. This fragment can be further cleaved using a thiol reducing agent, and optionally a blocking group for the sulfhydryl groups resulting from cleavage of disulfide linkages, to produce an approximate 50 Kd Fab' monovalent fragment. Alternatively, an enzymatic cleavage using papain produces two monovalent Fab fragments and an Fc fragment directly.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

Antibody Fusion Proteins and Multivalent Antibodies

Fusion proteins comprising the anti-pancreatic cancer antibodies of interest can be prepared by a variety of conventional procedures, ranging from glutaraldehyde linkage to more specific linkages between functional groups. The antibodies and/or antibody fragments that comprise the fusion proteins described herein are preferably covalently bound to one another, directly or through a linker moiety, through one or more functional groups on the antibody or fragment, e.g., amine, carboxyl, phenyl, thiol, or hydroxyl groups. Various conventional linkers in addition to glutaraldehyde can be used, e.g., diisocyanates, diiosothiocyanates, bis(hydroxysuccinimide)esters, carbodiimides, maleimidehydroxy succinimide esters, and the like.

A simple method for producing fusion proteins is to mix the antibodies or fragments in the presence of glutaraldehyde. The initial Schiff base linkages can be stabilized, e.g., by borohydride reduction to secondary amines. A diiosothiocyanate or carbodiimide can be used in place of glutaraldehyde as a non-site-specific linker. In one embodiment, an antibody fusion protein comprises an anti-pancreatic cancer MAb, or fragment thereof, wherein the MAb binds to an epitope located within the second to fourth cysteine-rich domains of MUC5AC (amino acid residues 1575-2052), more preferably to an epitope located in amino acid residues 1575-1725 and 1903-2052 (Cys2 and Cys 4), even more preferably to an epitope located in amino acid residues 1575-1725 (Cys2+), most preferably, to an epitope located in Cys2. This fusion protein and fragments thereof preferentially bind pancreatic cancer cells. This monovalent, monospecific MAb is useful for direct targeting of an antigen, where the MAb is attached to a therapeutic agent, a diagnostic agent, or a combination thereof, and the protein is administered directly to a patient.

The fusion proteins may instead comprise at least two anti-pancreatic cancer MAbs that bind to distinct epitopes of MUC5AC. For example, the MAbs can produce antigen specific diabodies, triabodies and tetrabodies, which are multivalent but monospecific to the MUC5AC. The non-covalent association of two or more scFv molecules can form functional diabodies, triabodies and tetrabodies. Monospecific diabodies are homodimers of the same scFv, where each scFv comprises the V$_H$ domain from the selected antibody connected by a short linker to the V$_L$ domain of the same antibody. A diabody is a bivalent dimer formed by the non-covalent association of two scFvs, yielding two Fv binding sites. A triabody results from the formation of a trivalent trimer of three scFvs, yielding three binding sites, and a tetrabody is a tetravalent tetramer of four scFvs, resulting in four binding sites. Several monospecific diabodies have been made using an expression vector that contains a recombinant gene construct comprising V$_H$1-linker-V$_L$1. See Holliger et al., Proc Natl. Acad. Sci USA 90: 6444-6448 (1993); Atwell et al., Molecular Immunology 33: 1301-1302 (1996); Holliger et al., Nature Biotechnology 15: 632-631(1997); Helfrich et al., Int J Cancer 76: 232-239 (1998); Kipriyanov et al., Int J Cancer 77: 763-772 (1998); Holiger et al., Cancer Research 59: 2909-2916(1999)). Methods of constructing scFvs are disclosed in U.S. Pat. No. 4,946,778 (1990) and U.S. Pat. No. 5,132,405 (1992), the Examples section of each of which is incorporated herein by reference. Methods of producing multivalent, monospecific antibodies based on scFv are disclosed in U.S. Pat. No. 5,837,242 (1998), U.S. Pat. No. 5,844,094 (1998) and WO-98/44001 (1998), the Examples section of each of which is incorporated herein by reference. The multivalent, monospecific antibody fusion protein binds to two or more of the same type of epitopes that can be situated on the same antigen or on separate antigens. The increased valency allows for additional interaction, increased affinity, and longer residence times. These antibody fusion proteins can be utilized in direct targeting systems, where the antibody fusion protein is conjugated to a therapeutic agent, a diagnostic agent, or a combination thereof, and administered directly to a patient in need thereof.

A preferred embodiment is a multivalent, multispecific antibody or fragment thereof comprising one or more antigen binding sites having an affinity toward a PAM4 target epitope and one or more additional binding sites for other epitopes associated with pancreatic cancer. This fusion protein is multispecific because it binds at least two different epitopes, which can reside on the same or different antigens. For example, the fusion protein may comprise more than one antigen binding site, the first with an affinity toward an epitope of MUC5AC as discussed above and the second with an affinity toward another target antigen such as TAG-72 or CEA. Another example is a bispecific antibody fusion protein which may comprise a CA19.9 MAb (or fragment thereof) and a PAM4 MAb (or fragment thereof). Such a fusion protein will have an affinity toward CA19.9 as well as MUC5AC. The antibody fusion proteins and fragments thereof can be utilized in direct targeting systems, where the antibody fusion protein is conjugated to a therapeutic agent, a diagnostic agent, or a combination thereof, and administered directly to a patient in need thereof.

Another preferred embodiment is a multivalent, multispecific antibody comprising at least one binding site having affinity toward a PAM4 target epitope and at least one hapten binding site having affinity towards hapten molecules. For example, a bispecific fusion protein may comprise the 679 MAb (or fragment thereof) and the PAM4 MAb (or fragment thereof). The monoclonal 679 antibody binds with high affinity to molecules containing the tri-peptide moiety histamine succinyl glycyl (HSG). Such a bispecific PAM4 antibody fusion protein can be prepared, for example, by obtaining a F(ab')$_2$ fragment from 679, as described above. The interchain disulfide bridges of the 679 F(ab')$_2$ fragment are gently reduced with DTT, taking care to avoid light-heavy chain linkage, to form Fab'-SH fragments. The SH group(s) is (are) activated with an excess of bis-maleimide linker (1,1'-(methylenedi-4,1-phenylene)b-is-maleimide). The PAM4 MAb is converted to Fab'-SH and then reacted with the activated 679 Fab'-SH fragment to obtain a bispecific antibody fusion protein. Bispecific antibody fusion proteins such as this one can be utilized in affinity enhancing systems, where the target antigen is pretargeted with the fusion protein and is subsequently targeted with a diagnostic or therapeutic agent attached to a carrier moiety (targetable construct) containing one or more HSG haptens. In alternative preferred embodiments, a DNL™-based hPAM4-679 construct, such as TF10, may be prepared and used as described in the Examples below.

Bispecific antibodies can be made by a variety of conventional methods, e.g., disulfide cleavage and reformation of mixtures of whole IgG or, preferably F(ab')$_2$ fragments, fusions of more than one hybridoma to form polyomas that produce antibodies having more than one specificity, and by genetic engineering. Bispecific antibody fusion proteins have been prepared by oxidative cleavage of Fab' fragments resulting from reductive cleavage of different antibodies. This is advantageously carried out by mixing two different F(ab')$_2$ fragments produced by pepsin digestion of two different antibodies, reductive cleavage to form a mixture of Fab' fragments, followed by oxidative reformation of the disulfide linkages to produce a mixture of F(ab')$_2$ fragments including bispecific antibody fusion proteins containing a Fab' portion specific to each of the original epitopes. General techniques for the preparation of antibody fusion proteins may be found, for example, in Nisonoff et al., Arch Biochem Biophys. 93: 470 (1961), Hammerling et al., J Exp Med. 128: 1461 (1968), and U.S. Pat. No. 4,331,647.

More selective linkage can be achieved by using a heterobifunctional linker such as maleimidehydroxysuccinimide ester. Reaction of the ester with an antibody or fragment will derivatize amine groups on the antibody or fragment, and the derivative can then be reacted with, e.g., an antibody Fab fragment having free sulfhydryl groups (or, a larger fragment or intact antibody with sulfhydryl groups appended thereto by, e.g., Traut's Reagent). Such a linker is less likely to crosslink groups in the same antibody and improves the selectivity of the linkage.

It is advantageous to link the antibodies or fragments at sites remote from the antigen-binding sites. This can be accomplished by, e.g., linkage to cleaved interchain sulfhydryl groups, as noted above. Another method involves reacting an antibody having an oxidized carbohydrate portion with another antibody that has at lease one free amine function. This results in an initial Schiff base linkage, which is preferably stabilized by reduction to a secondary amine, e.g., by borohydride reduction, to form the final composite. Such site-specific linkages are disclosed, for small molecules, in U.S. Pat. No. 4,671,958, and for larger addends in U.S. Pat. No. 4,699,784, the Examples section of each of which is incorporated herein by reference.

ScFvs with linkers greater than 12 amino acid residues in length (for example, 15- or 18-residue linkers) allow interactions between the $V_H$ and $V_L$ domains on the same chain and generally form a mixture of monomers, dimers (termed diabodies) and small amounts of higher mass multimers, (Kortt et al., Eur J Biochem. (1994) 221: 151-157). ScFvs with linkers of 5 or less amino acid residues, however, prohibit intramolecular pairing of the $V_H$ and $V_L$ domains on the same chain, forcing pairing with $V_H$ and $V_L$ domains on a different chain. Linkers between 5- and 12-residues form predominantly dimers (Atwell et al., Protein Engineering (1999) 12: 597-604). With linkers between 0 and 2 residues, trimeric (termed triabodies), tetrameric (termed tetrabodies) or higher oligomeric structures of scFvs are formed; however, the exact patterns of oligomerization appear to depend on the composition as well as the orientation of the V-domains, in addition to the linker length.

More recently, a novel technique for construction of mixtures of antibodies, antibody fragments and/or other effector moieties in virtually any combination has been described in U.S. Pat. Nos. 7,550,143; 7,521,056; 7,534,866; 7,527,787; and 7,666,400, the Examples section of each of which is incorporated herein by reference. The technique, known generally as DOCK-AND-LOCK™ (DNL™) involves the production of fusion proteins that comprise at their N- or C-terminal ends one of two complementary peptide sequences, called dimerization and docking domain (DDD) and anchoring domain (AD) sequences. In preferred embodiments, the DDD sequences are derived from the regulatory subunits of cAMP-dependent protein kinase and the AD sequence is derived from the sequence of A-kinase anchoring protein (AKAP). The DDD sequences form dimers that bind to the AD sequence, which allows formation of trimers, tetramers, hexamers or any of a variety of other complexes. By attaching effector moieties, such as antibodies or antibody fragments, to the DDD and AD sequences, complexes may be formed of any selected combination of antibodies or antibody fragments. The DNL™ complexes may be covalently stabilized by formation of disulfide bonds or other linkages.

Pretargeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct or targetable conjugate) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are well known in the art, for example, as disclosed in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. No. 6,077,499; U.S. Pat. No. 6,090,381; U.S. Pat. No. 6,472,511; and U.S. Pat. No. 6,962,702.

A pre-targeting method of treating or diagnosing a disease or disorder in a subject may be provided by: (1) administering to the subject a bispecific antibody or antigen binding antibody fragment; (2) optionally administering to the subject a clearing composition, and allowing the composition to clear the antibody from circulation; and (3) administering to the subject the targetable construct, containing one or more chelated or chemically bound therapeutic or diagnostic agents. The technique may also be utilized for antibody dependent enzyme prodrug therapy (ADEPT) by administering an enzyme conjugated to a targetable construct, followed by a prodrug that is converted into active form by the enzyme.

Known Antibodies

In various embodiments, the claimed methods and compositions may utilize any of a variety of antibodies known in the art, for example for combination antibody therapy. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953; 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art (see, e.g., U.S. Pat. Nos. 7,531,327; 7,537,930; 7,608,425 and 7,785,880, the Examples section of each of which is incorporated herein by reference).

Particular antibodies that may be of use for therapy of cancer within the scope of the claimed methods and compositions include, but are not limited to, LL1 (anti-CD74), LL2 or RFB4 (anti-CD22), veltuzumab (hA20, anti-CD20), rituxumab (anti-CD20), obinutuzumab (GA101, anti-CD20), lambrolizumab (anti-PD-1 receptor), nivolumab (anti-PD-1 receptor), ipilimumab (anti-CTLA-4), RS7 (anti-epithelial glycoprotein-1 (EGP-1, also known as TROP-2)), KC4 (anti-mucin), MN-14 (anti-carcinoembryonic antigen (anti-CEA, also known as CD66e or CEACAM5), MN-15 or MN-3 (anti-CEACAM6), Mu-9 (anti-colon-specific antigen-p), Immu 31 (an anti-alpha-fetoprotein), R1 (anti-IGF-1R), A19 (anti-CD19), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); tositumomab (anti-CD20); PAM4 (aka clivatuzumab, anti-MUC5AC) and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20050271671; 20060193865; 20060210475; 20070087001; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU-31 (U.S. Pat. No. 7,300,655), hLL1 (U.S. Pat. No. 7,312,318,), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406), D2/B (WO 2009/130575), BWA-3 (anti-histone H4), LG2-1 (anti-histone H3) and LG2-2 (anti-histone H2B) (U.S. patent application Ser. No. 14/180,646, filed Feb. 14, 2014) the text of each recited patent or application is incorporated herein by reference with respect to the Figures and Examples sections.

Other useful antigens that may be targeted using the described conjugates include carbonic anhydrase IX, B7, CCL19, CCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD47, CD52, CD54, CD55, CD59, CD64, CD67, CD70, CD74, CD79a, CD80, CD83, CD95, CD126, CD133, CD138, CD147, CD154, CEACAM5, CEACAM6, CTLA-4, CXCR4, alpha-fetoprotein (AFP), VEGF (e.g., AVASTIN®, fibronectin splice variant), ED-B fibronectin (e.g., L19), EGP-1 (TROP-2), EGP-2 (e.g., 17-1A), EGF receptor (ErbB1) (e.g., ERBITUX®), ErbB2, ErbB3, Factor H, FHL-1, Flt-3, folate receptor, Ga 733, GRO-β, HMGB-1, hypoxia inducible factor (HIF), HM1.24, HER-2/neu, histone H2B, histone H3, histone H4, insulin-like growth factor (ILGF), IFN-γ, IFN-α, IFN-β, IFN-λ, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5AC, placental growth factor (PlGF), PSA (prostate-specific antigen), PSMA, PD-1, PD-L1, TIM-3, LAG-3, matrix metalloproteinase-1 (MMP-1), MMP-2, MMP-7, MMP-9, MMP-14, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), TROP-2, VEGFR, RANTES, T101, as well as cancer stem cell antigens, complement factors C3, C3a, C3b, C5a, C5, and an oncogene product.

A comprehensive analysis of suitable antigen (Cluster Designation, or CD) targets on hematopoietic malignant cells, as shown by flow cytometry and which can be a guide to selecting suitable antibodies for drug-conjugated immunotherapy, is Craig and Foon, Blood prepublished online Jan. 15, 2008; DOL 10.1182/blood-2007-11-120535.

The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens (e.g., CEACAM6) are expressed mainly in granulocytes, normal epithelial cells of the digestive tract and tumor cells of various tissues. Also included as suitable targets for cancers are cancer testis antigens, such as NY-ESO-1 (Theurillat et al., *Int. J. Cancer* 2007; 120(11):2411-7), as well as CD79a in myeloid leukemia (Kozlov et al., *Cancer Genet. Cytogenet.* 2005; 163(1):62-7) and also B-cell diseases, and CD79b for non-Hodgkin's lymphoma (Poison et al., *Blood* 110(2):616-623). A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002. Cancer stem cells, which are ascribed to be more therapy-resistant precursor malignant cell populations (Hill and Penis, *J. Natl. Cancer Inst.* 2007; 99:1435-40), have antigens that can be targeted in certain cancer types, such as CD133 in prostate cancer (Maitland et al., *Ernst Schering Found. Sympos. Proc.* 2006; 5:155-79), non-small-cell lung cancer (Donnenberg et al., *J. Control Release* 2007; 122(3):385-91), and glioblastoma (Beier et al., *Cancer Res.* 2007; 67(9):4010-5), and CD44 in colorectal cancer (Dalerba er al., *Proc. Natl. Acad. Sci. USA* 2007; 104(24)10158-63), pancreatic cancer (Li et al., *Cancer Res.* 2007; 67(3):1030-7), and in head and neck squamous cell carcinoma (Prince et al., *Proc. Natl. Acad. Sci. USA* 2007; 104(3)973-8). Another useful target for breast cancer therapy is the LIV-1 antigen described by Taylor et al. (*Biochem. J.* 2003; 375:51-9).

For multiple myeloma therapy, suitable targeting antibodies have been described against, for example, CD38 and CD138 (Stevenson, *Mol Med* 2006; 12(11-12):345-346; Tassone et al., *Blood* 2004; 104(12):3688-96), CD74 (Stein et al., ibid.), CS1 (Tai et al., *Blood* 2008; 112(4):1329-37, and CD40 (Tai et al., 2005; *Cancer Res.* 65(13):5898-5906).

Macrophage migration inhibitory factor (MIF) is an important regulator of innate and adaptive immunity and apoptosis. It has been reported that CD74 is the endogenous receptor for MIF (Leng et al., 2003, *J Exp Med* 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, *BMC Cancer* 12:34; Shachar & Haran, 2011, *Leuk Lymphoma* 52:1446-54); autoimmune diseases such as rheumatoid arthritis and systemic lupus erythematosus (Morand & Leech, 2005, *Front Biosci* 10:12-22; Shachar & Haran, 2011, *Leuk Lymphoma* 52:1446-54); kidney diseases such as renal allograft rejection (Lan, 2008, *Nephron Exp Nephrol.* 109:e79-83); and numerous inflammatory diseases (Meyer-Siegler et al., 2009, *Mediators Inflamm* epub Mar. 22, 2009; Takahashi et al., 2009, *Respir Res* 10:33; Milatuzumab (hLL1) is an exemplary anti-CD74 antibody of therapeutic use for treatment of MIF-mediated diseases.

Anti-TNF-α antibodies are known in the art and may be of use to treat immune diseases, such as autoimmune disease, immune dysfunction (e.g., graft-versus-host disease, organ transplant rejection) or diabetes. Known antibodies against TNF-α include the human antibody CDP571 (Ofei et al., 2011, *Diabetes* 45:881-85); murine antibodies MTNFAI, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-α antibodies may be used in the claimed methods and compositions. Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); anti-CD40L (UCB, Brussels, Belgium); natalizumab (anti-α4 integrin) and omalizumab (anti-IgE).

Checkpoint inhibitor antibodies have been used primarily in cancer therapy. Immune checkpoints refer to inhibitory pathways in the immune system that are responsible for maintaining self-tolerance and modulating the degree of immune system response to minimize peripheral tissue damage. However, tumor cells can also activate immune system checkpoints to decrease the effectiveness of immune response against tumor tissues. Exemplary checkpoint inhibitor antibodies against cytotoxic T-lymphocyte antigen 4 (CTLA-4, also known as CD152), programmed cell death protein 1 (PD-1, also known as CD279) and programmed cell death 1 ligand 1 (PD-L1, also known as CD274), may be used in combination with one or more other agents to enhance the effectiveness of immune response against disease cells, tissues or pathogens. Exemplary anti-PD1 antibodies include lambrolizumab (MK-3475, MERCK), nivolumab (BMS-936558, BRISTOL-MYERS SQUIBB), AMP-224 (MERCK), and pidilizumab (CT-011, CURETECH LTD.). Anti-PD1 antibodies are commercially available, for example from ABCAM® (AB137132), BIOLEGEND® (EH12.2H7, RMP1-14) and AFFYMETRIX EBIOSCIENCE (J105, J116, MIH4). Exemplary anti-PD-L1 antibodies include MDX-1105 (MEDAREX), MEDI4736 (MEDIMMUNE) MPDL3280A (GENENTECH) and BMS-936559 (BRISTOL-MYERS SQUIBB). Anti-PD-L1 antibodies are also commercially available, for example from AFFYMETRIX EBIOSCIENCE (MIH1). Exemplary anti-CTLA4 antibodies include ipilimumab (Bristol-Myers Squibb) and tremelimumab (PFIZER). Anti-PD1 antibodies are commercially available, for example from ABCAM® (AB134090), SINO BIOLOGICAL INC. (11159-H03H, 11159-H08H), and THERMO SCIENTIFIC PIERCE (PA5-29572, PA5-23967, PA5-26465, MA1-12205, MA1-35914). Ipilimumab has recently received FDA approval for treatment of metastatic melanoma (Wada et al., 2013, *J Transl Med* 11:89). More recently, other checkpoint inhibitory receptors have been identified, including TIM-3 and LAG-3 (Stagg, 2013, *Ther Adv Med Oncol* 5:169-81). Antibodies against TIM-3 and LAG-3 may also be used in combination with the anti-MUC5AC antibodies disclosed herein.

Antibodies against matrix metalloproteinases, for example matrix metalloproteinase-1 (MMP-1), MMP-2, MMP-7, MMP-9 and MMP-14, are also of use in combination anti-cancer therapies. (See, e.g., Agarwal A, et al., Mol Cancer Ther 2008; 7:2746-57; Freije J M, et al. Adv Exp Med Biol 2003; 532:91-107; Coticchia C M, et al. Gynecol Oncol 2011; 123:295-300; Boiire D, et al., Cell 2005; 120:303-13; Belotti D, et al., Cancer Res 2003; 63:5224-9; Barbolina M V, et al., J Biol Chem 2007; 282:4924-31; Kaimal R, et al., Cancer Res 2013; 73:2457-67; Denzel S, et al, Int J Exp Pathol 2012; 93:341-53.)

Other antibodies of use may include anti-histone antibodies and/or antigen-binding fragments thereof, such as the BWA-3 (anti-H4), LG2-1 (anti-H3) and LG2-2 (anti-H2B) antibodies. Exemplary anti-histone antibodies are disclosed, for example, in U.S. patent application Ser. No. 14/180,646, filed Feb. 14, 2014 (the Examples section of which is incorporated herein by reference).

In another preferred embodiment, antibodies are used that internalize rapidly and are then re-expressed, processed and presented on cell surfaces, enabling continual uptake and accretion of circulating conjugate by the cell. An example of a most-preferred antibody/antigen pair is LL1, an anti-CD74 MAb (invariant chain, class II-specific chaperone, Ii) (see, e.g., U.S. Pat. Nos. 6,653,104; 7,312,318; the Examples section of each incorporated herein by reference). The CD74 antigen is highly expressed on B-cell lymphomas (including multiple myeloma) and leukemias, certain T-cell lymphomas, melanomas, colonic, lung, and renal cancers, glioblastomas, and certain other cancers (Ong et al., Immunology 98:296-302 (1999)). A review of the use of CD74 antibodies in cancer is contained in Stein et al., Clin Cancer Res. 2007 Sep. 15; 13(18 Pt 2):5556s-5563s, incorporated herein by reference.

The diseases that are preferably treated with anti-CD74 antibodies include, but are not limited to, non-Hodgkin's lymphoma, Hodgkin's disease, melanoma, lung, renal, colonic cancers, glioblastome multiforme, histiocytomas, myeloid leukemias, and multiple myeloma. Continual expression of the CD74 antigen for short periods of time on the surface of target cells, followed by internalization of the antigen, and re-expression of the antigen, enables the targeting LL1 antibody to be internalized along with any chemotherapeutic moiety it carries. This allows a high, and therapeutic, concentration of LL1-chemotherapeutic drug conjugate to be accumulated inside such cells. Internalized LL1-chemotherapeutic drug conjugates are cycled through lysosomes and endosomes, and the chemotherapeutic moiety is released in an active form within the target cells.

Antibody Use for Treatment and Diagnosis

Certain embodiments concern methods of diagnosing or treating a malignancy in a subject, comprising administering to the subject an anti-pancreatic cancer MAb, fusion protein or fragment thereof, wherein the MAb, fusion protein or fragment is bound to at least one diagnostic and/or therapeutic agent. The antibody preferably binds to an epitope located within the second to fourth cysteine-rich domains of MUC5AC (amino acid residues 1575-2052), more preferably to an epitope located in amino acid residues 1575-1725 and 1903-2052 (Cys2 and Cys 4), even more preferably to an epitope located in amino acid residues 1575-1725 (Cys2+), most preferably, to an epitope located in Cys2

Also preferred is a method for diagnosing or treating cancer, comprising administering to a subject a multivalent, multispecific antibody or fragment thereof comprising one or more antigen binding sites toward an epitope of MUC5AC as discussed above and one or more hapten binding sites, waiting a sufficient amount of time for non-bound antibody to clear the subject's blood stream; and then administering to the subject a carrier molecule comprising a diagnostic agent, a therapeutic agent, or a combination thereof, that binds to the hapten-binding site of the localized antibody. In a more preferred embodiment, the cancer is a non-endocrine pancreatic cancer.

The use of MAbs for in vitro diagnosis is well-known. See, for example, Carlsson et al., Bio/Technology 7 (6): 567 (1989). For example, MAbs can be used to detect the presence of a tumor-associated antigen in tissue from biopsy samples. MAbs also can be used to measure the amount of tumor-associated antigen in clinical fluid samples, such as blood or serum, using techniques such as radioimmunoassay, enzyme-linked immunosorbent assay, and fluorescence immunoassay. In vitro and in vivo methods of diagnosis are discussed in further detail below.

Conjugates of tumor-targeted MAbs and toxins can be used to selectively kill cancer cells in vivo (Spalding, Bio/Technology 9(8): 701 (1991); Goldenberg, Scientific American Science & Medicine 1(1): 64 (1994)). For example, therapeutic studies in experimental animal models have demonstrated the anti-tumor activity of antibodies carrying cytotoxic radionuclides. (Goldenberg et al., Cancer Res. 41: 4354 (1981), Cheung et al., J. Nat'l Cancer Inst. 77: 739 (1986), and Senekowitsch et al., J. Nucl. Med. 30: 531 (1989)). In a preferred embodiment, the conjugate comprises a $^{90}$Y-labeled hPAM4 antibody. The conjugate may optionally be administered in conjunction with one or more other therapeutic agents. In a preferred embodiment, $^{90}$Y-labeled hPAM4 is administered together with gemcitabine or 5-fluorouracil to a patient with pancreatic cancer. In a further preferred embodiment, $^{90}$Y is conjugated to a DOTA chelate for attachment to hPAM4. In a more preferred embodiment, the $^{90}$Y-DOTA-hPAM4 is combined with gemcitabine in fractionated doses comprising a treatment cycle, such as with repeated, lower, less-toxic doses of gemcitabine combined with lower, fractionated doses of $^{90}$Y-DOTA-hPAM4. Alternatively, a radiolabeled or other conjugated PAM4 antibody may be administered in combination with another immunoconjugate, such as an SN-38 conjugated antibody. A particularly preferred combination is $^{90}$Y-hPAM4 and SN-38-hRS7 (anti-TROP2 antibody) (see, e.g., U.S. Pat. No. 8,586,050, the Examples section incorporated herein by reference).

As tolerated, repeated cycles of a fractionated dose schedule are indicated. By way of example, 4 weekly doses of 200 mg/m$^2$ of gemcitabine are combined with three weekly doses of 8 mg/m$^2$ of $^{90}$Y-DOTA-hPAM4, with the latter commencing in the second week of gemcitabine administration, constitutes a single therapy cycle. Still other doses, higher or lower of each component, may constitute a fractionated dose, which is determined by conventional means of assessing hematopoietic toxicity (see, e.g., U.S. Pat. Nos. 6,649,352; 7,112,409; 7,279,289; 7,465,551), since myelosuppressive effects of both agents can be cumulative. A skilled physician in such therapy interventions can adjust these doses based on the patient's bone marrow status and general health status based on many factors, including prior exposure to myelosuppressive therapeutic agents. These principles can also apply to combinations of radiolabeled hPAM4 with other therapeutic agents, including radiosensitizing drugs such as 5-fluorouracil and cisplatin.

Chimeric, humanized and human antibodies and fragments thereof have been used for in vivo therapeutic and diagnostic methods. Accordingly contemplated is a method of delivering a diagnostic or therapeutic agent, or a combination thereof, to a target comprising (i) providing a composition that comprises an anti-pancreatic cancer antibody or fragment thereof, such as a chimeric, humanized or human PAM4 antibody, conjugated to at least one diagnostic and/or therapeutic agent and (ii) administering to a subject the diagnostic or therapeutic antibody conjugate. In a preferred embodiment, the anti-pancreatic cancer antibodies and fragments thereof are humanized or fully human.

Another embodiment concerns a method for treating a malignancy comprising administering a naked or conjugated anti-pancreatic cancer antibody, antibody fragment or fusion protein that binds to an epitope located within the second to fourth cysteine-rich domains of MUC5AC (amino acid residues 1575-2052), more preferably to an epitope located in amino acid residues 1575-1725 and 1903-2052 (Cys2 and Cys 4), even more preferably to an epitope located in amino acid residues 1575-1725 (Cys2+), most preferably, to an epitope located in Cys2, such as a PAM4 antibody, either alone or in conjunction with one or more other therapeutic agents. The other therapeutic agent may be added before, simultaneously with or after the antibody. In a preferred embodiment, the therapeutic agent is gemcitabine, and in a more preferred embodiment, gemcitabine is given with the hPAM4 radioconjugate in a fractionated dose schedule at lower doses than the conventional 800-1,000 mg/m$^2$ doses of gemcitabine given weekly for 6 weeks. For example, when combined with fractionated therapeutic doses of $^{90}$Y-PAM4, repeated fractionated doses intended to function as a radiosensitizing agent of 200-380 mg/m$^2$ gemcitabine are infused. The skilled artisan will realize that the antibodies, fusion proteins and/or fragments thereof described and claimed herein may be administered with any known or described therapeutic agent, including but not limited to heat shock protein 90 (Hsp90).

In another form of multimodal therapy, subjects receive immunoconjugates in conjunction with standard cancer chemotherapy. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

The present invention contemplates the administration of anti-pancreatic cancer antibodies and fragments thereof, including fusion proteins and fragments thereof, alone, as a naked antibody or antibody fragment, or administered as a multimodal therapy. Preferably, the antibody is a humanized or fully human PAM4 antibody or fragment thereof. Multimodal therapies further include immunotherapy with a naked anti-pancreatic cancer antibody supplemented with administration of other antibodies in the form of naked antibodies, fusion proteins, or as immunoconjugates. For example, a humanized or fully human PAM4 antibody may be combined with another naked antibody, or a humanized PAM4 or other antibody conjugated to an isotope, one or more chemotherapeutic agents, cytokines, toxins or a combination thereof. For example, the present invention contemplates treatment of a naked or conjugated PAM4 antibody or fragments thereof before, in combination with, or after other pancreatic tumor associated antibodies such as CA19.9, DUPAN2, SPAN1, Nd2, B72.3, CC49, anti-Le$^a$ antibodies, and antibodies to other Lewis antigens (e.g., Le(y)), as well as antibodies against carcinoembryonic antigen (CEA or CEACAM5), CEACAM6, colon-specific antigen-p (CSAp), MUC1, MUC2, MUC3, MUC4, MUC5AC, MUC16, MUC17, HLA-DR, CD40, CD74, CD138, HER2/neu, EGFR, EGP-1, EGP-2, angiogenesis factors (e.g., VEGF, PlGF), insulin-like growth factor (IGF), tenascin, platelet-derived growth factor, and IL-6, as well as products of oncogenes (e.g., bcl-2, Kras, p53), cMET, and antibodies against tumor necrosis substances.

These solid tumor antibodies may be naked or conjugated to, inter alia, drugs, toxins, isotopes, radionuclides or immunomodulators. Many different antibody combinations may be constructed and used in either naked or conjugated form. Alternatively, different naked antibody combinations may be employed for administration in combination with other therapeutic agents, such as a cytotoxic drug or with radiation, given consecutively, simultaneously, or sequentially.

Administration of the antibodies and their fragments can be effected by intravenous, intraarterial, intraperitoneal, intramuscular, subcutaneous, intrapleural, intrathecal, perfusion through a regional catheter, or direct intralesional injection. When administering the antibody by injection, the administration may be by continuous infusion or by single or multiple boluses.

The immunoconjugate of the present invention can be formulated for intravenous administration via, for example, bolus injection or continuous infusion. Preferably, the antibody of the present invention is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic conjugate. Control release preparations can be prepared through the use of polymers to complex or adsorb the immunoconjugate. For example, biocompatible polymers include matrices of poly (ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate or antibody from such a matrix depends upon the molecular weight of the immunoconjugate or antibody, the amount of immunoconjugate or antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

More generally, the dosage of an administered immunoconjugate for humans will vary depending upon such factors as the patient's age, weight, height, sex, general medical condition and previous medical history. It may be desirable to provide the recipient with a dosage of immunoconjugate, antibody fusion protein that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, an antibody may be administered as one dosage every 2 or 3 weeks, repeated for a total of at least 3 dosages. Or, the antibodies may be administered twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

Immunoconjugates

Anti-pancreatic cancer antibodies and fragments thereof may be conjugated to at least one therapeutic and/or diagnostic agent for therapy or diagnosis. For immunotherapy, the objective is to deliver cytotoxic doses of radioactivity, toxin, antibody and/or drug to target cells, while minimizing exposure to non-target tissues. Preferably, anti-pancreatic cancer antibodies are used to diagnose and/or treat pancreatic tumors.

Any of the antibodies, antibody fragments and fusion proteins can be conjugated with one or more therapeutic or diagnostic agents, using a variety of techniques known in the art. One or more therapeutic or diagnostic agents may be attached to each antibody, antibody fragment or fusion protein, for example by conjugating an agent to a carbohydrate moiety in the Fc region of the antibody. If the Fc region is absent (for example with certain antibody fragments), it is possible to introduce a carbohydrate moiety into the light chain variable region of either an antibody or antibody fragment to which a therapeutic or diagnostic agent may be attached. See, for example, Leung et al., J Immunol. 154: 5919 (1995); Hansen et al., U.S. Pat. No. 5,443,953 (1995), Leung et al., U.S. Pat. No. 6,254,868, the Examples section of each patent incorporated herein by reference.

Methods for conjugating peptides to antibody components via an antibody carbohydrate moiety are well-known to those of skill in the art. See, for example, Shih et al., Int J Cancer 41: 832 (1988); Shih et al., Int J Cancer 46: 1101 (1990); and Shih et al., U.S. Pat. No. 5,057,313, the Examples section of which is incorporated herein by reference. The general method involves reacting an antibody component having an oxidized carbohydrate portion with a carrier polymer that has at least one free amine function and that is loaded with a plurality of therapeutic agents, such as peptides or drugs. This reaction results in an initial Schiff base (imine) linkage, which can be stabilized by reduction to a secondary amine to form the final conjugate.

Antibody fusion proteins or multispecific antibodies comprise two or more antibodies or fragments thereof, each of which may be attached to at least one therapeutic agent and/or diagnostic agent. Accordingly, one or more of the antibodies or fragments thereof of the antibody fusion protein can have more than one therapeutic and/or diagnostic agent attached. Further, the therapeutic agents do not need to be the same but can be different therapeutic agents, for example, one can attach a drug and a radioisotope to the same fusion protein. For example, an IgG can be radiolabeled with $^{131}$I and attached to a drug. The $^{131}$I can be incorporated into the tyrosine of the IgG and the drug attached to the epsilon amino group of the IgG lysines. Both therapeutic and diagnostic agents also can be attached to reduced SH groups and to the carbohydrate side chains of antibodies. Alternatively, a bispecific antibody may comprise one antibody or fragment thereof against a disease antigen and another against a hapten attached to a targetable construct, for use in pretargeting techniques as discussed above.

A therapeutic or diagnostic agent can be attached at the hinge region of a reduced antibody component via disulfide bond formation. As an alternative, such agents can be attached to the antibody component using a heterobifunctional cross-linker, such as N-succinyl 3-(2-pyridyldithio) proprionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995).

Click Chemistry

An alternative method for attaching chelating moieties, drugs or other functional groups to an antibody, fragment or fusion protein involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.) For example, cyclooctyne is a 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted alkyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrones were prepared by the condensation of appropriate aldehydes with N-methylhydroxylamine and the cycloaddition reaction took place in a mixture of acetonitrile and water (Id.) These and other known click chemistry reactions may be used to attach chelating moieties to antibodies or other targeting molecules in vitro.

Therapeutic Agents

A wide variety of therapeutic reagents can be administered concurrently or sequentially, or advantageously conjugated to the antibodies of the invention, for example, drugs, toxins, oligonucleotides (e.g., siRNA), immunomodulators, hormones, hormone antagonists, enzymes, enzyme inhibitors, radionuclides, angiogenesis inhibitors, pro-apoptotic agents, etc. The therapeutic agents recited here are those agents that are useful for either conjugated to an antibody, fragment or fusion protein or for administration separately with a naked antibody as described above.

Therapeutic agents include, for example, chemotherapeutic drugs such as vinca alkaloids, anthracyclines, gemcitabine, epipodophyllotoxins, taxanes, antimetabolites, alkylating agents, antibiotics, SN-38, COX-2 inhibitors, antimitotics, antiangiogenic and apoptotic agents, particularly doxorubicin, methotrexate, taxol, CPT-11, camptothecans, proteosome inhibitors, mTOR inhibitors, HDAC inhibitors, tyrosine kinase inhibitors, and others from these and other classes of anticancer agents.

Other useful cancer chemotherapeutic drugs include nitrogen mustards, alkyl sulfonates, nitrosoureas, triazenes, folic acid analogs, COX-2 inhibitors, antimetabolites, pyrimidine analogs, purine analogs, platinum coordination complexes, mTOR inhibitors, tyrosine kinase inhibitors, proteosome inhibitors, HDAC inhibitors, camptothecins and hormones. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Specific drugs of use may include 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamicin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2-PDOX), pro-2PDOX, cyano-morpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, vinca alkaloids and ZD1839.

In a preferred embodiment, conjugates of camptothecins and related compounds, such as SN-38, may be conjugated to hPAM4 or other anti-pancreatic cancer antibodies, for example as disclosed in U.S. Pat. No. 7,591,994; and U.S. patent application Ser. No. 11/388,032, filed Mar. 23, 2006, the Examples section of each of which is incorporated herein by reference.

In another preferred embodiment, prodrug forms of 2-PDOX, as disclosed in U.S. patent application Ser. No. 14/175,089 (the Examples section of which is incorporated herein by reference) may be used as an immunoconjugate with an anti-pancreatic cancer antibody that binds to an epitope of MUC5AC as discussed above.

In another preferred embodiment, an hPAM4 antibody is given with gemcitabine, which may be given before, after, or concurrently with a naked or conjugated chimeric, humanized or human PAM4 antibody. Preferably, the conjugated hPAM4 antibody or antibody fragment is conjugated to a radionuclide.

A toxin can be of animal, plant or microbial origin. A toxin, such as Pseudomonas exotoxin, may also be complexed to or form the therapeutic agent portion of an immunoconjugate of the anti-pancreatic cancer and hPAM4 antibodies. Other toxins suitably employed in the preparation of such conjugates or other fusion proteins, include ricin, abrin, ribonuclease (RNase), DNase I, Staphylococcal enterotoxin-A, pokeweed antiviral protein, gelonin, diphtheria toxin, ranpirnase, Pseudomonas exotoxin, and Pseudomonas endotoxin. See, for example, Pastan et al., Cell 47:641 (1986), Goldenberg, C A—A Cancer Journal for Clinicians 44:43 (1994), Sharkey and Goldenberg, C A—A Cancer Journal for Clinicians 56:226 (2006). Additional toxins suitable for use are known to those of skill in the art and are disclosed in U.S. Pat. No. 6,077,499, the Examples section of which is incorporated herein by reference.

An immunomodulator, such as a cytokine, may also be conjugated to, or form the therapeutic agent portion of the immunoconjugate, or may be administered with, but unconjugated to, an antibody, antibody fragment or fusion protein. The fusion protein may comprise one or more antibodies or fragments thereof binding to different antigens. For example, the fusion protein may bind to an epitope of MUC5AC as discussed above as well as to immunomodulating cells or factors. Alternatively, subjects can receive a naked antibody, antibody fragment or fusion protein and a separately administered cytokine, which can be administered before, concurrently or after administration of the naked antibodies. As used herein, the term "immunomodulator" includes a cytokine, a lymphokine, a monokine, a stem cell growth factor, a lymphotoxin, a hematopoietic factor, a colony stimulating factor (CSF), an interferon (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, a transforming growth factor (TGF), TGF-α, TGF-β, insulin-like growth factor (IGF), erythropoietin, thrombopoietin, tumor necrosis factor (TNF), TNF-α, TNF-β, a mullerian-inhibiting substance, mouse gonadotropin-associated peptide, inhibin, activin, vascular endothelial growth factor, integrin, interleukin (IL), granulocyte-colony stimulating factor (G-CSF), granulocyte macrophage-colony stimulating factor (GM-CSF), interferon-α, interferon-β, interfλeron-γ, S1 factor, IL-1, IL-1cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21 and IL-25, LIF, kit-ligand, FLT-3, angiostatin, thrombospondin, endostatin and lymphotoxin.

The therapeutic agent may comprise one or more radioactive isotopes useful for treating diseased tissue. Particularly useful therapeutic radionuclides include, but are not limited to $^{111}$In, $^{177}$Lu, $^{212}$Bi, $^{213}$Bi, $^{211}$Bi, $^{62}$Cu, $^{64}$Cn, $^{67}$Cn, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Rd, $^{225}$Ac, $^{59}$Fe, $^{75}$Se, $^{77}$As, $^{89}$Sr, $^{90}$Mo, $^{105}$Rh, $^{109}$Pd, $^{143}$Pr, $^{149}$Pm, $^{169}$Er, $^{194}$Ir, $^{198}$Au, $^{199}$Au, $^{211}$Pb and $^{227}$Th. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227 and Fm-255. Decay energies of useful alpha-particle-emitting radionuclides are preferably 2,000-10,000 keV, more preferably 3,000-8,000 keV, and most preferably 4,000-7,000 keV.

For example, $^{67}$Cu, considered one of the more promising radioisotopes for radioimmunotherapy due to its 61.5-hour half-life and abundant supply of beta particles and gamma rays, can be conjugated to an antibody using the chelating agent, p-bromoacetamido-benzyl-tetraethylaminetetraacetic acid (TETA). Alternatively, $^{90}$Y, which emits an energetic beta particle, can be coupled to an antibody, antibody fragment or fusion protein, using diethylenetriaminepentaacetic acid (DTPA), or more preferably using DOTA. Methods of conjugating $^{90}$Y to antibodies or targetable constructs are known in the art and any such known methods may be used. (See, e.g., U.S. Pat. No. 7,259,249, the Examples section of which is incorporated herein by reference. See also Linden et al., Clin Cancer Res. 11:5215-22, 2005; Sharkey et al., J Nucl Med. 46:620-33, 2005; Sharkey et al., J Nucl Med. 44:2000-18, 2003.)

Additional potential therapeutic radioisotopes include $^{11}$C, $^{13}$N, $^{15}$O, $^{75}$Br, $^{198}$Au, $^{224}$Ac, $^{126}$I, $^{133}$I, $^{177}$Br, $^{113m}$In, $^{95}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

In another embodiment, a radiosensitizer can be used in combination with a naked or conjugated antibody or antibody fragment. For example, the radiosensitizer can be used in combination with a radiolabeled antibody or antibody fragment. The addition of the radiosensitizer can result in enhanced efficacy when compared to treatment with the radiolabeled antibody or antibody fragment alone. Radiosensitizers are described in D. M. Goldenberg (ed.), CANCER THERAPY WITH RADIOLABELED ANTIBODIES, CRC Press (1995). Other typical radionsensitizers of interest for use with this technology include gemcitabine, 5-fluorouracil, and cisplatin, and have been used in combination with external irradiation in the therapy of diverse cancers, including pancreatic cancer. Therefore, we have studied the combination of gemcitabine at what is believed to be radiosensitizing doses (once weekly 200 mg/m$^2$ over 4 weeks) of gemcitabine combined with fractionated doses of $^{90}$Y-hPAM4, and have observed objective evidence of pancreatic cancer reduction after a single cycle of this combination that proved to be well-tolerated (no grade 3-4 toxicities by NCI-CTC v. 3 standard).

Antibodies or fragments thereof that have a boron addend-loaded carrier for thermal neutron activation therapy will normally be affected in similar ways. However, it will be advantageous to wait until non-targeted immunoconjugate clears before neutron irradiation is performed. Clearance can be accelerated using an anti-idiotypic antibody that binds to the anti-pancreatic cancer antibody. See U.S. Pat. No. 4,624,846 for a description of this general principle. For example, boron addends such as carboranes, can be attached to antibodies. Carboranes can be prepared with carboxyl functions on pendant side chains, as is well-known in the art. Attachment of carboranes to a carrier, such as aminodextran, can be achieved by activation of the carboxyl groups of the carboranes and condensation with amines on the carrier. The intermediate conjugate is then conjugated to the antibody. After administration of the antibody conjugate, a boron addend is activated by thermal neutron irradiation and converted to radioactive atoms which decay by alpha-emission to produce highly toxic, short-range effects.

Interference RNA

Another type of therapeutic agent is RNAi or siRNA. RNA interference (RNAi) is mediated by the RNA-induced silencing complex (RISC) and is initiated by short double-stranded RNA molecules that interact with the catalytic RISC component argonaute (Rand et al., 2005, Cell 123: 621-29). Types of RNAi molecules include microRNA (miRNA) and small interfering RNA (siRNA). RNAi species can bind with messenger RNA (mRNA) through complementary base-pairing and inhibits gene expression by post-transcriptional gene silencing. Upon binding to a complementary mRNA species, RNAi induces cleavage of the mRNA molecule by the argonaute component of RISC. Among other characteristics, miRNA and siRNA differ in the degree of specificity for particular gene targets, with siRNA being relatively specific for a particular target gene and miRNA inhibiting translation of multiple mRNA species.

Therapeutic use of RNAi by inhibition of selected gene expression has been attempted for a variety of disease states, such as macular degeneration and respiratory syncytial virus infection (Sah, 2006, Life Sci 79:1773-80). It has been suggested that siRNA functions in host cell defenses against viral infection and siRNA has been widely examined as an approach to antiviral therapy (see, e.g., Zhang et al., 2004, Nature Med 11:56-62; Novina et al., 2002, Nature Med 8:681-86; Palliser et al., 2006, Nature 439:89-94). The use of siRNA for cancer therapy has also been attempted. Fujii et al. (2006, Int J Oncol 29:541-48) transfected HPV positive cervical cancer cells with siRNA against HPV E6 and E7 and suppressed tumor growth. siRNA-mediated knockdown of metadherin expression in breast cancer cells was reported to inhibit experimental lung metastasis (Brown and Ruoslahti, 2004, Cancer Cell 5:365-74).

Attempts have been made to provide targeted delivery of siRNA to reduce the potential for off-target toxicity. Song et al. (2005, Nat Biotechnol 23:709-17) used protamine-conjugated Fab fragments against HIV envelope protein to deliver siRNA to circulating cells. Schiffelers et al. (2004, Nucl Acids Res 32:e149) conjugated RGD peptides to nanoparticles to deliver anti-VEGFR2 siRNA to tumors and inhibited tumor angiogenesis and growth rate in nude mice. Dickerson et al. (2010, Cancer 10:10) used nanogels functionalized with anti-EphA2 receptor peptides to chemosensitize ovarian cancer cells with siRNA against EGFR. Dendrimer-conjugated magnetic nanoparticles have been applied to the targeted delivery of antisense survivin oligodeoxynucleotides (Pan et al., 2007, Cancer Res 67:8156-63).

The skilled artisan will realize that any siRNA or interference RNA species may be attached to the subject antibodies. siRNA and RNAi species against a wide variety of targets are known in the art, and any such known oligonucleotide species may be utilized in the claimed methods and compositions.

Known siRNA species of potential use include those specific for IKK-gamma (U.S. Pat. No. 7,022,828); VEGF, Flt-1 and Flk-1/KDR (U.S. Pat. No. 7,148,342); Bcl2 and EGFR (U.S. Pat. No. 7,541,453); CDC20 (U.S. Pat. No. 7,550,572); transducin (beta)-like 3 (U.S. Pat. No. 7,576,196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); amyloid beta precursor protein (APP) (U.S. Pat. No. 7,635,771); IGF-1R (U.S. Pat. No. 7,638,621); ICAM1 (U.S. Pat. No. 7,642,349); complement factor B (U.S. Pat. No. 7,696,344); p53 (U.S. Pat. No. 7,781,575), and apolipoprotein B (U.S. Pat. No. 7,795,421), the Examples section of each of which is incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Minis Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either an siRNA species has already been designed, or one may readily be designed using publicly available software tools. Any such siRNA species may be delivered using the subject DNL™ complexes.

Exemplary siRNA species that have been reported are listed in Table 1. Although siRNA is delivered as a double-stranded molecule, for simplicity only the sense strand sequences are shown in Table 1.

TABLE 1

Exemplary siRNA Sequences

| Target | Sequence | SEQ ID NO |
|---|---|---|
| VEGF R2 | AATGCGGCGGTGGTGACAGTA | SEQ ID NO: 22 |
| VEGF R2 | AAGCTCAGCACACAGAAAGAC | SEQ ID NO: 23 |
| CXCR4 | UAAAAUCUUCCUGCCCACCdTdT | SEQ ID NO: 24 |
| CXCR4 | GGAAGCUGUUGGCUGAAAAdTdT | SEQ ID NO: 25 |
| PPARC1 | AAGACCAGCCUCUUUGCCCAG | SEQ ID NO: 26 |
| Dynamin 2 | GGACCAGGCAGAAAACGAG | SEQ ID NO: 27 |
| Catenin | CUAUCAGGAUGACGCGG | SEQ ID NO: 28 |
| E1A binding protein | UGACACAGGCAGGCUUGACUU | SEQ ID NO: 29 |
| Plasminogen activator | GGTGAAGAAGGGCGTCCAA | SEQ ID NO: 30 |

TABLE 1-continued

Exemplary siRNA Sequences

| Target | Sequence | SEQ ID NO |
|---|---|---|
| K-ras | GATCCGTTGGAGCTGTTGGCGTAGTTCAAGAGACTCGCCAACAGCTCCAACTTTTGGAAA | SEQ ID NO: 31 |
| Sortilin 1 | AGGTGGTGTTAACAGCAGAG | SEQ ID NO: 32 |
| Apolipoprotein E | AAGGTGGAGCAAGCGGTGGAG | SEQ ID NO: 33 |
| Apolipoprotein E | AAGGAGTTGAAGGCCGACAAA | SEQ ID NO: 34 |
| Bcl-X | UAUGGAGCUGCAGAGGAUGdTdT | SEQ ID NO: 35 |
| Raf-1 | TTTGAATATCTGTGCTGAGAACACAGTTCTCAGCACAGATATTCTTTTT | SEQ ID NO: 36 |
| Heat shock transcription factor 2 | aatgagaaaagcaaaaggtgccctgtctc | SEQ ID NO: 37 |
| IGFBP3 | AAUCAUCAUCAAGAAAGGGCA | SEQ ID NO: 38 |
| Thioredoxin | AUGACUGUCAGGAUGUUGCdTdT | SEQ ID NO: 39 |
| CD44 | GAACGAAUCCUGAAGACAUCU | SEQ ID NO: 40 |
| MMP14 | AAGCCTGGCTACAGCAATATGCCTGTCTC | SEQ ID NO: 41 |
| MAPKAPK2 | UGACCAUCACCGAGUUUAUdTdT | SEQ ID NO: 42 |
| FGFR1 | AAGTCGGACGCAACAGAGAAA | SEQ ID NO: 43 |
| ERBB2 | CUACCUUUCUACGGACGUGdTdT | SEQ ID NO: 44 |
| BCL2L1 | CTGCCTAAGGCGGATTTGAAT | SEQ ID NO: 45 |
| ABL1 | TTAUUCCUUCUUCGGGAAGUC | SEQ ID NO: 46 |
| CEACAM1 | AACCTTCTGGAACCCGCCCAC | SEQ ID NO: 47 |
| CD9 | GAGCATCTTCGAGCAAGAA | SEQ ID NO: 48 |
| CD151 | CATGTGGCACCGTTTGCCT | SEQ ID NO: 49 |
| Caspase 8 | AACTACCAGAAAGGTATACCT | SEQ ID NO: 50 |
| BRCA1 | UCACAGUGUCCUUUAUGUAdTdT | SEQ ID NO: 51 |
| p53 | GCAUGAACCGGAGGCCCAUTT | SEQ ID NO: 52 |
| CEACAM6 | CCGGACAGTTCCATGTATA | SEQ ID NO: 53 |

Diagnostic Agents

In the context of this application, the terms "diagnosis" or "detection" can be used interchangeably. Whereas diagnosis usually refers to defining a tissue's specific histological status, detection recognizes and locates a tissue, lesion or organism containing a particular antigen.

The subject antibodies and fragments can be detectably labeled by linking the antibody to an enzyme. When the antibody-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label antibody include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, alpha-galactosidase, ribonuclease, urease, catalase, glucose-6-phosphate dehydrogenase, glucoamylase and acetylcholinesterase.

The immunoconjugate may comprise one or more radioactive isotopes useful for detecting diseased tissue. Particularly useful diagnostic radionuclides include, but are not limited to, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters, preferably with a decay energy in the range of 20 to 4,000 keV, more preferably in the range of 25 to 4,000 keV, and even more preferably in the range of 25 to 1,000 keV, and still more preferably in the range of 70 to 700 keV. Total decay energies of useful positron-emitting radionuclides are preferably <2,000 keV, more preferably under 1,000 keV, and most preferably <700 keV. Radionuclides useful as diagnostic agents utilizing gamma-ray detection include, but are not limited to: $^{51}$Cr, $^{57}$Co, $^{58}$Co, $^{59}$Fe, $^{67}$Cu, $^{67}$Ga, $^{75}$Se, $^{97}$Ru, $^{99m}$Tc, $^{111}$In, $^{114m}$In, $^{123}$I, $^{125}$I, $^{131}$I, $^{169}$Yb, $^{197}$Hg, and $^{201}$Tl. Decay energies of useful gamma-ray emitting radionuclides are preferably 20-2000 keV, more preferably 60-600 keV, and most preferably 100-300 keV.

Methods of diagnosing cancer in a subject may be accomplished by administering a diagnostic immunoconjugate and detecting the diagnostic label attached to an immunoconjugate that is localized to a cancer or tumor. The antibodies, antibody fragments and fusion proteins may be conjugated to the diagnostic agent or may be administered in a pretargeting technique using targetable constructs attached to a diagnostic agent. Radioactive agents that can be used as diagnostic agents are discussed above. A suitable non-radioactive diagnostic agent is a contrast agent suitable for magnetic resonance imaging, X-rays, computed tomography or ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs. See U.S. Ser. No. 09/921,290 (now abandoned) filed on Oct. 10, 2001, the Examples section of which is incorporated herein by reference. Other imaging agents such as PET scanning nucleotides, preferably $^{18}$F, may also be used.

Contrast agents, such as MRI contrast agents, including, for example, gadolinium ions, lanthanum ions, dysprosium ions, iron ions, manganese ions or other comparable labels, CT contrast agents, and ultrasound contrast agents may be used as diagnostic agents. Paramagnetic ions suitable for use include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II) and bismuth (III). Fluorescent labels include rhodamine, fluorescein and renographin. Rhodamine and fluorescein are often linked via an isothiocyanate intermediate.

Metals are also useful in diagnostic agents, including those for magnetic resonance imaging techniques. These metals include, but are not limited to: gadolinium, manganese, iron, chromium, copper, cobalt, nickel, dysprosium, rhenium, europium, terbium, holmium and neodymium. In order to load an antibody with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

Chelates are coupled to an antibody, fusion protein, or fragments thereof using standard chemistries. The chelate is normally linked to the antibody by a group which enables formation of a bond to the molecule with minimal loss of immunoreactivity and minimal aggregation and/or internal cross-linking. Other, more unusual, methods and reagents for conjugating chelates to antibodies are disclosed in U.S. Pat. No. 4,824,659 to Hawthorne, entitled "Antibody Conjugates", issued Apr. 25, 1989, the Examples section of which is incorporated herein by reference. Particularly useful metal-chelate combinations include 2-benzyl-DTPA and its monomethyl and cyclohexyl analogs, used with diagnostic isotopes in the general energy range of 20 to 2,000 keV. The same chelates, when complexed with non-radioactive metals, such as manganese, iron and gadolinium are useful for MRI. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as 223Ra for RAIT are encompassed by the invention.

Radiopaque and contrast materials are used for enhancing X-rays and computed tomography, and include iodine compounds, barium compounds, gallium compounds, thallium compounds, etc. Specific compounds include barium, diatrizoate, ethiodized oil, gallium citrate, iocarmic acid, iocetamic acid, iodamide, iodipamide, iodoxamic acid, iogulamide, iohexol, iopamidol, iopanoic acid, iprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

The antibodies, antibody fragments and fusion proteins also can be labeled with a fluorescent compound. The presence of a fluorescent-labeled MAb is determined by exposing the antibody to light of the proper wavelength and detecting the resultant fluorescence. Fluorescent labeling compounds include Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, fluorescein isothiocyanate, fluorescamine, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, phthaldehyde, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, and Texas Red. Fluorescently-labeled antibodies are particularly useful for flow cytometry analysis, but can also be used in endoscopic and intravascular detection methods.

Alternatively, the antibodies, antibody fragments and fusion proteins can be detectably labeled by coupling the antibody to a chemiluminescent compound. The presence of the chemiluminescent-tagged MAb is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label the antibodies and fragments there. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Accordingly, a method of diagnosing a malignancy in a subject is described, comprising performing an in vitro diagnosis assay on a specimen (fluid, tissue or cells) from the subject with a composition comprising an anti-pancreatic cancer MAb, fusion protein or fragment thereof. Immunohistochemistry can be used to detect the presence of PAM4 antigen in a cell or tissue by the presence of bound antibody. Preferably, the malignancy that is being diagnosed is a cancer. Most preferably, the cancer is pancreatic cancer.

Additionally, a chelator such as DTPA, DOTA, TETA, or NOTA or a suitable peptide, to which a detectable label, such as a fluorescent molecule, or cytotoxic agent, such as a heavy metal or radionuclide, can be conjugated to a subject antibody. For example, a therapeutically useful immunoconjugate can be obtained by conjugating a photoactive agent or dye to an antibody fusion protein. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Joni et al. (eds.), PHOTODYNAMIC THERAPY OF TUMORS AND OTHER DISEASES (Libreria Progetto 1985); van den Bergh, Chem. Britain 22:430 (1986)). Moreover, monoclonal antibodies have been coupled with photoactivated dyes for achieving phototherapy. Mew et al., J. Immunol. 130: 1473 (1983); idem., Cancer Res. 45:4380 (1985); Oseroff et al., Proc Natl. Acad. Sci. USA 83:8744 (1986); idem., Photochem. Photobiol. 46:83 (1987); Hasan et al., Prog. Clin. Biol. Res. 288:471 (1989); Tatsuta et al., Lasers Surg. Med. 9:422 (1989); Pelegrin et al., Cancer 67:2529 (1991).

Fluorescent and radioactive agents conjugated to antibodies or used in bispecific, pretargeting methods, are particularly useful for endoscopic, intraoperative or intravascular detection of the targeted antigens associated with diseased tissues or clusters of cells, such as malignant tumors, as disclosed in Goldenberg U.S. Pat. Nos. 5,716,595; 6,096,289 and 6,387,350, the Examples section of each incorporated herein by reference, particularly with gamma-, beta- and positron-emitters. Endoscopic applications may be used when there is spread to a structure that allows an endoscope, such as the colon. Radionuclides useful for positron emission tomography include, but are not limited to: F-18, Mn-51, Mn-52m, Fe-52, Co-55, Cu-62, Cu-64, Ga-68, As-72, Br-75, Br-76, Rb-82m, Sr-83, Y-86, Zr-89, Tc-94m, In-110, I-120, and I-124. Total decay energies of useful positron-emitting radionuclides are preferably <2,000 keV, more preferably under 1,000 keV, and most preferably <700 keV. Radionuclides useful as diagnostic agents utilizing gamma-ray detection include, but are not limited to: Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201. Decay energies of useful gamma-ray emitting radionuclides are preferably 20-2000 keV, more preferably 60-600 keV, and most preferably 100-300 keV.

In Vitro Diagnosis

The present invention contemplates the use of anti-pancreatic cancer antibodies to screen biological samples in vitro for the presence of the PAM4 antigen. In such immunoassays, the antibody, antibody fragment or fusion protein may be utilized in liquid phase or bound to a solid-phase carrier, as described below. For purposes of in vitro diagnosis, any type of antibody such as murine, chimeric, humanized or human may be utilized, since there is no host immune response to consider.

One example of a screening method for determining whether a biological sample contains MUC5AC is the radioimmunoassay (RIA). For example, in one form of RIA, the substance under test is mixed with PAM4 MAb in the presence of radiolabeled MUC5AC. In this method, the concentration of the test substance will be inversely proportional to the amount of labeled MUC5AC bound to the MAb and directly related to the amount of free, labeled MUC5AC. Other suitable screening methods will be readily apparent to those of skill in the art.

Alternatively, in vitro assays can be performed in which an anti-pancreatic cancer antibody, antibody fragment or fusion protein is bound to a solid-phase carrier. For example, MAbs can be attached to a polymer, such as aminodextran, in order to link the MAb to an insoluble support such as a polymer-coated bead, a plate or a tube.

Other suitable in vitro assays will be readily apparent to those of skill in the art. The specific concentrations of detectably labeled antibody and MUC5AC, the temperature and time of incubation, as well as other assay conditions may be varied, depending on various factors including the concentration of MUC5AC in the sample, the nature of the sample, and the like. The binding activity of a sample of anti-pancreatic cancer antibody may be determined according to well-known methods. Those skilled in the art will be able to determine operative and optimal assay conditions for each determination by employing routine experimentation.

The presence of the PAM4 antigen in a biological sample can be determined using an enzyme-linked immunosorbent assay (ELISA) (e.g., Gold et al. J Clin Oncol. 24:252-58, 2006). In the direct competitive ELISA, a pure or semipure antigen preparation is bound to a solid support that is insoluble in the fluid or cellular extract being tested and a quantity of detectably labeled soluble antibody is added to permit detection and/or quantitation of the binary complex formed between solid-phase antigen and labeled antibody.

In contrast, a "double-determinant" ELISA, also known as a "two-site ELISA" or "sandwich assay," requires small amounts of antigen and the assay does not require extensive purification of the antigen. Thus, the double-determinant ELISA is preferred to the direct competitive ELISA for the detection of an antigen in a clinical sample. See, for example, the use of the double-determinant ELISA for quantitation of the c-myc oncoprotein in biopsy specimens. Field et al., Oncogene 4: 1463 (1989); Spandidos et al., AntiCancer Res. 9: 821 (1989).

In a double-determinant ELISA, a quantity of unlabeled MAb or antibody fragment (the "capture antibody") is bound to a solid support, the test sample is brought into contact with the capture antibody, and a quantity of detectably labeled soluble antibody (or antibody fragment) is added to permit detection and/or quantitation of the ternary complex formed between the capture antibody, antigen, and labeled antibody. In the present context, an antibody fragment is a portion of an anti-pancreatic cancer MAb that binds to an epitope of MUC5AC. Methods of performing a double-determinant ELISA are well-known. See, for example, Field et al., supra, Spandidos et al., supra, and Moore et al., "Twin-Site ELISAs for fos and myc Oncoproteins Using the AMPAK System," in METHODS IN MOLECULAR BIOLOGY, VOL. 10, pages 273-281 (The Humana Press, Inc. 1992).

In the double-determinant ELISA, the soluble antibody or antibody fragment must bind to a MUC5AC epitope that is distinct from the epitope recognized by the capture antibody.

The double-determinant ELISA can be performed to ascertain whether the PAM4 antigen is present in a biopsy sample. Alternatively, the assay can be performed to quantitate the amount of MUC5AC that is present in a clinical sample of body fluid. The quantitative assay can be performed by including dilutions of purified MUC5AC.

The anti-pancreatic cancer MAbs, fusion proteins, and fragments thereof also are suited for the preparation of an assay kit. Such a kit may comprise a carrier means that is compartmentalized to receive in close confinement one or more container means such as vials, tubes and the like, each of said container means comprising the separate elements of the immunoassay.

The subject antibodies, antibody fragments and fusion proteins also can be used to detect the presence of the PAM4 antigen in tissue sections prepared from a histological specimen. Such in situ detection can be used to determine the presence of MUC5AC and to determine the distribution of MUC5AC in the examined tissue. In situ detection can be accomplished by applying a detectably-labeled antibody to frozen tissue sections. Studies indicate that the PAM4 antigen is preserved in paraffin-embedded sections. General techniques of in situ detection are well-known to those of ordinary skill. See, for example, Ponder, "Cell Marking Techniques and Their Application," in MAMMALIAN DEVELOPMENT: A PRACTICAL APPROACH 113-38 Monk (ed.) (IRL Press 1987), and Coligan at pages 5.8.1-5.8.8.

Antibodies, antibody fragments and fusion proteins can be detectably labeled with any appropriate marker moiety, for example, a radioisotope, an enzyme, a fluorescent label, a dye, a chromogen, a chemiluminescent label, a bioluminescent labels or a paramagnetic label.

The marker moiety can be a radioisotope that is detected by such means as the use of a gamma counter or a scintillation counter or by autoradiography. In a preferred embodiment, the diagnostic conjugate is a gamma-, beta- or a positron-emitting isotope. A marker moiety in the present description refers to a molecule that will generate a signal under predetermined conditions. Examples of marker moieties include radioisotopes, enzymes, fluorescent labels, chemiluminescent labels, bioluminescent labels and paramagnetic labels.

The binding of marker moieties to anti-pancreatic cancer antibodies can be accomplished using standard techniques known to the art. Typical methodology in this regard is described by Kennedy et al., Clin Chim Acta 70: 1 (1976), Schurs et al., Clin. Chim. Acta 81: 1 (1977), Shih et al., Int J Cancer 46: 1101 (1990).

The above-described in vitro and in situ detection methods may be used to assist in the diagnosis or staging of a pathological condition. For example, such methods can be used to detect tumors that express the PAM4 antigen such as pancreatic cancer.

In Vivo Diagnosis/Detection

Various methods of in vivo diagnostic imaging with radiolabeled MAbs are well-known. In the technique of immunoscintigraphy, for example, antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY 227-49, Pezzuto et al. (eds.) (Chapman & Hall 1993).

For diagnostic imaging, radioisotopes may be bound to antibody either directly or indirectly by using an intermediary functional group. Useful intermediary functional groups include chelators such as ethylenediaminetetraacetic acid and diethylenetriaminepentaacetic acid. For example, see Shih et al., supra, and U.S. Pat. No. 5,057,313.

The radiation dose delivered to the patient is maintained at as low a level as possible through the choice of isotope for the best combination of minimum half-life, minimum retention in the body, and minimum quantity of isotope which will permit detection and accurate measurement. Examples of radioisotopes that can be bound to anti-pancreatic cancer antibody and are appropriate for diagnostic imaging include $^{99m}Tc$, $^{111}In$ and $^{18}F$.

The subject antibodies, antibody fragments and fusion proteins also can be labeled with paramagnetic ions and a variety of radiological contrast agents for purposes of in vivo diagnosis. Contrast agents that are particularly useful for magnetic resonance imaging comprise gadolinium, manganese, dysprosium, lanthanum, or iron ions. Additional agents include chromium, copper, cobalt, nickel, rhenium, europium, terbium, holmium, or neodymium. Antibodies and fragments thereof can also be conjugated to ultrasound contrast/enhancing agents. For example, one ultrasound contrast agent is a liposome. Also preferred, the ultrasound contrast agent is a liposome that is gas filled.

In a preferred embodiment, a bispecific antibody can be conjugated to a contrast agent. For example, the bispecific antibody may comprise more than one image-enhancing agent for use in ultrasound imaging. In another preferred embodiment, the contrast agent is a liposome. Preferably, the liposome comprises a bivalent DTPA-peptide covalently attached to the outside surface of the liposome.

Pharmaceutically Suitable Excipients

Additional pharmaceutical methods may be employed to control the duration of action of an anti-pancreatic cancer antibody in a therapeutic application. Control release preparations can be prepared through the use of polymers to complex or adsorb the antibody, antibody fragment or fusion protein. For example, biocompatible polymers include matrices of poly(ethylene-co-vinyl acetate) and matrices of a polyanhydride copolymer of a stearic acid dimer and sebacic acid. Sherwood et al., Bio/Technology 10: 1446 (1992). The rate of release of an antibody, antibody fragment or fusion protein from such a matrix depends upon the molecular weight of the antibody, antibody fragment or fusion protein, the amount of antibody within the matrix, and the size of dispersed particles. Saltzman et al., Biophys. J. 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The antibodies, fragments thereof or fusion proteins to be delivered to a subject can comprise one or more pharmaceutically suitable excipients, one or more additional ingredients, or some combination of these. The antibody can be formulated according to known methods to prepare pharmaceutically useful compositions, whereby the immunoconjugate or naked antibody is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or naked antibody can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The immunoconjugate, naked antibody, fragment thereof or fusion protein may also be administered to a mammal subcutaneously or by other parenteral routes. In a preferred embodiment, the antibody or fragment thereof is administered in a dosage of 20 to 2000 milligrams protein per dose. Moreover, the administration may be by continuous infusion or by single or multiple boluses. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of immunoconjugate, antibody fusion protein or naked antibody that is in the range of from about 1 mg/kg to 20 mg/kg as a single intravenous or infusion, although a lower or higher dosage also may be administered as circumstances dictate. This dosage may be repeated as needed, for example, once per week for four to ten weeks, preferably once per week for eight weeks, and more preferably, once per week for four weeks. It may also be given less frequently, such as every other week for several months, or more frequently, such as two- or three-time weekly. The dosage may be given through various parenteral routes, with appropriate adjustment of the dose and schedule.

Kits

Various embodiments may concern kits containing components suitable for treating or diagnosing diseased tissue in a patient. Exemplary kits may contain at least one antibody, antigen binding fragment or fusion protein as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, an anti-pancreatic cancer antibody or antigen binding fragment thereof may be provided in the form of a prefilled syringe or autoinjection pen containing a sterile, liquid formulation or lyophilized preparation of antibody (e.g., Kivitz et al., Clin. Ther. 2006, 28:1619-29).

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions for use of the kit.

EXAMPLES

The examples below are illustrative of embodiments of the current invention and are not limiting to the scope of the claims. The examples discuss studies employing an exemplary anti-pancreatic cancer monoclonal antibody (e.g., PAM4). Clinical studies with the PAM4 MAb have shown that a majority of pancreatic cancer lesions were targeted in patients and there was no indication of uptake in normal tissues. Dosimetry indicated that it was possible to deliver 10 to 20 cGy/mCi to tumors, with a tumor to red marrow dose ratio of 3:1 to 10:1. The data show that PAM4 is useful for the treatment of pancreatic cancer.

Example 1

Epitope of MUC5AC that Binds to hPAM4 Antibody

PAM4 is a murine monoclonal antibody showing high specificity for pancreatic ductal adenocarcinoma (PDAC) compared with normal tissues and other cancers. Humanized PAM4 labeled with $^{90}Y$ in combination with low-dose gemcitabine has shown promising therapeutic activity in patients with metastatic PDAC, and is being evaluated in a phase III registration trial. Prior efforts have suggested the mucin species recognized by PAM4 is human MUC5AC, a secretory mucin expressed de novo in early pancreatic intraepithelial neoplasia and retained throughout disease progression. In the present study, we provide further evidence validating MUC5AC as the PAM4 antigen, and locate the PAM4-reactive epitope within the N-terminal cysteine-rich subdomain 2 (Cys2), thus differentiating PAM4 from anti-MUC5AC antibodies known to-date. Specifically, we show (i) PAM4-antigen and MUC5AC were co-localized in the immunocytochemical analysis of multiple human cancer cell lines, including Capan-1, BxPC-3, HT-29, and MCF-7; (ii) MUC5AC-specific siRNA prominently reduced the expression of both MUC5AC and PAM4-antigen in CFPAC-1 cells; (iii) ELISA performed on Capan-1 culture supernatants following SEPHAROSE®-CL2B chromatography depicted the preferential binding of PAM4 to the void-volume fractions, which were further revealed by agarose gel electrophoresis and Western blot to display the ladder pattern characteristic of oligomeric MUC5AC; and (iv) by testing the reactivity of PAM4 with a panel of recombinant fragments of MUC5AC, we demonstrated the N-terminal region comprising Cys2 is essential for binding to PAM4.

Materials and Methods

Antibodies and Reagents—

Humanized PAM4 (hPAM4) was provided by Immunomedics, Inc. Horseradish peroxidase (HRP)-hPAM4 conjugate was generated using the SureLINK HRP Conjugation Kit (Kirkegaard & Perry Laboratories). MAN-5ACI, a rabbit antiserum against MUC5AC (Thornton et al., 1996, Biochem J 316:967-75) was a generous gift from Dr. David J. Thornton (University of Manchester). Commercially available antibodies acquired include the following: four mouse mAbs against MUC5AC (45M1, 2-11M1, 2-12M1, and 1-13M1) from Thermo Fisher Scientific, one mouse monoclonal (2Q445) and one rabbit polyclonal (H-160) antibodies against MUC5AC from Santa Cruz Biotechnology, one mouse mAb against human MUC1 (MAB6298, hereafter referred to as α-MUC1) from R&D Systems, one rabbit polyclonal antibody against full-length GFP (α-GFP) from Clontech Laboratories, one rabbit polyclonal Myc-tag antibody (α-Myc) from Cell Signaling Technology, one FITC-labeled goat anti-human IgG (FITC-GAH) from Jackson ImmunoResearch Laboratories, and one Cy3-labeled goat anti-mouse IgG (Cy3-GAM) from EMD Millipore. The MUC5AC double-strand siRNA targeting sequence 5'-GGAGCCTGATCATCCAGCA-3' (SEQ ID NO:54) was synthesized by GenScript. SEPHAROSE®® CL-2B was purchased from Sigma-Aldrich.

Cell Culture—

All cell lines were obtained from the American Type Culture Collection (ATCC) and have been authenticated by Promega using Short Tandem Repeat (STR) analysis. BxPC-3, HT-29, LS174T, MCF-7, and Calu-3 were grown in RPMI 1640 medium (Life Technologies) with 10% fetal bovine serum (FBS, Thermo Scientific HyClone); Capan-1 was grown in RPMI 1640 medium with 20% FBS; CFPAC-1 was grown in ATCC-formulated Iscove's Modified Dulbecco's Medium (IMDM) with 10% FBS; SW1990 was grown in ATCC-formulated Leibovitz's L-15 Medium with 10% FBS; and PANC-1 was grown in Dulbecco's Modified Eagle Medium (Life technologies) plus 10% FBS. All cell lines were incubated at 37° C. in 5% $CO_2$ except SW1990, which was cultured in 100% air.

Immunocytochemistry—

Cells were plated on 8-chamber slides (Thermo Fisher Scientific) at approximately $2\times10^4$ cells/chamber and incubated overnight at 37° C. Following removal of the medium, cells were fixed in 4% formalin (Sigma-Aldrich) for 15 min at RT, and then treated with 0.1% Triton X-100 in PBS for another 15 min. After washing twice with PBS, cells were incubated with 10 µg/ml of either hPAM4 or a murine mAb against MUC5AC or MUC1 in PBS plus 1% BSA for 45 min at RT. Afterwards, cells were washed twice and incubated with a mixture of FITC-GAH and Cy3-GAM in PBS plus 1% BSA for 30 min at RT. After three washes, chambers were dissembled. Slides were mounted with an antifade solution (VectaShield, Vector Laboratories) containing the nuclear counterstain, 4,6-diamidino-2-phenylindole (DAPI). Image acquisition and analyses were performed using an Olympus fluorescence microscope with a Kodak camera system.

RNA Interference—

CFPAC-1 cells grown to 90% confluence were used for transfection. MUC5AC SiRNA or PBS alone (Mock) was 1:100 diluted into Opti-MEM I Medium (Life Technologies) prior to the addition of 1/100 volume of LIPOFECTAMINE® RNAiMAX Reagent (Life Technologies). After 20 min incubation at RT, the siRNA or Mock mixture was dispersed onto 8-chamber slides (80 µl/chamber). Meanwhile, cells were trypsinized, washed, diluted in complete growth medium, and then added at $8\times10^3$ cells/400 µl/chamber. The final RNA concentration was 15.6 nM in a total volume of 480 µl. After 48-h incubation, cells were stained with hPAM4 and anti-MUC5AC mAbs and examined under fluorescence microscope as described above.

Gel Chromatography of Cell Culture Supernatant—

Capan-1 cells were cultured for 3-4 days to reach over 90% confluence. The spent media were collected, mixed with an equal volume of 8 M guanidine hydrochloride (GdmCl) in 20 mM sodium phosphate buffer (pH 7), and 10-fold concentrated using the Amicon ultrafiltration membrane with 30 kDa normal molecular weight limit (EMD Millipore). Gel chromatography was performed on a SEPHAROSE® CL-2B column (78 cm×2.6 cm) using 4 M GdmCl as the eluent and a flow rate of 40 ml/h. Fractions of 8 mL were collected and each analyzed for reactivity with hPAM4 and α-MUC-1 by ELISA as follows. Briefly, MaxiSorp 96-well plates (Nunc, Roskilde, Denmark) were coated with CL-2B-eluted fractions (100 µl/well) at 37° C. overnight, washed twice with PBS, and blocked with Casein Blocking Buffers (Thermo Fisher Scientific) for 1 h. HRP-hPAM4 or α-MUC1 was diluted in PBS and added at 100 µl/well. After 1-h incubation at RT, plates with α-MUC1 were washed and incubated further with HRP-GAM for 1 h. Plates were washed and bound HRP-hPAM4 or HRP-GAM was detected with o-phenylenediamine dihydrochloride (0.4 mg/ml) in PBS plus 0.03% hydrogen peroxide as a substrate. The optical density was read at 490 nm using the EnVision 2100 Multilabel Reader (PerkinElmer). The fractions eluted in the void-volume peak were also pooled, dialyzed against the PBS-AG buffer (35.2 mM $Na_2PO_4.7H_2O$; 0.4 M NaCl; 6.5 mM $NaH_2PO4.H_2O$; 150 mM arginine; 150 mM monosodium glutamate, pH 8.0), and concentrated with 30 kDa Amicon Ultra centrifugal filters (EMD Millipore) for further analysis.

MUC5AC Sandwich ELISA—

MaxiSorp 96-well plates were coated with 100 µl of 2-11M1 (20 µg/ml) in PBS and incubated at 4° C. overnight. After blocking with casein buffer, a 5-fold concentrated void-volume peak pooled from the CL-2B fractionation of Capan-1 supernatant (hereafter referred to as the Capan-1 void-volume peak) was 2-fold serially diluted and added to the plate at 100 µl/well. After overnight incubation at RT, plates were washed and detected by HRP-PAM4, or by Biotin-45M1 plus HRP-streptavidin as a positive control.

Agarose Gel Electrophoresis—

Agarose gel electrophoresis was performed as described (Sheehan et al., 2000, Biochem J 347:37-44), with modifications. Briefly, the Capan-1 void-volume peak was concentrated in PBS-AG buffer and diluted with gel running buffer (40 mM Tris-acetate/1 mM EDTA, 0.1% SDS, pH 8.0). In selective experiments, serum samples from normal subjects or pancreatic cancer patients were mixed with an equal volume of 8 M guanidine hydrochloride (GdmCl) and dialyzed into gel running buffer. All samples were supplemented with 1 M urea, 3% glycerol and 0.02% bromophenol blue before loading into thin wells shaped with a 0.8 mm-thick comb in 0.7% agarose gel (5.7 cm×8.3 cm). Electrophoresis was performed at 30 V for 4 to 8 h in the Horizon 58 Electrophoresis Apparatus (LABRepCo).

Construction of Expression Vectors for MUC5AC Recombinant Fragments—

The pSM-MUC5AC-CH-long expression vector (Lidell et al., 2008, FEBS J 275:481-9; Lidell & Hansson, 2006, Biochem J 399: 121-9), which encodes a signal sequence, a Myc tag (EQKLISEEDL, SEQ ID NO:55), the human MUC5AC (Swiss-Prot accession no. P98088)C-terminal cysteine-rich part (AA3993-5030), and a histidine tag, was kindly provided by Dr. Gunner Hansson of Gothenburg University (Gothenburg, Sweden). Additional vectors were constructed from pSM-MUC5AC-CH-long by replacing the DNA sequence of AA3993-5030 with that of AA1-1217, AA1218-2199, AA1218-1517, AA1575-2052, AA1725-2052, AA1575-1723/1903-2052, AA1575-1853, and AA1575-1725, to express D1-D2-D'-D3 (b-fragment), 11P15-Cys1-2-3-4-5 (c-fragment), 11P15-Cys1 (d-fragment), Cys2-3-4 (e-fragment), Cys3-4 (f-fragment), Cys2/4 (g-fragment), Cys2-3 (h-fragment), and Cys2+(i-fragment), respectively, as listed in Table 2. In addition, four GFP-fused fragments were produced by replacing the Myc tag with a full GFP sequence in the vectors encoding Cys2-3-4, Cys3-4, Cys2/4, and Cys2-3, resulting in the e*-, f*-, g*- and h*-fragment, respectively. Myc-tagged Cys2-3-4 and Cys2+ were also expressed in E. coli, and purified from the inclusion body using HIS-Select Nickel Affinity Gel (Sigma-Aldrich), and refolded.

TABLE 2

Recombinant MUC5AC fragments

| Fragment | Tag | MUC5AC Domains | AA # (P98088) | MW $^a$(Da) | Expression PANC-1 | E. coli |
|---|---|---|---|---|---|---|
| a | Myc | Cys9-D4-B-C-CK | 3992-5030 | 116,140 | + | |
| b | Myc | D1-D2-D'-D3 | 1-1217 | 136,727 | + | |
| c | Myc | 11P15-Cys1-2-3-4-5 | 1218-2199 | 109,380 | + | |
| d | Myc | 11P15-Cys1 | 1218-1517 | 35,704 | + | |
| e | Myc | Cys2-3-4 | 1575-2052 | 56,444 | + | + |
| f | Myc | Cys3-4 | 1725-2052 | 39,686 | + | |
| g | Myc | Cys2/4 | 1575-1725/1903-2052 | 37,171 | + | |
| h | Myc | Cys2-3 | 1575-1853 | 35,452 | + | |
| I | Myc | Cys2+ | 1575-1725 | 20,504 | | + |
| e* | GFP | Cys2-3-4 | 1575-2052 | 81,742 | + | |
| f* | GFP | Cys3-4 | 1725-2052 | 64,983 | | |
| g* | GFP | Cys2/4 | 1575-1725/1903-2052 | 62,468 | + | |
| h* | GFP | Cys2-3 | 1575-1853 | 60,749 | + | |

Transient Expression of Recombinant MUC5AC Fragments—

One day prior to transfection, PANC-1 cells were seeded in a 24-well plate at $2\times10^5$/well and held at 37° C. overnight. Transfection was performed using Lipofectamine 2000 (Life Technologies) with and without the recombinant plasmid DNA of interest. After 72 h, the spent media were collected and analyzed by Western blot following gel electrophoresis.

Western Blot—

Samples were electrophoresed in the same gel or different gels under the same conditions. After electrophoresis, samples were transferred (100V, 1 h) onto a nitrocellulose membrane using the Mini TRANS-BLOT® cell system (Bio-Rad Laboratories) and probed with hPAM4, an anti-MUC5AC antibody, α-GFP, or α-Myc, as indicated. The signals were developed with SUPERSIGNAL™ West Dura Chemiluminescent Substrate (Thermo Fisher Scientific).

Results

Co-Localization of the hPAM4 Antigen and MUC5AC in Different Cell Lines—

Several cell lines were subjected to cytofluorometry in order to evaluate localization patterns (heterogeneous and/or homogenous) of MUC1, MUC5AC, and/or MUC17, as detected by hPAM4 and other mucin-specific mAbs. The cell lines examined included those derived from human pancreatic (CaPan-1, BxPC3, CFPAC-1, and AsPC-1), colorectal (HT-29 and LS174 T), breast (MCF-7), and lung (A549) carcinomas. As shown in FIG. 1, in each of the cell lines examined, hPAM4 exclusively co-localized with MUC5AC (as identified by two anti-MUC5AC mAbs, 2-11M1 and 2-12M1), but not with MUC1 or MUC17 (data not shown), suggesting that MUC5AC is the hPAM4-reactive antigen.

Co-Knockdown of the hPAM4 Antigen and MUC5AC by MUC5AC-Specific siRNA—

The disparate localization between PAM4 and anti-MUC1 or anti-MUC17 indicates that PAM4 reacts with neither MUC1 nor MUC17. On the other hand, the co-localization of PAM4 and the two anti-MUC5AC mAbs (2-11M1 and 2-12M1) is consistent with PAM4 being specific for MUC5AC (Gold et al., 2013, Mol Cancer 12:143). To investigate if hPAM4 associates with MUC5AC, we employed the RNAi method to specifically knockdown MUC5AC. As shown in the upper panel of FIG. 2, hPAM4 and 2-11M1 are co-localized in untreated CFPAC-1 cells, as well as the mock-treated (transfection agent alone) cells. In contrast, treatment with MUC5AC-specific siRNA resulted in substantially reduced immunostaining for both 2-11M1 and hPAM4. Moreover, as shown in the bottom panel of FIG. 2, siRNA knockdown of MUC5AC did not alter the anti-MUC1 immunostaining, providing further evidence that hPAM4 is not reactive with MUC1.

Presence of the hPAM4 Antigen in the Culture Supernatant of Mucin-Producing Carcinoma Cell Lines—

MUC5AC is a highly oligomeric secretory mucin that has been isolated from cell culture and in vivo mucous secretions (Sheehan et al., 2000, Biochem J 347:37-44; Hovenberg et al., 1996, Glycoconj J 13:839-47). Our early studies showed that hPAM4 reacts with mucin derived from the CaPan-1 xenografted human PDAC (Gold et al., 1994, Int J Cancer 57:204-10). In the current study, we used SEPHAROSE® CL-2B molecular sieve chromatography to separate the mucin species secreted into the supernatant of CaPan-1. The eluted fractions were then examined for immunoreactivity with hPAM4 and α-MUC1. As shown in FIG. 3A, PAM4-reactive substance was present predominantly in the void-volume peak, whereas only subsequently eluted fractions were found reactive with α-MUC1. When the Capan-1 void-volume peak was probed with anti-MUC5AC antibodies, we found a positive response with 45M1, 1-13M1, and H-160, but not 2Q445, as shown in FIG. 3B. It is noted that the void-volume peaks obtained from other cancer cell lines known to secret MUC5AC, such as HT-29 (Sheehan et al., 2000, Biochem J 347:37-44), LS 174T (Asker et al., 1998, Biochem J 335:381-7), SW1990 (Hoshi et al, 2011, Int J Oncol 38:619-27), CFPAC-1 (Luka et al., 2011, J Biomed Biotechnol 2011:93475728), and Calu-3 (Rose et al., 2000, J Aerosol Med 13:245-61), all tested positive for reactivity with hPAM4 (data not shown).

Direct evidence that correlates the hPAM4-reactive substance in the Capan-1 void-volume peak with MUC5AC is provided by a sandwich ELISA formatted to quantify the MUC5AC captured by 2-11M1, which reacts with the N-terminal domains of MUC5AC (Nollet et al., 2004, Hybrid Hybridomics 23:93-930). As shown in FIG. 3C, 2-11M1-captured MUC5AC could be detected by hPAM4 in a dose-dependent manner, demonstrating that hPAM4 binds to a different region of MUC5AC from 2-11M1. The additional results obtained with 45M1, which serves as a positive control, also support the previous conclusions that the epitopes of 45M1 (Lidell et al., 2008, FEBS J 275:481-9) and 2-11M1 on MUC5AC are non-overlapping.

Electrophoretic Resolution of the hPAM4-Reactive Void-Volume Fractions on Agarose Gel—

To further verify that the hPAM4-reactive substance is MUC5AC, the Capan-1 void-volume peak was separated by electrophoresis on 0.7% agarose gel, and subsequently probed with hPAM4 (FIG. 4A, left panel), 45M1 (FIG. 4A, middle panel), or MAN-5ACI (FIG. 4A, right panel) by Western blotting. Under non-reducing conditions, a group of bands resembling the ladder-like pattern reported for MUC5AC (Sheehan et al., 2000, Biochem J 347:37-44, Sheehan et al., 2004, J Biol Chem 279:15698-705) was clearly discerned by all three antibodies in the same gel. In contrast, under reducing conditions, two bands were revealed by MAN-5ACI, but undetectable by either hPAM4 or 45M1, which corroborate the previous findings that the predominant fast-migrating band and the minor band trailing behind represent the MUC5AC monomer and a reduction-resistant dimer, respectively (Sheehan et al., 2000, Biochem J 347:37-44), and that neither 45M1 (Lidell et al., 2008, FEBS J 275:481-9) nor hPAM4 (Gold et al., 1994, Int J Cancer 57:204-10) should react with a reduced mucin.

Detection of hPAM4-Reactive Substance in Serum Samples of Pancreatic Cancer Patients—

The visualization of MUC5AC by hPAM4 as a characteristic ladder in Western blot following agarose gel electrophoresis prompted us to examine whether such a pattern could be demonstrated for patient serum found positive with the presently formulated PAM4-based assay (Picozzi et al., 2014, J Clin Oncol 132:4026; Gold et al., 2010, Cancer Epidemiol Biomarkers Prev 19:2786-94). As shown in FIG. 4B, a broad band migrating faster than MUC5AC monomer was detected by hPAM4 and several MUC5AC-specific antibodies, such as 2-11M and H-160, but not by 45M1, suggesting the PAM4-reactive antigen in patient serum could be derived from an immature MUC5AC variant, or a breakdown product of mature MUC5AC.

Mapping of the hPAM4 Epitope on MUC5AC—

The disparity in the reactivity of hPAM4 and 2Q445 with the Capan-1 void-volume peak, as noted in FIG. 3B, suggests that the hPAM4 epitope is not in the tandem repeat region of MUC5AC recognized by 2Q445 (Perez-Vilar et al., 2006, J Biol Chem 281:4844-55). Therefore, we excluded the tandem repeat region (AA2199-3992) and decided to express in PANC-1 cells three large recombinant fragments (designated as a, b, and c) that comprise the remainder of MUC5AC (FIG. 5A). We found that hPAM4 did not react with the C-terminal a-fragment (AA3992-5030) or the N-terminal b-fragment (AA1-1217), suggesting its epitope was located outside the N-terminal D1-D2-D'-D3 domains and the C-terminal region encompassing Cys9-D4-B-C-CK domains. In contrast, the c-fragment (AA1218-2199), which spans the five N-terminal cysteine-rich subdomains (Cys1-2-3-4-5), reacted with hPAM4 as shown by Western blot (FIG. 5B, left panel). Expectedly, the c-fragment was found to react also with 1-13M1 (data not shown) and 45M1 (FIG. 5B, right panel), which recognize cysteine-rich subdomains of class-2 (Cys2 and Cys4) and class-3 (Cys3, 5, 6, 7 and 9), respectively. We next expressed two sub-fragments (d and e) within the c-fragment and showed (FIG. 5C, left panel) that hPAM4 failed to react with the d-fragment (AA1218-1517) comprising 11P15-Cys1, but strongly stained the e-fragment (AA1575-2052) comprising Cys2-3-4. We then expressed three overlapping sub-fragments (f, g, and h) of the e-fragment and showed (FIG. 5D, left panel) hPAM4 stained the g-fragment (AA1575-1725 joined to AA1903-2052, comprising Cys2 and Cys4 with Cys3 deleted), but barely the f-fragment (AA1725-2052, comprising Cys3-4) or the h-fragment (AA1575-1853, comprising Cys2-3). The differential reactivity of hPAM4 observed for the e-, f-, g-, and h-fragments was confirmed (FIG. 5E, left panel) with the respective GFP-fused counterparts (the e*-, f-, g*- and h*-fragments); the expression of each was clearly shown by Western blot with anti-GFP (FIG. 5E, right panel). Together, these results indicate that (i) the hPAM4 epitope resides within the e-fragment, which contains the Cys2-3-4 region; (ii) the presence of Cys2 or Cys4, or both, is needed for recognition by hPAM4; (iii) Cys3 is essential for the binding of 45M1, since it stained each of the c- (FIG. 5B, right panel; FIG. 5C, rightmost panel), e-, f-, and h-fragments (FIG. 5C, rightmost panel; FIG. 5D, right panel), all of which contains Cys3; but not the g-fragment (FIG. 5D, right panel), which lacks Cys3; and (iv) the validity of the d-fragment was supported by its positive staining with H-160 (FIG. 5C, middle panel), whose epitope was reported to reside in AA1214-1373 (33) contained in the d-fragment.

The successful expression of Cys2-3-4 (AA1575-2052) and Cys2+(AA1575-1725) in E. coli, as evidenced by the coomassie blue staining (FIG. 6A) and Western blot using anti-Myc (FIG. 6B), was instrumental in further defining the location of the hPAM4 epitope to the Cys2 subdomain. The unglycosylated Cys2-3-4 and Cys2+ were isolated predominantly as monomeric species of 55.4 and 20.5 kDa, respectively. As shown in FIG. 6C, hPAM4 reacts with non-reduced, but not the reduced, Cys2-3-4 and Cys2+. Although 1-13M1 also targets Cys2 or Cys4, its binding to both non-reduced and reduced Cys2+(FIG. 6D) differentiates it from hPAM4. Thus, we further establish that the hPAM4 epitope, being reduction-sensitive, is conformational, located within the Cys2 subdomain, and unlikely involving carbohydrates. We speculate that the weakly positive bands observed for hPAM4 in lanes 3 and 4 of FIG. 6C could result from reformation of the disulfide bond to a varying degree in the process of blotting, which would restore the hPAM4 epitope.

DISCUSSION

In the past decade, concerted efforts in the search of biomarkers for PDAC have produced compelling evidence that mucins are aberrantly expressed in this devastating malignancy, and have diverse biological functions in tumor development, progression, metastasis, and drug resistance (Kaur et al., 2013, Nat Rev Gastroenterol Hepatol 10:607-20). Moreover, a number of studies (Kaur et al., 2013, Nat Rev Gastroenterol Hepatol 10:607-20; Lau et al., 2004, Am J Clin Pathol 122:61-9; Remmers et al., 2013, Clin Cancer Res 19:1981-93) have shown that both cell-tethered and secreted mucins display different expression profiles in pancreatic cancer when compared to normal pancreas. As a de novo mucin in pancreatic cancer, MUC5AC could be detected as early as the pre-malignant/dysplastic stages (Nagata et al., 2007, J Hepatobiliary Pancreat Surg 14:243-54), and was identified in a high percentage of PDAC (Remmers et al., 2013, Clin Cancer Res 19:1981-93; Yamazoe et al., 2011, Pancreas 40:896-904; Kanno et al., 2006, Pancreas 33:391-6).

Our own endeavors for over 20 years have focused on the exploration of mucin-reactive PAM4 as a potential diagnostic and therapeutic agent for PDAC. Although we have recently proposed MUC5AC to be the PAM4 antigen (Gold et al., 2013, Mol Cancer 12:143), the identification of the PAM4 epitope has lagged behind its clinical development, mainly due to the challenges encountered in characterizing MUC5AC, which is polymeric, heavily 0-glycosylated, and present in several variant forms (Thornton et al., 2008, Annu Rev Physiol 70:459-86; Silverman et al., 2001, Glycobiology 2001; 11:459-71; Guo et al., 2014, Am J Respir Cell Mol Biol 50:223-32).

In the current Example, we provide additional evidence from immunocytochemistry, RNA interference, and biochemical studies that authenticates MUC5AC as the hPAM4 antigen; and more importantly, have located the PAM epitope to the N-terminal region comprising Cys2 through the recombinant expression of MUC5AC domains (Backstrom et al., 2013, Mol Biotechnol 54:250-6). We should note that DEGYTFCESPR (SEQ ID NO:56), one of the 6

MUC5AC peptides most frequently detected in the pancreatic cystic lesions with malignant potential, and not in the benign lesions, is located in the Cys2 and Cys4 subdomains, as reported in a very recent study of mucin proteomics (Jabbar et al., 2014, J Natl Cancer Inst 106:djt439).

Based on their sequence similarity (Escande et al., 2001, Biochem J 358:763-72), the 9 Cys subdomains of MUC5AC have been characterized (Guo et al., 2014, Am J Respir Cell Mol Biol 50:223-32) as Class I (Cys1), Class II (Cys2, Cys4; 98% identical), and Class III (Cys3, Cys5-9; 96% identical). Whereas each subdomain contains about 110 amino acid residues, including 10 remarkably conserved cysteine residues involved in intramolecular disulfide bonds, there is only one potential O-glycosylation site and no potential N-glycosylation site. These structural features appear to match the characteristics of the hPAM4 epitope. Earlier work (Gold et al., Int J Cancer 1994, 57:204-10) showed that the reactivity between PAM4 and its mucin antigen was negatively affected by heating, reduction of disulfide bonds, or certain protease digestion, suggesting that the PAM4 epitope is a conformational glycopeptide. While we have confirmed that reduced MUC5AC no longer reacts with hPAM4, the results obtained from the unglycosylated Cys2-3-4 and Cys2+ of this study also indicate that the hPAM epitope is retained under denaturing conditions (or can be readily restored following blotting or immobilization and washing), and unlikely to involve carbohydrates. Because Cys2 and Cys4 are 98% identical in amino acid sequence, including all of the 10 conserved cysteine residues, we expect the hPAM4 epitope is present on Cys4 also.

It is worthy of note that among the various anti-MUC5AC antibodies with mapped epitopes, which include the mouse mAbs of the M1 series: 1-13M1 (Rose et al., 2000, J Aerosol Med 13:245-61), 2-11M1 (Rose et al., 2000), 9-13M1 (Rose et al., 2000), 19M1 (Rose et al., 2000), 21M1 (Rose et al., 2000), 62M1 (Rose et al., 2000), 45M1 (Sheehan et al., 2000, Biochem J 347:37-44), and 2-12M1 (Sheehan et al., 2000); other murine mAbs such as CLH2 (Reis et al., 1997, Int J Cancer 74:112-21), SOMU1 (Rose et al., 2000, J Aerosol Med 13:245-61), 2Q445 (Sheehan et al., 2004, J Biol Chem 279:15698-705), and NPC-1C (U.S. Pat. No. 7,763,720); and two rabbit polyclonal antibodies, H-160 (Perez-Vilar et al., 2006, J Biol Chem 281:4844-55) and MAN-5ACI (Thornton et al., 1996, Biochem J 316:967-75), 1-13M1 is the only mAb reported to react with Cys2/4 subdomains of MUC5AC. Our data, however, indicate that 1-13M1 binds to a reduction-insensitive epitope, thus being different from that of hPAM4.

Because the Cys2, Cys3 and Cys4 subdomains are flanked by threonine/serine/proline (TSP)-rich sequences, which contain numerous O-glycosylation sites, we further note that the accessibility of hPAM4 to its epitope on Cys2 (or Cys4) could be masked by the surrounding oligosaccharides either structurally or in a conformation-dependent manner, or both. Accordingly, hPAM4 would prevail for underglycosylated MUC5AC, whose expression in epithelial cancers in general, and PDAC in particular, including the early-stage pancreatic cancer precursors, has not been as well studied as that of underglycosylated MUC1 (Reis et al., 1998, Int J Cancer 79:402-10).

In conclusion, we have located the hPAM4 antigen to the N-terminal Cys2 of MUC5AC and characterized it as a reduction-sensitive, carbohydrate-free epitope, whose access may be restricted by the surrounding oligosaccharides in the flanking TSP-domains. We believe the ultimate delineation of the hPAM4 epitope may lead to its exploration as a candidate for vaccine development, while providing valuable insight for diagnosis and treatment of MUC5AC-expressing cancers, such as biliary tract cancer (Wongkham et al., 2003, Cancer Lett 195:93-9), colorectal cancer (Bu et al., 2010, World J Gastroenterol 16:4089-94), and gastric cancer (Wang et al., 2003, J Surg Oncol 83:453-60), in addition to PDAC.

Example 2

Therapeutic Dosages of $^{90}$Y-Labeled Anti-MUC5AC Antibody for Human Pancreatic Cancer For patients with metastatic pancreatic adenocarcinoma, there are no approved or established treatments beyond $2^{nd}$ line. A study of fractionated radioimmunotherapy was undertaken, administering $^{90}$Y-clivatuzumab tetraxetan (yttrium-90-radiolabeled hPAM4 anti-MUC5AC antibody) with or without low radiosensitizing doses of gemcitabine.

Methods:

Fifty-eight patients with 3 median (range 2-7) prior treatments were treated on Arm A (N=29, $^{90}$Y-clivatuzumab tetraxetan, weekly 6.5 mCi/m$^2$ doses×3, plus gemcitabine, weekly 200 mg/m$^2$ doses×4 starting one week earlier) or Arm B (N=29, $^{90}$Y-clivatuzumab tetraxetan alone, weekly 6.5 mCi/m$^2$ doses×3), repeating cycles after 4-week delays. Safety and efficacy were evaluated.

Results:

Cytopenias (predominantly transient thrombocytopenia) were the only significant toxicities. Fifty-three patients (27 Arm A, 26 Arm B, 91% overall) completed ≥1 full treatment cycles, with 23 (12 Arm A, 11 Arm B; 40%) receiving multiple cycles, including 7 (6 Arm A, 1 Arm B; 12%) given 3-9 cycles. Two patients in Arm A had partial responses by RECIST criteria. Kaplan-Meier overall survival (OS) appeared improved in Arm A v B (hazard ratio [HR] 0.55, 95% CI: 0.29-0.86; P=0.017, log-rank) and the median OS for Arm A v Arm B increased to 7.9 v 3.4 months with multiple cycles (HR 0.32, P=0.004), including 3 patients in Arm A surviving >1 year.

Conclusions:

With these surprising results, clinical use of $^{90}$Y-clivatuzumab tetraxetan and low-dose gemcitabine is feasible in metastatic pancreatic cancer patients beyond $2^{nd}$ line. A Phase III trial is now underway in this setting.

Introduction

The outlook for patients with advanced pancreatic adenocarcinoma remains poor (Hidalgo, 2010, N Engl J Med 362:1605-17). In the frontline, median survival was 6.2-6.7 months with gemcitabine alone (Burris et al., 1997, J Clin Oncol 15:2403-13) or with erlotinib (Moore et al., 2007, J Clin Oncol 25:1960-6), 8.5 months combined with albumin-bound paclitaxel (Von Hoff et al., 2013, N Engl J Med 369:1691-1703), and 11.1 months for those able to tolerate combination chemotherapy (FOLFIRINOX) (Conroy et al., 2011, N Engl J Med 364:1817-25). Beyond 1st line, the survival advantage with chemotherapy remains limited (Rahma et al., 2013, Ann Oncol 24:1972-9; Oettle et al., 2014, J Clin Oncol 32:2423-9) and after two prior treatments (one usually gemcitabine-based, the other fluoropyrimidine-based), there are no accepted treatments (Seufferlein et al., 2012, Ann Oncol 23(suppl 7):vii33-40; Almhanna & Kim, 2008, Oncology (Williston Park) 22:1176-83).

We pursued radioimmunotherapy to target and directly irradiate tumor sites without needing to physically overcome transport barriers in pancreatic cancer (high interstitial pressure, dense stromal reaction) or be incorporated into the tumor cells to be effective (Koay et al., 2014, J Clin Invest 124:1525-36). PAM4, an anti-MUC5AC monoclonal antibody selectively binding to pancreatic adenocarcinoma mucin, proved active when radiolabeled in preclinical models of human pancreatic cancer (Cardillo et al., 2001, Clin Cancer Res 7:3186-92; Gold et al., 1997, Int J Cancer 71:660-7). However, dosage studies in animal model systems are generally not predictive of effective therapeutic dosages in humans (Reagan-Shaw et al., 2007, FASEB J 22:659-61), requiring clinical studies in human subjects to establish safe and effective therapeutic dosages.

After humanization and conjugation with DOTA (1,4,7, 10-tetraazacyclododecane-N,N',N'',N'''-tetraacetic acid), the chelate-hPAM4 conjugate (clivatuzumab tetraxetan) was labeled with 90-yttrium ($^{90}Y$), a beta-emitting radionuclide with a radiation path-length of ~5 mm suitable for bulky tumors. $^{90}Y$-clivatuzumab tetraxetan was initially administered as a single dose (Gulec et al., 2011, Clin Cancer Res 17:4091-100), but fractionated doses should be more effective (DeNardo et al., 2002, Cancer 94:1332-48). Gemcitabine is a known radiosensitizer (Morgan et al., 2008, Clin Cancer Res 14:6744-50), tolerated clinically at low doses with external radiotherapy (Pauwels et al., 2005, Oncologist 10:34-51), and preclinical studies showed enhanced antitumor activity combining $^{90}Y$-labeled PAM4 with gemcitabine (Cardillo et al., 2002, Int J Cancer 97:386-92; Gold et al., 2003, Clin Cancer Res 9:3929S-37S; Gold et al., 2004, Int J Cancer 109:618-26).

In the frontline, fractionated doses of $^{90}Y$-clivatuzumab tetraxetan combined with 200 mg/m$^2$ doses of gemcitabine achieved 11.8 months median survival for those patients given repeated treatment cycles; manageable myelosuppression was the principal side-effect (Ocean et al., 2012, Cancer 118:5497-505). There is an unmet medical need for further therapy in pancreatic cancer patients who have received and shown resistance to or relapsed from two or more prior therapies. Radioimmunotherapy may be particularly attractive for patients considering continued treatment, but unable or unwilling to tolerate the side effects of further chemotherapy.

Methods

This Example reports the results of an open-label, multicenter phase Ib study of $^{90}Y$-clivatuzumab tetraxetan administered with or without 200 mg/m$^2$ gemcitabine in patients with metastatic pancreatic adenocarcinoma after ≥2 prior therapies. Primary study objectives included evaluating treatment safety and tolerability in this setting. Additional objectives were to obtain evidence of efficacy based on survival, CT imaging and CA19-9 serum levels, assess the contribution of gemcitabine to this treatment regimen, and evaluate any immunogenicity toward this antibody-based regimen.

Population.

Adults ≥18 years old with metastatic pancreatic adenocarcinoma had received ≥2 prior chemotherapy regimens for their advanced disease and had measureable disease by CT imaging, but no CNS metastases or bulky disease (no single mass ≥10 cm). Other requirements included Karnofsky performance status ≥70%, hemoglobin ≥9 g/dL, neutrophils [ANC] ≥1500/mm$^3$, platelets ≥100,000/mm$^3$, creatinine and bilirubin ≤1.5×IULN (institutional upper limit of normal), AST and ALT ≤2.0×IULN, with any prior external radiation therapy <2000 cGy to lungs and kidneys, <3000 cGy to liver, <30% of red marrow, and with ≤Grade 2 nausea/vomiting, anorexia, or signs of intestinal obstruction.

Treatment and Assessments.

Immunomedics, Inc., (Morris Plains, N.J.) provided clivatuzumab tetraxetan to local commercial radiopharmacies for $^{90}Y$-radiolabeling. Based on the prior study (Ocean et al., 2012, Cancer 118:5497-5506), a 6.5 mCi/m$^2$ dose was selected for this population, with $^{90}Y$-clivatuzumab tetraxetan administered in the hospital nuclear medicine department by slow injection over 5-10 minutes. Commercially available gemcitabine prepared by the hospital pharmacy was given intravenously over 30 minutes.

Patients were alternately assigned to treatment arms, without consideration of prior history other than meeting eligibility criteria. In Arm A, patients received 6.5 mCi/m$^2$ $_{90}Y$-clivatuzumab tetraxetan once-weekly for 3 weeks together with 200 mg/m$^2$ gemcitabine once-weekly for 4 weeks starting 5 days before beginning $^{90}Y$-clivatuzumab tetraxetan and then 2 days after each dose. In Arm B, patients received only 6.5 mCi/m$^{290}Y$-clivatuzumab tetraxetan once-weekly for 3 weeks. For both arms, treatment cycles were repeated after 4 weeks following the last dose until unacceptable toxicity, progressive disease, or patient withdrawal. The full $^{90}Y$-clivatuzumab tetraxetan dose was administered for ANC ≥1000/mm$^3$ and platelets ≥100,000/mm$^3$; otherwise, a 75% dose for ANC ≥750/mm$^3$ and platelets ≥75,000/mm$^3$, or a 50% dose for lower values with ANC ≥500/mm$^3$ and platelets ≥50,000/mm$^3$, with the dose held if ANC <500/mm$^3$ or platelets <50,000/mm$^3$ and treatment delayed on a weekly basis until blood levels permitted dosing to continue. Gemcitabine doses were held if $^{90}Y$-clivatuzumab tetraxetan doses were held, but were otherwise given without reduction.

Adverse events were graded by NCI-CTCAE v4.0 (National Cancer Institute (NCI). Common terminology criteria for adverse events (CTCAE) version 4.0). Vital signs, physical examination, blood counts, serum chemistries, and CA19-9 serum levels were evaluated during treatment cycles, then 4, 8, and 12 weeks after last cycle. Serum samples were evaluated by enzyme immunoassay for any human anti-hPAM4 antibodies (HAHA). CT scans were interpreted by local radiologists every 4 weeks after each cycle until progression or 12 weeks post-treatment. Tumor lesion changes were categorized as a complete response (CR), partial response (PR), stable (SD), or progressive disease (PD) by RECIST v1.0 [27]. $^{18}F$-FDG-PET or PET/CT imaging was optional. All patients were followed for survival.

Statistical Analysis.

Overall survival (OS) from first dose to death or last contact was analyzed by Kaplan-Meier methods. Other results were summarized by descriptive statistics. To determine if this approach is sufficiently active in this population, and if low-dose gemcitabine adds to the therapeutic activity, a SWOG two-stage design was used with a treatment target of ≥25% disease control (PR or CR, or else SD for at least 8 weeks from treatment initiation) versus ≥5% for an inactive therapy, resulting in a sample size of ≥50 patients (25 per arm) for this study.

Results

Patients and Study Treatment.

Fifty-eight patients with a median of 3 (range, 2-7) prior chemotherapy regimens were enrolled. All had received gemcitabine-containing regimens (21% with nab-paclitaxel) while 97% had received fluoropyrimidine-containing regimens (50% with FOLFIRINOX). Twenty-nine patients were treated in both Arm A (gemcitabine) and Arm B (no gemcitabine). Table 3 summarizes patient demographics and baseline characteristics for each arm.

TABLE 3

Demographics and baseline characteristics

| | Arm A | Arm B |
|---|---|---|
| Patients, N | 29 | 29 |
| Sex, M/F | 19/10 | 14/15 |
| Age, median (range) | 62 (39-73) | 66 (51-80) |
| Karnofsky performance status, N | | |
| 90-100 | 14 | 10 |
| 70-80 | 15 | 19 |
| Hematology, median (range) | | |
| Platelets (x 1000/μL) | 211 (100-577) | 224 (113-570) |
| Neutrophils (x 1000/μL) | 5.2 (1.9-15.1) | 5.4 (3.0-13.4) |
| Hemoglobin (g/dL) | 11.3 (9.2-15.1) | 11.6 (9.4-15.8) |
| Years from diagnosis, median (range) | 1.8 (0.3-4.1) | 1.5 (0.4-3.7) |
| Stage IV disease, N (%) | 29 (100%) | 29 (100%) |
| Extent of disease, median (range) | | |
| CA19-9 (U/mL) | 863 (0.8-UL*) | 2720 (6.5-UL*) |
| Sum of index lesions (cm) | 9.8 (1.7-19.0) | 7.1 (1.2-22.2) |
| Tumor location, N (%) | | |
| Pancreas, including resection bed | 11 (38%) | 15 (52%) |
| Liver | 14 (48%) | 17 (59%) |
| Other abdomen sites | 13 (45%) | 16 (55%) |
| Lung | 13 (45%) | 12 (41%) |
| Prior therapies | | |
| Pancreatectomy, N (%) | 15 (52%) | 9 (31%) |
| External radiation, N (%) | 10 (34%) | 8 (28%) |
| Chemotherapy regimens | | |
| Median (range) | 3 (2-7) | 3 (2-6) |
| Most frequent, N (%) | | |
| Gemcitabine-containing | 29 (100%) | 29 (100%) |
| Gemcitabine/nab-paclitaxel | 6 (21%) | 6 (21%) |
| Fluoropyrimidine-containing | 28 (97%) | 28 (97%) |
| FOLFIRINOX† | 17 (59%) | 12 (41%) |

*UL = upper limit of quantitation, nominally >200,000 U/mL.
†Irinotecan, oxaliplatin, and 5-fluorouracil/leucovorin combination.

No drug-related interruptions, discontinuations or adverse reactions occurred with treatment administrations. Five patients rapidly deteriorated before finishing one cycle (stroke, entered hospice, biliary obstruction, pulmonary embolism, severe constipation). Patients terminated further treatment due to disease progression/clinical deterioration or other treatment-unrelated events, with 30/58 (52%) patients (15 per arm) completing only one cycle, and 23 (40%) patients (12 Arm A, 11 Arm B) receiving multiple cycles, including 16 (6 Arm A, 10 Arm B) given 2 cycles and 7 (6 Arm A, 1 Arm B) given 3 to 9 cycles. For cycle 1, 8/58 (14%) patients had ≥1 doses of $^{90}$Y-clivatuzumab tetraxetan reduced to 75%; but, besides the 5 patients who rapidly deteriorated, no doses were held. For repeated cycles, 16/23 (70%) patients had ≥1 doses reduced to 75% (N=7) or 50% (N=9), including 11 (48%) who also had ≥1 doses held.

Adverse Events.

Events considered at least possibly treatment-related were thrombocytopenia, 50% of patients; fatigue, 26%; anemia, 22%; nausea, 16%; leukopenia, neutropenia, 12% each; abdominal pain, anorexia, vomiting, diarrhea, 9% each; bleeding, fever, chills, 7% each; dyspnea, hyperbilirubinemia, headache, 5% each; others <5%. These included Grade ≥3 events of thrombocytopenia, 19%; anemia, leukopenia, neutropenia, 7% each; others ≤2%.

Comparison of events regardless of assumed treatment relationship shows limited differences between treatment arms, and AEs occurring more frequently (>10% difference) in arm A (fatigue, neutropenia, leukopenia, nausea, diarrhea, dyspnea, alkaline phosphatase, headache) or arm B (ascites, asthenia, gastrointestinal pain or tenderness) were primarily limited to Grade 1-2 events (Table 4).

TABLE 4

Patient Incidence of Most Frequent Adverse Events Regardless of Assumed Relationship to Treatment*

| | Arm A | | Arm B | |
|---|---|---|---|---|
| Adverse event, % | All Grades | Grade ≥3 | All Grades | Grade ≥3 |
| Laboratories | | | | |
| Thrombocytopenia | 62 | 21 | 52 | 17 |
| Anemia | 45 | 14 | 38 | 10 |
| Neutropenia | 28 | 10 | 3 | 3 |
| Leukopenia | 24 | 14 | 3 | 3 |
| Alkaline phosphatase | 24 | 3 | 10 | 0 |
| Hyponatremia | 21 | 7 | 14 | 7 |
| Aspartate aminotransferase | 17 | 0 | 7 | 7 |
| Lymphopenia | 14 | 10 | 17 | 10 |
| Hyperbilirubinemia | 14 | 3 | 21 | 3 |
| Hyperglycemia | 14 | 3 | 14 | 7 |
| Hypoalbuminemia | 14 | 0 | 3 | 3 |
| Clinical Events | | | | |
| Fatigue | 76 | 3 | 38 | 7 |
| Nausea | 41 | 0 | 24 | 3 |
| Anorexia | 31 | 0 | 24 | 7 |
| Abdominal/gastrointestinal pain or tenderness | 31 | 3 | 48 | 10 |
| Constipation | 28 | 0 | 28 | 3 |
| Diarrhea | 28 | 0 | 10 | 0 |
| Dyspnea | 28 | 7 | 14 | 0 |
| Infection | 24 | 7 | 17 | 7 |
| Vomiting | 21 | 3 | 28 | 3 |
| Abdominal distension | 17 | 0 | 7 | 0 |
| Bleeding | 17 | 3 | 14 | 7 |
| Back Pain | 17 | 7 | 14 | 0 |
| Cough | 17 | 0 | 7 | 0 |
| Dehydration | 14 | 3 | 17 | 3 |
| Headache | 14 | 0 | 0 | 0 |
| Hypertension | 14 | 7 | 3 | 0 |
| Fever | 14 | 0 | 14 | 0 |
| Pleural effusion | 10 | 7 | 17 | 7 |
| Peripheral edema | 10 | 0 | 14 | 0 |
| Ascites | 0 | 0 | 14 | 3 |
| Asthenia | 0 | 0 | 14 | 3 |

*Events occurring in >10% of the 29 patients in either treatment arm

Six patients (3 per arm) had serious events considered at least possibly treatment-related. Two patients had cerebrovascular accidents due to thromboembolic or watershed events, one after the first dose and the other one month after cycle 1, and two other patients developed consumptive coagulopathies, one after cycle 1 with thrombocytopenia, deep venous thrombosis and sub-acute cerebral infarcts, the other after cycle 2 with thrombocytopenia, acute renal failure and fatal gastrointestinal hemorrhage. One patient developed fever after cycle 3 with negative cultures but responded to antibiotics, while another patient with a history of severe infections developed fatal Gram-negative bacteremia during cycle 2; both had undergone recent biliary stent placements and were not neutropenic at time of event.

Overall, 20/58 (34%) patients (10 per arm) developed Grade ≥3 thrombocytopenia (4 given platelets), 14 (11 Arm A, 3 Arm B; 24% overall) developed Grade ≥3 neutropenia (4 given cytokine support), and 11 (7 Arm A, 4 Arm B; 19% overall) developed Grade ≥3 anemia (8 transfused). In patients with follow-up data, only 4 events (all thrombocytopenia) remained at Grade 4 levels >7 days, while all Grade 3 cytopenias recovered to Grade 2 levels within 12 weeks.

Grade ≥3 cytopenias generally increased with repeated cycles but Grade 4 occurrences generally remaining limited (Table 5).

TABLE 5

Grade 3 and 4 Hematological Toxicity by Treatment Cycle

| Cycle | N | Thrombocytopenia Grade 3 | Thrombocytopenia Grade 4 | Neutropenia Grade 3 | Neutropenia Grade 4 | Anemia Grade 3 | Anemia Grade 4 |
|---|---|---|---|---|---|---|---|
| Cycle 1 | 58 | 4 (7%) | 6 (10%) | 10 (17%) | 1 (2%) | 5 (9%) | 0 (0%) |
| Cycle 2 | 23 | 7 (30%) | 2 (9%) | 3 (13%) | 0 (0%) | 4 (17%) | 0 (0%) |
| Cycle 3-9 | 7 | 3 (43%) | 2 (29%) | 1 (14%) | 1 (14%) | 3 (43%) | 0 (0%) |

Infections occurred in 11 (19%) patients, including 4 serious events [fatal septic entercolitis from pre-study pancreatectomy (Sump syndrome); fatal septic bacteremia from unidentified source; post-interventional Grade 3 acute cholangitis; Grade 3 pneumonia responding to antibiotics]; and 10 Grade 1-2 events [upper respiratory infection (URI)×4, urinary tract infection (UTI)×3, superficial fungal infection× 2, pneumonia, Lyme disease). The fatal bacteremia was considered possibly-related although the patient had a history of severe infections and recent biliary stent placement; other infections were considered unrelated by the investigators. Furthermore, only 3 patients were neutropenic (700-900 cells/4) at time of infection (pneumonia, UTI, URI).

Bleeding occurred in 9 (16%) patients, including 3 serious events (fatal GI bleeding from consumptive coagulopathy, Grade 3 melena from concomitant medications, Grade 3 GI bleeding from underlying disease), and 7 minor Grade 1 events (bruising×4, epistaxis, hemorrhoids, conjunctival). Minor bruising was considered at least possibly study drug related, but the other bleeding events were all considered unrelated by the investigators, and only 3 patients had Grade 3-4 thrombocytopenia at time of event (consumptive coagulopathy, bruising×2).

Efficacy.

Figure 7:
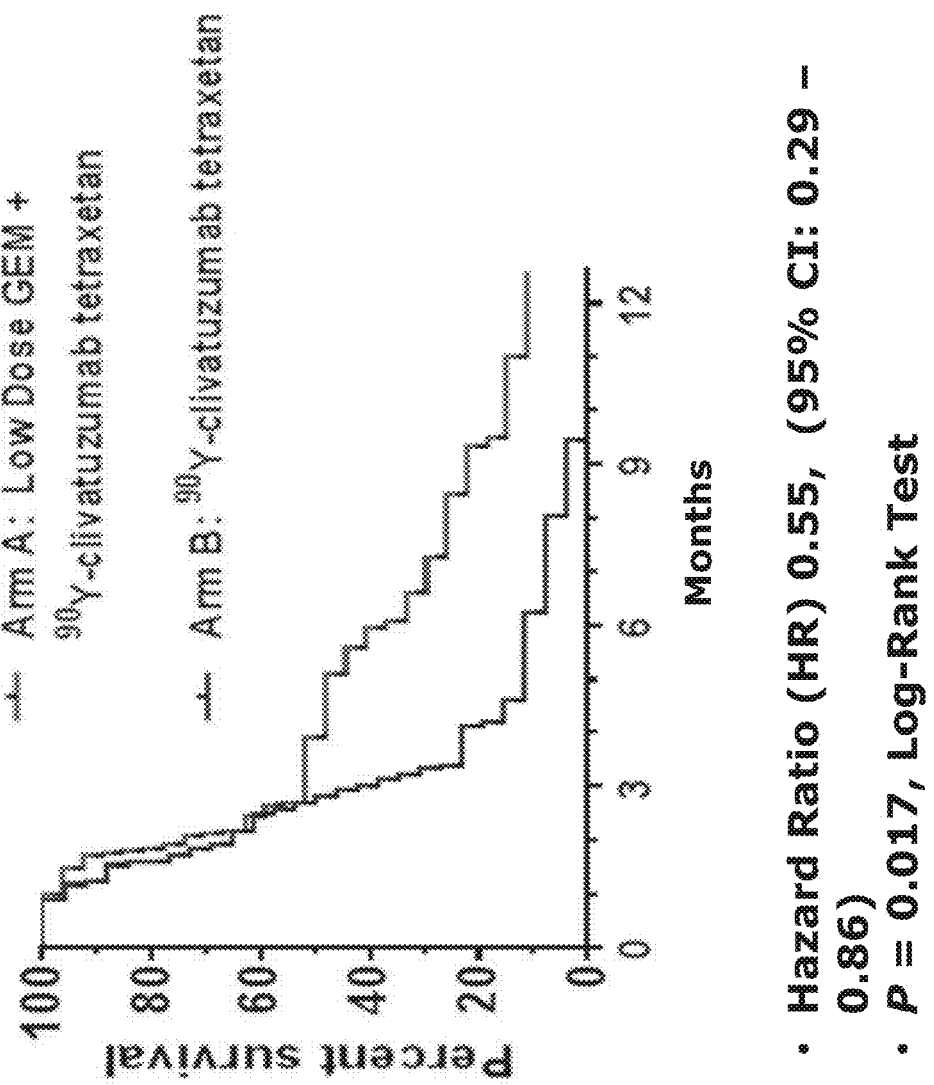
FIG. 7. Overall survival. Kaplan-Meier curves and time-point analyses for all 29 patients in Arm A ($^{90}$Y-clivatuzumab tetraxetan combined with low-dose gemcitabine) and all 29 patients in Arm B ($^{90}$Y-clivatuzumab tetraxetan alone).

The median overall survival (OS) for all 58 patients was 2.7 months, with 2 patients (both Arm A) currently alive 22 and 23 months from treatment initiation. Kaplan-Meier survival curves (FIG. 7) showed improvement in Arm A v B beginning at about 3 months, with the relative number of patients remaining alive in Arm A v B then progressively increasing with time (hazard ratio [HR] 0.55, 95% CI: 0.29-0.86; P=0.017, log-rank test). Median OS for Arm A v B (Table 6) was only 2.7 v 2.6 months overall, but increased to 7.9 v 3.4 months for those patients who received multiple cycles (HR 0.32, P=0.004), including 3 patients in Arm A surviving >1 year (one for 1.5 years, the others still alive). OS generally increased with better performance status and lower CA19-9 serum levels at study entry, and to a lesser degree with fewer prior therapies and smaller tumor burden estimated by summing lengths of index lesions (Table 6).

TABLE 6

Dependence of overall survival (OS) on treatment and patient factors

| | N | Median (range), months |
|---|---|---|
| Treatment | | |
| Arm A, Overall | 29 | 2.7 (0.4-22.8+) |
| Single Cycle | 17 | 1.9 (0.4-11.0) |
| Multiple Cycles | 12 | 7.9 (3.9-22.8+) |

TABLE 6-continued

Dependence of overall survival (OS) on treatment and patient factors

| | N | Median (range), months |
|---|---|---|
| Arm B, Overall | 29 | 2.6 (0.7-9.4) |
| Single Cycle | 18 | 1.7 (0.7-4.1) |
| Multiple Cycles | 11 | 3.4 (1.7-9.4) |
| Patient Factors | | |
| Karnofsky Performance Status | | |
| 90-100 | 24 | 4.0 (0.4-22.8+) |
| 70-80 | 34 | 2.0 (0.7-21.7+) |
| Number of Prior Systemic Treatments | | |
| 2 | 19 | 2.9 (0.4-21.7+) |
| 3 | 18 | 3.1 (0.9-22.8+) |
| >3 | 21 | 2.4 (0.7-17.5) |
| Sum of Index Lesions (cm) | | |
| 1.2-8.1 | 29 | 2.9 (0.7-22.8+) |
| 8.3-22.2 | 29 | 2.6 (0.4-21.7+) |
| Serum CA19-9 (U/mL) | | |
| ≤1257 | 29 | 3.9 (0.4-22.8+) |
| >1257 | 28* | 2.1 (0.7-8.4) | f.n. +indicates value from patient currently alive
*Baseline CA19-9 unavailable in one patient.

There was >25% disease control (PR+SD) in both treatment arms at interim evaluation, thus meeting the SWOG two-stage criteria to complete enrollment. By RECIST criteria, there were 2 PRs (both Arm A) and 22 SDs (10 Arm A, 12 Arm B) as best response, with other patients having progressed by first CT evaluation 4 weeks after cycle 1. Median OS for those with PR, SD and PD was 11.5, 5.1 and 1.8 months, respectively. Eleven patients had elevated CA19-9 levels at baseline that decreased with treatment, either 20-50% and considered a minor response (N=8), or >50% and considered an objective response (N=3). Median OS for patients with CA19-9 responses was 3.9 v 2.5 months for the remaining population.

Immunogenicity.

Five patients (1 arm A, 4 arm B) with baseline serum samples that were HAHA-negative (<50 ng/mL) became HAHA-positive after their first (N=3) or second (N=2) cycle, developing maximum titers of 135-21,611 ng/mL. These were isolated laboratory findings without event and of uncertain clinical significance.

DISCUSSION

Despite having 3 median (2 to 7) prior chemotherapies, 58 patients with metastatic pancreatic cancer were enrolled within 8 months, demonstrating the feasibility of using $^{90}$Y-clivatuzumab tetraxetan in this setting. All had received gemcitabine-containing regimens (21% with nab-paclitaxel), and 97% had received fluoropyrimidine-containing regimens (50% with FOLFIRINOX), underscoring the importance of developing treatments beyond 2nd line for pancreatic cancer.

There were no infusion reactions and, as expected, cytopenias (predominantly thrombocytopenia) were the only significant toxicities. Even in this population, these were mostly transient and reversible events, with infrequent hematologic support required. Treatment-related myelosuppression may have exacerbated two cases of consumptive coagulopathy, but otherwise, the few infections or major bleeding events that occurred could be attributed to complications of underlying disease. Most other AEs were mild-moderate constitutional and gastrointestinal events also expected in advanced pancreatic cancer, and comparison of events between treatment arms showed no substantial differences. Thus this combination approach appears to be an acceptable regimen in this advanced population.

Although median survival was only 2.7 months overall, the addition of low-dose gemcitabine to this regimen showed survival progressively improving with time (48% v 35% alive at 3 months, 35% v 10% at 6 months, 21% v 3% at 9 months, 10% v 0% at 1 year). For patients receiving only one cycle, gemcitabine made little difference, but with multiple cycles median OS increased (3.4 v 7.9 months), including 3 patients surviving >1 year. Patients undergoing multiple cycles could reflect a healthier population, but this would not explain survival results favoring combining radioimmunotherapy with low-dose gemcitabine. Although more limited than previously seen with $^{90}$Y-clivatuzumab tetraxetan in less heavily treated patients (Gulec et al., 2011, Clin Cancer Res 17:4091-100; Ocean et al., 2012, Cancer 118:5497-505), tumor response assessed by CT imaging or CA19-9 levels still showed treatment activity, and the improvement of survival with better responses and patient risk factors also supported the consistency of results in this advanced population. However, to additionally examine the role of low-dose gemcitabine in the treatment regimen before pursuing a large, randomized, controlled trial, the study was powered to demonstrate prespecified criteria for treatment arm activity, not survival.

In conclusion, this trial demonstrated the feasibility of using $^{90}$Y-clivatuzumab tetraxetan in metastatic pancreatic cancer patients after ≥2 prior chemotherapy regimens ($3^{rd}$ line and beyond). This is important, because the benefits of current second-line therapies appear modest, at the cost of drug toxicity (Rahma et al., 2013, Ann Oncol 24:1972-9; Seufferlein et al., 2012, Ann Oncol 23(suppl 7):vii33-40; Almhanna & Kim, 2008, Oncology (Williston Park) 22:1176-83). $^{90}$Y-clivatuzumab tetraxetan combined with low-dose gemcitabine appears promising in this difficult-to-treat population.

Example 3

Humanized PAM4 MAb

In preferred embodiments, the claimed methods and compositions utilize the antibody hPAM4 which is a humanized IgG of the murine PAM4 MAb raised against pancreatic cancer mucin. Humanization of the murine PAM4 sequences was utilized to reduce the human antimouse antibody (HAMA) response. To produce the humanized PAM4, murine complementarity determining regions (CDR) were transferred from heavy and light variable chains of the mouse immunoglobulin into human framework region (FR) antibody sequences, followed by the replacement of some human FR residues with their murine counterparts. Humanized monoclonal antibodies are suitable for use in in vitro and in vivo diagnostic and therapeutic methods.

Comparison of the variable region framework sequences of the murine PAM4 MAb (FIG. 8A and FIG. 8B) to known human antibodies in the Kabat database showed that the FRs of PAM4 $V_K$ and $V_H$ exhibited the highest degree of sequence homology to that of the human antibodies Walker $V_K$ (FIG. 10A) and Wil2 $V_H$ (FIG. 10B), respectively. Therefore, the Walker $V_K$ (FIG. 10A) and Wil2 $V_H$ (FIG. 10B) FRs were selected as the human frameworks into which the murine CDRs for PAM4 $V_K$ and $V_H$ were grafted, respectively. The FR4 sequence of the human antibody, NEWM, however, was used to replace the Wil2 FR4 sequence for the humanization of the PAM4 heavy chain (FIG. 10B). A few amino acid residues in PAM4 FRs that flank the putative CDRs were maintained in hPAM4 based on the consideration that these residues have more impact on Ag binding than other FR residues. These residues were 21M, 47W, 59P, 60A, 85S, 87F, and 100G of $V_K$ (FIG. 10A) and 27Y, 30P, 38K, 48I, 66K, 67A, and 69L of $V_H$ (FIG. 10B). The DNA and amino acid sequences of hPAM4 $V_K$ (SEQ ID NO:16) and $V_H$ (SEQ ID NO:19) are shown in FIGS. 11A and 11B, respectively.

A modified strategy as described by Leung et al. (Leung et al., 1994)) was used to construct the designed $V_K$ (FIG. 11A) and $V_H$ (FIG. 11B) genes for hPAM4 using a combination of long oligonucleotide syntheses and PCR. For the construction of the hPAM4 $V_H$ domain, two long oligonucleotides, hPAM4 $V_H$A (173-mer) and hPAM4 $V_H$B (173-mer) were synthesized on an automated DNA synthesizer (Applied Biosystems). hPAM4 $V_H$A represents nt 17 to 189 of the hPAM4 $V_H$ domain.

```
                                         (SEQ ID NO: 57)
5'-AGTCTGGGGC TGAGGTGAAG AAGCCTGGGG CCTCAGTGAA

GGTCTCCTGC GAGGCTTCTG GATACACATT CCCTAGCTAT

GTTTTGCACT GGGTGAAGCA GGCCCCTGGA CAAGGGCTTG

AGTGGATTGG ATATATTAAT CCTTACAATG ATGGTACTCA

GTACAATGAG AAG-3'
``` hPAM4 $V_H$B represents the minus strand of the hPAM4 $V_H$ domain complementary to nt 169 to 341.

```
                                         (SEQ ID NO: 58)
5'-AGGGTTCCCT GGCCCCAGTA AGCAAATCCG TAGCTACCAC

CGAAGCCTCT TGCACAGTAA TACACGGCCG TGTCGTCAGA

TCTCAGCCTG CTCAGCTCCA TGTAGGCTGT GTTGATGGAC

GTGTCCCTGG TCAGTGTGGC CTTGCCTTTG AACTTCTCAT

TGTACTGAGT ACC-3'
```

The 3'-terminal sequences (21 nt residues) of hPAM4 $V_H$A and $V_H$B are complementary to each other. Under defined PCR condition, the 3'-ends of hPAM4 $V_H$A and $V_H$B anneal to form a short double stranded DNA flanked by the rest of the long oligonucleotides. Each annealed end serves as a primer for the transcription of the single stranded DNA, resulting in a double strand DNA composed of the nt 17 to 341 of hPAM4 $V_H$. This DNA was further amplified in the presence of two short oligonucleotides, hPAM4 $V_H$BACK and hPAM4 $V_H$FOR to form the full-length hPAM4 $V_H$. The underlined portions are restriction sites for subcloning as shown in FIG. 11B.

hPAM4 $V_H$BACK
```
                                         (SEQ ID NO: 59)
5'-CAG GTG CAG CTG CAG CAG TCT GGG GCT GAG GTG A-3'
``` hPAM4 $V_H$FOR
```
                                         (SEQ ID NO: 60)
5'-TGA GGA GAC GGT GAC CAG GGT TCC CTG GCC CCA-3'
```

A minimal amount of hPAM4 $V_H$A and $V_H$B (determined empirically) was amplified in the presence of 104, of 10×PCR Buffer (500 mM KCl, 100 mM Tris HCl buffer, pH 8.3, 15 mM MgCl$_2$), 2 µmol of hPAM4 V$_H$BACK and hPAM4 V$_K$FOR, and 2.5 units of Taq DNA polymerase (Perkin Elmer Cetus, Norwalk, Conn.). This reaction mixture was subjected to three cycles of polymerase chain reaction (PCR) consisting of denaturation at 94° C. for 1 minute, annealing at 45° C. for 1 minute, and polymerization at 72° C. for 1.5 minutes. This procedure was followed by 27 cycles of PCR reaction consisting of denaturation at 94° C. for 1 minute, annealing at 55° C. for 1 minute, and polymerization at 72° C. for 1 minute. Double-stranded PCR-amplified product for hPAM4 V$_H$ was gel-purified, restriction-digested with PstI and BstEII restriction sites and cloned into the complementary PstI/BstEII restriction sites of the heavy chain staging vector, V$_H$pBS2, in which the V$_H$ sequence was fully assembled with the DNA sequence encoding the translation initiation codon and a secretion signal peptide in-frame ligated at the 5'-end and an intron sequence at the 3'-end. V$_H$pBS2 is a modified staging vector of V$_H$pBS (Leung et al., Hybridoma, 13:469, 1994), into which a XhoI restriction site was introduced at sixteen bases upstream of the translation initiation codon to facilitate the next subcloning step. The assembled V$_H$ gene was subcloned as a XhoI-BamHI restriction fragment into the expression vector, pdHL2, which contains the expression cassettes for both human IgG heavy and light chains under the control of IgH enhancer and MT1 promoter, as well as a mouse d/fr gene as a marker for selection and amplification. Since the heavy chain region of pdHL2 lacks a BamHI restriction site, this ligation requires use of a linker to provide a bridge between the BamHI site of the variable chain and the HindIII site present in the pdHL2 vector. The resulting expression vectors were designated as hPAM4 V$_H$pdHL2.

For constructing the full length DNA of the humanized V$_K$ sequence (FIG. 11A), hPAM4 V$_K$A (157-mer) and hPAM4 V$_K$B (156-mer) were synthesized as described above. hPAM4 V$_K$A and V$_K$B were amplified by two short oligonucleotides hPAM4 V$_K$BACK and hPAM4 V$_K$FOR as described above. hPAM4 V$_K$A represents nt 16 to 172 of the hPAM4 V$_K$ domain.

(SEQ ID NO: 61)
5'-CAGTCTCCAT CCTCCCTGTC TGCATCTGTA GGAGACAGAG

TCACCATGAC CTGCAGTGCC AGCTCAAGTG TAAGTTCCAG

CTACTTGTAC TGGTACCAAC AGAAACCAGG GAAAGCCCCC

AAACTCTGGA TTTATAGCAC ATCCAACCTG GCTTCTG-3' hPAM4 V$_K$B represents the minus strand of the hPAM4 V$_K$ domain complementary to nt 153 to 308.

(SEQ ID NO: 62)
5'-GTCCCCCCTC CGAACGTGTA CGGGTACCTA TTCCACTGAT

GGCAGAAATA AGAGGCAGAA TCTTCAGGTT GCAGACTGCT

GATGGTGAGA GTGAAGTCTG TCCCAGATCC ACTGCCACTG

AAGCGAGCAG GGACTCCAGA AGCCAGGTTG GATGTG-3'

The 3'-terminal sequences (20 nt residues) of hPAM4 V$_K$A and V$_K$B are complementary to each other. Under defined PCR condition, the 3'-ends of hPAM4 V$_K$A and V$_K$B anneal to form a short double-stranded DNA flanked by the rest of the long oligonucleotides. Each annealed end served as a primer for the transcription of the single stranded DNA, resulting in a double strand DNA composed of nt 16 to 308 of hPAM4 V$_K$. This DNA was further amplified in the presence of two short oligonucleotides, hPAM4 V$_K$BACK and hPAM4 V$_K$FOR to form the full-length hPAM4 V$_K$. The underlined portions are restriction sites for subcloning as described below.

hPAM4 V$_K$BACK
(SEQ ID NO: 63)
5'-GAC ATC CAG CTG ACC CAG TCT CCA TCC TCC CTG-3' hPAM4 V$_K$FOR
(SEQ ID NO: 64)
5'-TTA GAT CTC CAG TCG TGT CCC CCC TCC GAA CGT-3'

Gel-purified PCR products for hPAM4 V$_K$ were restriction-digested with PvuII and BglII and cloned into the complementary PvuII/BclI sites of the light chain staging vector, V$_K$pBR2. V$_K$pBR2 is a modified staging vector of V$_K$pBR (Leung et al., Hybridoma, 13:469, 1994), into which a XbaI restriction site was introduced at sixteen bases upstream of the translation initiation codon. The assembled V$_K$ genes were subcloned as XbaI-BamHI restriction fragments into the expression vector containing the V$_H$ sequence, hPAM4 V$_H$pdHL2. The resulting expression vectors were designated as hPAM4pdHL2.

Approximately 30 µg of hPAM4pdHL2 was linearized by digestion with SalI and transfected into Sp2/0-Ag14 cells by electroporation at 450 V and 25 µF. The transfected cells were plated into 96-well plates and incubated in a CO$_2$ cell culture incubator for two days and then selected for MTX resistance. Colonies surviving selection emerged in two to three weeks and were screened for human antibody secretion by ELISA assay. Briefly, supernatants (~100 ul) from the surviving colonies were added into the wells of an ELISA microplate precoated with goat anti-human IgG F(ab')$_2$ fragment-specific Ab. The plate was incubated for one hour at room temperature. Unbound proteins were removed by washing three times with wash buffer (PBS containing 0.05% Tween-20). Horseradish peroxidase-conjugated goat anti-human IgG Fc fragment-specific Ab was added to the wells. Following incubation for one hour, a substrate solution (100 µL/well) containing 4 mM o-phenylenediamine dihydrochloride (OPD) and 0.04% H$_2$O$_2$ in PBS was added to the wells after washing. Color was allowed to develop in the dark for 30 minutes and the reaction was stopped by the addition of 50 µL of 4 N H$_2$SO$_4$ solution. The bound human IgG was measured by reading the absorbance at 490 nm on an ELISA reader. Positive cell clones were expanded and hPAM4 was purified from cell culture supernatant by affinity chromatography on a Protein A column.

Figure 12:
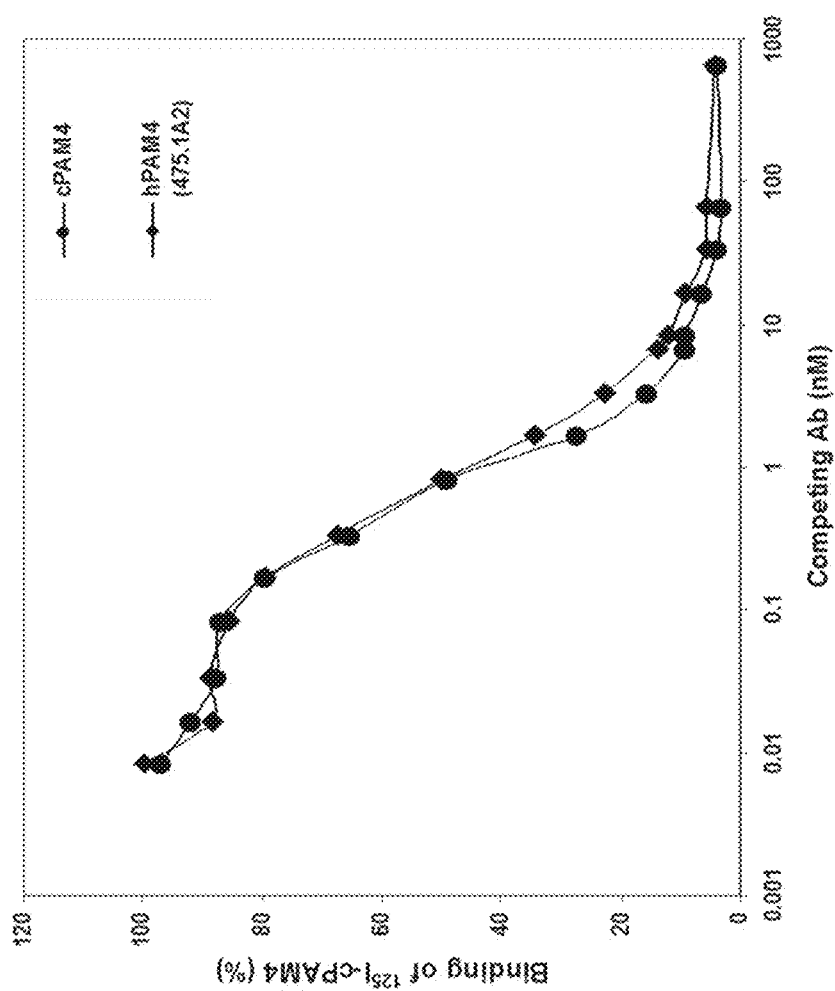
FIG. 12. Binding activity of humanized PAM4 antibody, hPAM4, as compared to the chimeric PAM4, cPAM4. hPAM4 is shown by diamonds and cPAM4 is shown by closed circles. Results indicate comparable binding activity of the hPAM4 antibody and cPAM4 when competing with $^{125}$I-cPAM4 binding to CaPan1 antigens.

The Ag-binding activity of hPAM4 was confirmed by ELISA assay in a microtiter plate coated with pancreas cancer cell extracts. An ELISA competitive binding assay using PAM4-antigen coated plates was developed to assess the Ag-binding affinity of hPAM4 in comparison with that of a chimeric PAM4 composed of murine V and human C domains. Constant amounts of the HRP-conjugated cPAM4 mixed with varying concentrations of cPAM4 or hPAM4 were added to the coated wells and incubated at room temperature for 1-2 h. The amount of HRP-conjugated cPAM4 bound to the CaPan1 Ag was revealed by reading the absorbance at 490 nm after the addition of a substrate solution containing 4 mM o-phenylenediamine dihydrochloride and 0.04% H$_2$O$_2$. As shown by the competition assays in FIG. 12, hPAM4 and cPAM4 antibodies exhibited similar binding activities.

Example 4

Immunohistochemistry Staining Studies

Immunohistochemistry on normal adult tissues showed that the PAM4 reactive epitope was restricted to the gastrointestinal tract where staining was weak, yet positive (Table 7). Normal pancreatic tissue, including ducts, ductules, acini, and islet cells, were negative for staining A PAM4 based enzyme immunoassay with tissue homogenates as antigens generally supported the immunohistology data (Table 8). The PAM4 epitope was absent from normal pancreas and other non-gastrointestinal tissues. In neoplastic tissues, PAM4 was reactive with twenty one out of twenty five (85%) pancreatic cancers (Table 9 and Table 10) and ten out of twenty six colon cancers, but only limited reactivity with tumors of the stomach, lung, breast, ovary, prostate, liver or kidney (Table 10). PAM4 reactivity appeared to correlate with the stage of tumor differentiation, with a greater percentage of staining observed in well differentiated pancreatic cancers than in moderately differentiated or poorly differentiated tumors. Generally, poorly differentiated tumors represent less than 10% of all pancreatic cancers.

These studies have shown the PAM4 reactivity and tissue distribution (both normal and cancer) to be unlike that reported for the CA19.9, DUPAN2, SPAN1, Nd2 and B72.3 antibodies and antibodies against the Lewis antigens. Together with crossblocking studies performed with certain of these MAbs, the data suggests that the PAM4 MAb recognizes a unique and novel epitope. When compared to the antigens recognized by the CA19.9, DUPAN2, and anti-Le' antibodies, the PAM4 antigen appears to be more restricted in its tissue distribution and is reactive with a higher percentage of pancreatic tumors. Moreover, it gives a greater overall intensity of reaction at equivalent concentrations and is reactive with a higher percentage of cells within the pancreatic tumors. Finally, PAM4 was found to be only weakly reactive with three out of twelve chronic pancreatitis specimens, whereas CA19.9 and DUPAN2 were strongly reactive with all twelve specimens. Although it is recognized that specificity is dependent in part upon the type of assay employed and the range and number of tissues examined, the ability of PAM4 to discriminate between normal and neoplastic pancreatic tissue, its ability to react with a large percentage of the cancer specimens, the high intensity of the reactions, and the ability to distinguish between early stage pancreatic cancer and benign conditions such as pancreatitis are important characteristics of this exemplary anti-pancreatic cancer antibody.

TABLE 7

Immunoperoxidase Staining of Normal Adult Tissues with MAb PAM4

| Tissue | Staining Reaction |
| --- | --- |
| Pancreas (22)[a] | − |
| Ducts | − |
| Acini | − |
| Islets | − |
| Submaxillary gland (2) | − |
| Esophagus (2) | − |
| Stomach (3) | + mucus secreting cells |
| Duodenum (3) | + goblet cells |
| Jejunum (3) | + goblet cells |
| Ileum (3) | + goblet cells |
| Colon (5) | + goblet cells |
| Liver (3) | − |
| Gallbladder (2) | − |
| Bronchus (3) | − |
| Lung (3) | − |
| Heart (3) | − |
| Spleen (3) | − |
| Kidney (3) | − |
| Bladder (3) | − |
| Prostate (2) | − |
| Testes (2) | − |
| Uterus (2) | − |
| Ovary (2) | − |

[a]number of individual specimens examined in parentheses

TABLE 8

Monoclonal Antibody PAM4 Reactivity with Normal Adult Tissue

| Homogenates by EIA Tissue | μg/g tissue[a] |
| --- | --- |
| Pancreas | 6.4 |
| Esophagus | 8.1 |
| Stomach | 61.3 |
| Duodenum | 44.7 |
| Jejunum | 60.6 |
| Colon | 74.5 |
| Liver | 0.0 |
| Gallbladder | 5.6 |
| Heart | 3.7 |
| Spleen | 3.4 |
| Kidney | 6.6 |
| Bladder | 4.9 |
| Thyroid | 3.5 |
| Adrenal | 1.3 |
| Ureter | 2.6 |
| Testes | 3.9 |
| CaPan1 Pancreatic Tumor | 569 |

[a]values are mean from two autopsy specimens

TABLE 9

Immunohistochemical Reactivity of Several Monoclonal Antibodies with Pancreatic Tumors

| | Differentiation | PAM4 | CA19.9 | Le[a] | DUPAN2 |
| --- | --- | --- | --- | --- | --- |
| 1 | W | +++ | − | − | +++ |
| 2 | M | ++ | +++ | +++ | + |
| 3 | M | + | − | + | + |
| 4 | M | +++ | +++ | +++ | + |
| 5 | M | ++ | + | − | − |
| 6 | M | + | ND | ND | ND |
| 7 | M* | +++ | +++ | +++ | +++ |
| 8 | M | + | − | − | +++ |
| 9 | M | ++ | + | ++ | − |
| 10 | M* | ++ | ++ | ++ | +++ |
| 11 | M | ++ | +++ | +++ | + |
| 12 | M | ++ | + | + | +++ |
| 13 | M | + | +++ | +++ | + |
| 14 | M | ++ | + | + | ++ |
| 15 | M | +++ | + | + | ++ |
| 16 | M | + | + | ++ | − |
| 17 | M | − | + | + | − |
| 18 | M | ++ | ++ | ++ | ++ |
| 19 | M | +++ | + | +++ | ++ |
| 20 | M | + | − | − | − |
| 21 | M | +++ | +++ | + | ++ |
| 22 | P | + | + | + | +++ |
| 23 | P | − | − | − | − |
| 24 | P | − | − | − | − |

TABLE 9-continued

Immunohistochemical Reactivity of Several Monoclonal
Antibodies with Pancreatic Tumors

| | Differentiation | PAM4 | CA19.9 | Le$^a$ | DUPAN2 |
|---|---|---|---|---|---|
| 25 | P | − | − | + | − |
| TOTAL | | 21/25 | 17/24 | 18/24 | 16/24 |

−: Negative; +: 5-20% of tissue is stained; ++: 21-50% of tissue is stained; +++: >50% of tissue is stained; W, M, P: Well, moderate, or poor differentiation; : Metastatic tissue; ND: Not Done

TABLE 10

Immunoperoxidase Staining of Neoplastic
Tissues with MAb PAM4

| Cancer Tissue | Positive/Total |
|---|---|
| Pancreas | 21/25 |
| Colon | 10/26 |
| Stomach | 1/5 |
| Lung | 1/15 |
| Breast | 0/30 |
| Ovarian | 0/10 |
| Prostate | 0/4 |
| Liver | 0/10 |
| Kidney | 0/4 |

Example 5

In Vivo Biodistribution and Tumor Targeting of
Radiolabeled PAM4

Initial biodistribution studies of PAM4 were carried out in a series of four different xenografted human pancreatic tumors covering the range of expected differentiation. Each of the four tumor lines employed, AsPc1, BxPc3, Hs766T and CaPan1, exhibited concentrations of $^{131}$I-PAM4 within the tumors (range: 21%-48% ID/g on day three) that were significantly (P<0.01-0.001) higher than concomitantly administered nonspecific, isotype-matched Ag8 antibody (range: 3.6%-9.3% ID/g on day three). The biodistribution data were used to estimate potential radiation doses to the tumor of 12,230; 10,684; 6,835; and 15,843 cGy/mCi of injected dose to AsPc1, BxPc3, Hs766T and CaPan1, respectively. With an actual maximum tolerated dose (MTD) of 0.7 mCi, PAM4 could provide substantial rad dose to each of the xenografted tumor models. In each tumor line the blood levels of radiolabeled PAM4 were significantly (P<0.01-0.001) lower than the nonspecific Ag8. Potential radiation doses to the blood from PAM4 were 1.4-4.4 fold lower than from Ag8. When radiation doses to the tumor from PAM4 were normalized to the blood doses from PAM4, the tumors received doses that were 2.2; 3.3; 3.4; and 13.1-fold higher than blood, respectively. Importantly, potential radiation doses to non-tumor tissues were minimal.

The biodistribution of PAM4 was compared with an anti-CEA antibody, MN-14, using the CaPan1 tumor model. The concentration of PAM4 within the tumor was much greater than MN-14 at early timepoints, yielding tumor:blood ratios at day three of 12.7±2.3 for PAM4 compared to 2.7±1.9 for MN-14. Although PAM4 uptake within the tumor was significantly higher than for MN-14 at early timepoints (day one—P<0.001; day three—P<0.01), dosimetry analyses indicated only a 3.2-fold higher dose to the tumor from PAM4 as compared to MN-14 over the fourteen day study period. This was due to a rapid clearance of PAM4 from the tumor, such that at later timepoints similar concentrations of the two antibodies were present within the tumors. A rapid clearance of PAM4 from the tumor was also noted in the BxPc3 and Hs766T but not AsPc1 tumor models. These observations were unlike those reported for other anti-mucin antibodies, as for example G9 and B72.3 in colorectal cancer, where each exhibited longer retention times as compared to the MN-14 antibody. Results from studies on the metabolism of PAM4, indicate that after initial binding to the tumor cell, antibody is rapidly released, possibly being catabolized or being shed as an antigen:antibody complex. The blood clearance is also very rapid. These data suggest that $^{131}$I may not be the appropriate choice of isotope for therapeutic applications. A short-lived isotope, such as $^{90}$Y or $^{188}$Re, which can be administered frequently may be a more effective reagent.

PAM4 showed no evidence of targeting to normal tissues, except in the CaPan1 tumor model, where a small but statistically significant splenic uptake was observed (range 3.1-7.5% ID/g on day-3). This type of splenic targeting has been observed in the clinical application of the anti-mucin antibodies B72.3 and CC49. Importantly, these studies also reported that splenic targeting did not affect tumor uptake of antibody nor did it interfere with interpretation of the nuclear scans. These studies suggested that splenic targeting was not due to crossreactive antigens in the spleen, nor to binding by Fc receptors, but rather to one or more of the following possibilities: direct targeting of antigen trapped in the spleen, or indirect uptake of antigen:antibody complexes formed either in the blood or released from the tumor site. The latter would require the presence of immune complexes in the blood. However, these were not observed when specimens as early as five minutes and as late as seven days were examined by gel filtration (HPLC, GF-250 column); radiolabeled antibody eluted as native material. The former explanation seems more likely in view of the fact that the CaPan1 tumor produced large quantities of PAM4-reactive antigen, 100- to 1000-fold higher than for the other tumor cell lines examined. The lack of splenic targeting by PAM4 in these other tumor lines suggests that this phenomenon was related to excessive antigen production. Splenic targeting can be overcome by increasing the protein dose to 10 μg from the original 2 μg dose. A greater amount of the splenic entrapped antigen presumably was complexed with unlabeled PAM4 rather than radiolabeled antibody. Increasing the protein dose had no adverse effect upon targeting of PAM4 to the tumor or nontumor tissues. In fact, an increase of the protein dose to 100 μg more than doubled the concentration of radiolabeled PAM4 within the CaPan1 tumor.

Example 6

Development of Orthotopic Pancreatic Tumor
Model in Athymic Nude Mice

In order to resemble the clinical presentation of pancreatic cancer in an animal model more closely, we developed an orthotopic model by injecting tumor cells directly into the head of the pancreas. Orthotopic CaPan1 tumors grew progressively without overt symptoms until the development of ascites and death at ten to fourteen weeks. By three to four weeks post-implantation, animals developed a palpable tumor of approximately 0.2 g. Within eight weeks of growth, primary tumors of approximately 1.2 g along with metastases to the liver and spleen were observed (1-3 metastatic tumors/animal; each tumor <0.1 g). At ten to fourteen weeks seeding of the diaphragm with development of ascites were evident. Ascites formation and occasional jaundice were usually the first overt indications of tumor growth. At this time tumors were quite large, 1 to 2 g, and animals had at most only three to four weeks until death occurred.

Radiolabeled $^{131}$I-PAM4, administered to animals bearing four week old orthotopic tumors (approximately 0.2 g) showed specific targeting to the primary tumor with localization indices of 7.9±3.0 at day one increasing to 22.8±15.3 at day fourteen. No evidence of specific targeting to other tissues was noted. In one case where tumor metastases to the liver and spleen were observed, both metastases were targeted, and had high concentrations of radiolabeled antibody. In addition, approximately half of the animals developed a subcutaneous tumor at the incision site. No significant differences were noted in the targeting of orthotopic and subcutaneous tumors within the same animal, and no significant differences were observed in the targeting of orthotopic tumor whether or not the animal had an additional subcutaneous tumor. The estimated radiation doses from PAM4 were 6,704 and 1,655 cGy/mCi to the primary tumor and blood, respectively.

Example 7

Radioimmunotherapy of Pancreatic Cancer

The initial studies on the use of $^{131}$I-PAM4 for therapy were carried out with the CaPan1 tumor, which was grown as a subcutaneous xenograft in athymic mice. Animals bearing a 0.25 g tumor were administered 350 µCi, $^{131}$I-PAM4 in an experiment that also compared the therapeutic effects of a similar dose of nonspecific Ag8. The MTD for administration of $^{131}$I-PAM4 to animals bearing 1 cm$^3$ tumors is 700 µCi. By weeks five and six, the PAM4 treated animals showed a dramatic regression of tumor, and even at week twenty seven, five out of eight remained tumor free. The untreated, as well as Ag8-treated animals, showed rapid progression of tumor growth although a significant difference was noted between these two control groups. At seven weeks, tumors from the untreated group had grown 20.0±14.6-fold from the initial timepoint whereas the $^{131}$I-Ag8-treated tumors had grown only 4.9±1.8-fold. At this time point, the PAM4 tumors had regressed to 0.1±0.1-fold of their original size, a significant difference from both untreated (P<0.001) and nonspecific Ag8-treated (P<0.01) animals.

These data show that CaPan1 tumors were sensitive to treatment with $^{131}$I-PAM4. The outcome, that is, regression or progression of the tumor, was dependent upon several factors including initial tumor size. Thus, groups of animals bearing CaPan1 tumor burdens of 0.25 g, 0.5 g, 1.0 g, or 2.0 g were treated with a single dose of the 350 µCi $^{131}$I-PAM4. The majority of animals having tumors of initial size 0.25 g and 0.5 g (nine of ten animals in each group) showed tumor regression or growth inhibition for at least sixteen weeks post treatment. In the 1.0 g tumor group five out of seven showed no tumor growth for the sixteen week period and in the 2.0 g tumor group six out of nine showed no tumor growth for a period of six weeks before progression occurred. Although a single 350 µCi dose was not as effective against larger tumors, a single dose may not be the appropriate regimen for large tumors.

Toxicity studies indicate the ability to give multiple cycles of radioimmunotherapy, which may be more effective with a larger tumor burden. Animals bearing CaPan1 tumors averaging 1.0 g, were given either a single dose of 350 µCi $^{131}$I-PAM4, two doses given at times zero and four weeks or were left untreated. The untreated group had a mean survival time of 3.7±1.0 weeks (survival defined as time for tumor to reach 5 cm$^3$). Animals died as early as three weeks, with no animal surviving past six weeks. A single dose of 350 µCi $^{131}$I-PAM4 produced a significant increase in the survival time to 18.8±4.2 weeks (P<0.0001). The range of animal deaths extended from weeks thirteen to twenty five. None of the animals were alive at the end of the study period of twenty six weeks.

A significant increase in survival time was observed for the two dose group as compared to the single dose group. Half of the animals were alive at the twenty six week timepoint with tumor sizes from 1.0-2.8 cm$^3$, and a mean tumor growth rate of 1.6±0.7 fold from initial tumor size. For those animals that were non-survivors at twenty six weeks, the mean survival time (17.7±5.3 weeks) was similar to the single dose group.

Therapy studies with PAM4 were also conducted using the orthotopic tumor model. Groups of animals bearing four week old orthotopic tumors (estimated tumor weight of 0.25 g) were either left untreated or treated with a single dose of either 350 µCi $^{131}$I-PAM4 or 350 µCi of $^{131}$I-nonspecific Ag8. The untreated animals had a 50% death rate by week ten with no survivors at week fifteen. Animals administered nonspecific $^{131}$I-Ag8 at four weeks of tumor growth, showed a 50% death rate at week seven with no survivors at week fourteen. Although statistically (logrank analysis) there were no differences between these two groups, it is possible that radiation toxicity had occurred in the Ag8 treated animals. Radiolabeled PAM4 provided a significant survival advantage (P<0.001) as compared to the untreated or Ag8 treated animals, with 70% survival at sixteen weeks, the end of the experiment. At this time the surviving animals were sacrificed to determine tumor size. All animals had tumor with an average weight of 1.2 g, as well as one or two small (<0.1 g) metastases evident in four of the seven animals. At sixteen weeks of growth, these tumors were more representative of an eight-week-old tumor.

Example 8

Combined Modality GEMZAR® Chemotherapy and $^{131}$I-PAM4 Experimental Radioimmunotherapy Initial studies into the combined use of gemcitabine (GEMZAR®) with $^{131}$I-PAM4 radioimmunotherapy were performed as a checkerboard array; a single dose of gemcitabine (0, 100, 200, 500 mg/kg) versus a single dose of $^{131}$I-PAM4 ([MTD=700 µCi] 100%, 75%, 50%, 0% of the MTD). The combined MTD was found to be 500 mg/kg gemcitabine with 350 µCi $^{131}$I-PAM4 (50% MTD). Toxicity, as measured by loss of body weight, went to the maximum considered as nontoxic; that is 20% loss in body weight. Although the combined treatment protocol was significantly more effective than gemcitabine alone, the treatment was no more effective than radioimmunotherapy alone. The next studies were performed at a low dose of gemcitabine and radioimmunotherapy to examine if a true synergistic therapeutic effect would be observed. Athymic nude mice bearing tumors of approximately 1 cm$^3$ (approximately 5% of body weight) were administered gemcitabine, 100 mg/kg on days zero, three, six, nine, and twelve, with 100 µCi of $^{131}$I-PAM4 given on day zero. A therapeutic effect was observed with statistically significant (P<0.0001) regression (two of five tumors less than 0.1 cm$^3$) and/or growth inhibition of the tumors compared to gemcitabine alone. Thus, at lower dosages of therapeutic agent, there surprisingly appears to be a synergistic effect of the combination of gemcitabine and radioimmunotherapy. Of additional note, in terms of body weight, toxicity was not observed. The combination treatment protocol can, if necessary, be delivered in multiple cycles, with the second treatment cycle beginning in week-four, as was done with the radioimmunotherapy-alone studies described above.

Example 9

Effects of Reagent Treatment on Immunoreactivity of PAM4 Antigen

Treatment of pancreatic mucin with DTT (15 min at room temp), completely abolished reactivity with PAM4 (DTT-$EC_{50}$, 0.60±0.00 μM). The only cysteines (cystine bridges) within MUC-1 are present within the transmembrane domain and should not be accessible to DTT. The secreted form of MUC-1 does not contain the transmembrane domain and therefore has no intramolecular cystine bridges. Data from periodate oxidation treatment of pancreatic cancer mucin with 0.05 M sodium periodate for 2 hrs at room temperature yielded 40% loss of immunoreactivity with PAM4 antibody (not shown). Further periodate studies have shown as high as a 60% loss of immunoreactivity with PAM4 antibody (not shown). The results of periodate and DTT studies suggest that the PAM4 epitope is conformationally dependent upon some minimal form of glycosylation, and may be affected by intermolecular disulfide bond formation.

Example 10

Distribution and Cross-Reactivity of the PAM4 Antigen

The expression of the PAM4-epitope within PanINs is atypical for MUC-1. It is similar to the expression reported for MUC5AC as detected by the commercially available MAb-CLH2-2. However, an attempted sandwich immunoassay with PAM4 capture and MAb-CLH2-2 as probe gave negative results. Although this possibly suggests the PAM4 and CLH2-2 epitopes may overlap and thus block each other, the CLH2-2 was reported to be reactive with 42/66 (64%) gastric carcinomas whereas the PAM4 MAb showed reactivity with only 6/40 (15%) of gastric carcinomas and, of these, only in focal reactivity.

Use of the commercially available 45M1, an anti-MUC5AC MAb, as a probe reagent in EIA (with PAM4 as capture) provided positive results, indicating that the two epitopes may be present on the same antigenic molecule. Blocking studies (either direction) indicated that the epitopes bound by 45M1 and PAM4 are in fact two distinct epitopes, as no blocking was observed. Labeling of tissue microarrays consisting of cores from invasive pancreatic carcinoma has demonstrated significant differences for expression of the 45M1 and PAM4 epitopes in individual patient specimens. Of 28 specimens, concordance was observed in only 17 cases (61%). PAM4 was reactive with 24/28 cases (86%) while 45M1 was reactive with 13/28 (46%) cases (not shown).

The results of periodate studies are consistent with glycosylation as a factor in MUC5AC immunoreactivity with the PAM4 antibody. Thus, results of studies with apomucins may not be definitive for antigen determination.

Although based on EIA capture, the PAM4 antibody appears to bind to the same antigenic protein as the 45M1 anti-MUC5AC MAb, it is noted that MUC5AC is not specific to pancreas cancer and it is found in a number of normal tissues (other than the gastric mucosa with which PAM4 is reactive). For example, MUC5AC is found in normal lung, colon and other tissues. PAM4 antibody does not bind to normal lung tissues, except as indicated above in few samples and to a limited or minimal amount.

With respect to the effects of DTT and periodate, it is probable that the peptide core disulfide bridges are identical no matter what tissue produces the protein. A specific amino acid sequence should fold in a specific manner, independent of the tissue source. However, glycosylation patterns may differ dependent upon tissue source.

Example 11

Phage Display Peptide Binding of PAM4 Antibody

PAM4 antibody binding was examined with two different phage display peptide libraries. The first was a linear peptide library consisting of 12 amino acid sequences and the second was a cyclic peptide consisting of 7 amino acid sequences cyclized by a disulfide bridge. We panned the individual libraries alternately against hPAM4 and hLL2 (negative selection with anti-CD22 antibody) for a combined total of 4 rounds, and then screened the phage displayed peptide for reactivity with both hPAM4 and mPAM4 with little to no reactivity against hLL2. Phage binding in a non-specific manner (i.e., binding to epratuzumab [hLL2]) were discarded.

For the linear phage-displayed peptide, the sequence WTWNITKAYPLP (SEQ ID NO:7) was identified 30 times (in 35 sequenced phage), each of which were shown to have reactivity with PAM4 antibodies. A mutational analysis was conducted in which a library based on this sequence and having 7.5% degeneracy at each position, was constructed, panned and screened as before. Variability was noted in the 19 obtained peptide sequences that were positive for PAM4 binding with 7 being identical to the parental sequence, 5 having the sequence WTWNITKEYPQP (SEQ ID NO:65) and the rest being uniquely present. Table 11 shows the results of this mutational analysis. The upper row lists the sequences identified and the lower row lists the frequency with which each of the amino acids was identified in that position. The parent sequence is most frequent (bold) with the next highest variation a substitution of E for A at position 8 and a substitution of Q for L at position 11. It does not appear that these substitutions had any great effect upon immunoreactivity.

TABLE 11

Phage Display Amino Acid Sequence (SEQ ID NO: 116) Variation with Linear Peptide Binding to PAM4 Antibody

| | | | | | | | A | | | | |
|---|---|---|---|---|---|---|---|---|---|---|---|
| | | | | | | K | E | | | L | |
| | | | | | | R | T | | | Q | |
| | | | | | | T | R | | | I | |
| | | | N | | T | N | F | Y | P | M | |
| W | T | W | D | I | R | G | C | T | R | C | P |
| number of occurrences (out of 19 sequences) | | | | | | | | | | | |
| 19 | 19 | 19 | 18 | 19 | 17 | 14 | 10 | 18 | 17 | 11 | 19 |
| | | | 1 | | 2 | 1 | 5 | 1 | 2 | 5 | |
| | | | | | | 2 | 1 | | | 1 | |
| | | | | | | 1 | 1 | | | 1 | |

TABLE 11-continued

Phage Display Amino Acid Sequence
(SEQ ID NO: 116) Variation with Linear
Peptide Binding to PAM4 Antibody

|   |   |   |   |   |   |   | A |   |   |   |
|---|---|---|---|---|---|---|---|---|---|---|
|   |   |   |   |   | K | E |   | L |   |   |
|   |   |   |   |   | R | T |   | Q |   |   |
|   |   |   |   |   | T | R |   | I |   |   |
|   |   |   | N |   | T | N | F | Y | P | M |
| W | T | W | D | I | R | G | C | T | R | C | P |
| analyzed) |   |   |   |   | 1 | 1 |   | 1 |   |   |
|   |   |   |   |   |   | 1 |   |   |   |   |

Results with the phage displayed cyclic library were significantly different from the linear library (Table 12). The sequence ACPEWWGTTC (SEQ ID NO:66) was present in 33 of 35 peptide sequences examined. Analysis of the cyclic library presented the following results (positions with an asterisk were invariant and not subject to selective pressure in the library).

TABLE 12

Phage Display Amino Acid Sequence
(SEQ ID NO: 117) Variation with Linear
Peptide Binding to PAM4 Antibody

|   |   |   |   |   |   |   |   | T |   |
|---|---|---|---|---|---|---|---|---|---|
|   |   |   |   |   |   |   |   | M |   |
|   |   |   |   |   |   |   | T | S |   |
|   |   | P |   |   |   | G | G | Q |   |
| A | C | Y | E | W | W | S | S | P | C |
| number of | * | * | 33 | 35 | 35 | 35 | 34 | 29 | 28 | * |
| occurrences |   | 2 |   |   |   |   | 1 | 5 | 4 |   |
| (out of 19 |   |   |   |   |   |   |   | 1 | 1 |   |
| sequences |   |   |   |   |   |   |   |   | 1 |   |
| analyzed) |   |   |   |   |   |   |   |   | 1 |   |

The two cysteines (at positions 2 and 10) formed a disulfide bridge. Substitution of T at position 9 with any amino acid greatly affected immunoreactivity. The sequence GTTGTTC (SEQ ID NO:67) is present within the MUC5AC protein towards the amino terminus as compared to the cyclic peptide sequence shown above, which shows homology at the C-terminal end of the consensus peptide sequence. However, the cyclic peptide only showed approximately 10% of the immunoreactivity of the linear sequence with the PAM4 antibody. Both linear and cyclic consensus sequences are associated with a cysteine, which may or may not relate to the effect of DTT on MUC5AC immunoreactivity.

The results reported herein indicate that the PAM4 epitope is dependent upon a specific conformation which may be produced by disulfide bridges, as well as a specific glycosylation pattern.

Example 12

Immunohistology of Pancreatic Cancer in a Pancreatitis Specimen

Several pathologic conditions predispose patients to the development of pancreatic carcinoma, such as pancreatitis, diabetes, smoking and others. Within this pre-selected group of patients, screening measures are particularly important for the early detection of pancreatic neoplasia. We examined 9 specimens of chronic pancreatitis tissue from patients having primary diagnosis of this disease. We employed an anti-CD74 MAb, LL1, as an indicator of inflammatory infiltrate, and MAb-MA5 as a positive control for pancreatic ductal and acinar cells. Whereas the two control MAbs provided immunohistologic evidence consistent with pancreatitis, in no instance did PAM4 react with inflamed pancreatic tissue. However, in one case, a moderately differentiated pancreatic adenocarcinoma was also present within the tissue specimen. PAM4 gave an intense stain of the neoplastic cells within this tumor. In a second case, while the inflamed tissue was negative with PAM4, a small PanIN precursor lesion was identified that was labeled with PAM4. Labeling of the PanIN within this latter specimen is consistent with early detection of pancreatic neoplasia in a patient diagnosed with a non-malignant disease. These results show that detection and/or diagnosis using the PAM4 antibody may be performed with high sensitivity and selectivity for pancreatic neoplasia against a background of benign pancreatic tissues.

Example 13

Therapy of a Patient with Inoperable and Metastatic Pancreatic Carcinoma

Figure 13:
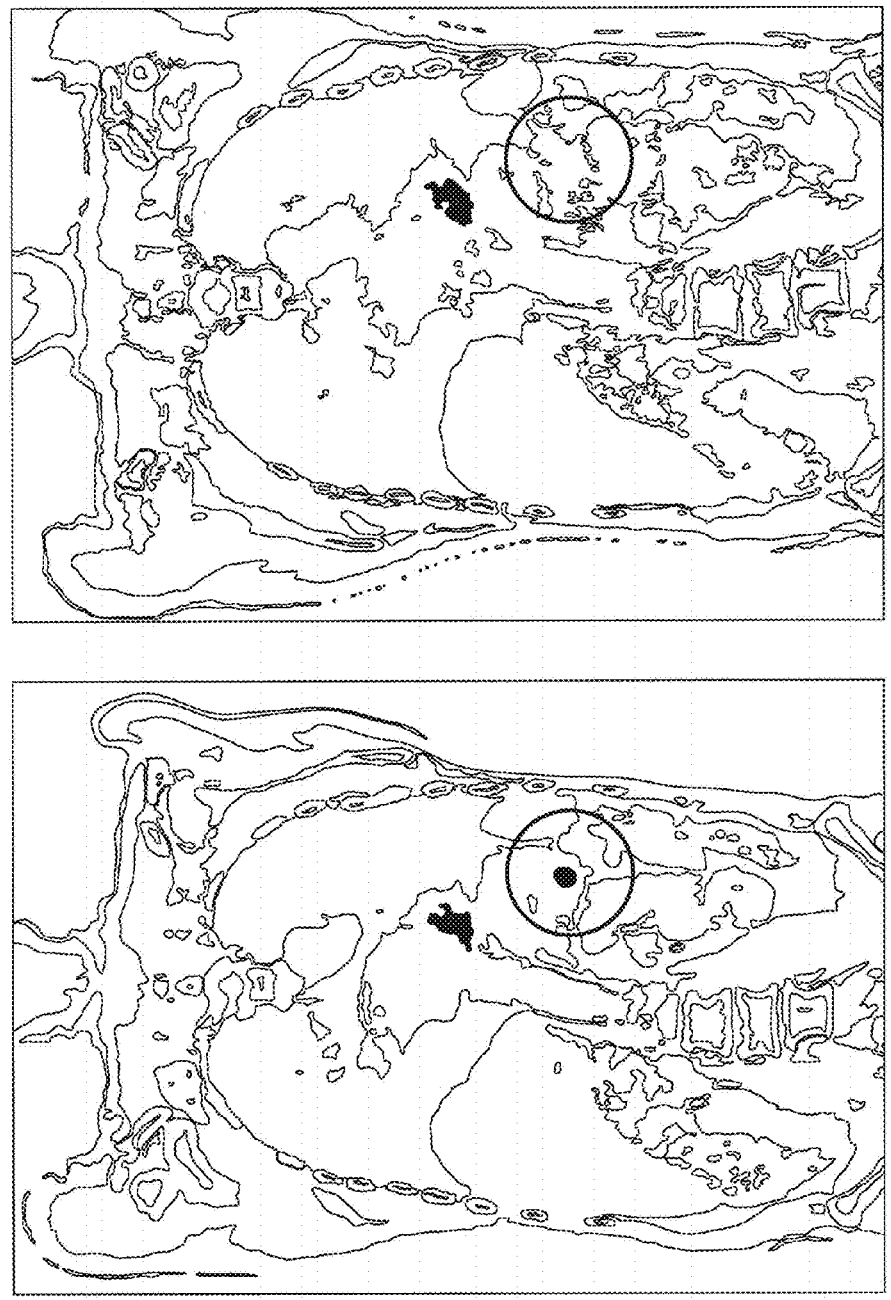
FIG. 13. PET/CT fusion images for a patient with inoperable metastatic pancreatic cancer treated with fractionated $^{90}$Y-hPAM4 plus gemcitabine, before therapy (left side) and post-therapy (right side). The circle indicates the location of the primary lesion, which shows a significant decrease in PET/CT intensity following therapy.
Figure 14:
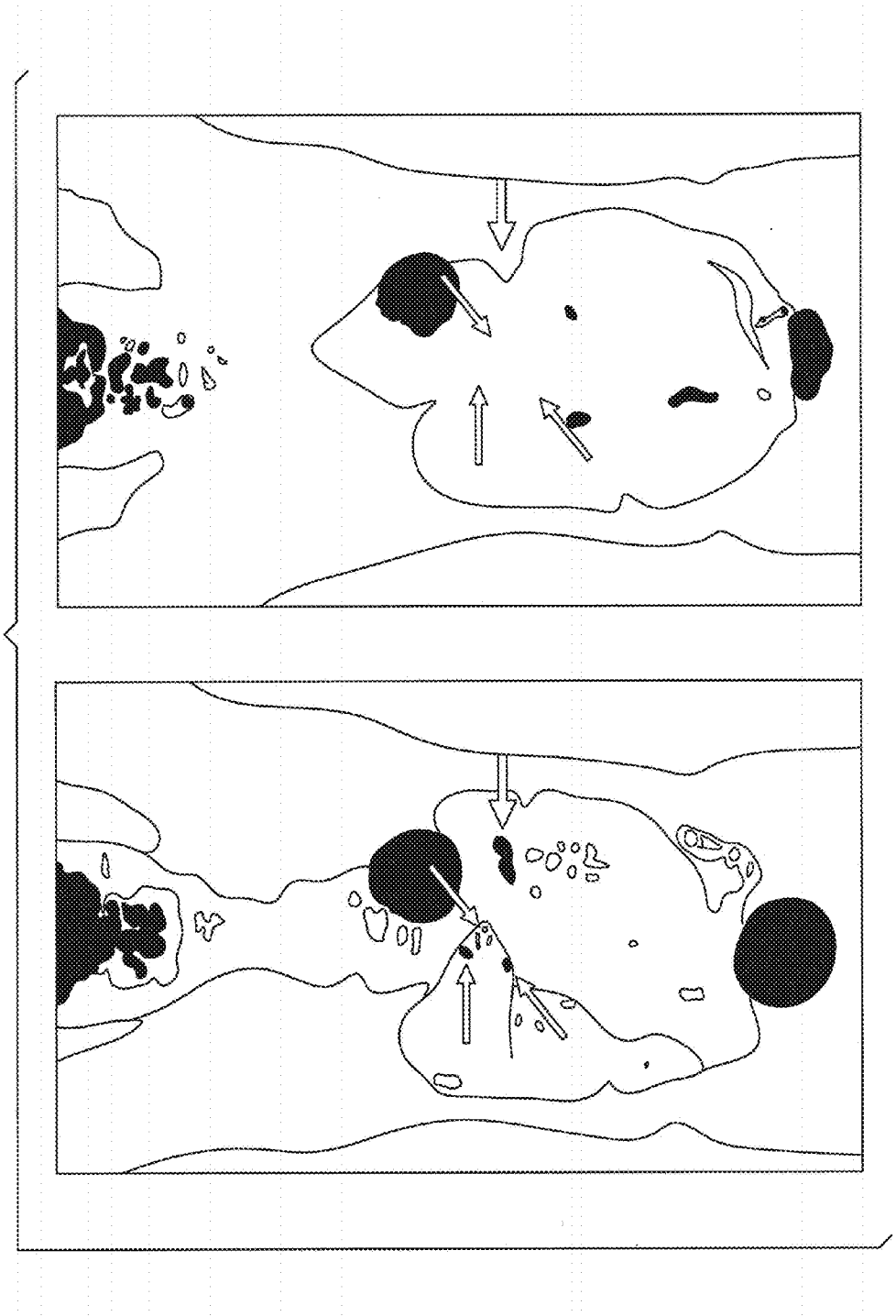
FIG. 14. 3D PET images for a patient with inoperable metastatic pancreatic cancer treated with fractionated $^{90}$Y-hPAM4 plus gemcitabine, before therapy (left side) and post-therapy (right side). Arrows point to the locations of the primary lesion (on right) and metastases (on left), each of which shows a significant decrease in PET image intensity after therapy with radiolabeled hPAM4 plus gemcitabine.

Patient 118-001, CWG, is a 63-year-old man with Stage-IV pancreatic adenocarcinoma with multiple liver metastases, diagnosed in November of 2007. He agreed to undertake combined radioimmunotherapy and gemcitabine chemotherapy as a first treatment strategy, and was then given a first therapy cycle of 6.5 mCi/m$^2$ of $^{90}$Y-hPAM4, combined with 200 mg/m$^2$ gemcitabine, whereby the gemcitabine was given once weekly on weeks 1-4 and $^{90}$Y-hPAM4 was given once-weekly on weeks 2-4 (3 doses). Two months later, the same therapy cycle was repeated, because no major toxicities were noted after the first cycle. Already 4 weeks after the first therapy cycle, CT evidence of a reduction in the diameters of the primary tumor and 2 of the 3 liver metastases surprisingly was noted, and this was consistent with significant decreases in the SUV values of FDG-PET scans, with 3 of the 4 tumors returning to normal background SUV levels at this time (FIG. 13 and FIG. 14). The patient's pre-therapy CA-19.9 level of 1,297 dropped to a low level of 77, further supportive of the therapy being effective. Table 13 shows the effects of combined radioimmunotherapy with $^{90}$Y-hPAM4 and gemcitabine chemotherapy in this patient. It was surprising and unexpected that such low doses of the radionuclide conjugated to the antibody combined with such low, nontoxic, doses of gemcitabine showed such antitumor activity even after only a single course of this therapy.

TABLE 13

Effects of Combined Radioimmunotherapy with $^{90}$Y-hPAM4 and Gemcitabine Chemotherapy in Metastatic Pancreatic Carcinoma

| Tumor Location | Baseline Longest Diameter (cm) | 4 wk post-Tx Longest Diameter (cm) | Baseline PET (SUV) | 4 wk post-Tx PET (SUV) |
|---|---|---|---|---|
| Pancreatic tail (primary) | 4.5 | 4.3 | 9.2 | 4.2 |
| L hepatic met | 1.9 | 1.9 | 4.1 | Background |
| R post hepatic met | 1.7 | 1.6 | 3.7 | Background |
| R central hepatic met | 1.9 | 1.2 | 3.2 | Background |

Example 14

Therapy of a Patient with Inoperable Metastatic Pancreatic Carcinoma

A 56-year-old male with extensive, inoperable adenocarcinoma of the pancreas, with several liver metastases ranging from 1 to 4 cm in diameter, substantial weight loss (30 lbs of weight or more), mild jaundice, lethargy and weakness, as well as abdominal pains requiring medication, is given 4 weekly infusions of gemcitabine at doses of 200 mg/m² each. On the last three gemcitabine infusions, $^{90}$Y-DOTA-hPAM4 radiolabeled humanized antibody is administered at a dose of 10 mCi/m² of $^{90}$Y and 20 mg antibody protein, in a two-hour i.v. infusion. Two weeks later, the patient is given a course of gemcitabine chemotherapy consisting of 3 weekly doses of 600 mg/m² by i.v. infusion. The patient is then evaluated 4 weeks later, and has a mild leukopenia (grade-2), no other major blood or enzyme changes over baseline, but shows an improvement in the blood CA19.9 titer from 5,700 to 1,200 and a decrease in jaundice, with an overall subjective improvement. This follows 3 weeks later with a repeat of the cycle of lower-dose gemcitabine (weekly×4), with 3 doses of $^{90}$Y-DOTA-hPAM4. Four weeks later, the patient is reevaluated, and the CT and PET scans confirm an approximately 40% reduction of total tumor mass (primary cancer and metastases), with a further reduction of the CA19.9 titer to 870. The patient regains appetite and activity, and is able to return to more usual daily activities without the need for pain medication. He gains 12 lbs after beginning this experimental therapy. A repeat of the scans and blood values indicates that this response is maintained 6 weeks later.

Example 15

Preparation of DNL™ Constructs for Pretargeting

DDD and AD Fusion Proteins

The DNL™ technique can be used to make dimers, trimers, tetramers, hexamers, etc. comprising virtually any antibodies or fragments thereof or other effector moieties. For certain preferred embodiments, IgG antibodies or Fab antibody fragments may be produced as fusion proteins containing either a dimerization and docking domain (DDD) or anchoring domain (AD) sequence. Although in preferred embodiments the DDD and AD moieties are produced as fusion proteins, the skilled artisan will realize that other methods of conjugation, such as chemical cross-linking or click chemistry, may be utilized within the scope of the claimed methods and compositions.

Bispecific antibodies may be formed by combining a Fab-DDD fusion protein of a first antibody with a Fab-AD fusion protein of a second antibody. Alternatively, constructs may be made that combine IgG-AD fusion proteins with Fab-DDD fusion proteins. The technique is not limiting and any protein or peptide of use may be produced as an AD or DDD fusion protein for incorporation into a DNL™ construct. Where chemical cross-linking is utilized, the AD and DDD conjugates are not limited to proteins or peptides and may comprise any molecule that may be cross-linked to an AD or DDD sequence using any cross-linking technique known in the art. In certain exemplary embodiments, a polyethylene glycol (PEG) or other polymeric moiety may be incorporated into a DNL™ construct, as described in further detail below.

For pretargeting applications, an antibody or fragment containing a binding site for an antigen associated with a diseased tissue, such as a tumor-associated antigen (TAA), may be combined with a second antibody or fragment that binds a hapten on a targetable construct, to which a therapeutic and/or diagnostic agent is attached. The DNL™-based bispecific antibody is administered to a subject, circulating antibody is allowed to clear from the blood and localize to target tissue, and the conjugated targetable construct is added and binds to the localized antibody for diagnosis or therapy.

Independent transgenic cell lines may be developed for each Fab or IgG fusion protein. Once produced, the modules can be purified if desired or maintained in the cell culture supernatant fluid. Following production, any DDD-fusion protein module can be combined with any AD-fusion protein module to generate a bispecific DNL™ construct. For different types of constructs, different AD or DDD sequences may be utilized. Exemplary DDD and AD sequences are provided below.

```
DDD1:
                                        (SEQ ID NO: 68)
SHIQIPPGLTELLQGYTVEVLRQQPPDLVEFAVEYFTRLREARA

DDD2:
                                        (SEQ ID NO: 69)
CGHIQIPPGLTELLQGYTVEVLRQQPPDLVEFAVEYFTRLREARA

AD1:
                                        (SEQ ID NO: 70)
QIEYLAKQIVDNAIQQA

AD2:
                                        (SEQ ID NO: 71)
CGQIEYLAKQIVDNAIQQAGC
```

The skilled artisan will realize that DDD1 and DDD2 comprise the DDD sequence of the human RIIα form of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                        (SEQ ID NO: 72)
SLRECELYVQKHNIQALLKDSIVQLCTARPERPMAFLREYFERLEKEEAK

DDD3C
                                        (SEQ ID NO: 73)
MSCGGSLRECELYVQKHNIQALLKDSIVQLCTARPERPMAFLREYF

ERLEKEEAK

AD3
                                        (SEQ ID NO: 74)
CGFEELAWKIAKMIWSDVFQQGC
```

Expression Vectors

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The dicistronic mammalian expression vector directs the synthesis of the heavy and light chains of IgG. The vector sequences are mostly identical for many different IgG-pdHL2 constructs, with the only differences existing in the variable domain ($V_H$ and $V_L$) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human RIIα (referred to as DDD1). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD1), which was generated using bioinformatics and peptide array technology and shown to bind RIIα dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge (PKSC (SEQ ID NO: 118)) followed by four glycines and a serine, with the final two codons (GS) comprising a Bam HI restriction site. The 410 bp PCR amplimer was cloned into the PGEMT® PCR cloning vector (PROMEGA®, Inc.) and clones were screened for inserts in the T7 (5') orientation.

A duplex oligonucleotide, designated (G$_4$S)$_2$DDD1 ('(G$_4$S)$_2$' disclosed as SEQ ID NO: 119), was synthesized by Sigma GENOSYS® (Haverhill, UK) to code for the amino acid sequence of DDD1 preceded by 11 residues of the linker peptide, with the first two codons comprising a BamHI restriction site. A stop codon and an EagI restriction site are appended to the 3' end. The encoded polypeptide sequence is shown below.

(SEQ ID NO: 75)
GSGGGGSGGGGSHIQIPPGLTELLQGYTVEVLRQQPPDLVEFAVEYFTR

LREARA

Two oligonucleotides, designated RIIA1-44 top and RIIA1-44 bottom, which overlap by 30 base pairs on their 3' ends, were synthesized and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into PGEMT® and screened for inserts in the T7 (5') orientation.

A duplex oligonucleotide was synthesized to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below.

(SEQ ID NO: 76)
GSGGGGSGGGGSQIEYLAKQIVDNAIQQA

Two complimentary overlapping oligonucleotides encoding the above peptide sequence, designated AKAP-IS Top and AKAP-IS Bottom, were synthesized and annealed. The duplex was amplified by PCR. The amplimer was cloned into the PGEMT® vector and screened for inserts in the T7 (5') orientation.

Ligating DDR1 with CH1

A 190 bp fragment encoding the DDD1 sequence was excised from PGEMT® with BamHI and NotI restriction enzymes and then ligated into the same sites in CH1-PGEMT® to generate the shuttle vector CH1-DDD1-PGEMT®.

Ligating AD1 with CH1

A 110 bp fragment containing the AD1 sequence was excised from PGEMT® with BamHI and NotI and then ligated into the same sites in CH1-PGEMT® to generate the shuttle vector CH1-AD1-PGEMT®.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective pGemT shuttle vector.

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN-14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA19, hA20 and many others. Generally, the antibody variable region coding sequences were present in a pdHL2 expression vector and the expression vector was converted for production of an AD- or DDD-fusion protein as described above. The AD- and DDD-fusion proteins comprising a Fab fragment of any of such antibodies may be combined, in an approximate ratio of two DDD-fusion proteins per one AD-fusion protein, to generate a trimeric DNL™ construct comprising two Fab fragments of a first antibody and one Fab fragment of a second antibody.

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

The expression vector was engineered as follows. Two overlapping, complimentary oligonucleotides, which comprise the coding sequence for part of the linker peptide and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-PGEMT®, which was prepared by digestion with BamHI and PstI, to generate the shuttle vector CH1-DDD2-PGEMT®. A 507 bp fragment was excised from CH1-DDD2-PGEMT® with SacII and EagI and ligated with the IgG expression vector hMN-14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

h679-Fd-AD2-pdHL2 h679-Fab-AD2, was designed to pair as B to C-DDD2-Fab-hMN-14 as A. h679-Fd-AD2-pdHL2 is an expression vector for the production of h679-Fab-AD2, which possesses an anchoring domain sequence of AD2 appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-PGEMT®, which was prepared by digestion with BamHI and SpeI, to generate the shuttle vector CH1-AD2-PGEMT®. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Example 16

Production of AD- and DDD-Linked Fab and IgG Fusion Proteins from Multiple Antibodies Using the techniques described in the preceding Example, the IgG and Fab fusion proteins shown in Table 14 were constructed and incorporated into DNL™ constructs. The fusion proteins retained the antigen-binding characteristics of the parent antibodies and the DNL™ constructs exhibited the antigen-binding activities of the incorporated antibodies or antibody fragments.

TABLE 14

Fusion proteins comprising IgG or Fab

| Fusion Protein | Binding Specificity |
| --- | --- |
| C-AD1-Fab-h679 | HSG |
| C-AD2-Fab-h679 | HSG |
| C-(AD)$_2$-Fab-h679 | HSG |
| C-AD2-Fab-h734 | Indium-DTPA |
| C-AD2-Fab-hA20 | CD20 |
| C-AD2-Fab-hA20L | CD20 |
| C-AD2-Fab-hL243 | HLA-DR |
| C-AD2-Fab-hLL2 | CD22 |
| N-AD2-Fab-hLL2 | CD22 |
| C-AD2-IgG-hMN-14 | CEACAM5 |
| C-AD2-IgG-hR1 | IGF-1R |
| C-AD2-IgG-hRS7 | EGP-1 |
| C-AD2-IgG-hPAM4 | MUC |
| C-AD2-IgG-hLL1 | CD74 |
| C-DDD1-Fab-hMN-14 | CEACAM5 |
| C-DDD2-Fab-hMN-14 | CEACAM5 |
| C-DDD2-Fab-h679 | HSG |
| C-DDD2-Fab-hA19 | CD19 |
| C-DDD2-Fab-hA20 | CD20 |
| C-DDD2-Fab-hAFP | AFP |
| C-DDD2-Fab-hL243 | HLA-DR |
| C-DDD2-Fab-hLL1 | CD74 |
| C-DDD2-Fab-hLL2 | CD22 |
| C-DDD2-Fab-hMN-3 | CEACAM6 |
| C-DDD2-Fab-hMN-15 | CEACAM6 |
| C-DDD2-Fab-hPAM4 | MUC |
| C-DDD2-Fab-hR1 | IGF-1R |
| C-DDD2-Fab-hRS7 | EGP-1 |
| N-DDD2-Fab-hMN-14 | CEACAM5 |

Example 17

Sequence Variants for DNL™

In certain preferred embodiments, the AD and DDD sequences incorporated into the DNL™ construct comprise the amino acid sequences of AD1, AD2, AD3, DDD1, DDD2, DDD3 or DDD3C as discussed above. However, in alternative embodiments sequence variants of AD and/or DDD moieties may be utilized in construction of the DNL™ complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

PKA RIα
(SEQ ID NO: 77)
SLRECELYVQKHNIQALLKDVSIVQLCTARPERPMAFLREYFEKLEK

EEAK

PKA RIβ
(SEQ ID NO: 78)
SLKGCELYVQLHGIQQVLKDCIVHLCISKPERPMKFLREHFEKLEKEE

NRQILA

PKA RIIα
(SEQ ID NO: 79)
SHIQIPPGLTELLQGYTVEVGQQPPDLVDFAVEYFTRLREARRQ

PKA RIIβ

```
                                     (SEQ ID NO: 80)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006) examined the crystal structure of the AD-DDD binding interaction and concluded that the human DDD sequence contained a number of conserved amino acid residues that were important in either dimer formation or AKAP binding, underlined in SEQ ID NO:68 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                     (SEQ ID NO: 68)
SHIQIPPGLTELLQGYTVEVLRQQPPDLVEFAVEYFTRLREARA
```

Alto et al. (2003) performed a bioinformatic analysis of the AD sequence of various AKAP proteins to design an RII selective AD sequence called AKAP-IS (SEQ ID NO:70), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:70. The skilled artisan will realize that in designing sequence variants of the AD sequence, one would desirably avoid changing any of the underlined residues, while conservative amino acid substitutions might be made for residues that are less critical for DDD binding.

AKAP-IS Sequence

```
QIEYLAKQIVDNAIQQA        (SEQ ID NO: 70)
```

Gold (2006) utilized crystallography and peptide screening to develop a SuperAKAP-IS sequence (SEQ ID NO:81), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL™ constructs. Other alternative sequences that might be substituted for the AKAP-IS AD sequence are shown in SEQ ID NO:82-84. Substitutions relative to the AKAP-IS sequence are underlined. It is anticipated that, as with the AD2 sequence shown in SEQ ID NO:68, the AD moiety may also include the additional N-terminal residues cysteine and glycine and C-terminal residues glycine and cysteine.

SuperAKAP-IS

```
QIEYVAKQIVDYAIHQA        (SEQ ID NO: 81)
```

Alternative AKAP Sequences

```
QIEYKAKQIVDHAIHQA        (SEQ ID NO: 82)

QIEYHAKQIVDHAIHQA        (SEQ ID NO: 83)

QIEYVAKQIVDHAIHQA        (SEQ ID NO: 84)
```

Figure 2:
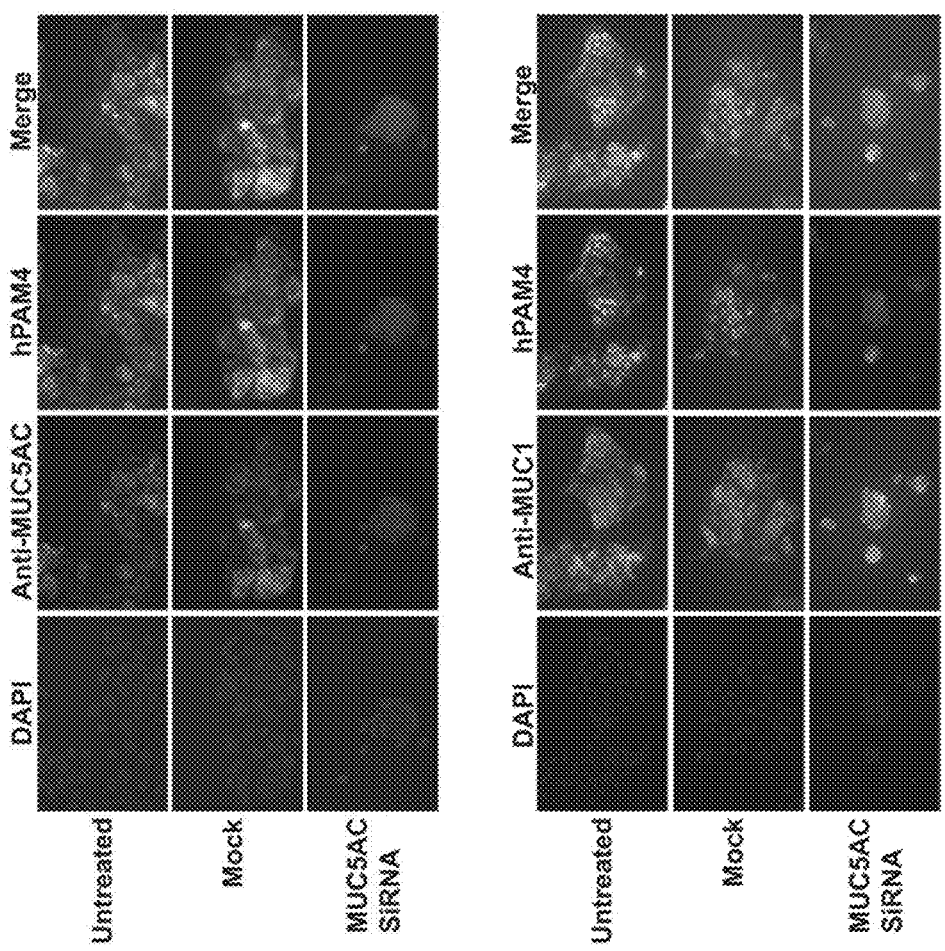
FIG. 2. Co-knockdown of PAM4 antigen and MUC5AC by MUC5AC-specific siRNA. CFPAC-1 cells were treated with a MUC5AC-specific siRNA, followed by immunostaining with DAPI, hPAM4, and 2-11M1 (anti-MUC5AC), or with DAPI, hPAM4 and anti-MUC1. Untreated Cells or cells treated with only the transfection agent (Mock) served as controls. Cells treated with MUC5AC-specific siRNA lost the binding to anti-MUC5AC and hPAM4 concurrently, with little effect on the binding to anti-MUC1.

FIG. 2 of Gold et al. disclosed additional DDD-binding sequences from a variety of AKAP proteins, shown below.

```
RII-SPECIFIC AKAPS
AKAP-KL
                         (SEQ ID NO: 85)
PLEYQAGLLVQNAIQQAI

AKAP79
                         (SEQ ID NO: 86)
LLIETASSLVKNAIQLSI

AKAP-LBC
                         (SEQ ID NO: 87)
LIEEAASRIVDAVIEQVK

RI-SPECIFIC AKAPS
AKAPCE
                         (SEQ ID NO: 88)
ALYQFADRFSELVISEAL

RIAD
                         (SEQ ID NO: 89)
LEQVANQLADQIIKEAT

PV38
                         (SEQ ID NO: 90)
FEELAWKIAKMIWSDVF

DUAL-SPECIFICITY AKAPS
AKAP7
                         (SEQ ID NO: 91)
ELVRLSKRLVENAVLKAV

MAP2D
                         (SEQ ID NO: 92)
TAEEVSARIVQVVTAEAV

DAKAP1
                         (SEQ ID NO: 93)
QIKQAAFQLISQVILEAT

DAKAP2
                         (SEQ ID NO: 94)
LAWKIAKMIVSDVMQQ
```

Stokka et al. (2006) also developed peptide competitors of AKAP binding to PKA, shown in SEQ ID NO:95-97. The peptide antagonists were designated as Ht31 (SEQ ID NO:95), RIAD (SEQ ID NO:96) and PV-38 (SEQ ID NO:97). The Ht-31 peptide exhibited a greater affinity for the RII isoform of PKA, while the RIAD and PV-38 showed higher affinity for RI.

```
Ht31
                         (SEQ ID NO: 95)
DLIEEAASRIVDAVIEQVKAAGAY
```

-continued

RIAD
LEQYANQLADQIIKEATE (SEQ ID NO: 96)

PV-38
FEELAWKIAKMIWSDVFQQC (SEQ ID NO: 97)

Hundsrucker et al. (2006) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 15 below. AKAPIS represents a synthetic RII subunit-binding peptide. All other peptides are derived from the RII-binding domains of the indicated AKAPs.

TABLE 15

AKAP Peptide sequences
Peptide Sequence

| | |
|---|---|
| AKAPIS | QIEYLAKQIVDNAIQQA (SEQ ID NO: 70) |
| AKAPIS-P | QIEYLAKQIPDNAIQQA (SEQ ID NO: 98) |
| Ht31 | KGADLIEEAASRIVDAVIEQVKAAG (SEQ ID NO: 99) |
| Ht31-P | KGADLIEEAASRIPDAPIEQVKAAG (SEQ ID NO: 100) |
| AKAP7δ-wt-pep | PEDAELVRLSKRLVENAVLKAVQQY (SEQ ID NO: 101) |
| AKAP7δ-L304T-pep | PEDAELVRTSKRLVENAVLKAVQQY (SEQ ID NO: 102) |
| AKAP7δ-L308D-pep | PEDAELVRLSKRDVENAVLKAVQQY (SEQ ID NO: 103) |
| AKAP7δ-P-pep | PEDAELVRLSKRLPENAVLKAVQQY (SEQ ID NO: 104) |
| AKAP7δ-PP-pep | PEDAELVRLSKRLPENAPLKAVQQY (SEQ ID NO: 105) |
| AKAP7δ-L314E-pep | PEDAELVRLSKRLVENAVEKAVQQY (SEQ ID NO: 106) |
| AKAP1-pep | EEGLDRNEEIKRAAFQIISQVISEA (SEQ ID NO: 107) |
| AKAP2-pep | LVDDPLEYQAGLLVQNAIQQAIAEQ (SEQ ID NO: 108) |
| AKAP5-pep | QYETLLIETASSLVKNAIQLSIEQL (SEQ ID NO: 109) |
| AKAP9-pep | LEKQYQEQLEEEVAKVIVSMSIAFA (SEQ ID NO: 110) |
| AKAP10-pep | NTDEAQEELAWKIAKMIVSDIMQQA (SEQ ID NO: 111) |
| AKAP11-pep | VNLDKKAVLAEKIVAEAIEKAEREL (SEQ ID NO: 112) |
| AKAP12-pep | NGILELETKSSKLVQNIIQTAVDQF (SEQ ID NO: 113) |
| AKAP14-pep | TQDKNYEDELTQVALALVEDVINYA (SEQ ID NO: 114) |
| Rab32-pep | ETSAKDNINIEEAARFLVEKILVNH (SEQ ID NO: 115) |

Residues that were highly conserved among the AD domains of different AKAP proteins are indicated below by underlining with reference to the AKAP IS sequence (SEQ ID NO:70). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

AKAP-IS
QIEYL<u>AK</u>QIVDN<u>AI</u>QQA (SEQ ID NO: 70)

Can et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:68. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 68)
SH<u>*IQIPP*</u><u>*GL*</u>T<u>*ELLQGYT*</u>V<u>*EVLRQQ*</u>PP<u>*DLVE*</u>F<u>*AVE*</u>Y<u>*FT*</u>R<u>*LREA*</u>RA

The skilled artisan will realize that these and other amino acid substitutions in the antibody moiety or linker portions of the DNL™ constructs may be utilized to enhance the therapeutic and/or pharmacokinetic properties of the resulting DNL™ constructs.

Example 18

Generation of TF2 DNL™ Pretargeting Construct

A trimeric DNL™ construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP 291 affinity chromatography. Before the addition of TCEP, SE-HPLC did not show any evidence of $a_2b$ formation. Addition of 5 mM TCEP rapidly resulted in the formation of $a_2b$ complex consistent with a 157 kDa protein expected for the binary structure. TF2 was purified to near homogeneity by IMP 291 affinity chromatography (not shown). IMP 291 is a synthetic peptide containing the HSG hapten to which the 679 Fab binds (Rossi et al., 2005, Clin Cancer Res 11:7122s-29s). SE-HPLC analysis of the IMP 291 unbound fraction demonstrated the removal of $a_4$, $a_2$ and free kappa chains from the product (not shown).

Non-reducing SDS-PAGE analysis demonstrated that the majority of TF2 exists as a large, covalent structure with a relative mobility near that of IgG (not shown). The additional bands suggest that disulfide formation is incomplete under the experimental conditions (not shown). Reducing SDS-PAGE shows that any additional bands apparent in the non-reducing gel are product-related (not shown), as only bands representing the constituent polypeptides of TF2 were evident (not shown). However, the relative mobilities of each of the four polypeptides were too close to be resolved. MALDI-TOF mass spectrometry (not shown) revealed a single peak of 156,434 Da, which is within 99.5% of the calculated mass (157,319 Da) of TF2.

The functionality of TF2 was determined by BIACORE® assay. TF2, C-DDD1-hMN-14+h679-AD1 (used as a control sample of noncovalent $a_2b$ complex), or C-DDD2-hMN-14+ h679-AD2 (used as a control sample of unreduced $a_2$ and b components) were diluted to 1 µg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

Example 19

Production of TF10 Bispecific Antibody for Pretargeting

A similar protocol was used to generate a trimeric TF10 DNL™ construct, comprising two copies of a C-DDD2-Fab-hPAM4 and one copy of C-AD2-Fab-679. The cancer-targeting antibody component in TF10 was derived from hPAM4, a humanized anti-MUC5AC MAb that has been studied in detail as a radiolabeled MAb (e.g., Gold et al., Clin. Cancer Res. 13: 7380-7387, 2007). The hapten-binding component was derived from h679, a humanized anti-histaminyl-succinyl-glycine (HSG) MAb. The TF10 bispecific ([hPAM4]$_2$×h679) antibody was produced using the method disclosed for production of the (anti CEA)$_2$×anti HSG bsAb TF2, as described above. The TF10 construct bears two humanized PAM4 Fabs and one humanized 679 Fab.

The two fusion proteins (hPAM4-DDD and h679-AD2) were expressed independently in stably transfected myeloma cells. The tissue culture supernatant fluids were combined, resulting in a two-fold molar excess of hPAM4-DDD. The reaction mixture was incubated at room temperature for 24 hours under mild reducing conditions using 1 mM reduced glutathione. Following reduction, the DNL™ reaction was completed by mild oxidation using 2 mM oxidized glutathione. TF10 was isolated by affinity chromatography using IMP 291-affigel resin, which binds with high specificity to the h679 Fab.

A full tissue histology and blood cell binding panel has been examined for hPAM4 IgG and for an anti-CEA x anti-HSG bsMAb that is entering clinical trials. hPAM4 binding was restricted to very weak binding to the urinary bladder and stomach in ⅓ specimens (no binding was seen in vivo), and no binding to normal tissues was attributed to the anti-CEA x anti-HSG bsMAb. Furthermore, in vitro studies against cell lines bearing the H1 and H2 histamine receptors showed no antagonistic or agonistic activity with the IMP 288 di-HSG peptide, and animal studies in 2 different species showed no pharmacologic activity of the peptide related to the histamine component at doses 20,000 times higher than that used for imaging. Thus, the HSG-histamine derivative does not have pharmacologic activity.

Example 20

Figure 15A:
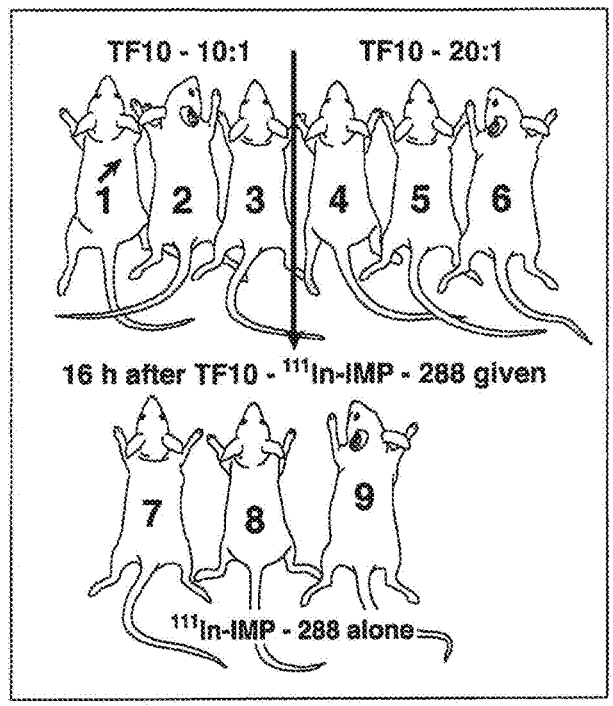
FIG. 15A. In vivo imaging of tumors using an $^{111}$In-labeled diHSG peptide (IMP 288) with or without pretargeting TF10 bispecific anti-pancreatic cancer MUC5AC antibody.
Figure 15B:
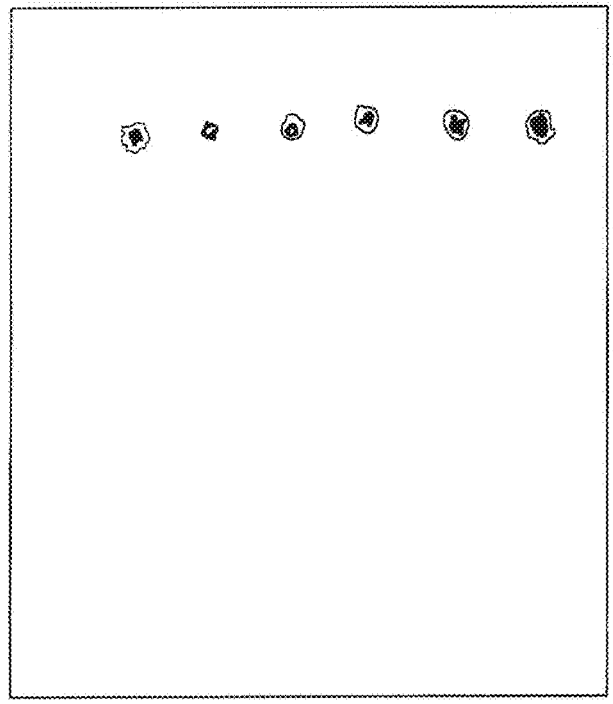
FIG. 15B In vivo imaging of tumors using an $^{111}$In-labeled diHSG peptide (IMP 288) with or without pretargeting TF10 bispecific anti-pancreatic cancer MUC5AC antibody.

Imaging Studies Using Pretargeting with TF10 Bispecific Antibody and $^{111}$In-Labeled Peptides The following study demonstrates the feasibility of in vivo imaging using the pretargeting technique with bispecific antibodies incorporating hPAM4 and labeled peptides. The TF10 bispecific antibody, comprising two copies of a C-DDD2-Fab-hPAM4 and one copy of C-AD2-Fab-679, was prepared as described in the preceding Example. Nude mice bearing 0.2 to 0.3 g human pancreatic cancer xenografts were imaged, using pretargeting with TF10 and $^{111}$In-IMP-288 peptide. The results, shown in FIG. 15A and FIG. 15B, demonstrate how clearly delineated tumors can be detected in animal models using a bsMAb pretargeting method, with $^{111}$In-labeled di-HSG peptide, IMP-288. The six animals in the top of FIG. 15A and FIG. 15B received 2 different doses of TF10 (10:1 and 20:1 mole ratio to the moles of peptide given), and the next day they were given an $^{111}$In-labeled diHSG peptide (IMP 288). The 3 other animals on the bottom of FIG. 15A and FIG. 15B received only the $^{111}$In-IMP-288 (no pretargeting). The images shown in FIG. 15B were taken 3 h after the injection of the labeled peptide and show clear localization of 0.2-0.3 g tumors in the pretargeted animals, with no localization in the animals given the $^{111}$In-peptide alone. Tumor uptake averaged 20-25% ID/g with tumor/blood ratios exceeding 2000:1, tumor/liver ratios of 170:1, and tumor/kidney ratios of 18/1.

Example 21

Production of Targeting Peptides for Use in Pretargeting and $^{18}$F Labeling

In a variety of embodiments, $^{18}$F-labeled proteins or peptides are prepared by a novel technique and used for diagnostic and/or imaging studies, such as PET imaging. The novel technique for $^{18}$F labeling involves preparation of an $^{18}$F-metal complex, preferably an $^{18}$F-aluminum complex, which is chelated to a chelating moiety, such as DOTA, NOTA or NETA or derivatives thereof. Chelating moieties may be attached to proteins, peptides or any other molecule using conjugation techniques well known in the art. In certain preferred embodiments, the $^{18}$F—Al complex is formed in solution first and then attached to a chelating moiety that is already conjugated to a protein or peptide. However, in alternative embodiments the aluminum may be first attached to the chelating moiety and the $^{18}$F added later.

Peptide Synthesis

Peptides were synthesized by solid phase peptide synthesis using the Fmoc strategy. Groups were added to the side chains of diamino amino acids by using Fmoc/Aloc protecting groups to allow differential deprotection. The Aloc groups were removed by the method of Dangles et. al. (*J. Org. Chem.* 1987, 52:4984-4993) except that piperidine was added in a 1:1 ratio to the acetic acid used. The unsymmetrical tetra-t-butyl DTPA was made as described in McBride et al. (US Patent Application Pub. No. 2005/0002945, the Examples section of which is incorporated herein by reference).

The tri-t-butyl DOTA, symmetrical tetra-t-butyl DTPA, ITC-benzyl DTPA, p-SCN-Bn-NOTA and TACN were obtained from MACROCYCLICS® (Dallas, Tex.). The DiBocTACN, NODA-GA(tBu)$_3$ and the NO2AtBu were purchased from CheMatech (Dijon, France). The Aloc/Fmoc Lysine and Dap (diaminopropionic acid derivatives (also Dpr)) were obtained from CREOSALUS® (Louisville, Ky.) or BACHEM® (Torrance, Calif.). The Sieber Amide resin was obtained from NOVABIOCHEM® (San Diego, Calif.). The remaining Fmoc amino acids were obtained from CREOSALUS®, BACHEM®, PEPTECH® (Burlington, Mass.), EMD BIOSCIENCES® (San Diego, Calif.), CHEM IMPEX® (Wood Dale, Ill.) or NOVABIOCHEM®. The aluminum chloride hexahydrate was purchased from SIGMA-ALDRICH® (Milwaukee, Wis.). The remaining solvents and reagents were purchased from FISHER SCIENTIFIC® (Pittsburgh, Pa.) or SIGMA-ALDRICH® (Milwaukee, Wis.). $^{18}$F was supplied by IBA MOLECULAR® (Somerset, N.J.)

$^{18}$F-Labeling of IMP 272

The first peptide that was prepared and $^{18}$F-labeled was IMP 272: DTPA-Gln-Ala-Lys(HSG)-D-Tyr-Lys(HSG)-NH$_2$ MH$^+$ 1512

IMP 272 was synthesized as described (U.S. Pat. No. 7,534,431, the Examples section of which is incorporated herein by reference).

Acetate buffer solution—Acetic acid, 1.509 g was diluted in ~160 mL water and the pH was adjusted by the addition of 1 M NaOH then diluted to 250 mL to make a 0.1 M solution at pH 4.03.

Aluminum acetate buffer solution—A solution of aluminum was prepared by dissolving 0.1028 g of AlCl$_3$ hexahydrate in 42.6 mL DI water. A 4 mL aliquot of the aluminum solution was mixed with 16 mL of a 0.1 M NaOAc solution at pH 4 to provide a 2 mM Al stock solution.

IMP 272 acetate buffer solution—Peptide, 0.0011 g, 7.28×10$^{-7}$ mol IMP 272 was dissolved in 364 µL of the 0.1 M pH 4 acetate buffer solution to obtain a 2 mM stock solution of the peptide.

F-18 Labeling of IMP 272-A 3 µL aliquot of the aluminum stock solution was placed in a REACTI-VIAL™ and mixed with 50 µL $^{18}$F (as received) and 3 µL of the IMP 272 solution. The solution was heated in a heating block at 110° C. for 15 min and analyzed by reverse phase HPLC. HPLC analysis (not shown) showed 93% free $^{18}$F and 7% bound to the peptide. An additional 10 µL of the IMP 272 solution was added to the reaction and it was heated again and analyzed by reverse phase HPLC (not shown). The HPLC trace showed 8% $^{18}$F at the void volume and 92% of the activity attached to the peptide. The remainder of the peptide solution was incubated at room temperature with 150 µL PBS for ~1 hr and then examined by reverse phase HPLC. The HPLC (not shown) showed 58% $^{18}$F unbound and 42% still attached to the peptide. The data indicate that $^{18}$F—Al-DTPA complex may be unstable when mixed with phosphate.

The labeled peptide was purified by applying the labeled peptide solution onto a 1 cc (30 mg) WATERS® HLB column (Part #186001879) and washing with 300 µL water to remove unbound F-18. The peptide was eluted by washing the column with 2×100 µL 1:1 EtOH/H$_2$O. The purified peptide was incubated in water at 25° C. and analyzed by reverse phase HPLC (not shown). The HPLC analysis showed that the $^{18}$F-labeled IMP 272 was not stable in water. After 40 min incubation in water about 17% of the $^{18}$F was released from the peptide, while 83% was retained (not shown).

The peptide (16 µL 2 mM IMP 272, 48 µg) was labeled with $^{18}$F and analyzed for antibody binding by size exclusion HPLC. The size exclusion HPLC showed that the peptide bound hMN-14×679 but did not bind to the irrelevant bispecific antibody hMN-14×734 (not shown).

IMP 272 $^{18}$F Labeling with Other Metals

A ~3 µL aliquot of the metal stock solution (6×10$^{-9}$ mol) was placed in a polypropylene cone vial and mixed with 75 µL $^{18}$F (as received), incubated at room temperature for ~2 min and then mixed with 20 µL of a 2 mM (4×10$^{-8}$ mol) IMP 272 solution in 0.1 M NaOAc pH 4 buffer. The solution was heated in a heating block at 100° C. for 15 min and analyzed by reverse phase HPLC. IMP 272 was labeled with indium (24%), gallium (36%), zirconium (15%), lutetium (37%) and yttrium (2%) (not shown). These results demonstrate that the $^{18}$F metal labeling technique is not limited to an aluminum ligand, but can also utilize other metals as well. With different metal ligands, different chelating moieties may be utilized to optimize binding of an F-18-metal conjugate.

Production and Use of a Serum-Stable $^{18}$F-Labeled Peptide IMP 449

The peptide, IMP 448 D-Ala-D-Lys(HSG)-D-Tyr-D-Lys(HSG)-NH$_2$ MH$^+$ 1009 was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH, the Aloc was cleaved, Fmoc-D-Ala-OH with final Fmoc cleavage to make the desired peptide. The peptide was then cleaved from the resin and purified by HPLC to produce IMP 448, which was then coupled to ITC-benzyl NOTA. The peptide, IMP 448, 0.0757 g (7.5×10$^{-5}$ mol) was mixed with 0.0509 g (9.09×10$^{-5}$ mol) ITC benzyl NOTA and dissolved in 1 mL water. Potassium carbonate anhydrous (0.2171 g) was then slowly added to the stirred peptide/NOTA solution. The reaction solution was pH 10.6 after the addition of all the carbonate. The reaction was allowed to stir at room temperature overnight. The reaction was carefully quenched with 1 M HCl after 14 hr and purified by HPLC to obtain 48 mg of IMP 449.

$^{18}$F Labeling of IMP 449

The peptide IMP 449 (0.002 g, 1.37×10$^{-6}$ mol) was dissolved in 686 µL (2 mM peptide solution) 0.1 M NaOAc pH 4.02. Three microliters of a 2 mM solution of Al in a pH 4 acetate buffer was mixed with 15 µL, 1.3 mCi of $^{18}$F. The solution was then mixed with 20 µL of the 2 mM IMP 449 solution and heated at 105° C. for 15 min. Reverse Phase HPLC analysis showed 35% ($t_R$~10 min) of the activity was attached to the peptide and 65% of the activity was eluted at the void volume of the column (3.1 min, not shown) indicating that the majority of activity was not associated with the peptide. The crude labeled mixture (5 µL) was mixed with pooled human serum and incubated at 37° C. An aliquot was removed after 15 min and analyzed by HPLC. The HPLC showed 9.8% of the activity was still attached to the peptide (down from 35%). Another aliquot was removed after 1 hr and analyzed by HPLC. The HPLC showed 7.6% of the activity was still attached to the peptide (down from 35%), which was essentially the same as the 15 min trace (data not shown).

High Dose $^{18}$F Labeling

Further studies with purified IMP 449 demonstrated that the $^{18}$F-labeled peptide was highly stable (91%, not shown) in human serum at 37° C. for at least one hour and was partially stable (76%, not shown) in human serum at 37° C. for at least four hours. Additional studies were performed in which the IMP 449 was prepared in the presence of ascorbic acid as a stabilizing agent. In those studies (not shown), the metal-$^{18}$F-peptide complex showed no detectable decomposition in serum after 4 hr at 37° C. The mouse urine 30 min after injection of $^{18}$F-labeled peptide was found to contain $^{18}$F bound to the peptide (not shown). These results demonstrate that the $^{18}$F-labeled peptides disclosed herein exhibit sufficient stability under approximated in vivo conditions to be used for $^{18}$F imaging studies.

For studies in the absence of ascorbic acid, $^{18}$F ~21 mCi in ~400 µL of water was mixed with 9 µL of 2 mM AlCl$_3$ in 0.1 M pH 4 NaOAc. The peptide, IMP 449, 60 µL (0.01 M, 6×10$^{-7}$ mol in 0.5 NaOH pH 4.13) was added and the solution was heated to 110° C. for 15 min. The crude labeled peptide was then purified by placing the reaction solution in the barrel of a 1 cc WATERS® HLB column and eluting with water to remove unbound $^{18}$F followed by 1:1 EtOH/H$_2$O to elute the $^{18}$F-labeled peptide. The crude reaction solution was pulled through the column into a waste vial and the column was washed with 3×1 mL fractions of water (18.97 mCi). The HLB column was then placed on a new vial and eluted with 2×200 µL 1:1 EtOH/H$_2$O to collect the labeled peptide (1.83 mCi). The column retained 0.1 mCi of activity after all of the elutions were complete. An aliquot of the purified $^{18}$F-labeled peptide (20 µL) was mixed with 200 µL of pooled human serum and heated at 37° C. Aliquots were analyzed by reverse phase HPLC. The results showed the relative stability of $^{18}$F-labeled purified IMP 449 at 37° C. at time zero, one hour (91% labeled peptide), two hours (77% labeled peptide) and four hours (76% labeled peptide) of incubation in human serum (not shown). It was also observed that $^{18}$F-labeled IMP 449 was stable in TFA solution, which was occasionally used during reverse phase HPLC chromatography. There appears to be a general correlation between stability in TFA and stability in human serum observed for the exemplary $^{18}$F-labeled molecules described herein. These results demonstrate that $^{18}$F-labeled peptide, produced according to the methods disclosed herein, shows sufficient stability in human serum to be successfully used for in vivo labeling and imaging studies, for example using PET scanning to detect labeled cells or tissues. Finally, since IMP 449 peptide contains a thiourea linkage, which is sensitive to radiolysis, several products are observed by RP-HPLC. However, when ascorbic acid is added to the reaction mixture, the side products generated were markedly reduced.

Example 22

In Vivo Studies with Pretargeting TF10 DNL™ Construct and $^{18}$F-Labeled Peptide $^{18}$F-labeled IMP 449 was prepared as follows. The $^{18}$F, 54.7 mCi in ~0.5 mL was mixed with 3 µL 2 mM Al in 0.1 M NaOAc pH 4 buffer. After 3 min 10 µL of 0.05 M IMP 449 in 0.5 M pH 4 NaOAc buffer was added and the reaction was heated in a 96° C. heating block for 15 min. The contents of the reaction were removed with a syringe. The crude labeled peptide was then purified by HPLC on a C$_{18}$ column. The flow rate was 3 mL/min. Buffer A was 0.1% TFA in water and Buffer B was 90% acetonitrile in water with 0.1% TFA. The gradient went from 100% A to 75/25 A:B over 15 min. There was about 1 min difference in retention time ($t_R$) between the labeled peptide, which eluted first and the unlabeled peptide. The HPLC eluent was collected in 0.5 min (mL) fractions. The labeled peptide had a $t_R$ between 6 to 9 min depending on the column used. The HPLC purified peptide sample was further processed by diluting the fractions of interest two fold in water and placing the solution in the barrel of a 1 cc WATERS® HLB column. The cartridge was eluted with 3×1 mL water to remove acetonitrile and TFA followed by 400 µL 1:1 EtOH/H$_2$O to elute the $^{18}$F-labeled peptide. The purified [Al$^{18}$F] IMP 449 eluted as a single peak on an analytical HPLC C$_{18}$ column (not shown).

TACONIC® nude mice bearing the four slow-growing sc CaPan1 xenografts were used for in vivo studies. Three of the mice were injected with TF10 (162 µg) followed with [Al$^{18}$F] IMP 449 18 h later. TF10 is a humanized bispecific antibody of use for tumor imaging studies, with divalent binding to the PAM-4 defined tumor antigen and monovalent binding to HSG (see, e.g., Gold et al., 2007, J. Clin. Oncol. 25(185):4564). One mouse was injected with peptide alone. All of the mice were necropsied at 1 h post peptide injection. Tissues were counted immediately. Comparison of mean distributions showed substantially higher levels of $^{18}$F-labeled peptide localized in the tumor than in any normal tissues in the presence of tumor-targeting bispecific antibody (data not shown).

Tissue uptake was similar in animals given the [Al$^{18}$F] IMP 449 alone or in a pretargeting setting (data not shown). Uptake in the human pancreatic cancer xenograft, CaPan1, at 1 h was increased 5-fold in the pretargeted animals as compared to the peptide alone (4.6±0.9% ID/g vs. 0.89% ID/g). Exceptional tumor/nontumor ratios were achieved at this time (e.g., tumor/blood and liver ratios were 23.4±2.0 and 23.5±2.8, respectively).

The results demonstrate that $^{18}$F labeled peptide used in conjunction with a PAM4 containing antibody construct, such the TF10 DNL™ construct, provide suitable targeting of the $^{18}$F label to perform in vivo imaging, such as PET imaging analysis.

Example 23

Further Imaging Studies with TF10

Summary

Preclinical and clinical studies have demonstrated the application of radiolabeled mAb-PAM4 for nuclear imaging and radioimmunotherapy of pancreatic carcinoma. We have examined herein the ability of the TF10 construct to pretarget a radiolabeled peptide for improved imaging and therapy. Biodistribution studies and nuclear imaging of the radiolabeled TF10 and/or TF10-pretargeted hapten-peptide (IMP-288) were conducted in nude mice bearing CaPan1 human pancreatic cancer xenografts. $^{125}$I-TF10 cleared rapidly from the blood, with levels decreasing to <1% injected dose per gram (ID/g) by 16 hours. Tumor uptake was 3.47±0.66% ID/g at this time point with no accumulation in any normal tissue. To show the utility of the pretargeting approach, $^{111}$In-IMP-288 was administered 16 hours after TF10. At 3 hours postadministration of radiolabeled peptide, imaging showed intense uptake within the tumors and no evidence of accretion in any normal tissue. No targeting was observed in animals given only the $^{111}$In-peptide. Tumor uptake of the TF10-pretargeted $^{111}$In-IMP-288 was 24.3±1.7% ID/g, whereas for $^{111}$In-IMP-288 alone it was only 0.12±0.002% ID/g at 16 hours. Tumor/blood ratios were significantly greater for the pretargeting group (~1,000:1 at 3 hours) compared with $^{111}$In-PAM4-IgG (~5:1 at 24 hours; P<0.0003). Radiation dose estimates suggested that TF10/$^{90}$Y-peptide pretargeting would provide a greater antitumor effect than $^{90}$Y-PAM4-IgG. Thus, the results support that TF10 pretargeting may provide improved imaging for early detection, diagnosis, and treatment of pancreatic cancer as compared with directly radiolabeled PAM4-IgG. (Gold et al., Cancer Res 2008, 68(12):4819-26)

We have identified a unique biomarker present on mucin expressed by >85% of invasive pancreatic adenocarcinomas, including early stage I disease and the precursor lesions, pancreatic intraepithelial neoplasia and intraductal papillary mucinous neoplasia (Gold et al., Clin Cancer Res 2007, 13:7380-87). The specific epitope, as detected by mAb-PAM4 (Gold et al., Int J Cancer 1994, 57:204-10), is absent from normal and inflamed pancreatic tissues, as well as most other malignant tissues. Thus, detection of the epitope provides a high diagnostic likelihood for the presence of pancreatic neoplasia. Early clinical studies using $^{131}$I- and $^{99m}$Tc-labeled, murine PAM4 IgG or Fab', respectively, showed specific targeting in 8 of 10 patients with invasive pancreatic adenocarcinoma (Mariani et al., Cancer Res 1995, 55:5911s-15s; Gold et al., Crit Rev Oncol Hematol 2001, 39:147-54). Of the two negative patients, one had a poorly differentiated pancreatic carcinoma that did not express the PAM4-epitope, whereas the other patient was later found to have pancreatitis rather than a malignant lesion.

Accordingly, the high specificity of PAM4 for pancreatic cancer is of use for the detection and diagnosis of early disease. In addition to improved detection, $^{90}$Y-PAM4 IgG was found to be effective in treating large human pancreatic cancer xenografts in nude mice (Cardillo et al., Clin Cancer Res 2001, 7:3186-92), and when combined with gemcitabine, further improvements in therapeutic response were observed (Gold et al., Clin Cancer Res 2004, 10:3552-61; Gold et al., Int J Cancer 2004, 109:618-26). A Phase I therapy trial in patients who failed gemcitabine treatment was recently completed, finding the maximum tolerated dose of $^{90}$Y-humanized PAM4 IgG to be 20 mCi/m$^2$ (Gulec et al., Proc Amer Soc Clin Onc, 43rd Annual Meeting, J Clin Oncol 2007, 25(18S):636s). Although all patients showed disease progression at or after week 8, initial shrinkage of tumor was observed in several cases. Clinical studies are now underway to evaluate a fractionated dosing regimen of $^{90}$Y-hPAM4 IgG in combination with a radiosensitizing dose of gemcitabine.

We report herein the development of a novel recombinant, humanized bispecific monoclonal antibody (mAb), TF10, based on the targeting specificity of PAM4 to pancreatic cancer. This construct also binds to the unique synthetic hapten, histamine-succinyl-glycine (HSG), which has been incorporated in a number of small peptides that can be radiolabeled with a wide range of radionuclides suitable for single-photon emission computed tomography (SPECT) and positron emission tomography (PET) imaging, as well as for therapeutic purposes (Karacay et al., Clin Cancer Res 2005, 11:7879-85; Sharkey et al., Leukemia 2005, 19:1064-9; Rossi et al., Proc Natl Acad Sci USA 2006, 103:6841-6; McBride et al., J Nucl Med 2006, 47:1678-88). These studies illustrate the potential of this new construct to target pancreatic adenocarcinoma for imaging or therapeutic applications.

Methods and Materials

The TF2 and TF10 bispecific DNL™ constructs and the IMP 288 targeting peptide were prepared as described above. Sodium iodide ($^{125}$I) and indium chloride ($^{111}$In) were obtained from PERKIN-ELMER®. TF10 was routinely labeled with $^{125}$I by the iodogen method, with purification by use of size-exclusion spin columns. Radiolabeling of DOTA-peptide and DOTA-PAM4-IgG with $^{111}$InCl was done as previously described (Rossi et al., Proc Natl Acad Sci USA 2006, 103:6841-6; McBride et al., J Nucl Med 2006, 47:1678-88). Purity of the radiolabeled products was examined by size-exclusion high-performance liquid chromatography with the amount of free, unbound isotope determined by instant TLC.

For TF10 distribution studies, female athymic nude mice ~20 g (TACONIC® Farms), bearing s.c. CaPan1 human pancreatic cancer xenografts, were injected with $^{125}$I-TF10 (10 µCi; 40 µg, 2.50×10$^{-10}$ mol). At various time points, groups of mice (n=5) were necropsied, with tumor and nontumor tissues removed and counted in a gamma counter to determine the percentage of injected dose per gram of tissue (% ID/g), with these values used to calculate blood clearance rates and tumor/nontumor ratios.

For pretargeting biodistribution studies, a bispecific mAb/radiolabeled peptide molar ratio of 10:1 was used. For example, a group of athymic nude mice bearing s.c. CaPan1 human pancreatic cancer xenografts was administered TF10 (80 µg, 5.07×10$^{-10}$ mol), whereas a second group was left untreated. At 16 h postinjection of TF10, In-IMP-288 hapten-peptide (30 µCi, 5.07×10$^{-11}$ mol) was administered. Mice were necropsied at several time points, with tumor and nontumor tissues removed and counted in a gamma counter to determine the % ID/g. Tumor/nontumor ratios were calculated from these data. In a separate study, groups of mice were given $^{111}$In-DOTA-PAM4-IgG (20 µC, 50 µg, 3.13×10$^{-10}$ mol) for the purpose of comparing biodistribution, nuclear imaging, and potential therapeutic activity. Radiation dose estimates were calculated from the time-activity curves with the assumption of no activity at zero time. Student's t test was used to assess significant differences.

To perform nuclear immunoscintigraphy, at 3 h postinjection of radiolabeled peptide or 24 h postinjection of radiolabeled hPAM4-IgG, tumor-bearing mice were imaged with a dual-head Solus gamma camera fitted with medium energy collimator for $^{111}$In (ADAC Laboratories). Mice were imaged for a total of 100,000 cpm or 10 min, whichever came first.

Results

In Vitro Characterization of the Bispecific mAb TF10.

Figure 16:
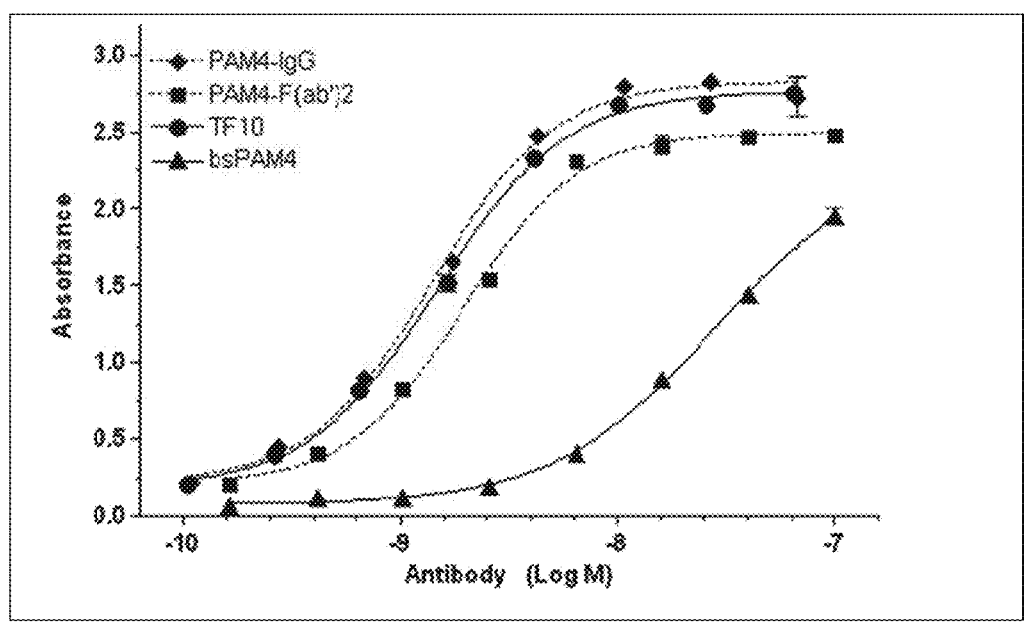
FIG. 16. Exemplary binding curves for TF10, PAM4-IgG, PAM4-F(ab')$_2$ and a monovalent bsPAM4 chemical conjugate (PAM4-Fab'×anti-DTPA-Fab'). Binding to target mucin antigen was measured by ELISA assay.

The binding of TF10 to the target mucin antigen was analyzed by ELISA (FIG. 16). The results showed nearly identical binding curves for the divalent TF10, PAM4-IgG, and PAM4-F(ab')$_2$ (half-maximal binding was calculated as 1.42±0.10, 1.31±0.12, and 1.83±0.16 nmol/L, respectively; P >0.05 for all), whereas the monovalent bsPAM4 chemical conjugate (PAM4-Fab'×anti-DTPA-Fab') had a significantly lower avidity (half-maximal binding, 30.61±2.05 nmol/L; P=0.0379, compared with TF10), suggesting that TF10 binds in a divalent manner. The immunoreactive fraction of $^{125}$I-TF10 bound to MUC5AC was 87%, with 9% found as unbound TF10 and 3% as free iodide (not shown). Ninety percent of the $^{111}$In-IMP-288 bound to TF10 (not shown). Of the total $^{111}$In-IMP-288 bound to TF10, 92% eluted at higher molecular weight when excess mucin (200 µg) was added, with only 3% eluting with the non-mucin-reactive TF10 fraction. An additional 5% of the radiolabeled peptide eluted in the free peptide volume. None of the radiolabeled peptide bound to the mucin antigen in the absence of TF10 (not shown).

Biodistribution of $^{125}$I-TF10 in CaPan1 Tumor-Bearing Nude Mice.

TF10 showed a rapid clearance from the blood, starting with 21.03±1.93% ID/g at 1 hour and decreasing to just 0.13±0.02% ID/g at 16 hours. The biological half-life was calculated to be 2.19 hours [95% confidence interval (95% CI), 2.11-2.27 hours]. Tissue uptake revealed enhanced activity in the liver, spleen, and kidneys at 1 hour, which cleared just as quickly by 16 hours [$T_{1/2}$=2.09 hours (95% CI, 2.08-2.10), 2.84 hours (95% CI, 2.49-3.29), and 2.44 hours (95% CI, 2.28-2.63) for liver, spleen, and kidney, respectively]. Activity in the stomach most likely reflects the accretion and excretion of radioiodine, suggesting that the radioiodinated TF10 was actively catabolized, presumably in the liver and spleen, thereby explaining its rapid clearance from the blood. Nevertheless, by 16 hours, the concentration of radioiodine within the stomach was below 1% ID/g. A group of five non-tumor-bearing nude mice given $^{125}$I-TF10 and necropsied at 16 hours showed similar tissue distribution, suggesting that the tumor had not affected the bispecific mAb distribution and clearance from normal tissues (data not shown). Of course, it is possible that differences occurred before the initial time point examined. Tumor uptake of TF10 peaked at 6 hours postinjection (7.16±1.10% ID/g) and had decreased to half maximum binding (3.47±0.66% ID/g) at 16 hours. Tumor uptake again decreased nearly 2-fold over the next 32 hours, but then was stable over the following 24 hours.

Biodistribution of TF10-Pretargeted, $^{111}$In-Labeled Peptide.

Although maximum tumor uptake of TF10 occurred at 6 hours, previous experience indicated that the radiolabeled peptide would need to be given at a time point when blood levels of TF had cleared to <1% ID/g (i.e., 16 hours). Higher levels of TF in the blood would lead to unacceptably high binding of the radiolabeled peptide within the blood (i.e., low tumor/blood ratios), whereas administering the peptide at a later time would mean the concentration of TF10 in the tumor would be decreased with consequently reduced concentration of radiolabeled peptide within the tumor. Thus, an initial pretargeting study was done using a 16-hour interval. With the amount of the $^{111}$In-IMP-288 held constant (30 µCi, 5.07×10$^{-11}$ mol), increasing amounts of TF10 were given so that the administered dose of TF10 and IMP-288 expressed as mole ratio varied from 5:1 to 20:1 (Table 16).

TABLE 16

Biodistribution of $^{111}$In-IMP-288 alone (no TF10) or pretargeted with varying amounts of TF10

| | % ID/g at 3 h (mean ± SD) | | | |
|---|---|---|---|---|
| | 5:1 | 10:1 | 20:1 | No TF10 |
| Tumor | 19.0 ± 3.49 | 24.3 ± 1.71 | 28.6 ± 0.73 | 0.12 ± 0.00 |
| Liver | 0.09 ± 0.01 | 0.21 ± 0.12 | 0.17 ± 0.01 | 0.07 ± 0.00 |
| Spleen | 0.12 ± 0.04 | 0.16 ± 0.07 | 0.26 ± 0.10 | 0.04 ± 0.01 |
| Kidneys | 1.59 ± 0.11 | 1.72 ± 0.24 | 1.53 ± 0.14 | 1.71 ± 0.22 |
| Lungs | 0.19 ± 0.06 | 0.26 ± 0.00 | 0.29 ± 0.04 | 0.03 ± 0.00 |
| Blood | 0.01 ± 0.00 | 0.01 ± 0.01 | 0.01 ± 0.00 | 0.00 ± 0.00 |
| Stomach | 0.03 ± 0.02 | 0.02 ± 0.02 | 0.01 ± 0.00 | 0.02 ± 0.01 |
| Small intestine | 0.12 ± 0.08 | 0.08 ± 0.03 | 0.04 ± 0.01 | 0.06 ± 0.02 |
| Large intestine | 0.23 ± 0.10 | 0.39 ± 0.08 | 0.25 ± 0.08 | 0.33 ± 0.02 |
| Pancreas | 0.02 ± 0.00 | 0.02 ± 0.01 | 0.02 ± 0.00 | 0.02 ± 0.00 |
| Tumor weight (g) | 0.12 ± 0.03 | 0.32 ± 0.09 | 0.27 ± 0.01 | 0.35 ± 0.03 |

At 3 hours the amount of $^{111}$In-IMP-288 in the blood was barely detectable (0.01%). Tumor uptake increased from 19.0±3.49% ID/g to 28.55±0.73% ID/g as the amount of bispecific mAb administered was increased 4-fold (statistically significant differences were observed for comparison of each TF10/peptide ratio, one group to another; P<0.03 or better), but without any appreciable increase in normal tissue uptake. Tumor uptake in the animals given TF10 was >100-fold higher than when $^{111}$In-IMP-288 was given alone. Comparison of $^{111}$In activity in the normal tissues of the animals that either received or did not receive prior administration of TF10 indicated similar absolute values, which in most instances were not significantly different. This suggests that the bispecific mAb had cleared sufficiently from all normal tissues by 16 hours to avoid appreciable peptide uptake in these tissues. Tumor/blood ratios were >2,000:1, with other tissue ratios exceeding 100:1. Even tumor/kidney ratios exceeded 10:1. The highest tumor uptake of radioisotope with minimal targeting to nontumor tissues resulted from the 20:1 ratio; however, either of the TF10/peptide ratios could be used to achieve exceptional targeting to tumor, both in terms of signal intensity and contrast ratios. The 10:1 ratio was chosen for further study because the absolute difference in tumor uptake of radiolabeled peptide was not substantially different between the 10:1 (24.3±1.71% ID/g) and 20:1 (28.6±0.73% ID/g) ratios.

Figure 17A:
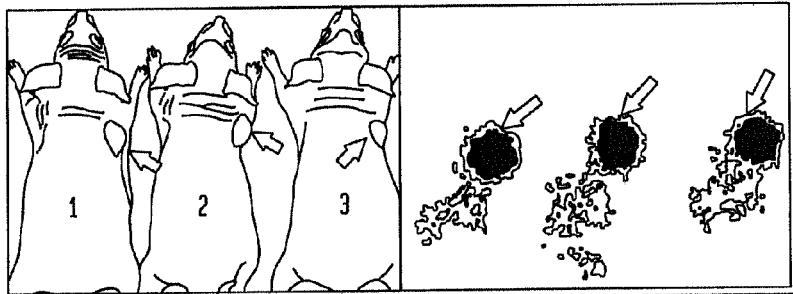
FIG. 17A. Immunoscintigraphy of CaPan1 human pancreatic cancer xenografts (~0.25 g). An image of mice that were injected with bispecific TF10 (80 μg, 5.07×10$^{-10}$ mol) followed 16 h later by administration of $^{111}$In-IMP-288 (30 μCi, 5.07×10$^{-11}$ mol). The image was taken 3 h later. The intensity of the image background was increased to match the intensity of the image obtained when $^{111}$In-IMP-288 was administered alone (30 μCi, 5.07×10$^{-11}$ mol).
Figure 17B:
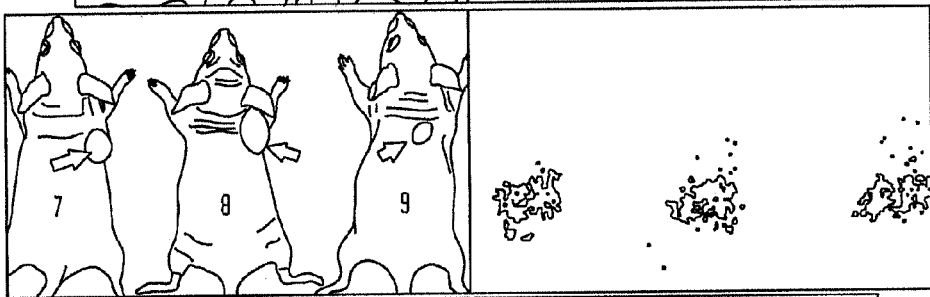
FIG. 17B. Immunoscintigraphy of CaPan1 human pancreatic cancer xenografts (~0.25 g). No targeting was observed in mice given $^{111}$In-IMP-288 alone.
Figure 17C:
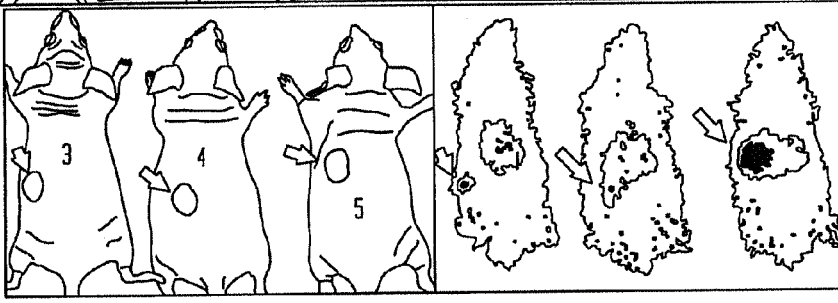
FIG. 17C. Immunoscintigraphy of CaPan1 human pancreatic cancer xenografts (0.25 g). An image of mice that were given $^{111}$In-DOTA-PAM4-IgG (20 μCi, 50 μg) with imaging done 24 h later. Although tumors are visible, considerable background activity is still present at this time point.

Images of the animals given TF10-pretargeted $^{111}$In-IMP-288 at a bispecific mAb/peptide ratio of 10:1, or the $^{111}$In-IMP-288 peptide alone, are shown in FIG. 17A, FIG. 17B and FIG. 17C. The majority of these tumors were <0.5 cm in diameter, weighing ~0.25 g. The images show highly intense uptake in the tumor of the TF10-pretargeted animals (FIG. 17A). The intensity of the image background for the TF10-pretargeted animals was increased to match the intensity of the image taken of the animals given the $^{111}$In-IMP-288 alone (FIG. 17B). However, when the images were optimized for the TF10-pretargeted mice, the signal intensity and contrast were so high that no additional activity was observed in the body. No tumor localization was seen in the animals given the $^{111}$In-IMP-288 alone, even when image intensity was enhanced (FIG. 17C).

An additional experiment was done to assess the kinetics of targeting $^{111}$In-hPAM4 whole-IgG compared with that of the TF10-pretargeted $^{111}$In-IMP-288 peptide. Tumor uptake of the $^{111}$In-peptide was highest at the initial time point examined, 3 hours (15.99±4.11% ID/g), whereas the blood concentration of radiolabeled peptide was only 0.02±0.01% ID/g, providing a mean tumor/blood ratio of 946.3±383.0. Over time, radiolabeled peptide cleared from the tumor with a biological half-life of 76.04 hours. Among nontumor tissues, uptake was highest in the kidneys, averaging 1.89±0.42% ID/g at 3 hours with a steady decrease over time (biological half-life, 33.6 hours). Liver uptake started at 0.15±0.06% ID/g and remained essentially unchanged over time. In contrast to the TF10-pretargeted $^{111}$In-IMP-288, the $^{111}$In-hPAM4-IgG had a slower clearance from the blood, albeit there was a substantial clearance within the first 24 hours, decreasing from 30.1% ID/g at 3 hours to just 11.5±1.7% ID/g at 24 hours. Variable elevated uptake in the spleen suggested that the antibody was likely being removed from the blood by targeting of secreted mucin that had become entrapped within the spleen. Tumor uptake peaked at 48 hours with 80.4±6.1% ID/g, and remained at an elevated level over the duration of the monitoring period. The high tumor uptake, paired with a more rapid than expected blood clearance for an IgG, produced tumor/blood ratios of 5.2±1.0 within 24 hours. FIG. 17C shows the images of the animals at 24 hours postadministration of $^{111}$In-PAM4-IgG, illustrating that tumors could be visualized at this early time, but there was still considerable activity within the abdomen. Tumor/nontumor ratios were mostly higher for TF10-pretargeted $^{111}$In-labeled hapten-peptide as compared with $^{111}$In-hPAM4-IgG, except for the kidneys, where tumor/kidney ratios with the $^{111}$In-IMP-288 and $^{111}$In-hPAM4-IgG were similar at later times. However, tumor/kidney ratios for the TF10-pretargeted $^{111}$In-IMP-288 were high enough (e.g., ~7:1) at 3 hours to easily discern tumor from normal tissue.

Figure 18A:
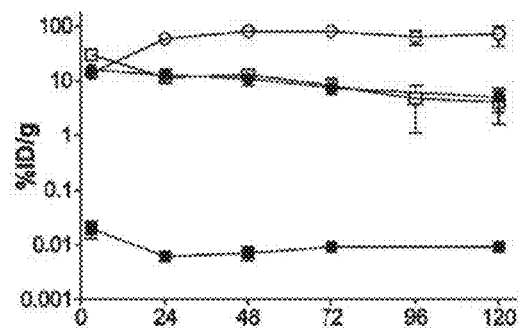
FIG. 18A. Extended biodistribution of $^{111}$In-DOTA-PAM4-IgG (20 μCi, 50 μg) and TF10-pretargeted $^{111}$In-IMP-288 (80 μg, 5.07×10$^{-10}$ mol TF10 followed 16 h later with 30 μCi, 5.07×10$^{-11}$ mol $^{111}$In-IMP-288) in nude mice bearing CaPan1 human pancreatic cancer xenografts (mean tumor weight+/−SD, 0.28+/−0.21 and 0.10+/−0.06 g for the pretargeting and IgG groups of animals, respectively).
Figure 18B:
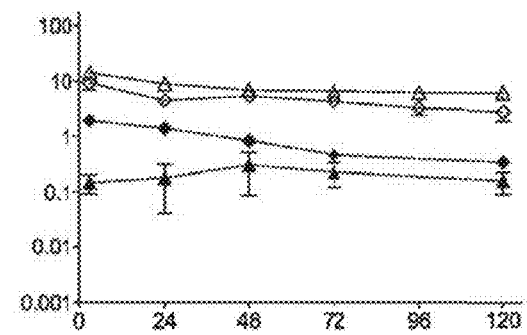
FIG. 18B. Extended biodistribution of $^{111}$In-DOTA-PAM4-IgG (20 μCi, 50 μg) and TF10-pretargeted $^{111}$In-IMP-288 (80 μg, 5.07×10$^{-10}$ mol TF10 followed 16 h later with 30 μCi, 5.07×10$^{-11}$ mol $^{111}$In-IMP-288) in nude mice bearing CaPan1 human pancreatic cancer xenografts (mean tumor weight+/−SD, 0.28+/−0.21 and 0.10+/−0.06 g for the pretargeting and IgG groups of animals, respectively).
Figure 18C:
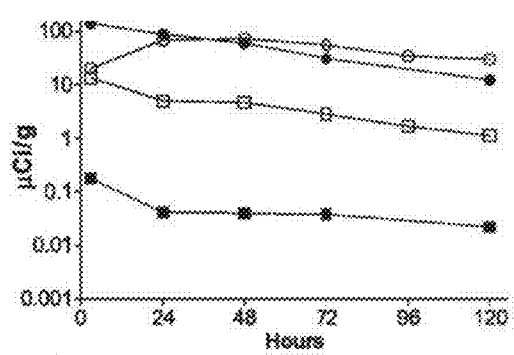
FIG. 18C. Extended biodistribution of $^{111}$In-DOTA-PAM4-IgG (20 μCi, 50 μg) and TF10-pretargeted $^{111}$In-IMP-288 (80 μg, 5.07×10$^{-10}$ mol TF10 followed 16 h later with 30 μCi, 5.07×10$^{-11}$ mol $^{111}$In-IMP-288) in nude mice bearing CaPan1 human pancreatic cancer xenografts (mean tumor weight+/−SD, 0.28+/−0.21 and 0.10+/−0.06 g for the pretargeting and IgG groups of animals, respectively).
Figure 18D:
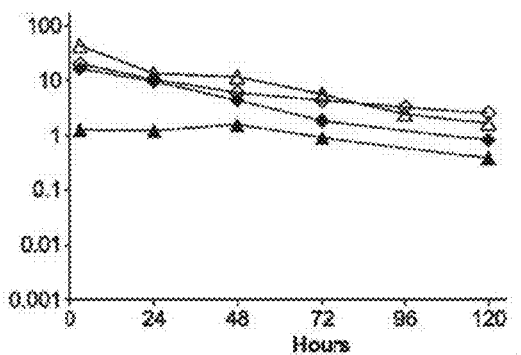
FIG. 18D. Extended biodistribution of $^{111}$In-DOTA-PAM4-IgG (20 μCi, 50 μg) and TF10-pretargeted $^{111}$In-IMP-288 (80 μg, 5.07×10$^{-10}$ mol TF10 followed 16 h later with 30 μCi, 5.07×10$^{-11}$ mol $^{111}$In-IMP-288) in nude mice bearing CaPan1 human pancreatic cancer xenografts (mean tumor weight+/−SD, 0.28+/−0.21 and 0.10+/−0.06 g for the pretargeting and IgG groups of animals, respectively).

FIG. 18A to FIG. 18D illustrates the potential therapeutic capability of the direct and pretargeted methods to deliver radionuclide ($^{90}$Y). Although the concentration (% ID/g) of radioisotope within the tumor seems to be much greater when delivered by PAM4-IgG than by pretargeted TF10 at their respective maximum tolerated dose (0.15 mCi for $^{90}$Y-hPAM4 and 0.9 mCi for TF10-pretargeted $^{90}$Y-IMP-288) (FIG. 18A), the radiation dose to tumor would be similar (10,080 and 9,229 cGy for $^{90}$Y-PAM4-IgG and TF10-pretargeted $^{90}$Y-IMP-288, respectively) (FIG. 18C). The advantage for the pretargeting method would be the exceptionally low activity in blood (9 cGy), almost 200-fold less than with the $^{90}$Y-hPAM4 IgG (1,623 cGy) (FIG. 18C). It is also important to note that the radiation dose to liver, as well as other nontumor organs, would be much lower with the TF10-pretargeted $^{90}$Y-IMP-288 (FIG. 18B, FIG. 18D). The exception would be the kidneys, where the radiation dose would be similar for both protocols at their respective maximum dose (612 and 784 cGy for $^{90}$Y-PAM4-IgG and TF10-$^{90}$Y-IMP-288, respectively) (FIG. 18B, FIG. 18D). The data suggest that for $^{90}$Y-PAM4-IgG, as with most other radiolabeled whole-IgG mAbs, the dose-limiting toxicity would be hematologic; however, for the TF10 pretargeting protocol, the dose-limiting toxicity would be the kidneys.

Discussion

Current diagnostic modalities such as ultrasound, computerized tomography (CT), and magnetic resonance imaging (MRI) technologies, which provide anatomic images, along with PET imaging of the metabolic environment, have routinely been found to provide high sensitivity in the detection of pancreatic masses. However, these data are, for the most part, based on detection of lesions >2 cm in a population that is already presenting clinical symptoms. At this time in the progression of the pancreatic carcinoma, the prognosis is rather dismal. To improve patient outcomes, detection of small, early pancreatic neoplasms in the asymptomatic patient is necessary.

Imaging with a mAb-targeted approach, such as is described herein with mAb-PAM4, may provide for the diagnosis of these small, early cancers. Of prime importance is the specificity of the mAb. We have presented considerable data, including immunohistochemical studies of tissue specimens (Gold et al., Clin Cancer Res 2007; 13:7380-7; Gold et al., Int J Cancer 1994; 57:204-10) and immunoassay of patient sera (Gold et al., J Clin Oncol 2006; 24:252-8), to show that mAb-PAM4 is highly reactive with a biomarker, the presence of which provides high diagnostic likelihood of pancreatic neoplasia. Furthermore, we determined that PAM4, although not reactive with normal adult pancreatic tissues nor active pancreatitis, is reactive with the earliest stages of neoplastic progression within the pancreas (pancreatic intraepithelial neoplasia 1 and intraductal papillary mucinous neoplasia) and that the biomarker remains at high levels of expression throughout the progression to invasive pancreatic adenocarcinoma (Gold et al., Clin Cancer Res 2007; 13:7380-7). Preclinical studies with athymic nude mice bearing human pancreatic tumor xenografts have shown specific targeting of radiolabeled murine, chimeric, and humanized versions of PAM4.

In the current studies, we have examined a next-generation, recombinant, bispecific PAM4-based construct, TF10, which is divalent for the PAM4 arm and monovalent for the anti-HSG hapten arm. There are several important characteristics of this pretargeting system's constructs, named DOCK-AND-LOCK™, including its general applicability and ease of synthesis. However, for the present consideration, the major differences from the previously reported chemical construct are the valency, which provides improved binding to tumor antigen, and, importantly, its pharmacokinetics. TF10 clearance from nontumor tissues is much more rapid than was observed for the chemical conjugate. Time for blood levels of the bispecific constructs to reach less than 1% ID/g was 40 hours postinjection for the chemical construct versus 16 hours for TF10. A more rapid clearance of the pretargeting agent has provided a vast improvement of the tumor/blood ratio, while maintaining high signal strength at the tumor site (% ID/g).

In addition to providing a means for early detection and diagnosis, the results support the use of the TF10 pretargeting system for cancer therapy. Consideration of the effective radiation dose to tumor and nontumor tissues favors the pretargeting method over directly radiolabeled PAM4-IgG. The dose estimates suggest that the two delivery systems have different dose-limiting toxicities: myelotoxicity for the directly radiolabeled PAM4 versus the kidney for the TF10 pretargeting system. This is of significance for the future clinical development of radiolabeled PAM4 as a therapeutic agent.

Gemcitabine, the frontline drug of choice for pancreatic cancer, can provide significant radiosensitization of tumor cells. In previous studies, we showed that combinations of gemcitabine and directly radiolabeled PAM4-IgG provided synergistic antitumor effects compared with either arm alone (Gold et al., Clin Cancer Res 2004, 10:3552-61; Gold et al., Int J Cancer 2004, 109:618-26). The dose-limiting factor with this combination was overlapping hematologic toxicity. However, because the dose-limiting organ for TF10 pretargeting seems to be the kidney rather than hematologic tissues, combinations with gemcitabine should be less toxic, thus allowing increased administration of radioisotope with consequently greater antitumor efficacy.

The superior imaging achieved with TF10 pretargeting in preclinical models, as compared with directly radiolabeled DOTA-PAM4-IgG, provides a compelling rationale to proceed to clinical trials with this imaging system. The specificity of the tumor-targeting mAb for pancreatic neoplasms, coupled with the bispecific antibody platform technology providing the ability to conjugate various imaging compounds to the HSG-hapten-peptide for SPECT ($^{111}$In), PET ($^{68}$Ga), ultrasound (Au), or other contrast agents, or for that matter $^{90}$Y or other radionuclides for therapy, provides high potential to improve overall patient outcomes (Goldenberg et al., J Nucl Med 2008, 49:158-63). In particular, we believe that a TF10-based ImmunoPET procedure will have major clinical value to screen individuals at high-risk for development of pancreatic cancer (e.g., genetic predisposition, chronic pancreatitis, smokers, etc.), as well as a means for follow-up of patients with suspicious abdominal images from conventional technologies and/or with indications due to the presence of specific biomarker(s) or abnormal biochemical findings. When used as part of an ongoing medical plan for following these patients, early detection of pancreatic cancer may be achieved. Finally, in combination with gemcitabine, TF10 pretargeting may provide a better opportunity for control of tumor growth than directly radiolabeled PAM4-IgG.

Example 24

Therapy of Pancreatic Cancer Xenografts with Gemcitabine and $^{90}$Y-Labeled Peptide Pretargeted Using TF10

Summary $^{90}$Y-hPAM4 IgG is currently being examined in Phase I/II trials in combination with gemcitabine in patients with Stage III/IV pancreatic cancer. We disclose a new approach for pretargeting radionuclides that is able to deliver a similar amount of radioactivity to pancreatic cancer xenografts, but with less hematological toxicity, which would be more amenable for combination with gemcitabine. Nude mice bearing ~0.4 cm$^3$ sc CaPan1 human pancreatic cancer were administered a recombinant bsMAb, TF10, followed 1 day later with a $^{90}$Y-labeled hapten-peptide (IMP-288). Various doses and schedules of gemcitabine were added to this treatment, and tumor progression monitored up to 28 weeks. 0.7 mCi PT-RAIT alone produce only a transient 60% loss in blood counts, and animals given 0.9 mCi of PT-RAIT alone and 0.7 mCi PT-RAIT+6 mg gemcitabine (human equivalent ~1000 mg/m$^2$) had no histological evidence of renal toxicity after 9 months. A single dose of 0.25 or 0.5 mCi PT-RAIT alone can completely ablate 20% and 80% of the tumors, respectively. Monthly fractionated PT-RAIT (0.25 mCi/dose given at the start of each gemcitabine cycle) added to a standard gemcitabine regimen (6 mg wkly×3; 1 wk off; repeat 3 times) significantly increased the median time for tumors to reach 3.0 cm$^3$ over PT-RAIT alone. Other treatment plans examining non-cytotoxic radiosensitizing dose regimens of gemcitabine added to PT-RAIT also showed significant improvements in treatment response over PT-RAIT alone. The results show that PT-RAIT is a promising new approach for treating pancreatic cancer. Current data indicate combining PT-RAIT with gemcitabine will enhance therapeutic responses.

Methods

TF10 bispecific antibody was prepared as described above. For pretargeting, TF10 was given to nude mice bearing the human pancreatic adenocarcinoma cell line, CaPan1. After allowing sufficient time for TF10 to clear from the blood (16 h), the radiolabeled divalent HSG-peptide was administered. The small molecular weight HSG-peptide (~1.4 kD) clears within minutes from the blood, entering the extravascular space where it can bind to anti-HSG arm of the pretargeted TF10 bsMAb. Within a few hours, >80% of the radiolabeled HSG-peptide is excreted in the urine, leaving the tumor localized peptide and a trace amount in the normal tissues.

Results

Figure 19:
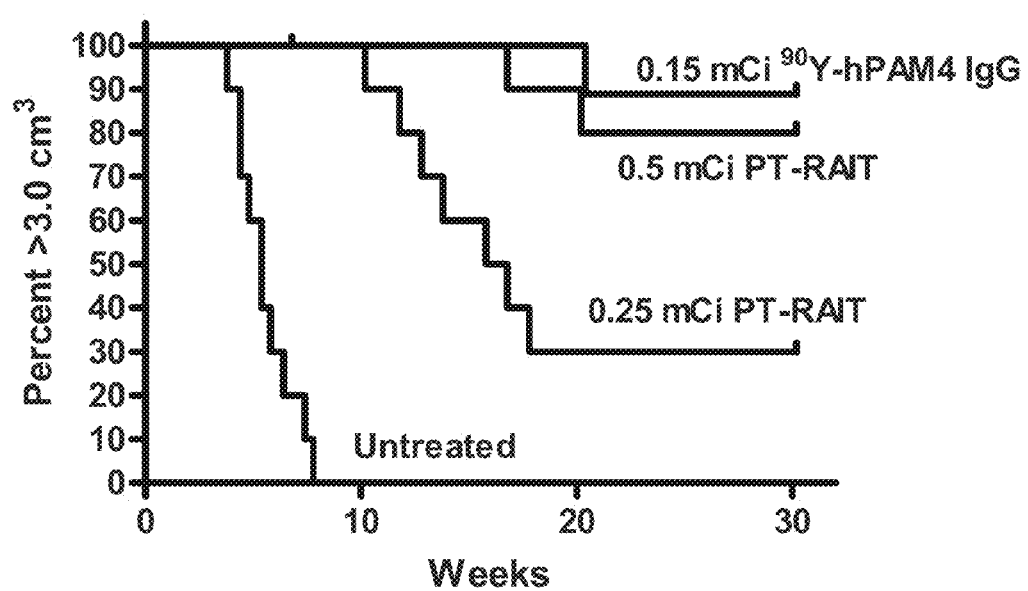
FIG. 19. Therapeutic activity of a single treatment of established (~0.4 cm$^3$) CaPan1 tumors with 0.15 mCi of $^{90}$Y-hPAM4 IgG, or 0.25 or 0.50 mCi of TF10-pretargeted $^{90}$Y-IMP-288.

FIG. 19 illustrates the therapeutic activity derived from a single treatment of established (~0.4 cm$^3$) CaPan1 tumors with 0.15 mCi of $^{90}$Y-hPAM4 IgG, or 0.25 or 0.50 mCi of TF10-pretargeted $^{90}$Y-IMP-288. Similar anti-tumor activity was observed for the 0.5-mCi pretargeted dose vs. 0.15-mCi dose of the directly radiolabeled IgG, but hematological toxicity was severe at this level of the direct conjugate (not shown), while the pretargeted dose was only moderately toxic (not shown). Indeed, the MTD for pretargeting using 90Y-IMP-288 is at least 0.9 mCi in nude mice.

Figure 20:
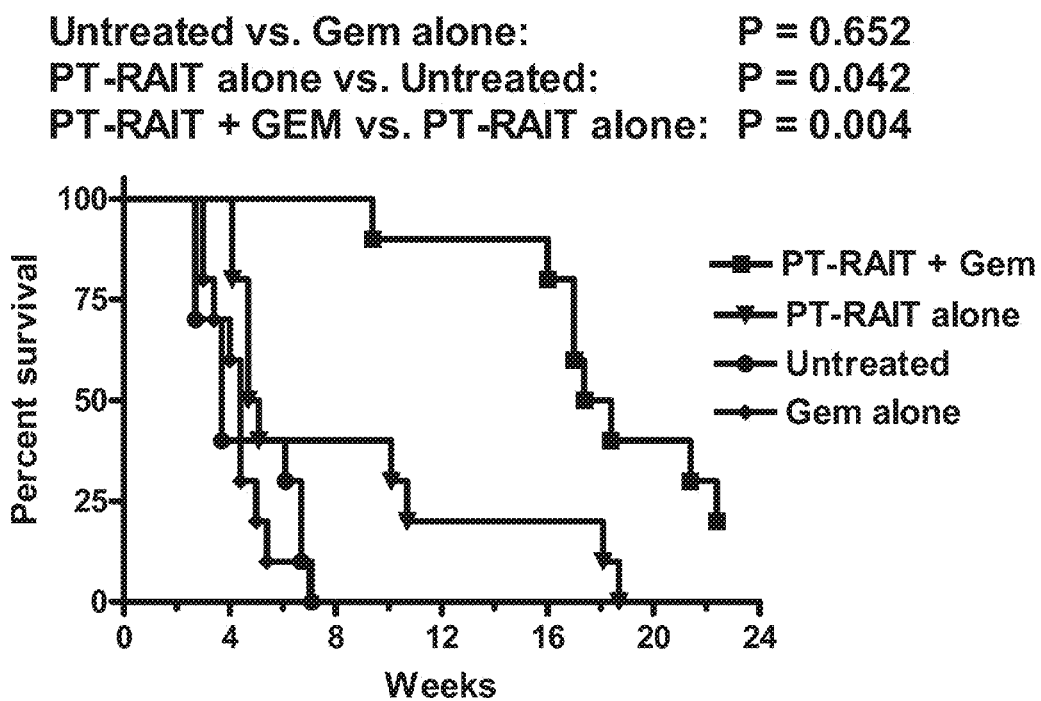
FIG. 20. Effect of gemcitabine potentiation of PT-RAIT therapy.

FIG. 20 shows that the combination of gemcitabine and PT-RAIT has a synergistic effect on anti-tumor therapy. Human equivalent doses of 1000 mg/m$^2$ (6 mg) of gemcitabine (GEM) were given intraperitoneally to mice weekly for 3 weeks, then after resting for 1 week, this regimen was repeated 2 twice. PT-RAIT (0.25 mCi of TF10-pretargeted $^{90}$Y-IMP-288) was given 1 day after the first GEM dose in each of the 3 cycles of treatment. Gem alone had no significant impact on tumor progression (survival based on time to progress to 3.0 cm$^3$). PT-RAIT alone improved survival compared to untreated animals, but the combined GEM with PT-RAIT regimen increased the median survival by nearly 10 weeks. Because hematological toxicity is NOT dose-limiting for PT-RAIT, but it is one of the limitations for gemcitabine therapy, these studies suggest that PT-RAIT could be added to a standard GEM therapy with the potential for enhanced responses. The significant synergistic effect of gemcitabine plus PT-RAIT was surprising and unexpected.

A further study examined the effect of the timing of administration on the potentiation of anti-tumor effect of gemcitabine plus PT-RAIT. A single 6-mg dose of GEM was given one day before or 1 day after 0.25 mCi of TF10-pretargeted $^{90}$Y-IMP-288 (not shown). This study confirmed what is already well known with GEM, i.e., radiosensitization is best given in advance of the radiation. Percent survival of treated mice showed little difference in survival time between PT-RAIT alone and PT-RAIT with gemcitabine given 22 hours after the radiolabeled peptide. However, administration of gemcitabine 19 hours prior to PT-RAIT resulted in a substantial increase in survival (not shown).

Figure 21:
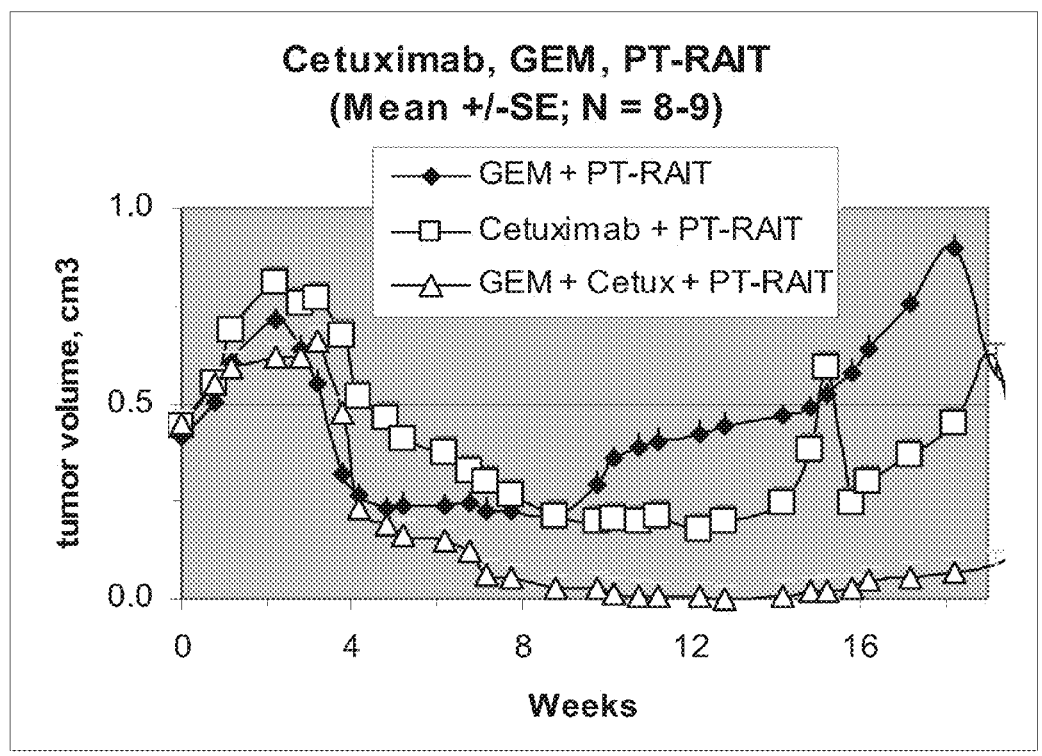
FIG. 21. Effect of combination of cetuximab with gemcitabine and PT-RAIT.

Single PT-RAIT (0.25 mCi) combined with cetuximab (1 mg weekly ip; 7 weeks) or with cetuximab+GEM (6 mg weekly×3) in animals bearing CaPan1 showed the GEM+ cetuximab combination with PT-RAIT providing a better initial response (FIG. 21), but the response associated with just cetuximab alone added to PT-RAIT was encouraging (FIG. 21), since it was as good or better than PT-RAIT+ GEM. Because the overall survival in this study was excellent, with only 2 tumors in each group progressing to >2.0 cm3 after 24 weeks when the study was terminated, these results indicate a potential role for cetuximab when added to PT-RAIT.

Example 25

Effect of Fractionated Pretargeted Radioimmunotherapy (PT-RAIT) for Pancreatic Cancer Therapy We evaluated fractionated therapy with $^{90}$Y-DOTA-di-HSG peptide (IMP-288) and TF10. Studies using TF10 and radiolabeled IMP-288 were performed in nude mice bearing s.c. CaPan1 human pancreatic cancer xenografts, 0.32-0.54 cm$^3$. For therapy, TF10-pretargeted $^{90}$Y-IMP-288 was given [A] once (0.6 mCi on wk 0) or [B] fractionated (0.3 mCi on wks 0 and 1), [C] (0.2 mCi on wks 0, 1 and 2) or [D] (0.2 mCi on wks 0, 1 and 4).

Tumor regression (>90%) was observed in the majority of mice, 9/10, 10/10, 9/10 and 8/10 in groups [A], [B], [C] and [D], respectively. In group [A], maximum tumor regression in 50% of the mice was reached at 3.7 wks, compared to 6.1, 8.1 and 7.1 wks in [B], [C] and [D], respectively. Some tumors showed regrowth. At week 14, the best therapeutic response was observed in the fractionated group (2×0.3 mCi), with 6/10 mice having no tumors (NT) compared to 3/10 in the 3×0.2 mCi groups and 1/10 in the 1×0.6 mCi group. No major body weight loss was observed. Fractionated PT-RAIT provides another alternative for treating pancreatic cancer with minimum toxicity.

Example 26

$^{90}$Y-hPAM4 Radioimmunotherapy (RAIT) Plus Radiosensitizing Gemcitabine (GEM) Treatment in Advanced Pancreatic Cancer (PC)

$^{90}$Y-hPAM4, a humanized antibody highly specific for PC, showed transient activity in patients with advanced disease, and GEM enhanced RAIT in preclinical studies. This study evaluated repeated treatment cycles of $^{90}$Y-hPAM4 plus GEM in patients with untreated, unresectable PC. The $^{90}$Y-dose was escalated by cohort, with patients repeating 4-wk cycles (once weekly 200 mg/m$^2$ GEM, $^{90}$Y-hPAM4 once-weekly wks 2-4) until progression or unacceptable toxicity. Response assessments used CT, FDG-PET, and CA19.9 serum levels.

Of 8 patients (3F/5M, 56-72 y.o.) at the 1$^{st}$ 2 dose levels (6.5 and 9.0 mCi/m$^2$ $^{90}$Y-hPAM4×3), hematologic toxicity has been transient Grade 1-2. Two patients responded to initial treatment with FDG SUV and CA19.9 decreases, and lesion regression by CT. Both patients continue in good performance status now after 9 and 11 mo. and after a total of 3 and 4 cycles, respectively, without additional toxicity. A 3$^{rd}$ patient with a stable response by PET and CT and decreases in CA19.9 levels after initial treatment is now undergoing a 2nd cycle. Four other patients had early disease progression and the remaining patient is still being evaluated. Dose escalation is continuing after fractionated RAIT with $^{90}$Y-hPAM4 plus low-dose gemcitabine demonstrated therapeutic activity at the initial $^{90}$Y-dose levels, with minimal hematologic toxicity, even after 4 therapy cycles.

Example 27

Early Detection of Pancreatic Carcinoma Using Mab-PAM4 and in Vitro Immunoassay

Immunohistochemistry studies were performed with PAM4 antibody. Results obtained with stained tissue sections showed no reaction of PAM4 with normal pancreatic ducts, ductules and acinar tissues (not shown). In contrast, use of the MA5 antibody applied to the same tissue samples showed diffuse positive staining of normal pancreatic ducts and acinar tissue (not shown). In tissue sections with well differentiated or moderately differentiated pancreatic adenocarcinoma, PAM4 staining was positive, with mostly cytoplasmic staining but intensification of at the cell surface. Normal pancreatic tissue in the same tissue sections was unstained.

Table 17 shows the results of immunohistochemical analysis with PAM4 MAb in pancreatic adenocarcinoma samples of various stages of differentiation. Overall, there was an 87% detection rate for all pancreatic cancer samples, with 100% detection of well differentiated and almost 90% detection of moderately differentiated pancreatic cancers.

TABLE 17

| PAM4 Labeling Pattern | | | | |
|---|---|---|---|---|
| Cancer | n | Focal | Diffuse | Total |
| Well Diff. | 13 | 2 | 11 | 13 (100%) |
| Moderately Diff. | 24 | 6 | 15 | 21 (88%) |
| Poorly Diff. | 18 | 5 | 9 | 14 (78%) |
| Total | 55 | 13 | 35 | 48 (87%) |

Table 18 shows that PAM4 immunohistochemical staining also detected a very high percentage of precursor lesions of pancreatic cancer, including PanIn-1A to PanIN-3, IPMN (intraductal papillary mucinous neoplasms) and MCN (mucinous cystic neoplasms). Overall, PAM4 staining detected 89% of all pancreatic precursor lesions. These results demonstrate that PAM4 antibody-based immunodetection is capable of detecting almost 90% of pancreatic cancers and precursor lesions by in vitro analysis. PAM4 expression was observed in the earliest phases of PanIN development. Intense staining was observed in IPMN and MCN samples (not shown). The PAM4 epitope was present at high concentrations (intense diffuse stain) in the great majority of pancreatic adenocarcinomas. PAM4 showed diffuse, intense reactivity with the earliest stages of pancreatic carcinoma precursor lesions, including PanIN-1, IPMN and MCN, yet was non-reactive with normal pancreatic tissue. Taken together, these results show that diagnosis and/or detection with the PAM4 antibody is capable of detecting, with very high specificity, the earliest stages of pancreatic cancer development.

TABLE 18

| PAM4 Labeling Pattern | | | | |
|---|---|---|---|---|
| | n | Focal | Diffuse | Total |
| PanIn-1A | 27 | 9 | 15 | 24 (89%) |
| PanIn-1B | 20 | 4 | 16 | 20 (100%) |

TABLE 18-continued

PAM4 Labeling Pattern

|  | n | Focal | Diffuse | Total |
|---|---|---|---|---|
| PanIn-2 | 11 | 6 | 4 | 10 (91%) |
| PanIn-3 | 5 | 2 | 0 | 2 (40%) |
| Total PanIn | 63 | 21 | 35 | 56 (89%) |
| IPMN | 36 | 6 | 25 | 31 (86%) |
| MCN | 27 | 3 | 22 | 25 (92%) |

Figure 22:
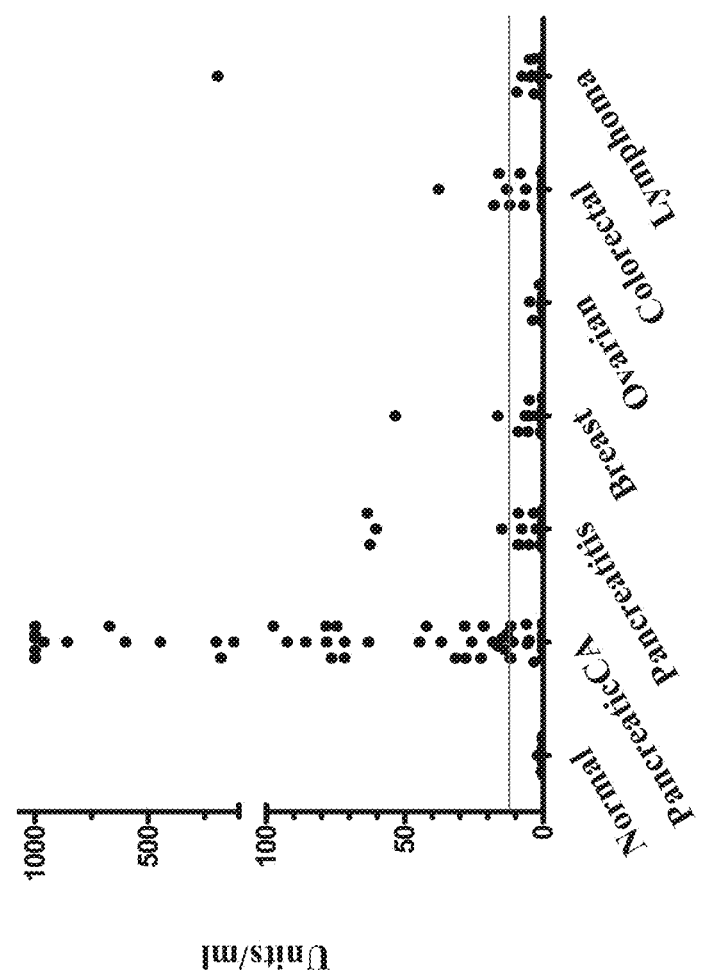
FIG. 22. Differential diagnosis of pancreatic cancer using PAM4-based immunoassay. The horizontal line shows the cutoff level selected for a positive result, based on ROC analysis.

An enzyme based immunoassay for PAM4 antigen in serum samples was developed. FIG. 22 shows the results of differential diagnosis using PAM4 immunoassay for pancreatic cancer versus normal tissues and other types of cancer. The results showed a sensitivity of detection of pancreatic cancer of 77.4%, with a specificity of detection of 94.3%, comparing pancreatic carcinoma (n=53) with all other specimens (n=233), including pancreatitis and breast, ovarian and colorectal cancer and lymphoma. The data of FIG. 22 are presented in tabular form in Table 19.

TABLE 19

PAM4-Reactive MUC5AC in Patient Sera

|  | n | Mean | SD | Median | Range | # Positive (%) |
|---|---|---|---|---|---|---|
| Normal | 43 | 0.1 | 0.3 | 0.0 | 0-2.0 | 0 (0) |
| Pancreatitis | 87 | 3.0 | 11.5 | 0.0 | 0-63.6 | 4 (5) |
| Pancreatic CA | 53 | 171 | 317 | 31.7 | 0-1000 | 41 (77) |
| Colorectal CA | 36 | 3.3 | 7.7 | 0.0 | 0-37.8 | 5 (14) |
| Breast CA | 30 | 3.7 | 10.1 | 0.0 | 0-53.5 | 2 (7) |
| Ovarian CA | 15 | 1.8 | 4.3 | 0.0 | 0-16.5 | 1 (7) |
| Lymphoma | 19 | 12.3 | 44.2 | 0.0 | 0-194 | 1 (5) |

An ROC curve (not shown) was constructed with the data from Table 19. Examining a total of 283 patients, including 53 with pancreatic carcinoma, and comparing the presence of circulating MUC5AC in patients with pancreatic cancer to all other samples, the ROC curve provided an AUC of 0.88±0.03 (95% ci, 0.84-0.92) with a P value <0.0001, a highly significant difference for discrimination of pancreatic carcinoma from non-pancreatic carcinoma samples. Comparing pancreatic CA with other tumors and normal tissue, the PAM4 based serum assay showed a sensitivity of 77% and a specificity of 95%.

Figure 23:
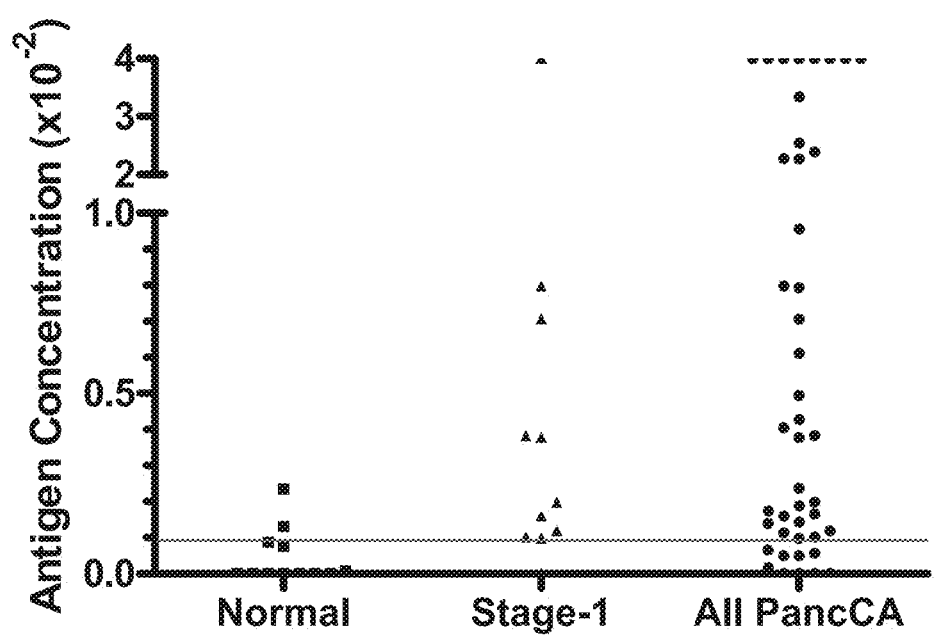
FIG. 23. Frequency distribution of PAM4 antigen in patient sera from healthy volunteers and individuals with varying stages of pancreatic cancer.
Figure 24:
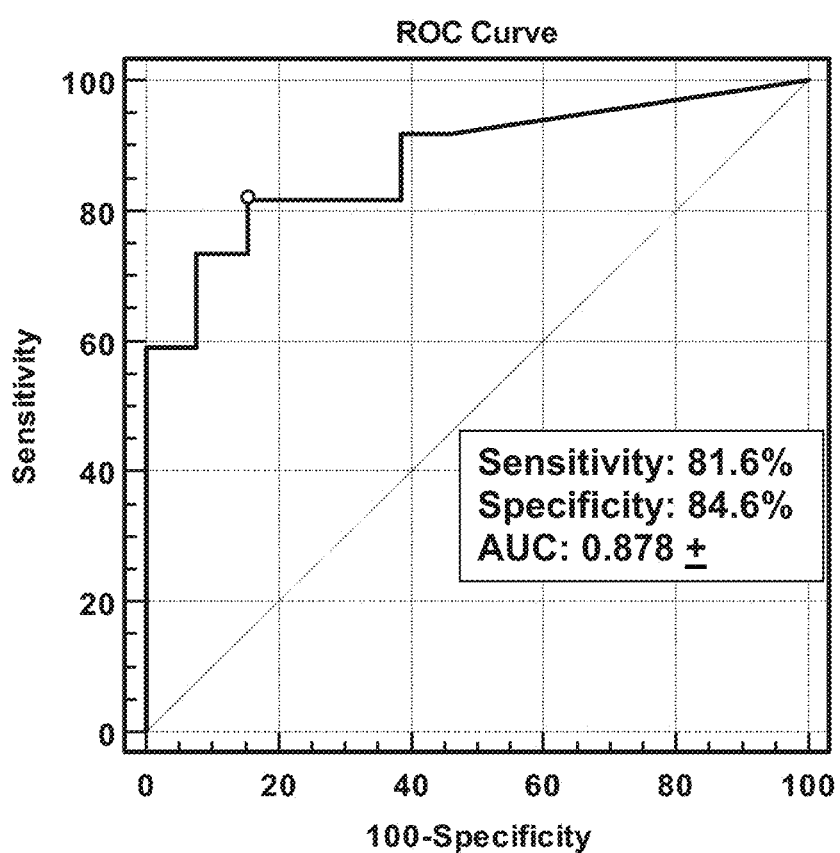
FIG. 24. ROC curve for PAM4 serum immunoassay, showing sensitivity for detection of 81.6% and specificity of 84.6%.

A comparison was made of MUC5AC concentration in serum samples from normal patients, "early" (stage 1) pancreatic carcinoma and all pancreatic carcinoma samples. The specimens included 13 sera from healthy volunteers, 12 sera from stage-1, 13 sera from stage-2 and 25 sera from stage-¾ (advanced) pancreatic carcinoma. A cutoff value of 8.8 units/ml (horizontal line) was used, as determined by ROC curve statistical analysis. The frequency distribution of PAM4 antigen concentration is shown in FIG. 23, which shows that 92% of "early" stage-1 pancreatic carcinomas were above the cutoff line for diagnosis of pancreatic cancer. An ROC curve for the PAM4 based assay is shown in FIG. 24, which demonstrates a sensitivity of 81.6% and specificity of 84.6% for the PAM4 assay in detection of pancreatic cancer.

These results confirm that an enzyme immunoassay based on PAM4 antibody binding can detect and quantitate PAM4-reactive antigen in the serum of pancreatic carcinoma patients. The immunoassay demonstrates high specificity and sensitivity for pancreatic carcinoma. The majority of patients with stage 1 disease were detectable using the PAM4 immunoassay.

In conclusion, an immunohistology procedure employing PAM4 antibody identified approximately 90% of invasive pancreatic carcinoma and its precursor lesions, PanIN, IPMN and MCN. A PAM4 based enzyme immunoassay to quantitate MUC5AC in human patient sera showed high sensitivity and specificity for detection of early pancreatic carcinoma. Due to the high specificity of PAM4 for pancreatic carcinoma, the mucin biomarker can also serve as a target for in vivo targeting of imaging and therapeutic agents. ImmunoPET imaging for detection of "early" pancreatic carcinoma is of use for the early diagnosis of pancreatic cancer, when it can be more effectively treated. Use of radioimmunotherapy with a humanized PAM4 antibody construct, preferably in combination with a radiosensitizing agent, is of use for the treatment of pancreatic cancer.

Example 28

Further Studies of In Vitro Detection of PAM4 Antigen in Human Serum

In certain embodiments, it is preferred to detect the presence of MUC5AC and/or to diagnose the presence of pancreatic cancer in a subject by in vitro analysis of samples that can be obtained by non-invasive techniques, such as blood, plasma or serum samples. Such ex vivo analysis may be preferred, for example, in screening procedures where there is no a priori reason to believe that an individual has a pancreatic tumor in a specific location. The objective of the present study was to develop a reliable, accurate, serum-based assay for detection of pancreatic cancer at the earliest stages of the disease.

Summary

A PAM4-based immunoassay was used to quantitate antigen in the serum of healthy volunteers (N=19), patients with known diagnosis of pancreatic adenocarcinoma (N=68), and patients with a primary diagnosis of chronic pancreatitis (N=29). Sensitivity for the detection of pancreatic adenocarcinoma was 82%, with a false-positive rate of 5% for the healthy controls. Patients with advanced disease had significantly higher antigen levels than those with early-stage disease (P<0.01), with a diagnostic sensitivity of 91%, 86%, and 62% for stage ¾ advanced disease, stage-2, and stage-1, respectively. We also evaluated chronic pancreatitis sera, finding 38% positive for antigen. However, this observation was discordant with immunohistochemical findings that suggest the PAM4-antigen is not produced by inflamed pancreatic tissue. Furthermore, several of the serum-positive pancreatitis patients, for whom tissue specimens were available for pathological interpretation, had evidence of neoplastic precursor lesions. Immunohistochemistry of additional pancreatitis specimens showed 90% to be PAM4-negative with the remainder only weakly positive. This suggested that positive levels of PAM4-antigen within the serum are not derived from inflamed pancreatic tissues, but may be an early indicator of pancreatic cancer.

These results show that the PAM4-serum assay may be used to detect early-stage pancreatic adenocarcinoma, and that positive serum levels of PAM4-antigen are not derived from inflamed pancreatic tissues, but rather may provide evidence of subclinical pancreatic neoplasia.

Materials and Methods

Human Specimens

Sera (N=68) were obtained from patients with a confirmed diagnosis of pancreatic adenocarcinoma being treated at the Johns Hopkins Medical Center, Baltimore, Md., and stored frozen <5 yrs. Each of these patients underwent surgical resection of the pancreas, providing an opportunity for accurate diagnosis and staging. For stage-1 disease, no neoplastic cells were observed outside of the pancreas. However, patients with pancreatic adenocarcinoma are likely to have undetected micrometastatic disease at presentation, including those patients reported with stage-1 disease. For this reason, we evaluated follow-up survival data. All patients described as having stage-1 disease survived at least 1 year (time to last recorded follow-up visit), with a median survival time of 2.70 years ($25^{th}$ percentile=1.32 years) in comparison to the latest SEER data (2002-2006), which reports a 1.42-year median survival for patients having stage-1 disease treated by surgical resection.

A total of 29 sera from patients with a diagnosis of chronic pancreatitis were obtained from the Johns Hopkins Medical Center and Zeptometrix Corp. (Franklin, Mass.). Healthy volunteers (N=19) provided blood for control specimens at the Center for Molecular Medicine and Immunology. All specimens were de-identified, with the only clinical data provided to the investigators being the diagnosis, stage of disease, follow-up survival time, and size of the primary tumor.

Reagents

A human pancreatic mucin preparation was isolated from CaPan1, a human pancreatic cancer grown as xenografts in athymic nude mice. Briefly, 1 g of tissue was homogenized in 10 mL of 0.1 M ammonium bicarbonate containing 0.5 M sodium chloride. The sample was then centrifuged to obtain a supernatant that was fractionated on a SEPHAROSE00-4B-CL column with the void volume material chromatographed on hydroxyapatite. The unadsorbed fraction was dialyzed extensively against deionized water and then lyophilized. A 1 mg/mL solution was prepared in 0.01 M sodium phosphate buffer (pH, 7.2) containing 0.15 M sodium chloride (phosphate-buffered saline [PBS]), and used as the stock solution for the immunoassay standards. A polyclonal, anti-mucin antiserum was prepared by immunization of rabbits, as described previously (Gold et al., Cancer Res 43:235-38, 1983). An IgG fraction was purified and assessed for purity by sodium dodecyl sulfate-polyacrylamide gel electrophoresis (SDS-PAGE) and molecular-sieve high-performance liquid chromatography. Murine MA5 antibody reactive with the MUC1 protein core was obtained from Immunomedics, Inc. (Morris Plains, N.J.). A non-binding isotype-matched control antibody, Ag8, was purified from the P3X63-Ag8 murine myeloma.

Sample Preparation

All assays were performed in a blinded fashion. To prepare the specimens for immunoassay, 300 μL of serum were placed in a 2.0 mL microcentrifuge tube and extracted with an equal volume of 1-butanol. The tubes were vortexed vigorously for 2 min at which time 300 μL of chloroform were added and the tubes again vortexed for 2 min; this latter step was included in the procedure in order to invert the aqueous and organic layers. The tubes were then centrifuged in a microfuge at a setting of 12,000 rpm for 5 min. The top aqueous layer was removed to a clean tube and the sample diluted 1:2 in 2.0% (w/v) casein-sodium salt in 0.1 M sodium phosphate buffer, pH 7.2, containing 0.15 M sodium chloride (PBS) for immunoassay.

Enzyme Immunoassay

The immunoassay was performed in a 96-well polyvinyl plate that had been coated with 100 μL of humanized-PAM4 IgG at 20 μg/mL in PBS with incubation at 4° C. overnight. The wells were then blocked by addition of 200 μL of a 2.0% (w/v) solution of casein in PBS and incubated for 1.5 h at 37° C. The blocking solution was removed from the wells and the plate washed 5-times with 250 μL of PBS containing 0.1% (v/v) Tween-20. The standards, or unknown specimens, 100 μL in triplicate, were added to the appropriate wells and incubated at 37° C. for 1.5 h. The plate was then washed 5-times with PBS-Tween-20 as above.

The polyclonal, rabbit anti-mucin antibody, diluted to 5 μg/mL in 1.0% (w/v) casein in PBS containing 50 μg/mL non-specific, human IgG, was added to each well and incubated for 1 h at 37° C. The polyclonal antibody was then washed from the wells as above, and peroxidase-labeled donkey anti-rabbit IgG (Jackson ImmunoResearch Laboratories, West Grove, Pa.), at a 1:2000 dilution in 1.0% (w/v) casein in PBS, also containing 50 μg/mL human IgG, was added to the wells and incubated at 37° C. for 1 h. After washing the plate as above, 100 μL of a 3,3',5,5'-tetramethylbenzidine substrate solution were added to the wells and incubated at room temperature for 30 min. The reaction was stopped by the addition of 50 μL 4.0 N sulfuric acid, and the optical density read at a wavelength of 450 nm using a SPECTRA-MAX® 250 spectrophotometer (Molecular Devices, Sunnyvale, Calif.). Because of the considerable microheterogeneity of the PAM4 antigen, we chose to report our results in arbitrary units/mL, based on an initial reference standard purified from xenografted CaPan-1 human pancreatic tumor.

Immunohistochemistry

Paraffin-embedded specimens obtained from the Cooperative Human Tissue Network were cut to 4 micron sections on superfrost plus adhesive slides (Thermo Scientific, Waltham, Mass.). Tissue sections were then heated to 95° C. for 20 min in a pH 9.0 Tris buffer, Target Retrieval Solution (Dako, Carpinteria, Calif.), allowed to cool to room temperature, and then quenched with 3% $H_2O_2$ for 15 min at room temperature. Primary antibodies were then used at 10 μg/mL with an ABC VECTASTAIN® kit (Vector Laboratories, Burlingame, Calif.) for labeling the tissues. The slides were scored independently by two pathologists using a paradigm consistent with that reported for earlier studies on biomarkers in pancreatic adenocarcinoma (Gold et al., 2007, Clin Cancer Res 13:7380-87): 0-negative, <1% of the tissue was labeled; 1-a weak, focal labeling of between 1%-25% of the tissue; 2-a strong, focal labeling of between 1%-25% of the tissue; 3-a weak, diffuse labeling >25% of the tissue; 4-a strong, diffuse labeling >25% of the tissue. Only the appropriate tissue components (e.g., adenocarcinoma cells, normal ducts, etc.) were considered for assessment.

Statistical Analyses

Standard curves were generated from the immunoassay data, with regression analyses performed to interpolate concentrations of the unknown samples (Prism 4.0 software, GraphPad, La Jolla, Calif.). Receiver operating characteristic (ROC) curves were generated by use of the Med-Calc statistical software package (version 7.5) (Med-Calc, Mariakerke Belgium). Student's t-test was used to compare variables in any two groups. The Cochran-Armitage test was used to detect a trend between detection rates and stage of disease.

Results

Accuracy and Precision of the Immunoassay

Figure 25:
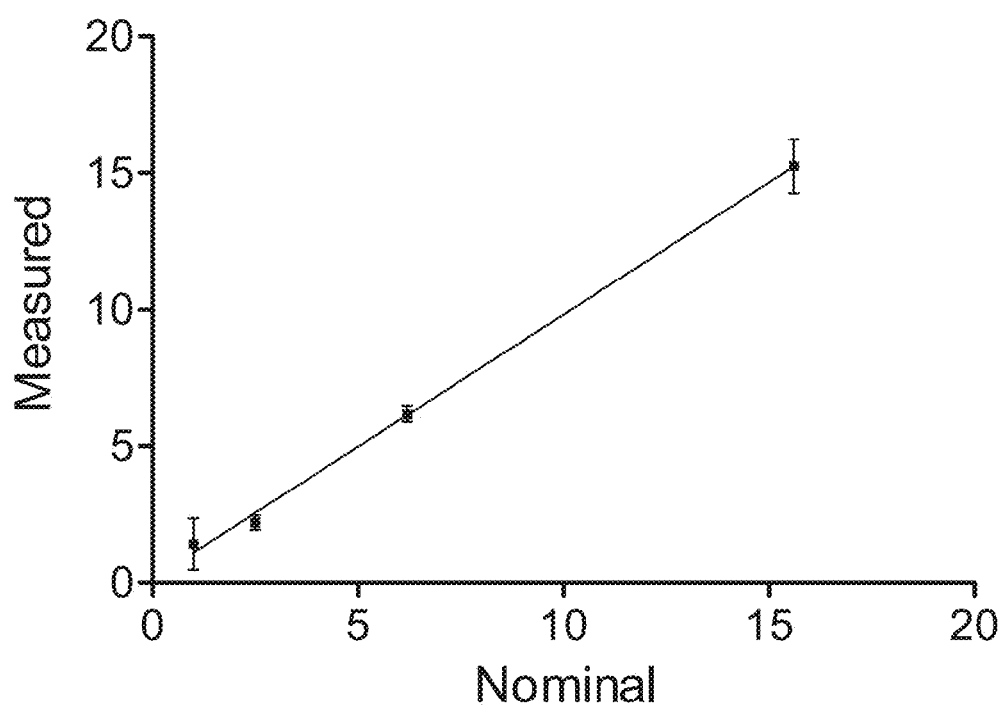
FIG. 25. Accuracy of the PAM4-immunoassay was determined to be within 10% of the nominal concentrations examined at or above the cutoff value of 2.40 units/mL. A linear trend was calculated with an equation of y=0.965x+ 0.174, and goodness of fit r$^2$=0.999.

A set of control standards with nominal concentrations of 15.60, 6.20, 2.50, and 1.00 units/mL was evaluated on several nonconsecutive days (N=7) for determination of accuracy and precision. Curve fitting for the standards generally gave resultant goodness of fit values for $r^2>0.990$. Accuracy was calculated to be within 8% of the nominal value for the first three concentrations, but fell to approximately 22% for the 1.00 units/mL standard. Linear regression of nominal vs. measured units/mL in this series of controls gave a trend-line with a slope of 0.965 and y intercept of 0.174 ($r^2$=0.999), where a slope of 1.00 with a y intercept of 0.00 would constitute 100% accuracy (FIG. 25). An average absolute difference between nominal and recovered mass equal to 0.190±0.173 units/mL for the two lowest concentration standards suggested a minimum absolute error of approximately 0.2 units/mL for the EIA. Values for the coefficient of variation (CV) were 6.40%, 4.85%, 12.0%, and 66.4%, respectively, for the 4 control standards. Taken together, the data suggest that the PAM4-immunoassay provides levels of accuracy and reproducibility that are within the guidelines suggested for an immunoassay measurement of an analyte; accuracy and precision were within 15% for concentrations above the cutoff value (2.40 units/mL), and within 20% at the cutoff value. To further test this, we examined 3 sera, two of which were from healthy controls, on 3 separate days. The two healthy controls gave average results of 0.27±0.06 and 0.30±0.27 units/mL, each of which was close to the minimum absolute error for the EIA with consequent high CV of 21.65% and 88.19%, respectively. The other patient serum gave an average of 19.45±2.51 units/mL with a CV of 12.9%.

Quantitation of Antigen in Patient Sera

In a preliminary study reported in the Example above, the PAM4 serum-based immunoassay had an apparent sensitivity of 77% and a specificity of 94% for pancreatic carcinoma. It should be noted that the overwhelming majority of cancer specimens of pancreatic and non-pancreatic origin had been obtained from patients enrolled in IRB-approved clinical trials conducted by the Garden State Cancer Center and stored frozen at −80° C. for more than 10 yrs. However, the specimens of pancreatitis had been stored frozen for a considerably shorter time. We evaluated a new group of 24 sera from patients diagnosed with pancreatic adenocarcinoma. Only two of the sera had levels of PAM4-reactive antigen considered to be positive. Therefore, we considered and evaluated reasons why the immunoassay had not performed as expected, including the quality of the immunoassay reagents, the possibility that the antigen was being degraded and/or removed from the serum, its presence in the form of immune complexes, or being bound by a blocking substance. We discovered that there is a substance in fresh human serum and/or specimens stored frozen for short periods of time (<5 yrs) that apparently binds to the PAM4-reactive epitope and blocks its binding to PAM4 antibody, thus preventing detection by immunoassay. Percent recovery of antigen from fresh normal human serum (N=2) spiked with PAM4-antigen at concentrations from 5-20 units/mL was on the order of 33% or less.

In a series of reports, Slomiany and co-workers disclosed that gastric mucin had covalenty bound and/or associated lipids and fatty-acids (Slomiany et al., 1984, Arch Biochem Biophys 229:560-67; Slomiany et al., 1986, Biochem Biophys Res Commun 141:387-93; Zalesna et al., 1989, Biochem Int 18:775-84), and that these lipids and fatty acids had specific effects upon the physicochemical properties of the mucin. Furthermore, it was reported that fatty-acid synthetase levels and activity are significantly elevated in pancreatic adenocarcinoma, as is also the case for other forms of cancer and other pathologic conditions (Walter et al., 2009, Cancer Epidemiol Biomarkers Prev 19:2380-85). Because the blocking substance might be lipid in nature, we performed organic extraction of sera from the group of 24 pancreatic adenocarcinoma patients that had been stored frozen for <5 years. As was noted above, without prior extraction, only 2 of the 24 specimens (8.3%) had levels of PAM4-antigen that were considered positive, whereas after organic extraction, 22 of the 24 specimens (92%) had positive levels of the PAM4-antigen.

We were also able to re-evaluate, from the study reported in the Example above, 10 pancreatic adenocarcinoma patient sera that had been stored frozen for >15 years to confirm the prior results. With or without extraction, all 10 specimens had levels of antigen that were considered to be positive. Regression analysis to compare paired results from extracted and non-extracted sera gave a trendline with slope of 1.10 ($r^2$=0.94), demonstrating that with or without extraction of these long-term frozen sera, the results were similar. It is considered that long-term storage of the specimens resulted in degradation of the inhibiting substance or decreased binding to and unmasking of the epitope. All further testing of sera was performed with organic extraction of specimens prior to immunoassay.

Figure 26:
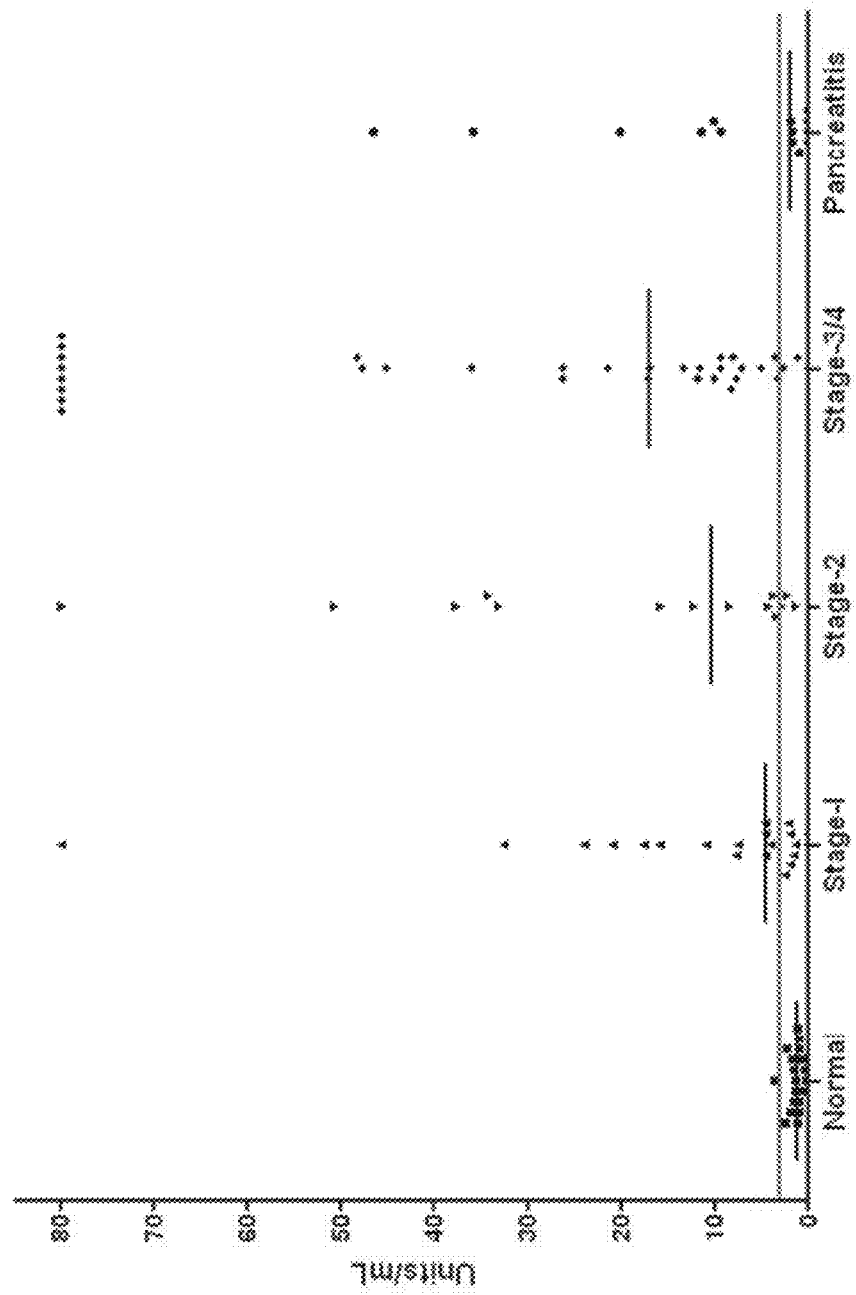
FIG. 26. Frequency distribution of PAM4-reactive antigen in patient sera by stage of disease. Cutoff value=2.4 units/mL (horizontal line). The median values (units/mL) are shown for each study group.
Figure 27:
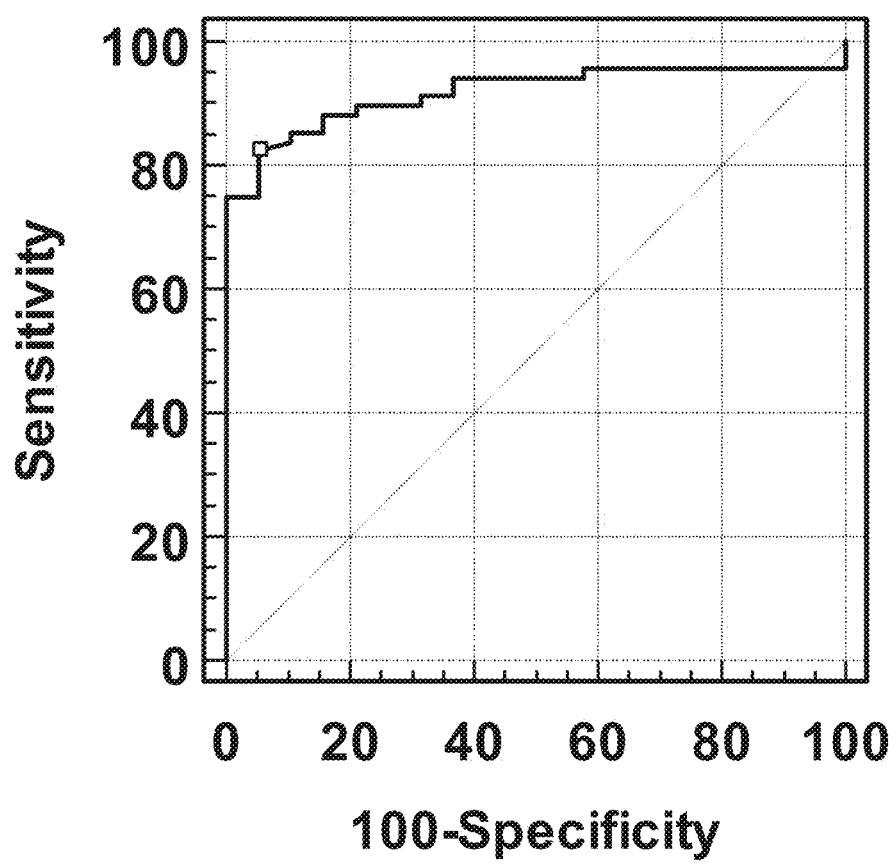
FIG. 27. Receiver Operator Characteristics (ROC) curve for the performance of the PAM4-based immunoassay; pancreatic adenocarcinoma vs. healthy adults. Values for the area under the curves (AUC) and 95% confidence limits are provided.

Specimens evaluated for PAM4-reactive antigen included 68 patients with confirmed pancreatic adenocarcinoma divided by stage: 21 from stage-1; 14 from stage-2; and 33 from stages-3 and -4 (advanced). In addition, 19 sera collected from healthy adult volunteers and 29 patients diagnosed with chronic pancreatitis were included as control groups. The maximum concentration shown in the dot-plot (FIG. 26) was 80 units/mL, because there were insufficient volumes of sera to perform additional dilution studies. Although a cutoff value of 10.2 units/mL was reported in the Example above, because of the use of an organic extraction procedure, as well as differences in the EIA protocol (reagent concentrations, inclusion of human IgG in buffers), we chose to treat the current data set independently of prior results. A positive cutoff value of 2.4 units/mL was calculated by ROC curve statistics (FIG. 27) for the comparison of all pancreatic adenocarcinoma specimens versus healthy adults. The overall sensitivity for detection of pancreatic adenocarcinoma was 82%, with an area under the curve of 0.92±0.03 (95% CI=0.84-0.97). At this level of sensitivity, a false-positive rate of 5% was observed for the healthy control group, the single positive case having 3.65 units/mL of circulating antigen, just above the cutoff value. Insufficient volumes of sera precluded CA19-9 immunoassays for comparison to the PAM4-immunoassay results.

As shown in Table 20, sensitivity for detection of early, stage-1 pancreatic adenocarcinoma was relatively high, with 13 of 21 (62%) specimens above the cutoff value. As expected, this detection rate was lower than that observed for the stage-2 (86%) and advanced stage-3 and -4 (91%) patient groups. A statistically significant trend (P<0.01) was noted for detection rate vs. stage of disease. We considered that this was most likely due to tumor size or burden. The average tumor sizes for stage-1, stage-2, and stage-¾ groups were 2.14±1.02 $cm^3$, 3.36±1.18 $cm^3$, and 3.45±1.06 $cm^3$, respectively. While there was no statistically significant difference in tumor size between the stage-2 and -¾ groups (P>0.41), a statistically significant difference was observed for each of these two groups when compared to stage-1 tumor size (P<0.004 or better). However, it should be noted that individual tumor size did not correlate with antigen concentration in the serum ($r^2$=0.0065).

Specimens reported as Stage-1 could be divided into stage-1A (N=13) and stage-1B (N=8) subgroups based on tumor size, with detection rates of 54% and 75%, respectively; however, caution is emphasized since the number of patients in each subgroup is small. The average tumor size for stage-1A was 1.41±0.58 cm$^3$ (range: 0.4 cm$^3$-2.0 cm$^3$) and for stage-1B was 3.15±0.44 cm$^3$ (range: 2.5 cm$^3$-4 cm$^3$); P<0.001 for comparison of the two groups. While, on the whole, tumor sizes were smaller in stage-1A disease than in stage-1B, there was no apparent statistical correlation between individual tumor size and concentration of the PAM4-antigen in the blood ($r^2$=0.03). Furthermore, it is important to note that of the 13 stage-1A specimens, 4 of the 7 positive cases had PAM4-antigen levels considerably higher than the cutoff value, with a range of 17.65-32.65 units/mL.

TABLE 20

PAM4-reactive antigen in the sera of patients

| | N | Median (units/mL) | True- Positive | T-test (P value)$^a$ |
|---|---|---|---|---|
| Total PC | 68 | 9.85 | 81% | <0.001 |
| Stage-1 | 21 | 4.53 | 62% | <0.002 |
| Stage-1A | 13 | 3.96 | 54% | <0.02 |
| Stage-1B | 8 | 6.05 | 75% | <0.02 |
| Stage-2 | 14 | 10.39 | 86% | <0.005 |
| Stage-3/4 | 33 | 13.37 | 91% | <0.001 |
| Chronic Pancreatitis | 29 | 1.28 | (38% FP) | |
| Healthy Volunteers | 19 | 1.18 | (5% FP) | |

$^a$All comparisons are to healthy volunteers

We also evaluated a set of 29 patient sera with the primary diagnosis of chronic pancreatitis. At the 2.4 units/mL cutoff established by ROC evaluation of normal and pancreatic adenocarcinoma patients, 11 pancreatitis patients (38%) were positive. ROC curve analysis of pancreatitis sera compared directly to the pancreatic adenocarcinoma specimens gave an area under the curve of 0.77±0.05 (95% CI=0.68-0.85). The median value for the pancreatitis group was 1.28 units/mL, comparable to the healthy volunteer group (1.18 units/mL), but considerably lower (3.5-fold) than the stage-1 pancreatic adenocarcinoma group (4.53 units/mL). It should be noted that our earlier results for pancreatitis specimens suggested a considerably lower false-positive rate, only 5%. However, those pancreatitis specimens were stored frozen for less than 5 years, and were not organic phase extracted prior to analysis.

Biopsy and/or surgical specimens were available from 14 of the chronic pancreatitis specimens, 6 of which were from patients who were considered positive for circulating MUC5AC. In 3 of these 6 positive cases, precursor lesions were identified within the tissue sections. It was then considered whether the positive serum test was due to pancreatitis or the presence of neoplastic precursor lesions. We performed immunohistochemistry on an additional 30 biopsy specimens from patients diagnosed with pancreatitis. Of the 30 specimens, one frank invasive pancreatic adenocarcinoma and one large PanIN-2-3 lesion were identified (in separate specimens) by use of PAM4 staining, while surrounding acinar-ductal metaplasia (ADM) and normal tissues were negative (data not shown). Of the remaining 28 specimens, 19 had sufficient parenchyma to be evaluated, 16 of which had evidence of ADM. PAM4 was negative in all but two of these cases, and in each of these gave only a very focal, weak labeling of ADM within the specimens (data not shown).

Validation Studies

We have begun putting together a panel of well-annotated serum specimens from patients with known diagnoses. A first set of patient sera (N~450) including healthy individuals and patients having invasive pancreatic cancers (carcinoma, neuroendocrine, and other forms), benign disease of the pancreas (adenomatous lesions, pancreatitis, etc.) and non-pancreatic cancers and benign disease (biliary, duodenal, ampullary carcinomas, cholecystitis, gastritis, etc.) is being evaluated (blind study) to both confirm and extend the prior results on PAM4 specificity in a much larger group of patients. Table 21 presents an interim analysis based upon studies completed to date; overall, the data are remarkably similar to our earlier data. Employing a cutoff value determined by ROC analysis of PC vs Healthy Adults, the overall sensitivity for detection of pancreatic carcinoma was 80% at a specificity of 96%. Only 2 of 16 neuroendocrine tumors were positive, just over the cutoff value.

To date, 14 of 53 (26%) patients with primary diagnosis of pancreatitis have been identified as PAM4 positive, lower than that reported in our recent publication. We are now attempting to correlate clinical data with results in this pancreatitis group, as well as provide for clinical and laboratory follow-up of these patients. Only 2 of 11 patients with benign adenomatous lesions (both cystadenoma) were considered positive. One other cystadenoma had PAM4-antigen levels greater than 200 units/mL. The pathology report describes the biopsy as "very suspicious for cancer".

TABLE 21

PAM4-reactive antigen in the sera of patients

| | N | Median$^a$ | Mean ± SD$^a$ | Positive (%) | ROC-AUC$^b$ (95% CI) | P value$^c$ |
|---|---|---|---|---|---|---|
| Pancreatic Carcinoma | 145 | 7.84 | 35.61 ± 64.58 | 80 | (comparisons are to PC) | |
| Neuro-endocrine | 16 | 0.00 | 1.73 ± 4.91 | 12.5 | | |
| Healthy | 27 | 0.40 | 0.54 ± 0.53 | 3.7 | 0.90 ± 0.02 (0.85-0.94) | <0.0001 |
| Pancreatitis | 53 | 0.37 | 1.56 ± 3.35 | 26 | 0.85 ± 0.28 (0.79-0.90) | <0.0001 |
| Pancreatic Adenoma | 11 | 0.00 | 0.64 ± 0.78 | 18 | 0.90 ± 0.03 (0.84-0.94) | <0.0001 |

$^a$Values for Median and Mean ± SD are in Units/mL
$^b$Receiver Operating Characteristic Curves (ROC); Area Under the Curve (AUC) with values for 95% Confidence Intervals presented.

Discussion

Studies reported in the Example above that employed both immunohistology of tissue specimens and EIA of circulating antigen demonstrated that the PAM4-reactive epitope is a biomarker for invasive pancreatic adenocarcinoma and is expressed at the earliest stages of pancreatic neoplasia (i.e., PanIN-1). It was not detectable within normal pancreatic tissues (ducts, acinar and islet cells), nor the majority of non-pancreatic cancers examined (breast, lung, gastric, and others). Thus, an elevation of the PAM4-epitope concentration in the serum provided a high positive likelihood ratio of 16.8 for pancreatic adenocarcinoma. Missing from the prior study was clinical information regarding the stage of disease. Consequently, we could not evaluate the value of the immunoassay for detection of potentially curable early disease until now.

We report herein that PAM4-based EIA using serum samples can detect patients having early-stage pancreatic adenocarcinoma, and can provide accurate discrimination from disease-free individuals. The assay's sensitivity for detection of early pancreatic adenocarcinoma was 62% for patients with stage-1 and 86% for patients with stage-2 disease and serum levels generally increased with advancing stage of disease. A high percentage of patients with stage-1 and -2 disease are clinically asymptomatic. We conclude that detection of tumor growth at these early stages using a PAM4 serum assay could provide improved prospects for survival.

The cancer patients in this study all underwent surgical resection, providing an opportunity to accurately stage each patient. However, many patients with pancreatic cancer are suspected of having micrometastatic disease at presentation, even if they do not have histologically-apparent regional lymph node involvement. This highlights a general problem in the study of early detection, particularly with a low-incidence disease such as pancreatic adenocarcinoma. The accrual of specimens that are well-defined is problematic. Further complicating the issue is that many of these pancreatic cancers occur in the presence of chronic pancreatitis, cholecystitis, and neoplastic precursor lesions, amongst other conditions.

Of 29 sera with a primary diagnosis of chronic pancreatitis, 38% were identified as positive for PAM4-antigen. However, several of these serum-positive patients, for whom tissue specimens for pathological interpretation were available, had evidence of neoplastic precursor lesions. Furthermore, a discrepancy was observed in the comparison of tissue reactivity by immunohistology and serum levels of antigen by immunoassay. By immunohistochemistry, only 10% of the evaluable specimens showed evidence of PAM4 staining within the ADM, although this was at considerably lower intensity than observed for the overwhelming majority of pancreatic adenocarcinoma specimens (Gold et al., 2007, Clin Cancer Res 13:7380-87). Therefore, the results suggest that positive levels of PAM4-antigen within the serum may not be derived from inflamed pancreatic tissues, but rather could provide evidence of subclinical pancreatic neoplasia, such as PanIN lesions, and that, at the very least, positive results provide the rationale for clinical follow-up of these patients.

Findings from genetically-engineered animal models of pancreatic adenocarcinoma suggest that human pancreatic neoplasia may arise before the PanIN-1 lesion (Leach, 2004, Cancer Cell 5:7-11). ADM was the earliest change observed in the mutant KRAS targeted model described by Zhu et al. (2007, Am J Pathol 171:263-73). On the other hand, Shi et al. (2009, Mol Cancer Res 7:230-36) reported that although KRAS gene mutations can occur within ADM, they occur predominantly within ADM that are associated with PanIN lesions. The authors suggest this may occur by retrograde extension of the PanIN to the surrounding ADM. As yet, there is no conclusive evidence that ADM progress to PanIN. The fact that PAM4 is reactive with ADM in two patients with pancreatitis is of interest.

At the present time, screening the general population for pancreatic cancer is not considered medically or economically worthwhile, because the disease is simply too infrequent. However, there is considerable interest in screening patients predicted to have an increased risk of developing pancreatic adenocarcinoma. Several studies have demonstrated that screening individuals with strong family histories of pancreatic cancer can identify precursor neoplasms of the pancreas that are amenable to surgical resection (Canto et al., 2006, Clin Gastroenterol Hepatol 4:766-81; Canto, 2005, Clin Gastroenterol Hepatol 3:S46-58; Brentnall et al., 1999, Ann Intern Med 131:247-55). For example, relatives of pancreatic cancer patients have a significantly higher risk of developing pancreatic cancer than the general population (Shi et al., 2009, Arch Pathol Lab Med 133:365-74). A small percentage of patients with familial pancreatic cancer harbor mutations of PALB2 (partner and localizer of BRCA2), a susceptibility gene for pancreatic cancer (Tischkowitz et al., 2009, Gastroenterology 137:1183-86). Similarly, patients with long-standing chronic pancreatitis are at increased risk of developing pancreatic cancer, and the risk is over 30%, among patients with early-onset (teenage) hereditary pancreatitis (Lowenfels et al., 1993, New Eng J Med 328:1433-37; Lowenfels et al., 1997, J Natl Cancer Inst 89:442-46). A 20- to 34-fold higher risk has been observed in individuals with familial atypical multiple mole (FAMMM) syndrome (Rutter et al., 2004, Cancer 101:2809-16). Also, several studies have shown a significantly increased risk of developing pancreatic cancer in diabetic individuals who meet certain criteria (Pannala et al., 2009, Lancet Oncol 10:88-95). Longitudinal surveillance of these patients by use of the PAM4-immunoassay may provide for early detection of neoplasia. A second potential use of the immunoassay could be as a means to detect recurrence of disease post-therapy, and in particular, following surgical resection for those patients where the tumor is supposedly confined to the pancreas.

The relatively high specificity of the PAM4 antibody provides a means to target both imaging and therapeutic agents with high tumor uptake and high tumor/nontumor ratios. We have demonstrated PAM4's potential as both a directly-radiolabeled or bispecific, pretargeting reagent for nuclear imaging and radioimmunotherapy of pancreatic cancer. Also, initial results of a clinical phase 1b trial to evaluate a fractionated dosing of $^{90}$Y-PAM4 whole IgG (clivatuzumab tetraxetan), in combination with a radiosensitizing regimen of gemcitabine, were reported recently (Pennington et al., 2009, J Clin Oncol 27:15s, abstract 4620). Of 22 patients with stage-¾ disease (mostly stage-4), 68% showed evidence of disease control, with 23% of patients having partial responses based on RECIST criteria. Thus, positive results by the PAM4-based immunoassay provides a rationale to pursue PAM4-targeted imaging and therapy, thus providing a personalized therapy.

The PAM4-based immunoassay can identify the majority of pancreatic adenocarcinoma patients of all stages. Although a direct comparison with CA19.9 was not possible in the current study, a prior comparison of the two biomarkers in a limited set of pancreatic adenocarcinoma sera (N=41) demonstrated a statistically significant difference (P<0.01) with PAM4-antigen levels positive in 71% of patient specimens and CA19.9-antigen levels positive in 59% of specimens. In general, it is thought that CA19.9 lacks the sensitivity and specificity to provide for early detection and/or diagnosis of pancreatic adenocarcinoma. However, the assay does have its use for management with continued elevation in CA19.9 serum levels post treatment indicative of a poor prognosis. Similarly, we recently reported in abstract form (Pennington et al., 2009, J Clin Oncol 27:15s, abstract 4620), the use of circulating PAM4-antigen levels for prediction of anti-tumor response.

These results show that the conditions under which specimens are stored (e.g., the length of time they are kept frozen) can have significant effects upon accessibility of the epitope under study. For the PAM4-based immunoassay, a fatty acid or lipid substance may be able to bind the specific epitope and interfere with the immunoassay. However, it is also possible this material was a low-molecular weight peptide or other substance soluble in organic solvents. The ability to remove this substance by organic extraction of the serum makes the PAM4-immunoassay reproducible. In addition, the question is raised as to the biological significance of the circulating inhibitor:MUC5AC interaction. However, when using the PAM4 antibody as an in vivo targeting agent (e.g., radioimmunotherapy), the presence of circulating PAM4-antigen is not a factor, since targeting of radiolabeled-PAM4 to sites of tumor growth has been observed in the majority of patients evaluated to date. Thus, it appears that the PAM4-antigen within tumor is free of the blocking substance.

Example 29

Phase IB/II Study of $^{90}$Y-Labeled hPAM4 Antibody and Gemcitabine in Advanced Pancreatic Cancer A phase IB/II study of $^{90}$Y-labeled hPAM4 antibody (clivatuzumab tetraxetan) in advanced pancreatic cancer patients was performed. A total of 100 patients with previously untreated Stage III or IV pancreatic cancer were enrolled into this open-label trial to receive gemcitabine once-weekly×4 with $^{90}$Y-clivatuzumab tetraxetan on weeks 2, 3 and 4 (therapy cycle). The therapy cycle could be repeated until disease progression or until the patient displayed unacceptable toxicity. Ten patients withdrew early, while 90 patients, of whom 82 had the Stage IV (metastatic) disease, received 1-4 therapy cycles. Tumor responses were assessed by CT, FDG/PET and serum CA19.9 after each cycle (initially every 4 wks).

In Part I of this study, 38 patients were treated with $^{90}$Y-clivatuzumab tetraxetan at 6.5, 9, 12 or 15 mCi/m$^2$×3, and a low, fixed gemcitabine dose of 200 mg/m$^2$×4 for radiosensitization. Thirteen patients were retreated with the same cycle 1-3 times. The overall disease control rate, which included complete response (CR), partial response (PR) and stable disease (SD), by CT-based RECIST criteria, was 58%, including 6 patients (16%) with PR and 16 patients (42%) with SD as best response.

The median overall survival (OS) for the 38 treated patients was 7.7 months, which compares favorably with other regimens for advanced pancreatic cancer. At the higher therapy doses (12 and 15 mCi/m$^2$ of $^{90}$Y-clivatuzumab tetraxetan×3), a median OS of 8.0 months was noted. For the 13 patients who received repeated cycles of the combination therapy, median OS improved to 11.8 months. Extended survival of up to 14.8 months post therapy onset has been observed, with 8 patients achieving a survival >6 months (3 patients >1 yr). Anecdotal reports indicate performance status and pain level improved with therapy.

Fifty-two patients who were treated in Part II of this study received 3 weekly $^{90}$Y doses of 12 mCi/m$^2$ and gemcitabine doses of 200, 600 or 1000 mg/m$^2$×4, with 14 patients receiving repeated therapy cycles at the same gemcitabine dose but $^{90}$Y doses of 6.5, 9 or 12 mCi/m$^2$. Results were available from 47 of the 52 patients. The disease control rate for the 200 mg/m$^2$ group was 72%, with 19% PR and 53% SD. For the 600 and 1000 mg/m$^2$ groups, the disease control rates were 63% (0% PR) and 68% (18% PR), respectively. Higher gemcitabine doses appeared to offer no advantage in treatment response over the lowest dose of 200 mg/m$^2$. At the time of reporting, survival data were not available for this group of patients. Treatments were well tolerated with no infusion reactions to radiolabeled clivatuzumab and few non-hematologic side effects. Hematologic suppression was transient after cycles 1 and 2.

These results showed that repeated cycles of fractionated doses of clivatuzumab tetraxetan, labeled with yttrium-90 ($^{90}$Y) and given in combination with gemcitabine, demonstrated therapeutic activity in patients with advanced, inoperable, pancreatic cancer. Therapy with repeated cycles of clivatuzumab tetraxetan plus low-dose gemcitabine improved overall survival over single-cycle therapy in patients with locally advanced or metastatic pancreatic cancer.

Example 30

Detection of Early-Stage Pancreatic Ductal Adenocarcinoma (PDAC): Sensitivity, Specificity, and Discriminatory Properties of Serum-Based PAM4-Immunoassay As disclosed in Example 28, a serum-based enzyme immunoassay employing the PAM4 antibody was able to correctly identify 81% of patients with known PDAC and this assay had promising sensitivity for detecting early-stage disease. These findings have been extended in a much larger patient population that included over 600 sera from both malignant and benign diseases of the pancreas and surrounding tissues. In a blinded analysis, sera from patients with confirmed PDAC (N=298), other cancers (N=99), benign disease of the pancreas (N=126), and healthy adults (N=79) were evaluated by enzyme immunoassay for concentration of PAM4-antigen levels.

Overall sensitivity for detection of PDAC was 76%, with 64% of stage-1 patients testing positive and a higher sensitivity (85%) for advanced disease. For the most part, sera from patients with neuroendocrine tumors of the pancreas or cancers of other origin (squamous, GIST, etc.) did not have elevated levels of the PAM4-antigen. Approximately half of the patients with ampullary (48%) and extrahepatic biliary (50%) adenocarcinomas had positive levels of circulating PAM4-antigen. Of 126 patients diagnosed with benign conditions of the pancreas, only 24 (19%) were positive and, in particular, 18 of 80 (23%) patients with chronic pancreatitis (CP) were positive. ROC curve analysis demonstrated a statistically significant difference between the PDAC and CP groups (P<0.0001), with an area under the curve of 0.84±0.02 (95% CI: 0.79-0.89). The positive- and negative-likelihood ratios for differentiating PDAC from benign conditions of the pancreas were 4.00 and 0.30, respectively.

In conclusion, the PAM4-immunoassay detected nearly two-thirds of stage-1 PDAC patients, and did so with high discriminatory power with respect to benign pancreatic disease. The results provide a rationale for longitudinal surveillance of patients considered at high-risk for PDAC (e.g., familial pancreatic cancer, new-onset diabetes, etc.) with the PAM4 assay.

Example 31

PAM4-Based Assay Differentiates Pancreatic Ductal Adenocarcinoma (PDAC) from Chronic Pancreatitis and Benign Nonmucinous Pancreatic Cysts We examined the expression of PAM4-reactive MUC5AC in chronic pancreatitis and benign non-mucinous cystic lesions of the pancreas. A tissue microarray of PDAC (N=14), as well as surgical specimens from chronic pancreatitis (N=32) and benign non-mucinous cystic lesions of the pancreas (N=19), were assessed by immunohistochemistry for expression of the PAM4-reactive MUC5AC, as well as MUC1 (mAb-MA5), MUC4 (mAb-8G7), and CEACAM6 (mAb-MN-15).

PAM4-reactive MUC5AC, MUC1, MUC4 and CEACAM6 were expressed in 79% (11/14), 100% (14/14), 86% (12/14) and 100% (14/14) of invasive pancreatic adenocarcinoma. PAM4 only weakly labeled 6% (1/19) of benign non-mucinous cystic lesions, 1 of 15 serous cystadenomas (SCAs) and 0 of 4 cysts with squamous epithelial lining (2 lymphoepithelial cysts, and 2 retention cysts with squamous metaplasia). However, the expression of MUC1, MUC4 and CEACAM6 was detected in 53% (8/15), 0% (0/15) and 13% (2/15) of SCAs, and in 4, 3 and 3 of the 4 cysts with squamous epithelial lining, respectively. PAM4 labeled 19% (6/32) of chronic pancreatitis specimens; however, this PAM4 reactivity was restricted to the PanIN precursor lesions associated with chronic pancreatitis. Inflamed tissue was negative. The expression of MUC1, MUC4 and CEACAM6 was detected in 90% (27/30), 78% (25/32), and 97% (31/32) of chronic pancreatitis. In all of the positively-labeled specimens, the reactivity was present in non-neoplastic inflamed pancreatic tissue in addition to PanIN.

In conclusion, the expression of PAM4 was detected in only 6% of benign non-mucinous cystic lesions and in the precursor lesions associated with chronic pancreatitis. These results suggest that PAM4, in contrast to MUC1, MUC4, and CEACAM6, may be useful to differentiate benign non-mucinous cystic lesions of the pancreas and chronic pancreatitis from PDAC.

Example 32

Combination of the PAM4 and CA19-9 Biomarkers for Improved Detection of Pancreatic Adenocarcinoma Pancreatic ductal adenocarcinoma (PDAC) is almost universally lethal, due mainly to the inability to detect early-stage disease. Thus, identification of biomarkers that can identify patients with early-stage PDAC may improve overall survival. In a blinded study, PAM4 and CA19-9 immunoassays were performed on sera from 480 patients, including those with confirmed PDAC (N=234), other cancers (N=84), benign diseases of the pancreas (N=89), and healthy adults (N=50).

Overall sensitivity for PDAC was similar, 74% and 77% for PAM4 and CA19-9, respectively. Sensitivity for detection of early, stage-1 disease (N=26), although somewhat higher for the PAM4-antigen, was also statistically similar, 65% and 58% for PAM4 and CA19-9, respectively (P=0.5775). However, specificity was significantly lower for CA19-9, particularly with respect to chronic pancreatitis (CP): 68% vs.86% for the PAM4 assay (P=0.014). Furthermore, CA19-9 results showed considerably higher detection rates for non-PDAC neoplasia, including patients with other cancers that metastasized to the pancreas. Thus, positive likelihood ratios (+LR) were lower for CA19-9 (+LR=2.41) than for the PAM4 assay (+LR=5.29).

PAM4 and CA19-9 antigen levels in PDAC were independent of each other ($r^2$=0.003, P=0.410); however, the positive and negative interpretations were concordant in 68% of the cases. Thus, a combined biomarker analysis improved the overall PDAC detection rate (84%), without a significant decrease in specificity (83%). Comparison of the ROC curves for PDAC vs. CP and PDAC vs. benign disease demonstrated a statistically significant improvement for the combined immunoassay, as compared to either assay alone (P<0.0001 in both comparisons), to detect and discriminate PDAC from benign disease.

While the PAM4-immunoassay provided high sensitivity and specificity for detection and diagnosis of PDAC, inclusion of the CA19-9 biomarker significantly enhanced positive identification of PDAC patients, from 74% to 84%.

Example 33

Use of PAM4-Immunoassay as a Correlate of Tumor Response

Figure 28A:
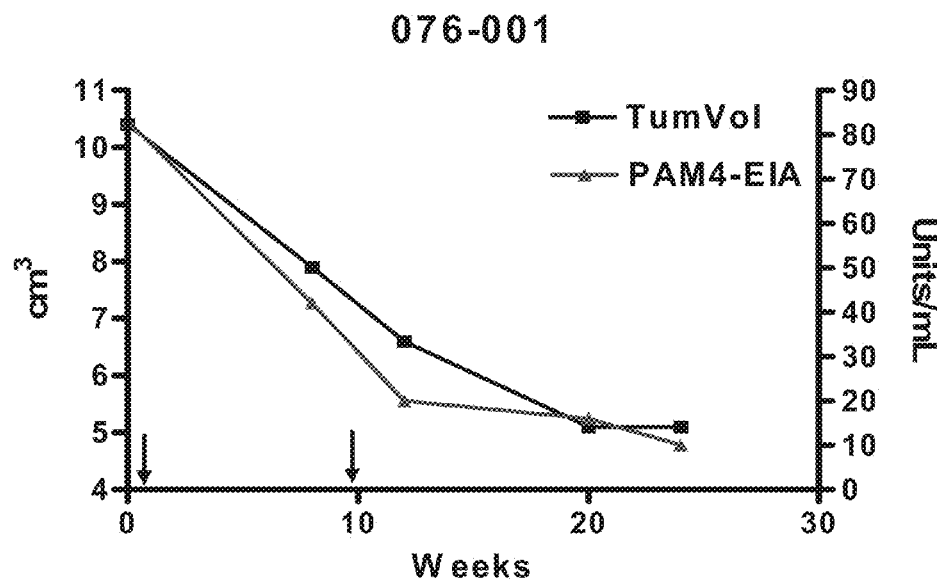
FIG. 28A. Circulating PAM4 antigen levels correlated with progression/regression of tumor volume (CT) following treatment with $^{90}$Y-PAM4-IgG plus gemcitabine. Patient 076-001 was responsive to therapy and serum PAM4 antigen decreased. Serum PAM4 levels correlated with tumor volume.
Figure 28B:
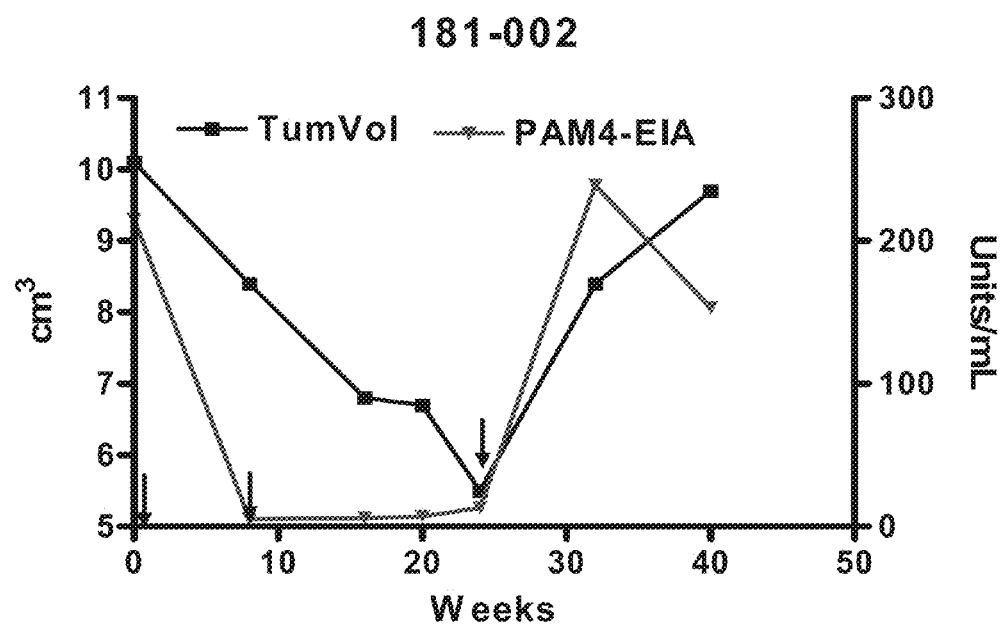
FIG. 28B. Circulating PAM4 antigen levels correlated with progression/regression of tumor volume (CT) following treatment with $^{90}$Y-PAM4-IgG plus gemcitabine. Patient 1810002 showed an initial response to therapy, followed by recurrence of the tumor. Serum PAM4 levels correlated with tumor volume.

We investigated whether specific trends in PAM4-reactive MUC5AC concentrations (within the individual patient) can be used as an indicator of tumor response after therapy. Several patients from a $^{90}$Y-hPAM4 phase-1b/II clinical trial now in progress were evaluated. When patients were evaluated 4 weeks after treatment had ended (a treatment cycle is 4 weeks), a decrease in serum antigen levels of >40% was suggestive of a response. All of the patients who had progressive disease had levels of PAM4 antigen that continued to rise. Trends are presented for two patients in FIG. 28A and FIG. 28B. In both cases, trends in the level of circulating MUC5AC were concordant with the trend in tumor volume as determined by CT. These results suggest that serum PAM4 levels are of use to monitor responsiveness to anti-cancer treatments for pancreatic cancer.

Example 34

Identification of Target Antigen for PAM4 Antibody

We performed a set of blocking and capture/probe paired enzyme immunoassays to evaluate the relationships between the PAM4 antibody and antibodies reactive with MUC1 (MA5, KC4, HMFG1, SM3, H23), MUC2 (G9), MUC4 (8G7) and MUC5AC (45M1). A mucin standard derived from the CaPan1 human tumor xenograft was shown to contain the reactive mucin species for all of these antibodies except those reactive with G9 (MUC2). Of all MAbs examined, only 1 (45M1) reported to be reactive with MUC5AC provided a positive reaction in sandwich EIA when PAM4 was used as the capture reagent. The 45M1 antibody is reactive with a much lower percentage of pancreatic carcinomas than PAM4 (by IHC on TMA) and so cannot be used as a single probe for the serum-based PAM4-immunoassay.

As described above, we performed a peptide-phage-display study by consecutive biopanning with the murine and humanized versions of PAM4-IgG. A consensus sequence (12mer-WTWNITKAYPLP (SEQ ID NO: 7)) was generated which when input into a BLAST protein search with query coverage set at 100%, identified MUC5AC and MUC16 with 7 of 12 and 5 of 12 identical amino acids within the 12mer sequence, respectively.

Studies were performed using mass spectrometry to identify PAM4-immunoprecipitated antigens from credentialed cyst fluids (these fluids were previously analyzed by mass spectrometry to identify specific MUCs present in the mixtures). By PAGE analyses of the PAM4-immunoprecipitated materials from 3 individual cyst fluid specimens, only two identical bands were present in each specimen (not shown). Both of these bands contained MUC5AC as the major mucin species.

Figure 29:
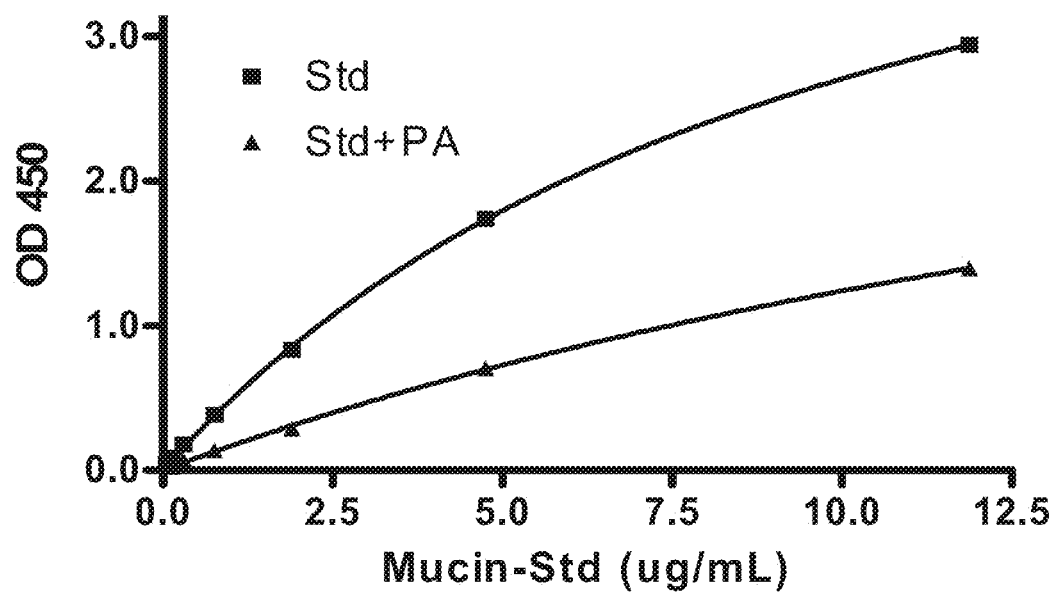
FIG. 29. Reactivity of PAM4 with mucin standards in the presence or absence of palmitic acid.

We have investigated the nature of the substance within human blood that binds to the PAM4-epitope, which necessitates organic extraction prior to immunoassay. As discussed above, Slomiany and co-workers have observed that gastric mucin had covalently bound and/or associated lipids and fatty-acids. Further, fatty-acid synthetase levels and activity are significantly elevated in pancreatic adenocarcinoma, as is also the case for other forms of cancer and other pathologic conditions. Speculating that the blocking substance might be lipid in nature, we performed an EIA (FIG. 29) in the presence and absence of 100 μM palmitic acid and observed a statistically signficant 69% reduction in reactivity at an OD450 equivalent of 1.0 (P<0.0001). It is noted that the normal adult serum level of palmitic acid is in the range of 1,480 to 3,730 μM, considerably higher than the concentration that was used in this EIA experiment.

Example 35

PAM4 Differentiates Between Pancreatic Ductal Adenocarcinoma (PDAC) and Chronic Pancreatitis (CP)

Current practice guidelines suggest that patients who present with signs and/or symptoms suspicious of pancreatic cancer undergo a pancreatic protocol CT imaging study for detection of tumor mass within the pancreas. Follow-up imaging by endoscopic technologies (e.g., EUS, ERCP) can provide high sensitivity for detection of disease, and when combined with fine-needle aspiration/biopsy, can provide good diagnostic accuracy. However, the majority of these procedures have been performed on patients with advanced disease; that is, tumors greater than 2 cm. Detection of early pancreatic cancer is still problematic, especially when occurring in a background of pancreatitis. Thus, the current reality is that only 7% of all cases detected are early disease. With no effective treatment for advanced PC, the prognosis for these patients is dismal.

Biomarkers that can reliably distinguish between cancer and benign conditions, and/or provide means to prioritize patients for follow-up evaluation, would be of significant clinical value, especially if the biomarker is capable of detecting early disease. We have developed monoclonal antibody PAM4 that demonstrates a high degree of specificity for pancreatic ductal adenocarcinoma (PDAC).

MAbs having defined reactivity with several mucin species, including MUC1, MUC2, MUC3, MUC4, MUC5AC, etc., were evaluated for signal response in a heterologous PAM4-capture sandwich EIA. The only MAbs able to provide signal response (45M1, 2-11M1) are known to react with specific domains of the MUC5AC mucin. Further, three additional anti-MUC5AC MAbs (21M1, 62M1, and 463M1) were each able to inhibit the interaction between PAM4 and its mucin antigen. These data suggest MUC5AC as an antigen to which PAM4 is reactive. PAM4, unlike other anti-MUC5AC MAbs (45M1, 2-11M1, CLH2, and others), demonstrates greater specificity for PDAC than cancers originating from other organs, and may serve as a useful biomarker for PDAC, as well as a target for antibody-directed imaging and therapy.

TABLE 22

PAM4-Antigen In the Serum of Patients with Known Disease

| Pancreatic Cancer | N | Median (units/mL) | Number of Positive Cases | Percent of Positive Cases |
| --- | --- | --- | --- | --- |
| Ductal Adenocarcinoma | 298 | 10.40 | 225 | 76 |
| Neuroendocrine | 20 | 0.08 | 2 | 10 |
| Other Morphology | 7 | 0.51 | 1 | 14 |
| Non-PC, Mets to the Pancreas | 11 | 0.00 | 2 | 18 |
| Ampullary Adenocarcinoma | 21 | 1.52 | 10 | 48 |
| Biliary Adenocarcinoma | 26 | 4.41 | 13 | 50 |
| Cholangiocarcinoma | 7 | 1.07 | 2 | 29 |
| Duodenal Adenocarcinoma | 7 | 2.80 | 4 | 57 |
| All Biliary and Periampullary | 61 | 1.78 | 29 | 48 |
| Colon Carcinoma | 32 | 0.15 | 5 | 16 |
| Chronic Pancreatitis (CP) | 80 | 0.41 | 18 | 23 |
| Benign Cystadenoma | 15 | 0.18 | 1 | 7 |
| Benign - Other | 25 | 0.20 | 5 | 20 |
| All Benign Disease | 120 | 0.26 | 24 | 20 |
| Healthy Volunteers | 79 | 0.27 | 3 | 4 |

All groups are statistically different from the pancreatic adenocarcinoma group with P values equal to or better than 0.0001; Mann-Whitney nonparametric test.
Gold D V, Gaedcke J, Ghadimi B M, et al. Cancer. 2013 Feb. 1; 119(3): 522-8.

Figure 30A:
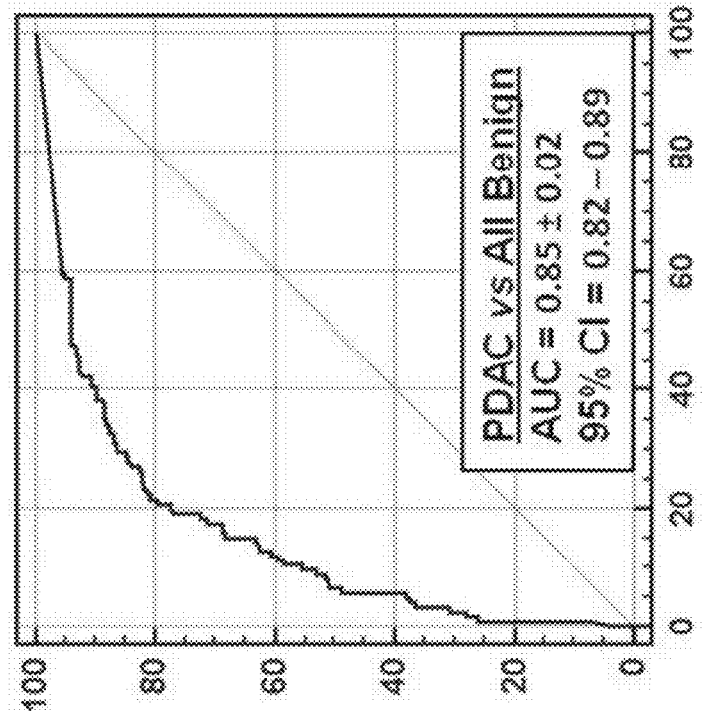
FIG. 30A. Sensitivity and specificity for PAM4 detection of PDAC vs. chronic pancreatitis (CP).
Figure 30B:
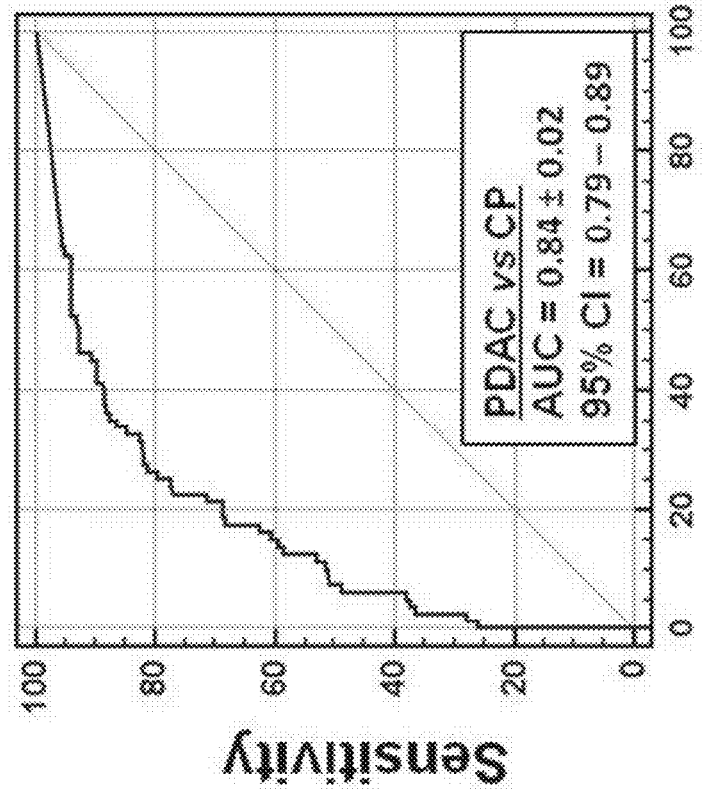
FIG. 30B. Sensitivity and specificity for PAM4 detection of PDAC vs. all benign tissue samples.

The PDAC group consisted of 40% early and 60% advanced stage patients. Detection rates were 64% and 85%, respectively. The sensitivity and specificity of the PAM4 assay was determined for PDAC vs. CP (FIG. 30A) and for PDAC vs. all benign tissue samples (FIG. 30B). The calculated values of AUC were 0.84 and 0.85, respectively.

Approximately 20% of patients with chronic pancreatitis (CP) are positive by use of the serum-based immunoassay. This issue is critical to the interpretation of the results with PAM4-positive CP patients being either false positives, or perhaps, the discovery of occult neoplasia. Thus, we undertook an extensive immunohistochemical evaluation of PAM4-reactivity in CP tissue specimens.

Figure 31:
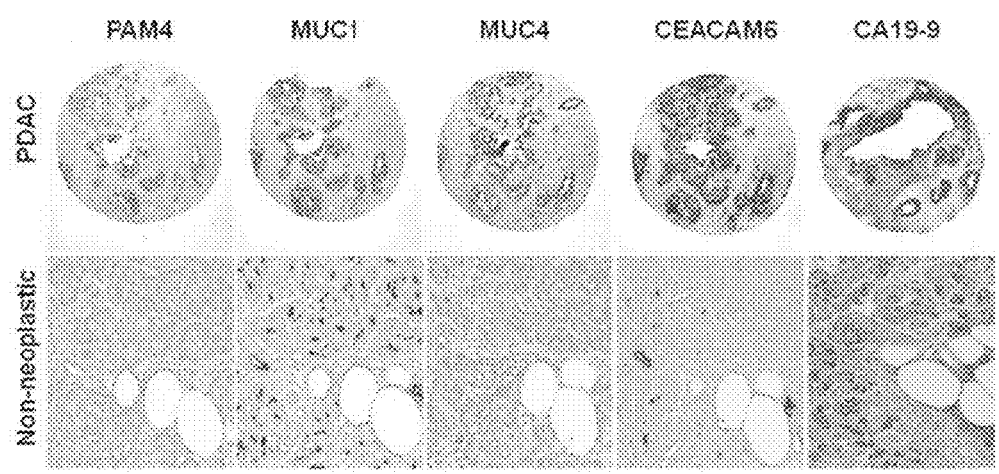
FIG. 31. Comparative labeling of PDAC vs. non-neoplastic prostate tissue with PAM4 vs. antibodies against MUC1, MUC4, CEACAM6 and CA19-9.

FIG. 31 shows comparative labeling of PDAC vs. non-neoplastic prostate tissue by PAM4 antibody vs. antibodies against MUC1, MUC4, CEACAM6 and CA19-9. Each of the antibodies reacted with PDAC. PAM4 showed no reactivity with normal tissue. The same antibodies were compared in a sample showing a PanIN-2 lesion arising within a background of CP, with partial loss of acinar cells, some fibrosis and PanIN-associated acinar-ductal metaplasia (ADM) (not shown). No labeling was observed with PAM4 in any of the tissues within CP, including isolated ADM (not shown). Each of the other antibodies showed some binding to non-neoplastic tissue (not shown). Table 23 and Table 24 show comparative results of labeling with PAM4 vs. antibodies against MUC1, MUC4, CEACAM6 and CA19-9.

TABLE 23

Expression of Biomarkers in Pancreatic Ductal Adenocarcinoma

|  | PAM4 | MUC1 | MUC4 | CEACAM6 | CA19-9 |
| --- | --- | --- | --- | --- | --- |
| Number | 43 | 43 | 43 | 42 | 43 |
| Focal Labeling a | 8 (24%)b | 1 (2%) | 4 (15%) | 3 (8%) | 2 (5%) |
| Diffuse Labeling | 26 (76%) | 42 (98%) | 22 (85%) | 35 (92%) | 37 (95%) |
| Total Labeled | 34 (79%) | 43 (100%) | 26 (60%) | 38 (90%) | 39 (91%) |
| Adjacent Normal (N = 14) | 0 (0%) | 14 (100%) | 6 (43%) | 14 (100%) | 14 (100%) | aFocal labeling, 5% to 25% of the appropriate tissue components labeled with the indicated MAb; Diffuse, >25% of the appropriate tissue components labeled with the indicated MAb; Total, focal + diffuse.
bvalue provided in parenthesis is the percentage of total N PDAC specimens evaluated

TABLE 24

Expression of Biomarkers in Chronic Pancreatitis

|  | N | PAM4 | MUC1 | MUC4 | CEACAM6 | CA19-9 |
|---|---|---|---|---|---|---|
| Chronic Pancreatitis | 32 | | | | | |
| PanIN1 | 5 | 2 | 2 | 1 | 5 | 5 |
| PanIN2 | 5 | 4 | 4 | 3 | 5 | 5 |
| Ducts | 32a | 0 | 22 | 25 | 31 | 29 |
| Acinar cells | 32a | 0 | 27 | 8 | 30 | 29 |
| Isolated ADM | 32a | 0 | 24 | 0 | 0 | 26 |

We conclude that PAM4 is not reactive with the non-neoplastic tissues from chronic pancreatitis (CP) patients, but rather with PDAC and its neoplastic precursor lesions, such as PanINs, which are known to develop within the inflamed parenchyma. Together with results from a prior study, we have evaluated a total of 51 specimens of CP, finding that in no instance was PAM4 reactive with the inflamed parenchyma. On the other hand, each of the other biomarkers investigated, MUC1, MUC4, CEACAM6, and CA19-9, were unable to differentiate PDAC and benign, non-neoplastic tissues. These latter biomarkers were expressed to varying extents in CP-associated PanIN lesions, but also in non-neoplastic ducts and isolated ADM. A PAM4-based EIA to quantitate antigen in patient sera shows high sensitivity and specificity for detection of PDAC. Approximately ⅔ of patients with stage-1 disease are positive for circulating PAM4-antigen. We speculate that CP patients (and perhaps others having disease with high risk for development of PDAC), who are found to have positive levels of PAM4-reactive antigen in the circulation, may have occult PDAC and/or significant mass of precursor lesions producing the PAM4-biomarker.

Example 36

Mapping the PAM4 Epitope on MUC5AC

Summary

Indirect and sandwich enzyme immunoassays (EIA) were performed to compare and contrast the reactivity of PAM4 with several anti-mucin antibodies having known reactivity to specific mucin species (e.g., MUC1, MUC4, MUC5AC, etc.). Studies designed to block reactivity of PAM4 with its specific antigen also were performed. We demonstrated that MAbs 2-11M1 and 45M1, each reactive with MUC5AC, are able to provide signal in a heterologous sandwich immunoassay where PAM4 is the capture antibody. Further, we identified MAbs 21M1, 62M1, and 463M1, each reactive with MUC5AC, as inhibiting the reaction of PAM4 with its specific epitope. MAbs directed to MUC1, MUC3, MUC4, MUC16 and CEACAM6 were not reactive with PAM4-captured antigen, nor are they able to block the reaction of PAM4 with its antigen. We concluded that MUC5AC is the mucin species to which PAM4 antibody is reactive.

Background

Mucin glycoproteins are high molecular weight, heavily glycosylated, proteins that include at least 19 species categorized on the basis of their unique protein cores. They can be found as either transmembrane components of the cell or as secreted products. Abnormal expression of mucins is a well-known occurrence in many forms of cancer (see Hollingsworth & Swanson, 2004, Nat Rev Cancer 4:45-60; Kufe, 2009, Nat Rev Cancer 9:874-85; Rachagani et al., 2009, Biofactors 35:509-27), including pancreatic ductal adenocarcinoma (PDAC) (Ringel & Lohr, 2003, Mo lancer 2:9-13; Andrianifahanana et al., 2001, Clin Cancer Res 7:4033-40; Torres et al., 2012, Curr Pharm Des 18:2472-81). Neo-expression and/or upregulation/downregulation of specific mucin species, with and without the generation of newly transcribed and translated splice variants (Schmid, 2003, Oncol Rep 10:1981-85), have been well-documented in the literature. Alteration of carbohydrate moieties through the addition of new terminal sugars (e.g., neuraminic acids), underglycosylation, and other abnormal biochemical pathways also have been observed (Brockhausen, 2006, EMBO Rep 7:599-604; Yue et al., 2009, Mol Cell Proteomics 8:1697-707; Haab et al., 2010, Ann Surg 251:937-45). These modifications may lead to changes in conformational structure and/or appearance or disappearance of specific epitopes. Additionally, changes may be observed for the intracellular distribution of the mucin species under consideration, such as MUC1, which in normal tissues is a transmembrane glycoprotein, but with neoplastic transformation is found in the cytoplasm as well (Jass et al., 1995, J Pathol 176:143-49; Cao et al., 1997, Virchows Arch 431:159-66). These events may prove to be of biological and clinical significance in the process of neoplastic development and progression, as well as provide new biomarkers/targets for early detection and targeted therapy of cancer.

Our laboratory initially reported the use of a polyclonal antiserum to identify a pancreatic ductal mucin, which at the level of sensitivity provided by indirect immunohistochemistry (IHC), was shown to contain an epitope relatively specific to the pancreas (Gold et al., 1983, Cancer Res 43:235-38), and ultimately resulted in the development of monoclonal antibody (MAb), PAM4 (Gold et al., 1994, Int J Cancer 57:204-10), also known as clivatuzumab in its humanized form. PAM4 demonstrates high specificity for PDAC with little to no reactivity towards normal and benign, non-neoplastic, pancreatic tissues, although it does show limited reactivity (approximately 10% of all specimens examined) with adenocarcinomas originating in certain other organs (e.g., stomach, colon, lung) (Gold et al., 1994, Int J Cancer 57:204-10; Gold et al., 2007, Clin Cancer Res 13:7380-87; Gold et al., 2010, Cancer Epidemiol Biomarkers Prev 19:2786-94). PAM4 identifies a biomarker that, if present, provides a high diagnostic likelihood of the presence of pancreatic neoplasia (Gold et al., 2010, Cancer Epidemiol Biomarkers Prev 19:2786-94; Gold et al., 2006, J Clin Oncol 24:252-58; Gold et al., 2013, Cancer 119:522-28). Thus, clinical applications for detection of early-stage disease (Gold et al., 2010, Cancer Epidemiol Biomarkers Prev 19:2786-94; Gold et al., 2013, Cancer 119:522-28), and antibody-targeted imaging and therapy, are being pursued (Gulec et al., 2011, Clin Cancer Res 17:4091-4100; Ocean et al., 2012, Cancer 118:5497-5506). In addition to PDAC, the PAM4-biomarker is expressed in the precursor lesions, pancreatic intraepithelial neoplasia (PanIN, including the earliest developing lesion, PanIN-1A), and intraductal papillary mucinous neoplasia (IPMN), suggesting that there may be oncogenic significance to its expression (Gold et al., 2007, Clin Cancer Res 13:7380-87). In the current study, we investigated the identity of the mucin species to which this clinically-relevant antibody is reactive, in order to understand what role this mucin may play in the development and progression of pancreatic cancers.

Methods

Antigen and Antibodies—

A mucin containing fraction, designated CPM1, was isolated, as described previously (Gold et al., 2006, J Clin Oncol 24:252-58), from the Capan-1 human PDAC xenograft in athymic nude mice. Briefly, this consisted of homogenization of the dissected tumor in 0.1M ammonium bicarbonate containing 0.5M sodium chloride. Following high-speed centrifugation (20,000 g×45 min), the soluble material was chromatographed on a SEPHAROSE® 4B-CL column, and then eluted with the identical ammonium bicarbonate-sodium chloride solution. The void volume material was collected, dialyzed against 0.01M sodium phosphate, pH 7.2, and then passed through hydroxyapatite to remove nucleic acids and proteins. The non-binding, mucin-containing fraction was again dialyzed extensively to remove salts and used as a source of antigen.

Antibodies used in the current study are listed in Table 25 with clone and source information. For sandwich and blocking studies, PAM4 was available in both murine (mPAM4) and humanized (hPAM4; clivatuzumab) versions provided by Immunomedics, Inc. (Morris Plains, N.J.). All other MAbs were murine IgG. Mouse ascites fluids containing MAbs 21M1, 45M1, 62M1 and 463M1 were kindly provided by Dr. J. Bara, INSERM, Paris, France. PAM4 antibodies and ascites fluid containing an anti-alpha-fetoprotein antibody, employed as a negative control for the blocking studies (reactive with Hep-G2, hepatoceullar carcinoma cells) were provided by Immunomedics, Inc. (Morris Plains, N.J.). A rabbit polyclonal anti-CPM1 (Gold et al., 1994, Int J Cancer 57:204-210; Gold et al., 2010, Cancer Epidemiol Biomarkers Prev 19:2786-94) IgG served as the positive control with detection by a horseradish peroxidase (HRP)-labeled donkey anti-rabbit IgG (Jackson ImmunoResearch, West Grove, Pa.).

TABLE 25

Monoclonal antibodies used

| Antigen | Clone name | Source |
| --- | --- | --- |
| MUC1 | MA5 | Immunomedics |
| MUC1 | KC4 | Immunomedics |
| MUC1 | CM1 | Gene Tex |
| MUC2 | 994/152 | Abcam |
| MUC3 | M3.1 | Abcam |
| MUC3 | M3A | LifeSpan Bio |
| MUC4 | 8G7 | Santa Cruz Biotech |
| MUC5AC | 2-11M1 | Santa Cruz Biotech |
| MUC5AC | 45M1 | Santa Cruz Biotech |
| MUC5AC | CLH2 | Santa Cruz Biotech |
| MUC16 | X306 | Novus Bio |
| MUC16 | X325 | Abcam |
| CEACAM5 | MN14 | Immunomedics |
| CEACAM6 | MN15 | Immunomedics |
| CA 19-9 | CA 19-9 | Santa Cruz Biotech |

Immunomedics, Inc. - Morris Plains, NJ; GeneTex - Irvine, CA; Abcam - Cambridge, MA; LifeSpan Biosciences, Inc. - Seattle, WA; Santa Cruz Biotechnology, Inc. - Santa Cruz, CA; Novus Biologicals - Littleton, CO.

Enzyme Immunoassay—

Procedures have been described for both indirect and sandwich enzyme immunoassays (Gold et al., 1994, Int J Cancer 57:204-210; Gold et al., 2010, Cancer Epidemiol Biomarkers Prev 19:2786-94). For indirect immunoassays, primary MAbs were used at a concentration of 10 μg/mL to provide high sensitivity for signal detection. For sandwich immunoassays, the capture MAb was coated onto the wells at a concentration of 10 μg/mL, followed by the addition of the CPM1 antigen at various concentrations up to 10 μg/mL. The MAb probe was then added at a high concentration of 10 μg/mL for detection of response to captured antigen. Secondary HRP-labeled anti-species-specific IgG (Jackson ImmunoResearch, West Grove, Pa.) was evaluated initially to determine optimum concentrations for use in the assay (usually 1:1000 or 1:2000). MAb inhibition studies were performed by adding the inhibiting MAb to wells coated with CPM1 antigen, starting at a high concentration of 100 μg/mL of pure MAb or 1:10 dilution of ascites fluid, and titrating to lower amounts. After incubating with the inhibiting antibody at 37° C. for 1 h, the plates were washed, and hPAM4 added to the wells at a concentration of 0.25 μg/mL. hPAM4 binding was then detected with a secondary probe, HRP-labeled anti-human IgG conjugate.

SDS-PAGE and Western-Blotting—

SDS-PAGE was performed under non-reducing conditions using 4-20% Tris-Glycine gels at 125V for about 2 h. Resolved proteins were transferred onto a nitrocellulose membrane using the Mini TRANS-BLOT® cell system (Bio-Rad Laboratories, Hercules, Calif.) at 100 V for 1 h. To examine the identity of recombinant proteins, triplicate samples were run in the same gel and membrane with transferred samples were cut into three pieces for probing with HRP-anti-Myc, HRP-hPAM4, and 45M1 plus HRP-GAM, respectively. The signals were developed with SUPERSIGNAL™ West Dura Chemiluminescent Substrate (Thermo Fisher Scientific, Waltham, Mass.).

Results

Figure 32:
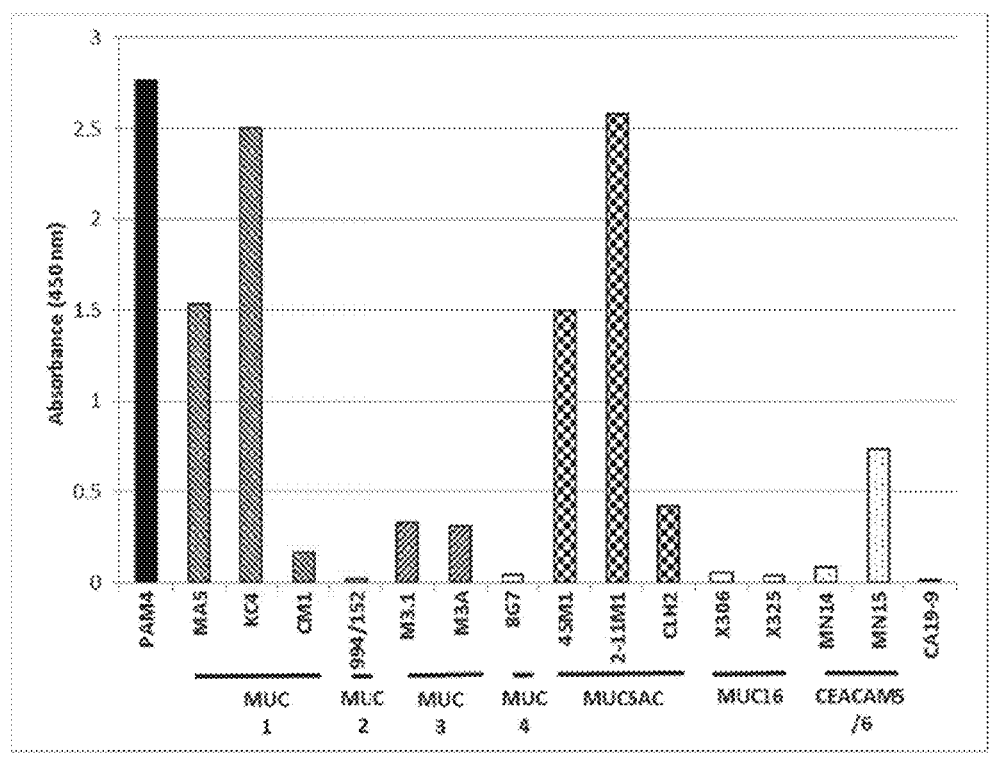
FIG. 32. Reactivity of several anti-mucin MAbs with a high molecular weight mucin containing fraction (CPM1) isolated from the Capan-1, human pancreatic adenocarcinoma. MAbs are identified by clone name with reactive species of mucin indicated by horizontal bars beneath MAb clone names. In addition to PAM4, substantial reactions were observed for anti-MUC1, MUC5AC, and CEACAM6 antibodies. All MAbs were employed at a constant 10 µg/mL.

Several MAbs were evaluated by indirect EIA for reactivity with plates coated with CPM1 (FIG. 32), a high molecular weight mucin fraction isolated from the Capan-1 human pancreatic cancer xenograft. Murine PAM4 and MAbs reactive specifically with MUC1 and MUC5AC mucins provided elevated reactivity in this indirect immunoassay, with minor reactivity also observed for MAbs directed to MUC3 and CEACAM6. Essentially no reaction was seen with MAbs to MUC2, MUC4, MUC16, and CEACAM5 glycoproteins, or the CA19-9 carbohydrate epitope.

It should be noted that a negative EIA reaction does not necessarily indicate absence of the mucin-antigen, because the specific epitope structure may be present, but inaccessible (i.e., cryptic). This is likely the case for MAb-CLH2 anti-MUC5AC generated against a peptide derived from the mucin's tandem repeat (Reis et al., 1997, Int J Cancer 74:112-21), since the other two anti-MUC5AC MAbs were highly reactive. Similarly, CM1 anti-MUC1 was considerably less reactive than MA5 and KC4 anti-MUC1 antibodies. Capan-1 cells produce well-differentiated tumors with highly glycosylated mucins. Thus, it is likely that both CLH2 and CM1, reactive with the tandem repeat domains of their respective mucins, would not be reactive with CPM1, since the tandem repeat epitopes are inaccessible.

Figure 33:
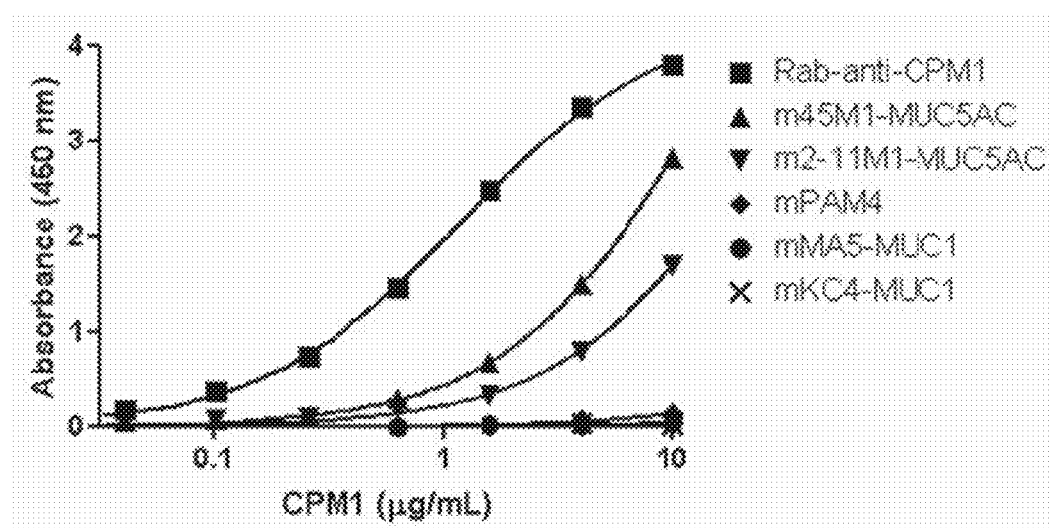
FIG. 33. Reaction of several anti-mucin MAbs with PAM4-captured antigen. Mucin antigens were captured on hPAM4 coated plates, and then probed with several murine anti-mucin MAbs for reaction signal. Both anti-MUC5AC MAbs (2-11M1 and 45M1) bound to the hPAM4-captured mucin, whereas the anti-MUC1 MAbs (MA5 and KC4) did not bind. The homologous hPAM4/mPAM4, capture/probe immunoassay gave no signal, suggesting the density of PAM4 epitopes within the mucin may be low, possibly only a single site. A rabbit polyclonal anti-CPM1, IgG, was used as a positive control for reaction with hPAM4-captured antigen.

We then evaluated whether the anti-mucin MAbs were reactive with PAM4-captured mucin. Humanized PAM4 (hPAM4)-coated plates were used to capture the specific mucin-antigen from the CPM1 fraction, which was then probed with various anti-mucin MAbs. Murine MAbs (mMAbs) specifically reactive with MUC1, MUC3, MUC4, MUC16 and CEACAM6 did not provide a signal in these heterologous sandwich immunoassays (not shown). On the other hand, both anti-MUC5AC mMAbs tested, 45M1 and 2-11M1, gave positive reactions with the hPAM4-captured antigen (FIG. 33), with 45M1 showing significantly greater reaction than 2-11M1 (Kd=14.32±1.08 μg/mL and 24.4±7.83 μg/mL, respectively, for MAbs 45M1 and 2-11M1; P<0.001). However, neither of these individual anti-MUC5AC MAbs provided as strong signal intensity as the rabbit anti-CPM1 polyclonal IgG fraction. Importantly, mPAM4 did not bind to the hPAM4-captured antigen, nor did hPAM4 bind to mPAM4-captured antigen, suggesting that the PAM4 epitope is present at low density, possibly only a single site within the mucin-antigen.

Figure 34A:
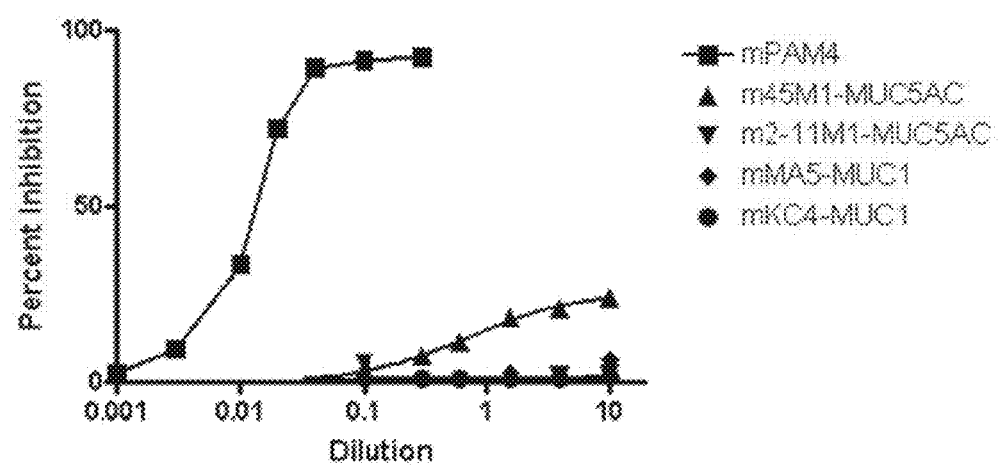
FIG. 34A. Inhibition of hPAM4/antigen binding reaction by murine anti-mucin MAbs. Anti-mucin mMAbs (purified IgG) were added to CPM1-coated plates as potential inhibitors prior to addition of hPAM4. mPAM4 provided almost complete inhibition of the reaction between hPAM4 and antigen with the 45M1 anti-MUC5AC providing limited inhibitory affect ($IC_{max}$=25.5%). Neither 2-11M1, anti-MUC5AC nor MA5 and KC4, anti-MUC1 MAbs were able to inhibit the specific hPAM4/antigen reaction.
Figure 34B:
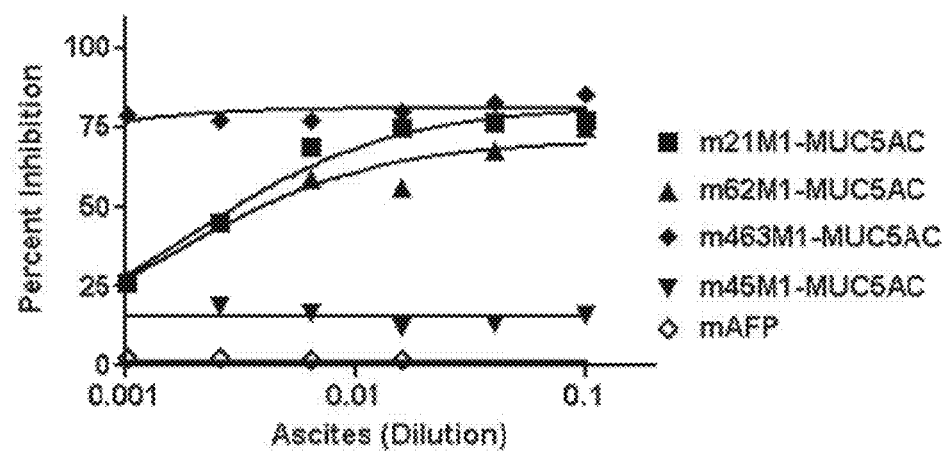
FIG. 34B. Inhibition of hPAM4/antigen binding reaction by murine anti-mucin MAbs. A similar inhibition study was performed with several anti-MUC5AC MAbs obtained as ascites fluids. MAbs 21M1, 62M1, and 463M1, anti-MUC5AC provided substantial inhibitory affect similar to that observed with mPAM4, IgG, self-inhibition. The ascites form of 45M1 yielded an inhibitory affect similar to that of the purified IgG. Ascites containing anti-alpha fetoprotein was employed as a negative control.

Follow-up studies were designed to inhibit the binding of hPAM4 to CPM1-coated plates (FIG. 34A-B). Although 2-11M1 anti-MUC5AC was unable to inhibit hPAM4-CPM1 binding, 45M1 anti-MUC5AC was able to provide a limited inhibitory effect, with $IC_{max}$=25.5% inhibition (FIG. 34A). mPAM4, included as a positive control, provided $IC_{max}$=92.4% self-inhibition at a concentration 0.1 μg/mL, while the MA5 and KC4 anti-MUC1 antibodies provided no inhibition, even at the highest concentration evaluated (10 μg/mL) (FIG. 34A). hPAM4 was unable to completely block mPAM4 binding to the CPM1 antigen ($IC_{max}$=52.8%) (not shown), a not unexpected finding since the humanized version of PAM4 is known to have a lower affinity than the murine parent. Ascites fluids containing mMAbs with known mapping to MUC5AC were serially diluted as inhibitory reagents, with results shown in FIG. 34B. mMAbs 21M1, 62M1, and 463M1 each provided inhibition similar to the results shown for mPAM4 self-blocking, with 45M1 ascites providing limited inhibition, similar to what was observed with the commercially available 45M1-IgG (FIG. 34B). Ascites fluid containing a murine anti-alpha-fetoprotein (AFP), included here as a negative control, provided no inhibition of the hPAM4 binding to CPM1 (FIG. 34B). Unfortunately, insufficient volumes of ascites precluded determination of MAb concentrations, so that relative blocking efficiency could not be calculated.

Discussion

Figure 35:
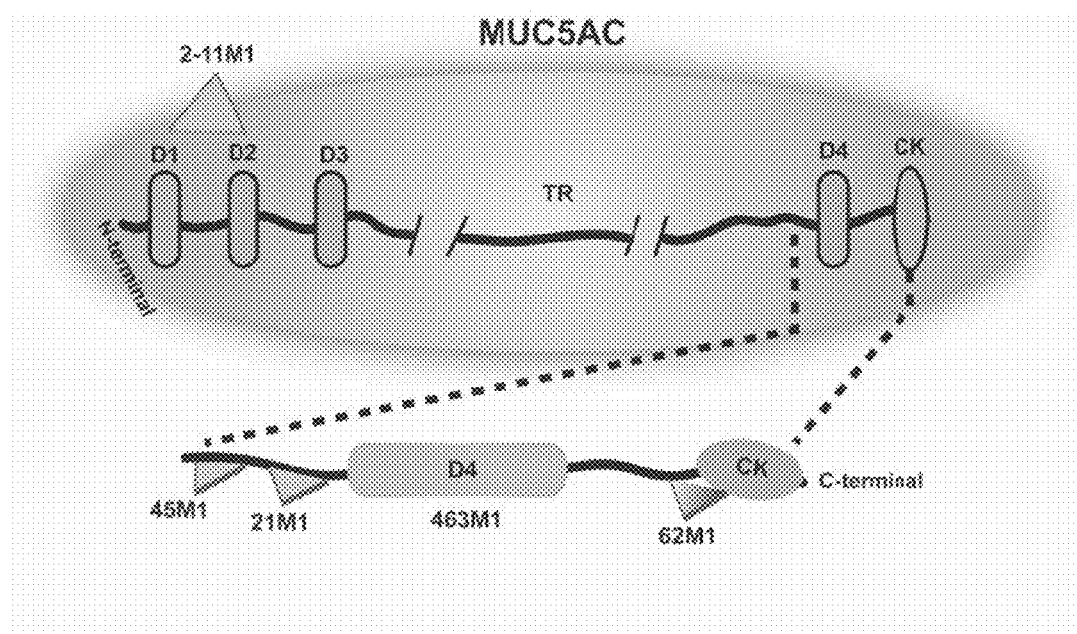
FIG. 35. Representation of the domains of the MUC5AC glycoprotein with reactive epitopes indicated for several anti-MUC5AC MAbs. Data derived by transfection with plasmid vectors containing the cDNA of the 3'-end of MUC5AC, along with derivative cDNA vectors obtained by restriction enzyme digestion, have identified the location of specific epitopes for anti-MUC5AC MAbs employed in the current studies. Specific blocking studies suggest the PAM4-epitope resides within the cysteine-rich C-terminus domain.

The current Example suggests that PAM4 is reactive with the MUC5AC mucin glycoprotein. FIG. 35 presents a map of the MUC5AC mucin domains with reactive epitopes indicated for several of the anti-MUC5AC MAbs employed in our studies (Nollet et al., 2002, Int J Cancer 99:336-43; Nollet et al., 2004, Hybrid Hybridomics 23:93-99; Lidell et al., 2008, FEBS J 275:481-89). CLH2 is reactive with the peptide core of the tandem repeat domain (Reis et al., 1997, Int J Cancer 74:112-21), and is likely a cryptic epitope within the Capan-1 tumor-derived MUC5AC. 2-11M1 is reactive with the N-terminus of the mucin (Nollet et al., 2004, Hybrid Hyridomics 23:93-99), and 45M1 at the furthest N-terminal region of the cysteine-rich, C-terminus (Lidell et al., 2008, FEBS J 275:481-89). Both of these MAbs were reactive with PAM4-captured mucin, whereas MAbs to MUCs 1, 3, 4, and 16 were not. We observed that 45M1 provides a significantly greater signal response than 2-11M1, suggesting a greater density of 45M1-epitopes than 2-11M1-epitopes within CPM1. However, this may simply be due to a loss of 2-11M1 epitopes through proteolytic digestion of the relatively non-glycosylated N-terminus, and/or molecular shear of this very large glycoprotein during purification. In any case, the 2-11M1 antibody provided no inhibition of the hPAM4-CPM1 interaction, suggesting the epitope is located distant to the PAM4-epitope.

On the other hand, 45M1 did inhibit the hPAM4-CPM1 interaction, albeit only partially, suggesting that the PAM4-epitope is within the C-terminal region of the mucin or conformationally altered by interaction of this antibody with the mucin molecule. MAbs 21M1, 62M1, and 463M1 have also been mapped to the C-terminal region of the MUC5AC mucin (Nollet et al., 2002 Int J Cancer 99:336-43; et al., 2004, Hybrid Hybridomics 23:93-99; Lidell et al., 2008, FEBS J 275:481-89), and each provided significant inhibition of the PAM4-mucin reaction. Taken together, our data provide direct evidence that PAM4 is reactive with the identical mucin (MUC5AC), and that the PAM4 epitope is either directly-blocked, or conformationally modified, by interaction of these MAbs with the MUC5AC antigen.

We had initially reported that PAM4 was reactive with the MUC1 mucin species (Gold et al., 2007, Clin Cancer Res 13:7380-87; Gold et al., 2006, J Clin Oncol 24:252-58). This was based upon MUC1-gene transfection studies, whereby PAM4 was observed to react with the gene-transfected, MUC1$^+$ cell line, but not the MUC1$^-$ parental cell line or vector control cell lines. However, other evidence acquired since then has questioned this interpretation, suggesting that MUC1 transfection may have upregulated other mucins as well. Prior results from our laboratory lend support to the current findings. The PAM4 epitope was found to be highly sensitive to mild reduction with dithiothreitol (0.02M, 15 min, 20° C.) or heat (100° C., 2 min), suggesting the epitope is peptide in nature, and highly dependent upon a specific conformation of the protein core kept intact by disulfide bridges (Gold et al., 1994, Int J Cancer 57:204-10). This is unlikely to be MUC1 with all of the cysteines located within the transmembrane domain of the mucin, but is consistent with the loss of reactivity shown by several anti-MUC5AC MAbs upon reduction of the mucin antigen. Further, employing immunohistochemical methods, we reported that frequency of expression and morphologic distribution of the PAM4-epitope within PDAC and its precursor lesions shared greater similarity to those described for MUC5AC than for MUC1 (Gold et al., 2007, Clin Cancer Res 13:7380-87).

In conclusion, antibodies that bind to the PAM4 epitope of MUC5AC are of use for detection and differential diagnosis of pancreatic cancer. Immunoconjugates of such antibodies are of use for pancreatic cancer therapy.

Example 37

DOTA Conjugates of PAM4

The hPAM4 antibody was prepared as described in Example The genes of CDR-grafted $V_H$ and $V_\kappa$ chains of hPAM4 were inserted into the pdHL2 plasmid vector, a DHFR-based amplifiable expression system. The plasmid was transfected into the murine myeloma cell line, Sp2/0-Ag14 (ATCC, Manassas, Va.) to generate the cell clones producing hPAM4. The complete mature amino acid sequence is shown below.

```
hPAM4 Heavy Chain
                                   (SEQ ID NO: 120)
QVQLQQSGAEVKKPGASVKVSCEASGYTFPSYVLHWVKQAPGQGLEWIGY

INPYNDGTQYNEKFKGKATLTRDTSINTAYMELSRLRSDDTAVYYCARGF

GGSYGFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

-continued hPAM4 light chain (SEQ ID NO: 121)

DIQLTQSPSSLSASVGDRVTMTCSASSSVSSSYLYWYQQKPGKAPKLWIY

STSNLASGVPARFSGSGSGTDFTLTISSLQPEDSASYFCHQWNRYPYTFG

GGTRLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Figure 4A:
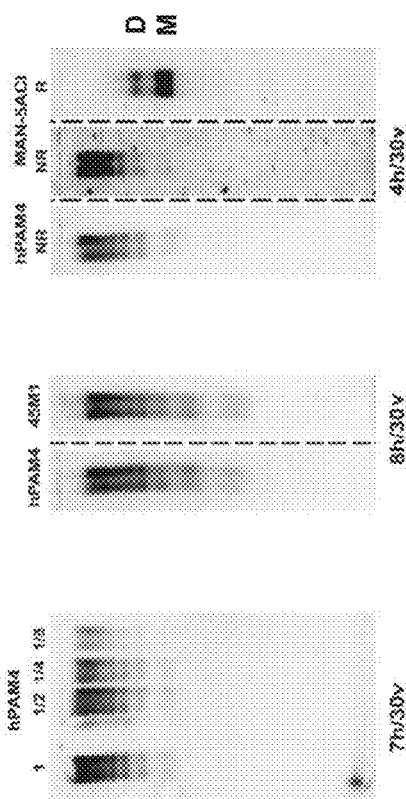
FIG. 4A. Agarose gel electrophoresis. The Capan-1 void-volume peak displayed the characteristic banding pattern of MUC5AC as revealed by Western blot analysis with hPAM4, 45M1, and MAN-5ACI. In the left panel, samples in the lanes marked as 1, ½, ¼, and ⅛ were tested undiluted, 2-, 4- and 8-fold diluted, respectively. In the far right panel, the monomeric and dimeric MUC5AC were indicated as M and D, respectively.
Figure 4B:
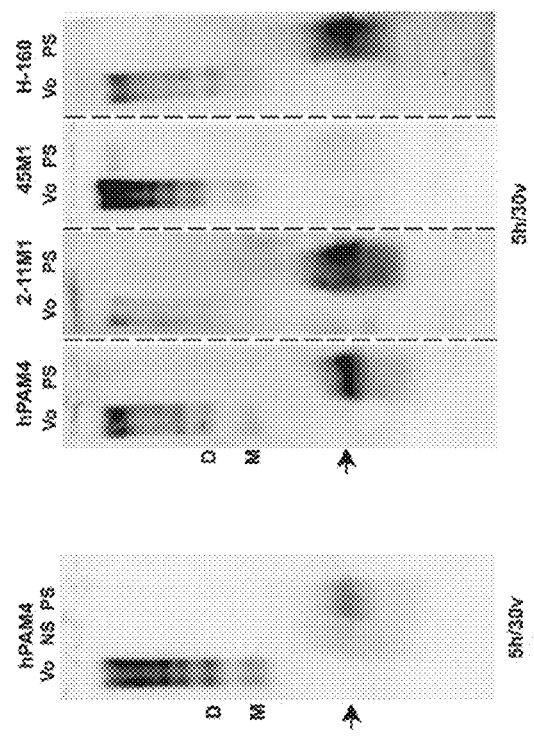
FIG. 4B. Agarose gel electrophoresis. The serum from a pancreatic cancer patient (PS) tested positive for hPAM4-reactive substance was differentially detected by hPAM4 and three anti-MUC5AC antibodies (2-11M1, 45M1, and H-160). The Capan-1 void-volume peak (Vo) and normal serum sample (NS) were included as controls.

The DNA and amino acid sequences of hPAM4 $V_K$ and $V_H$ are shown in FIG. 4A and FIG. 4B, respectively, with the CDRs identified in bold and underlined.

The current cell clone name is hPAM4-2E3 and is produced in Sp2/0 host cells, DHFR expression system. The antibody is a humanized $IgG_{1K}$ glycoprotein. A glycosylation site on the heavy chain (Asn299) has a composition per mole of hPAM4-DOTA: 0.5 Fuc, 6.3 GlcNAc, 6.3 Man, 0.3 Gal and 0.15 Neu5Gc; glycosylation species: GOF 70%, G1F 23%, G2F 2%, G1FS1 4%, G2FS1 1%. There are 16 S—S bonds (32 SH), identified and located exactly as theoretical prediction based on the above sequence.

An hPAM4-DOTA product was prepared from purified hPAM4 IgG that was coupled with the 12-membered macrocyclic chelating agent 1,4,7,10-tetraazacyclododecane-N, N',N',N'''-tetraacetic acid (DOTA).

DOTA was conjugated via one of the carboxyl moieties to reactive sites on the hPAM4 antibody to generate a stable conjugate. The coupling is assumed to be via stable amide bond to the antibody's lysine side-chain amino group.

The chemical conjugation was performed by first reacting DOTA with N-hydroxysulfo-succinimide (sulfo-NHS) in the presence of 1-ethyl-3-(3-dimethylaminopropyl)carbodiimide (EDC) to generate activated DOTA, then incubating activated DOTA with purified hPAM4 antibody. Conditions were optimized to yield a substitution ratio of 4-7 DOTA moieties per antibody molecule, as determined by mass spectrometry assays.

It will be apparent to those skilled in the art that various modifications and variations can be made to the products, compositions, methods and processes of this invention. Thus, it is intended that the present invention cover such modifications and variations, provided they come within the scope of the appended claims and their equivalents.

What is claimed is:

1. A method of detecting or diagnosing pancreatic cancer comprising:
   a) obtaining a fresh blood, serum, or plasma sample from an individual;
   b) removing an inhibitor of anti-MUC5AC antibody binding from the sample by organic phase extraction; and
   c) performing an immunoassay with an anti-MUC5AC antibody or antigen-binding fragment thereof that binds to an epitope located within the second cysteine-rich domain (Cys2, amino acid residues 1575-1725) of MUC5AC;
wherein binding of the antibody is indicative of pancreatic cancer in the individual and the immunoassay can detect early stage pancreatic cancer.

2. The method of claim 1, further comprising performing an immunoassay with one or more additional antibodies that bind to pancreatic cancer cells in the sample.

3. The method of claim 2, wherein the additional antibody binds to an antigen selected from the group consisting of CA19.9, DUPAN2, SPAN1, Nd2, B72.3, CC49, CTLA-4, PD-1, PD-L1, TIM-3, LAG-3, CEACAM5, CEACAM6, Le$^a$, Le(y), CSAp, insulin-like growth factor (IGF), epithelial glycoprotein-1 (EGP-1), epithelial glycoprotein-2 (EGP-2), TROP2, CD80, placental growth factor (P1GF), carbonic anhydrase IX, tenascin, IL-6, HLA-DR, CD40, CD74, CD138, MUC1, MUC2, MUC3, MUC4, MUC5AC, MUC16, MUC17, TAG-72, EGFR, platelet-derived growth factor (PDGF), VEGF, PlGF, bcl-2, Kras, p53, cMET and HER2/neu.

4. The method of claim 3, wherein the additional antibody binds to CA19.9.

5. The method of claim 4, wherein the immunoassay with anti-MUC5AC and anti-CA19.9 antibodies has a sensitivity of 84% and a specificity of 83% for detection of pancreatic cancer.

6. The method of claim 1, wherein the immunoassay can differentiate between individuals with benign non-mucinous pancreatic cystic lesions and individuals with stage 1A, stage 1B and stage 2 pancreatic cancer.

7. The method of claim 1, wherein the immunoassay has a false positive rate of 6% or less for individuals with benign pancreatic lesions.

8. The method of claim 1, wherein the serum immunoassay can detect pancreatic adenocarcinoma in asymptomatic individuals.

9. The method of claim 1, wherein the organic phase is butanol.

10. The method of claim 1, wherein the immunoassay detects the presence of PanIN-1A, PanIN-1B, PanIN-2, invasive pancreatic adenocarcinoma, pancreatic carcinoma, mucinous cyst neoplasms (MCN), intrapancreatic mucinous neoplasms (IPMN) and intraductal papillary mucinous neoplasia.

11. The method of claim 1, wherein the anti-MUC5AC antibody or fragment thereof is capable of binding to a linear peptide comprising the amino acid sequence WTWNIT-KAYPLP (SEQ ID NO: 7) or to a cyclic peptide comprising the amino acid sequence ACPEWWGTTC (SEQ ID NO: 8).

* * * * *